US012629419B2

(12) United States Patent (10) Patent No.: US 12,629,419 B2
Haegel et al. (45) Date of Patent: May 19, 2026

(54) PREVENTION OR MITIGATION OF T-CELL ENGAGING AGENT-RELATED ADVERSE EFFECTS

(71) Applicant: Hoffmann-La Roche Inc., Little Falls, NJ (US)

(72) Inventors: Hélène Cécile Haegel, Illkirch-Graffenstaden (FR); Christian Klein, Weilheim (DE); Gabrielle Leclercq, Zurich (CH); Alberto Toso, Basel (CH); Tina Zimmermann, Zurich (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/454,193

(22) Filed: Nov. 9, 2021

(65) Prior Publication Data

US 2022/0168418 A1 Jun. 2, 2022

(30) Foreign Application Priority Data

| Nov. 10, 2020 | (EP) | ..................................... | 20206567 |
| Feb. 8, 2021 | (EP) | ..................................... | 21155823 |
| May 7, 2021 | (EP) | ..................................... | 21172623 |
| Jul. 23, 2021 | (EP) | ..................................... | 21187472 |

(51) Int. Cl.

| A61K 39/395 | (2006.01) |
| A61K 31/436 | (2006.01) |
| A61K 31/506 | (2006.01) |
| A61K 31/519 | (2006.01) |
| A61K 38/17 | (2006.01) |
| A61K 39/00 | (2006.01) |
| A61K 40/11 | (2025.01) |
| A61K 40/33 | (2025.01) |
| A61K 40/42 | (2025.01) |
| A61P 35/00 | (2006.01) |
| C12N 5/0783 | (2010.01) |

(52) U.S. Cl.
CPC ...... *A61K 39/39558* (2013.01); *A61K 31/436* (2013.01); *A61K 31/506* (2013.01); *A61K 31/519* (2013.01); *A61K 38/1774* (2013.01); *A61K 40/11* (2025.01); *A61K 40/33* (2025.01); *A61K 40/4211* (2025.01); *A61K 40/4221* (2025.01); *A61K 40/4266* (2025.01); *A61K 40/4268* (2025.01); *A61P 35/00* (2018.01); *C12N 5/0636* (2013.01); *A61K 2039/505* (2013.01); *A61K 2239/38* (2023.05); *A61K 2239/51* (2023.05)

(58) Field of Classification Search
None
See application file for complete search history.

(56) References Cited

U.S. PATENT DOCUMENTS

| 5,571,894 A | 11/1996 | Wels et al. |
| 5,587,458 A | 12/1996 | King et al. |
| 5,731,168 A | 3/1998 | Carter et al. |
| 5,869,046 A | 2/1999 | Presta et al. |
| 6,248,516 B1 | 6/2001 | Winter et al. |
| 9,914,776 B2 * | 3/2018 | Ast .................... C07K 16/2809 |
| 2016/0075785 A1 | 3/2016 | Ast et al. |
| 2017/0340733 A1 * | 11/2017 | Cao ......................... A61K 38/13 |
| 2019/0112380 A1 | 4/2019 | Chaudhary |
| 2019/0336504 A1 * | 11/2019 | Gill ......................... A61P 35/02 |
| 2020/0172627 A1 | 6/2020 | Bacac et al. |

FOREIGN PATENT DOCUMENTS

| EP | 0404097 B1 | 12/1990 |
| WO | 93/01161 A1 | 1/1993 |
| WO | 93/16185 A2 | 8/1993 |
| WO | 2014/131712 A1 | 9/2014 |
| WO | 2016/020309 A1 | 2/2016 |
| WO | 2016/079076 A1 | 5/2016 |
| WO | 2017/055314 A1 | 4/2017 |
| WO | 2020/127618 A1 | 6/2020 |
| WO | 2020/127619 A1 | 6/2020 |
| WO | WO-2020/169698 A1 | 8/2020 |
| WO | 2021/122875 A1 | 6/2021 |

OTHER PUBLICATIONS

Ayyappan et al 2019 (Novel and emerging therapies for B-cell lymphoma, Journal of Hematology and Oncology, vol. 12, 2019). (Year: 2019).*
Frey et al (Cytokine release syndrome with novel therapeutics for acute lymphoblastic leukemia. Hematology Am Soc Hematol Educ Program. 2016;2016(1):567-572.), (Year: 2016).*
Dinner et al (Targeting the mTOR Pathway in Leukemia, Journal of Cellular Biochemistry, 117:1745-1752, 2016), (Year: 2016).*
Kaplan et al (Blinatumomab for the treatment of acute lymphoblastic leukemia, Invest New Drugs (2015) 33:1271-1279), (Year: 2015).*
Murthy et al (Cytokine Release Syndrome: Current Perspectives, Immuno Targets and Therapy, vol. 8, pp. 43-52, Published Oct. 29, 2019). (Year: 2019).*
Kamperschroer et al.(Summary of a workshop on preclinical and translational safety assessment of CD3 bispecifics, Journal of Immunotoxicology, vol. 17, pp. 67-85, Published Feb. 7, 2020), (Year: 2020).*
Carter, P., et al., "Bispecific human IgG by design" J Immunol Methods 248(1-2):7-15 (Feb. 1, 2001).
Claus, C., et al., "Tumor-targeted 4-1BB agonists for combination with T cell bispecific antibodies as off-the-shelf therapy" Sci Transl Med 11(496):eaav5989 (1-13) (Jun. 12, 2019).
(Continued)

*Primary Examiner* — Janet L Epps-Smith
*Assistant Examiner* — Sarah A Alsomairy
(74) *Attorney, Agent, or Firm* — Clark & Elbing LLP; Karen L. Elbing

(57) ABSTRACT

The present invention relates to the prevention or mitigation of adverse effects related to T cell engaging agents, such as cytokine release syndrome. Specifically, the invention relates to the prevention or mitigation of such side effects using an inhibitor of JAK and/or mTOR.

41 Claims, 121 Drawing Sheets

Specification includes a Sequence Listing.

(56)                    References Cited

OTHER PUBLICATIONS

F. Hoffmann-La Roche, AG et al., "European Patent Application No. 20181056.1 filed Jun. 19, 2020" (Unpublished),:1-140 (Jun. 19, 2020).

F. Hoffmann-Laroche, AG et al., "European Patent Application No. 20180968.8 filed Jun. 19, 2020" (Unpublished),:1-195 (Jun. 19, 2020).

Holliger, P., et al., "Diabodies: Small Bivalent and Bispecific Antibody Fragments" PNAS 90(14):6444-6448 (Jul. 15, 1993).

Hudson, P., et al., "Engineered antibodies" Nat Med 9(1):129-134 (Jan. 1, 2003).

Husain, B., et al., "Expanding the Boundaries of Biotherapeutics with Bispecific Antibodies" Biodrugs 32(5):441-464 (Oct. 1, 2018).

"International Search Report—PCT/EP2021/066346" (w/Written Opinion),:1-20 (Sep. 7, 2021).

"International Search Report—PCT/EP2021/066366" (w/Written Opinion),:1-17 (Sep. 10, 2021).

Leclercq, G., et al., "653 Dasatinib as a rapid pharmacological On/Off switch for T cell bispecific antibody-induced T cell activation and cytokine release" J Immunother Cancer 8( Suppl 3):1-2 (Nov. 1, 2020).

Li, J., et al., "CD3 bispecific antibody-induced cytokine release is dispensable for cytotoxic T cell activity" Sci Transl Med 11(508):eaax8861 (1-13) (Sep. 4, 2019).

Mestermann, K., et al., "The tyrosine kinase inhibitor dasatinib acts as a pharmacologic on/off switch for CAR-T cells" Sci Transl Med 11(499):eaau5907 (1-12) (Jul. 3, 2019).

Pluckthun, A. et al. The Pharmacology of Monoclonal Antibodies "Antibodies from *Escherichia coli*" (Antibodies from *Escherichia coli*), Rosenberg & Moore, vol. 113:269-315 (1994).

Ridgway, J., et al., "Knobs-into-holes' engineering of antibody CH3 domains for heavy chain heterodimerization" Protein Eng 9(7):617-621 (Jul. 1, 1996).

Shimabukuro-Vornhagen, A., et al., "Cytokine release syndrome" J Immunother Cancer 6(56):1-14 (Jun. 15, 2018).

Stubenrauch, K., et al., "Impact of molecular processing in the hinge region of therapeutic IgG4 antibodies on disposition profiles in cynomolgus monkeys" Drug Metab Dispos 38(1):84-91 (Jan. 1, 2010).

uniprot.org et al., Other Database, B-lymphocyte antigen CD20, P11836, (Last Modified Date: Sep. 29, 2021), pp. 1-13; Creation Date Oct. 1, 1989 https://www.uniprot.org/uniprot/P11836.

Weber, E., et al., "Pharmacologic control of CAR-T cell function using dasatinib" Blood Adv 3(5):711-717 (Mar. 12, 2019).

World Health Organization [WHO] et al., "International Nonproprietary Names for Pharmaceutical Substances (INN)—Cibisatamab" WHO Drug Information 32(3):438 (Oct. 31, 2018).

World Health Organization [WHO] et al., "International Nonproprietary Names for Pharmaceutical Substances (INN)—Glofitamab" WHO Drug Information 34(1):39-42 (Mar. 30, 2020).

Crombie et al., "Consensus recommendations on the management of toxicity associated with CD3xCD20 bispecific antibody therapy," Blood. 143(16): 1565-1575 (Apr. 2024).

Huarte et al., "Prophylactic Itacitinib (INCB039110) for the Prevention of Cytokine Release Syndrome Induced By Chimeric Antigen Receptor T-Cells (CAR-T-cells) Therapy," Blood. 134 (Supplement 1):1934 (Nov. 2019) (2 pages).

Khadka et al., "Management of Cytokine Release Syndrome: An Update On Emerging Antigen-Specific T Cell Engaging Immunotherapies", Immunotherapy, 11:10, 851-857, (Jun. 2019) (8 pages).

* cited by examiner

FIG. 4
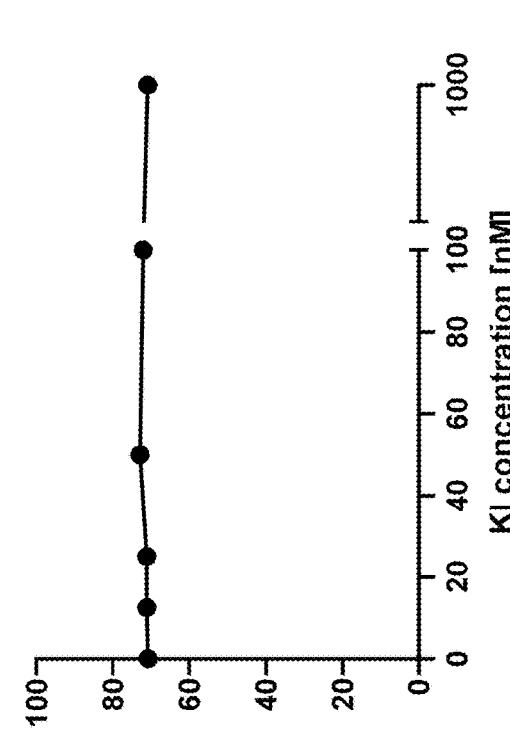
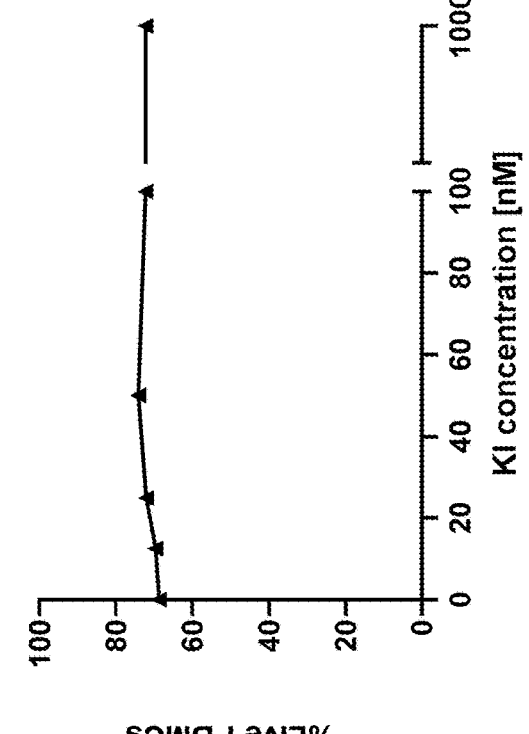
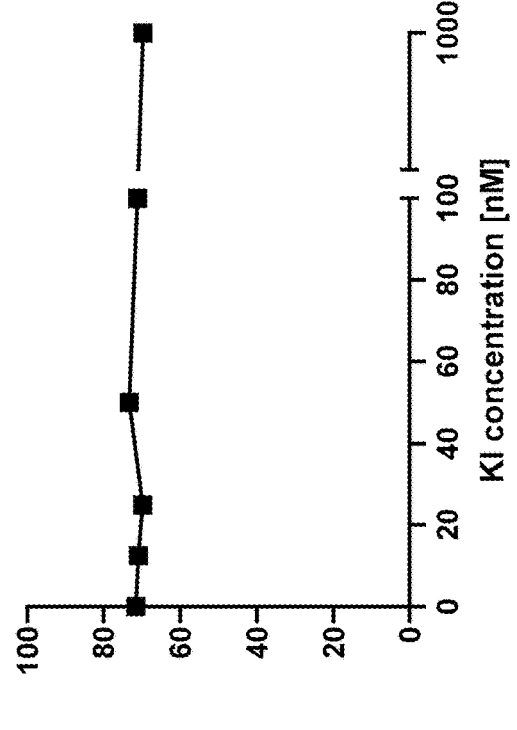

A

CD4%CD69

KI concentration [nM]

B

CD4%CD25

KI concentration [nM]

C

CD8%CD69

KI concentration [nM]

D

CD8%CD25

KI concentration [nM]

FIG. 16

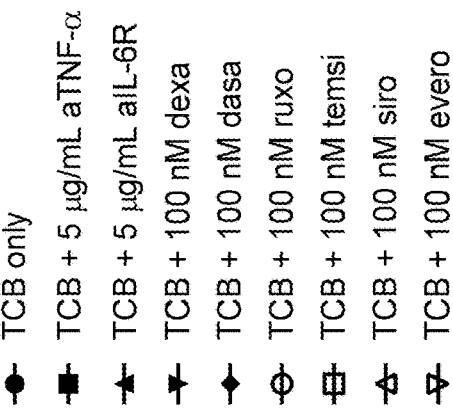
- TCB only
- TCB + 5 μg/mL aTNF-α
- TCB + 5 μg/mL aIL-6R
- TCB + 100 nM dexa
- TCB + 100 nM dasa
- TCB + 100 nM ruxo
- TCB + 100 nM temsi
- TCB + 100 nM siro
- TCB + 100 nM evero
FIG. 29
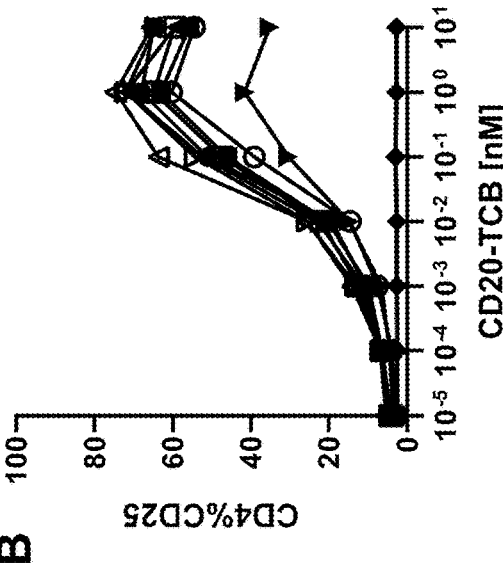
B
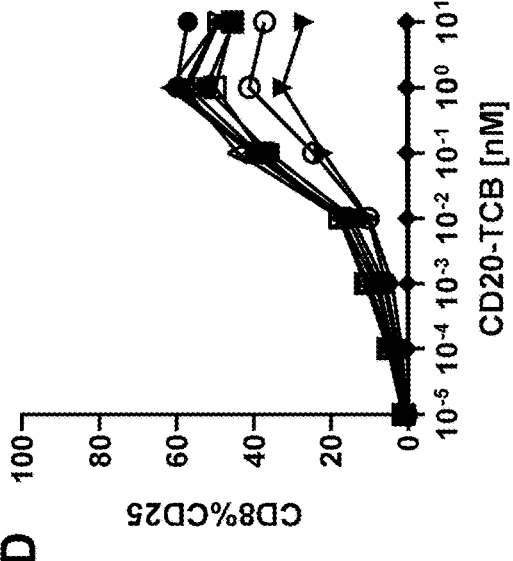
D
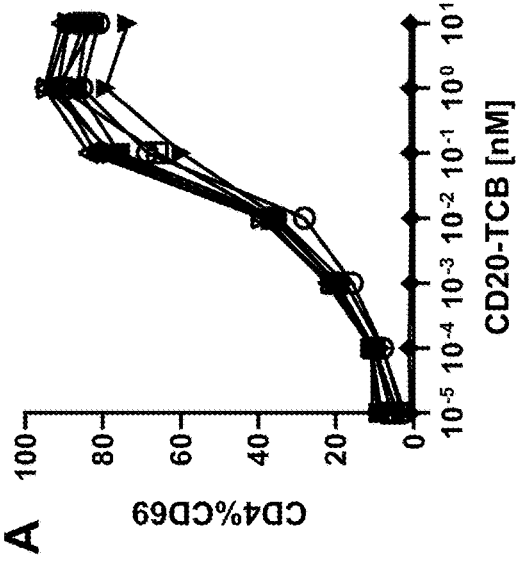
A
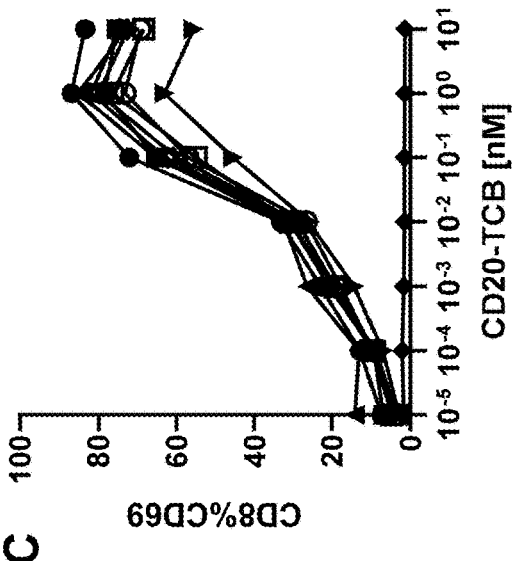
C

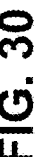
FIG. 30
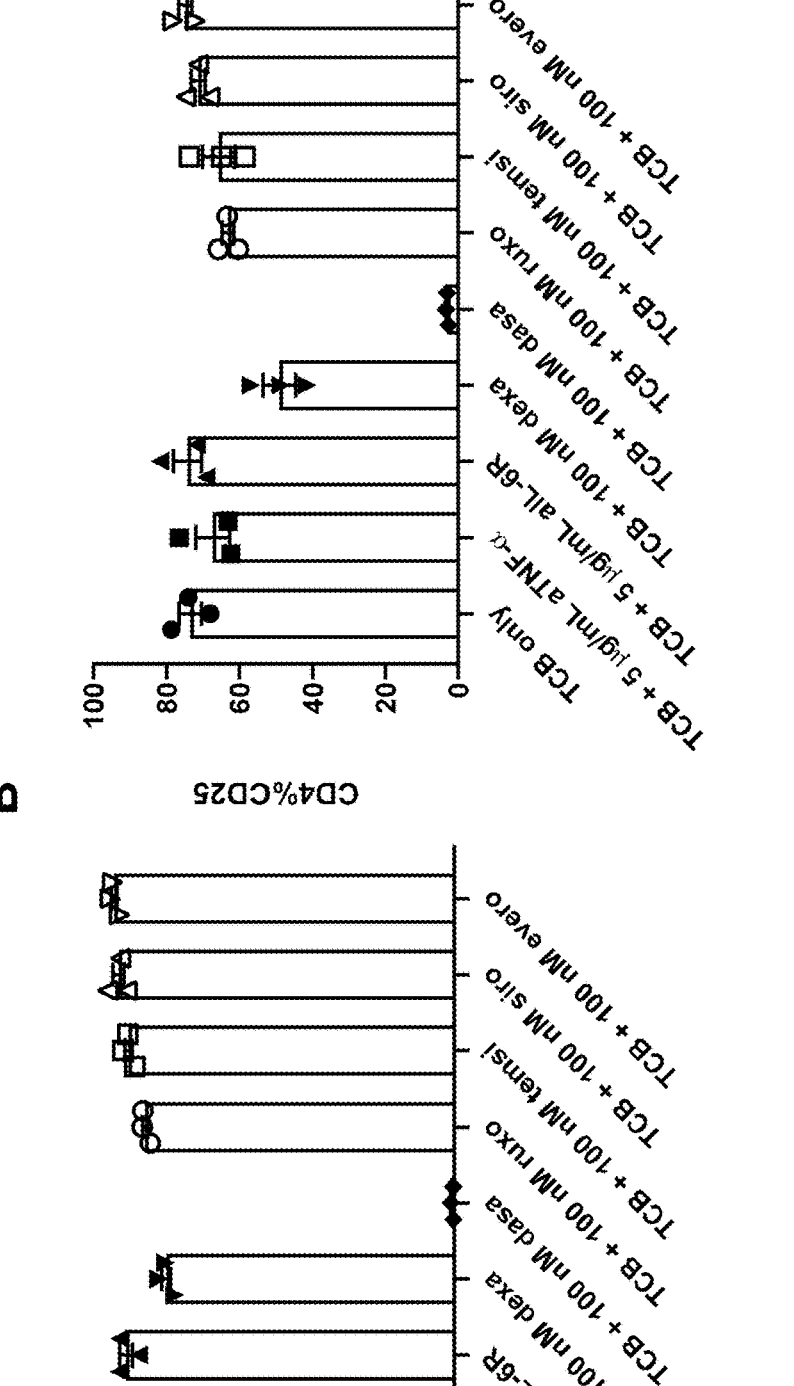

TCB only
TCB + 5μg/mL aTNF-α
TCB + 5μg/mL aIL-6R
TCB + 0.1μM dexa
TCB + 100nM dasa
TCB + 100nM ruxo
TCB + 100nM temsi
TCB + 100nM siro
TCB + 100nM evero

A

TNF-α (pg/mL)

CD20-TCB [nM]

B

IFN-γ (pg/mL)

CD20-TCB [nM]

C

IL-2 (pg/mL)

CD20-TCB [nM]

D

IL-1β (pg/mL)

CD20-TCB [nM]

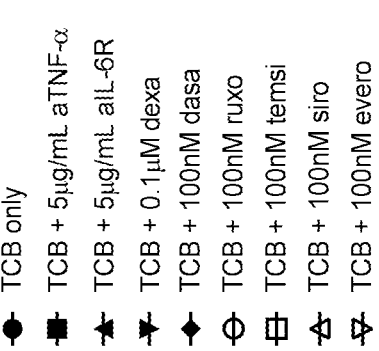
- TCB only
- TCB + 5μg/mL aTNF-α
- TCB + 5μg/mL aIL-6R
- TCB + 0.1μM dexa
- TCB + 100nM dasa
- TCB + 100nM ruxo
- TCB + 100nM temsi
- TCB + 100nM siro
- TCB + 100nM evero
FIG. 32
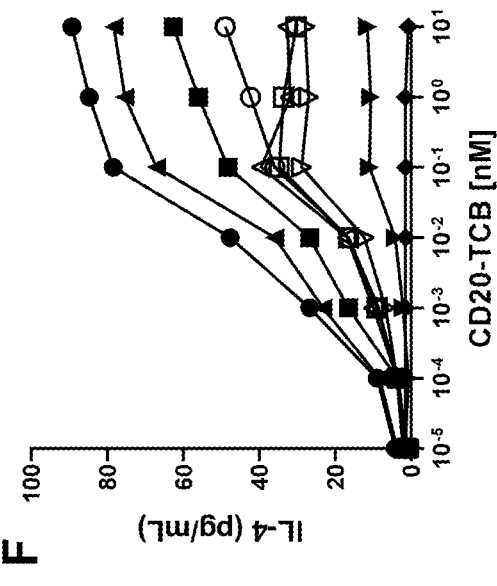
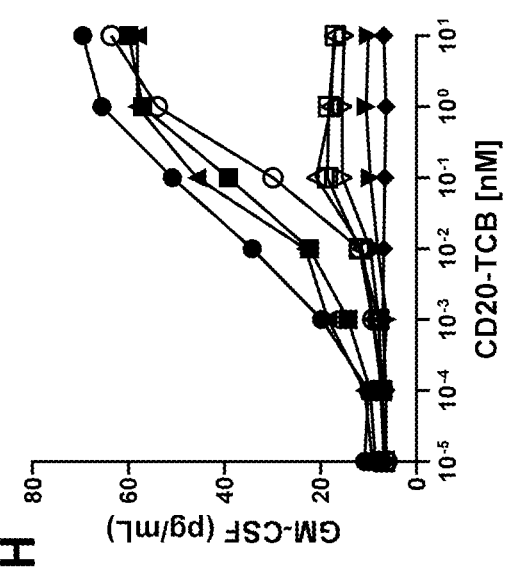
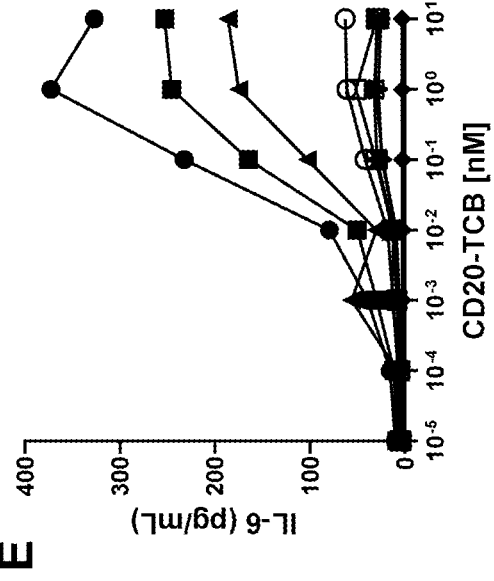
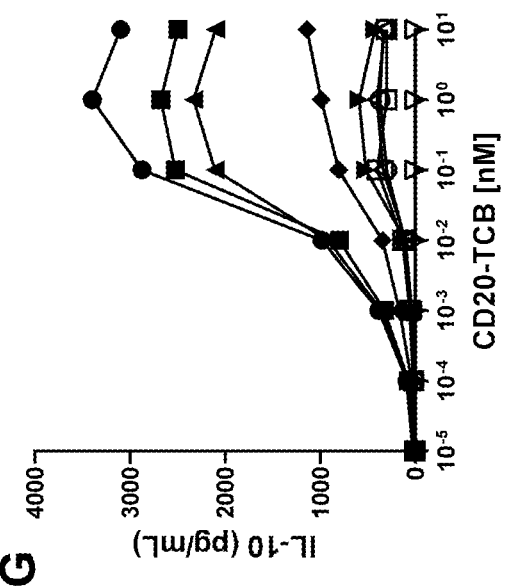

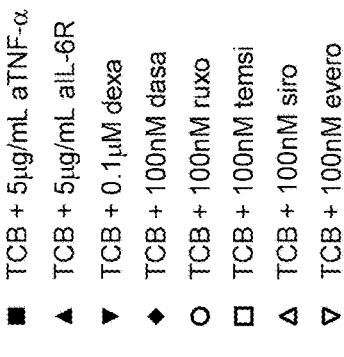
■　TCB + 5μg/mL aTNF-α
▲　TCB + 5μg/mL aIL-6R
▶　TCB + 0.1μM dexa
◆　TCB + 100nM dasa
○　TCB + 100nM ruxo
□　TCB + 100nM temsi
◁　TCB + 100nM siro
▽　TCB + 100nM evero
FIG. 33
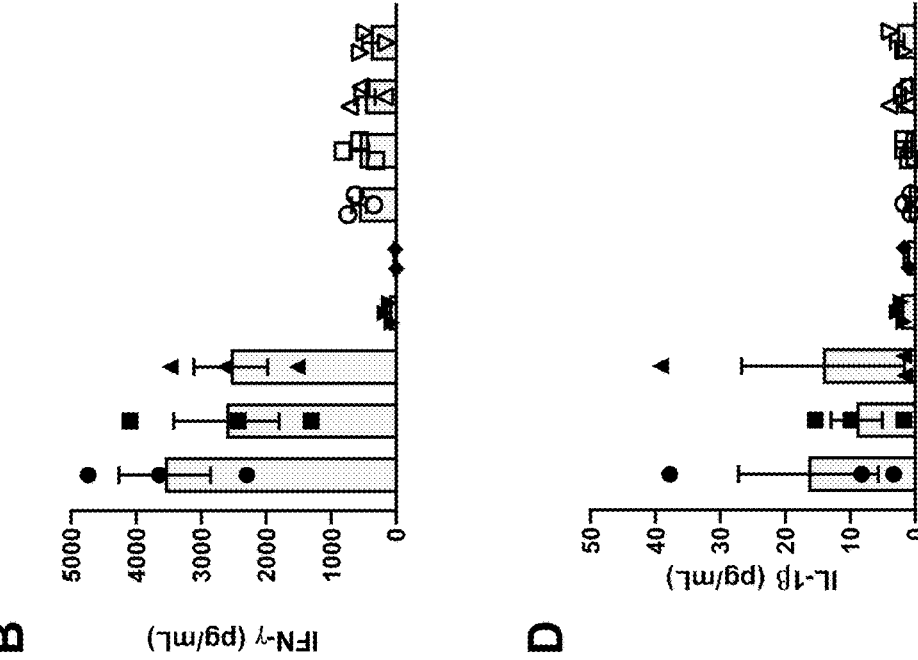
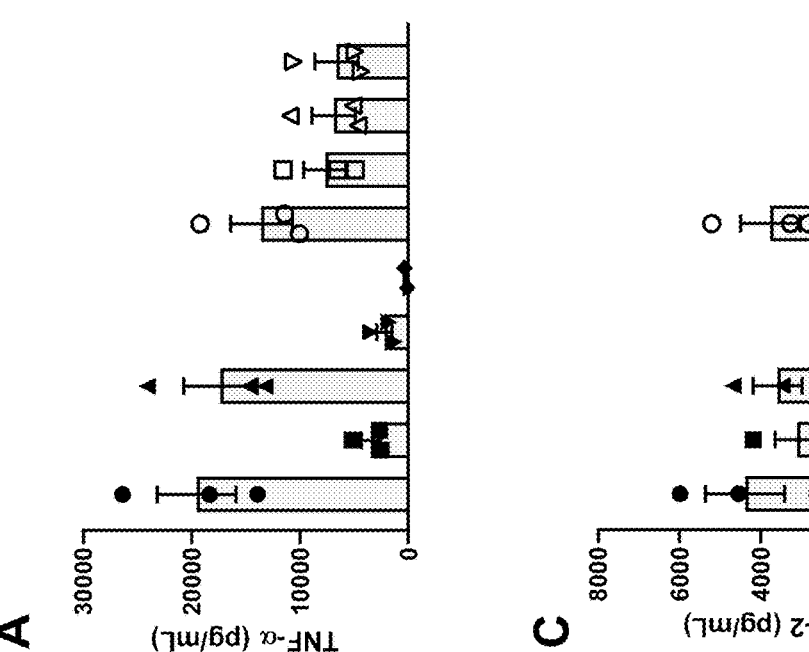

B

A

FIG. 43
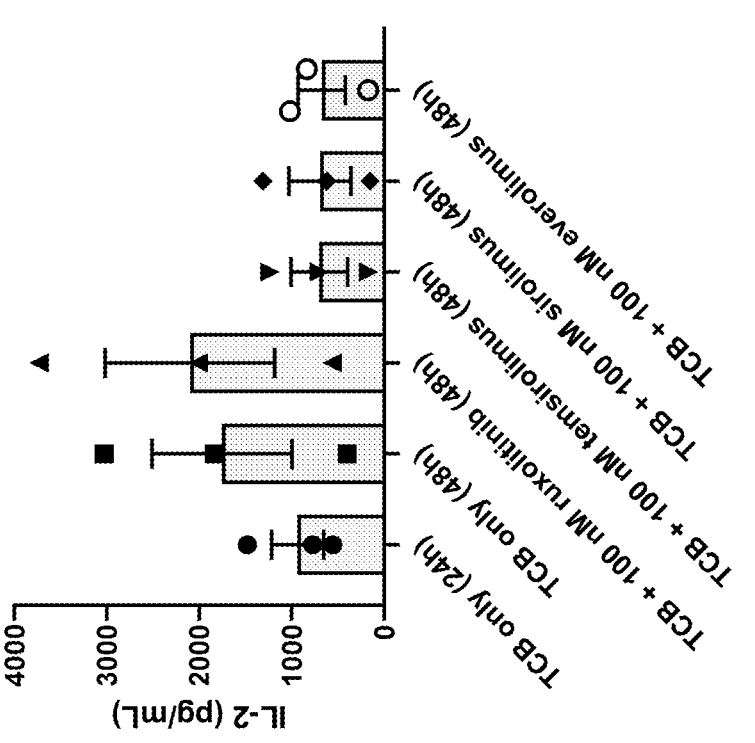
B
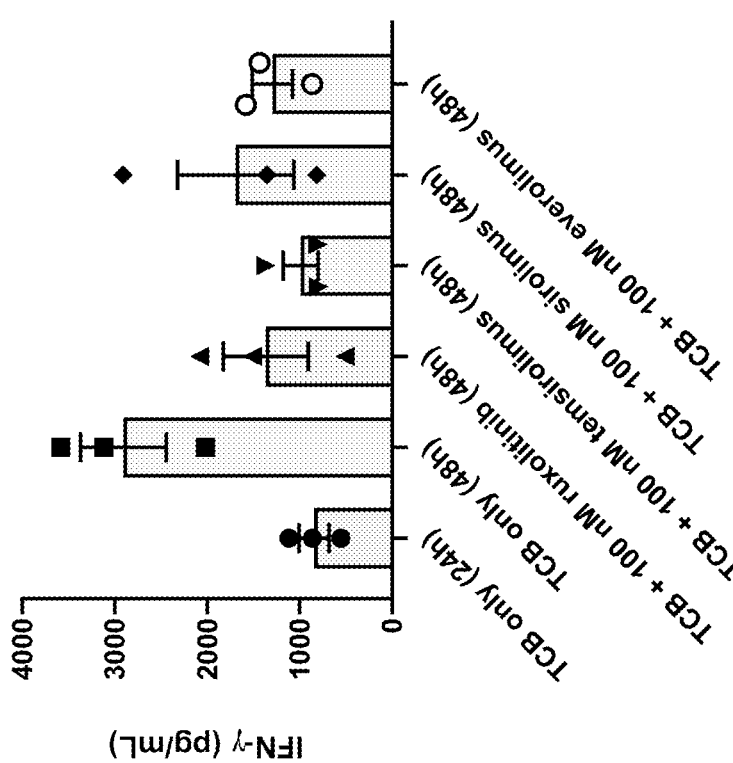
A no KI 0.0061uM 0.05uM 0.1uM 0.0025uM 0.00125uM

A

Killing [%]

Time [h]

B

Killing [%]

Time [h]

C

Killing [%]

Time [h]

1000 nM baricitinib
100 nM baricitinib
50 nM baricitinib
25 nM baricitinib
12.5 nM baricitinib
0 nM baricitinib

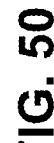
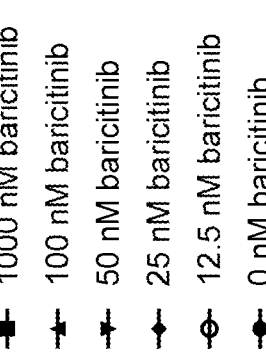
1000 nM baricitinib
100 nM baricitinib
50 nM baricitinib
25 nM baricitinib
12.5 nM baricitinib
0 nM baricitinib
FIG. 50
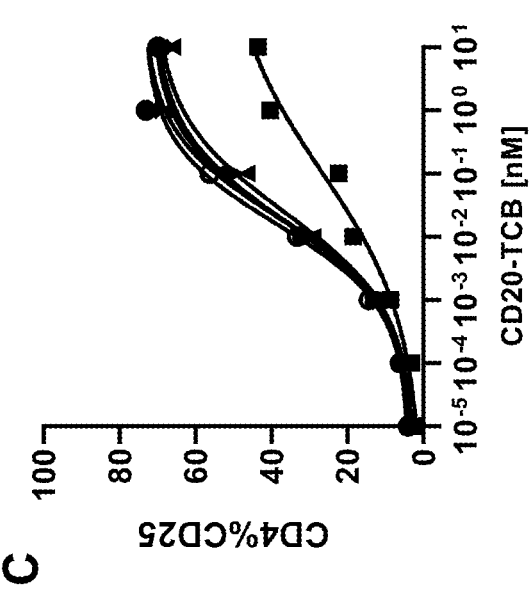
C
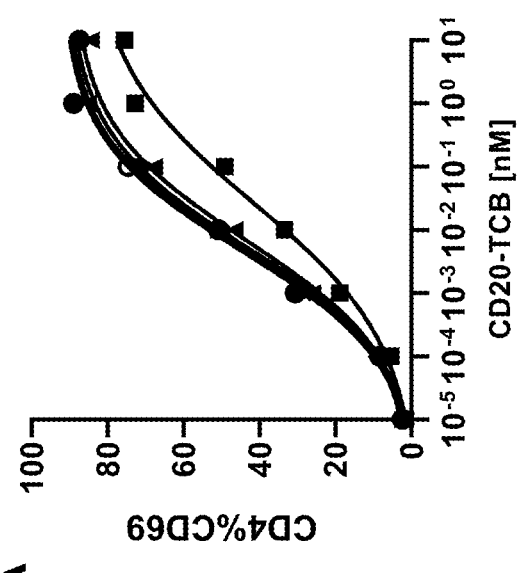
A
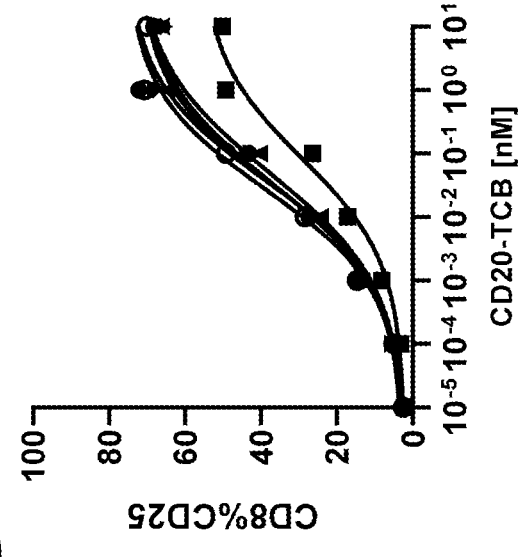
D
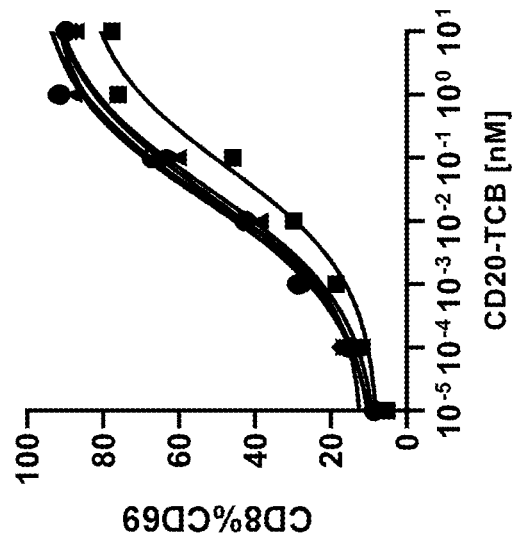
B

FIG. 52
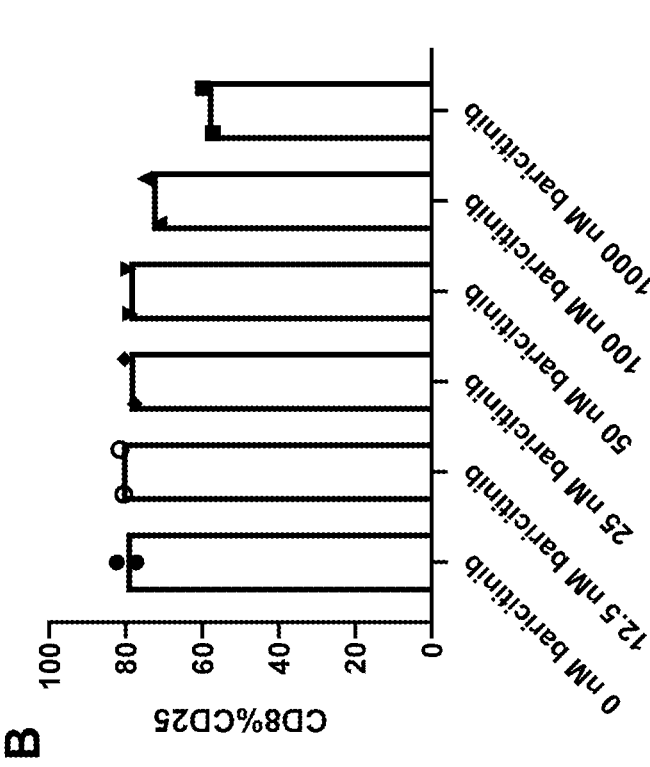
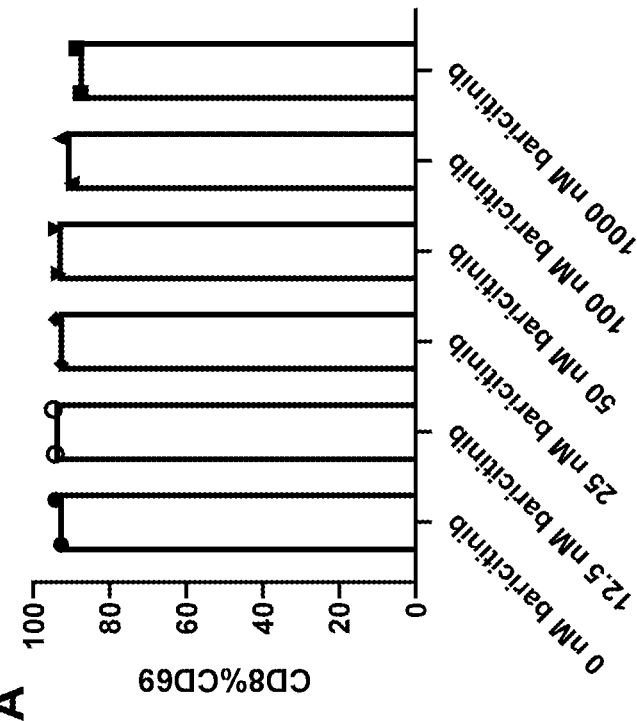

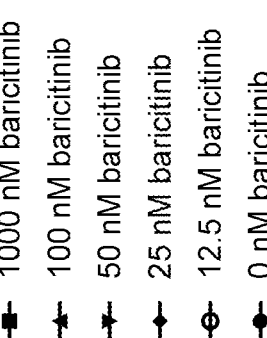
1000 nM baricitinib
100 nM baricitinib
50 nM baricitinib
25 nM baricitinib
12.5 nM baricitinib
0 nM baricitinib
FIG. 53
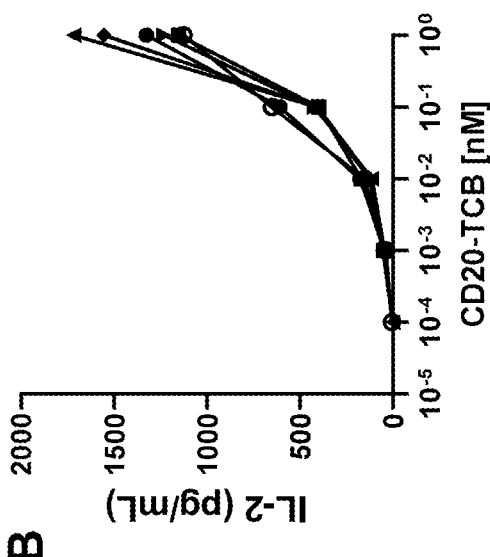
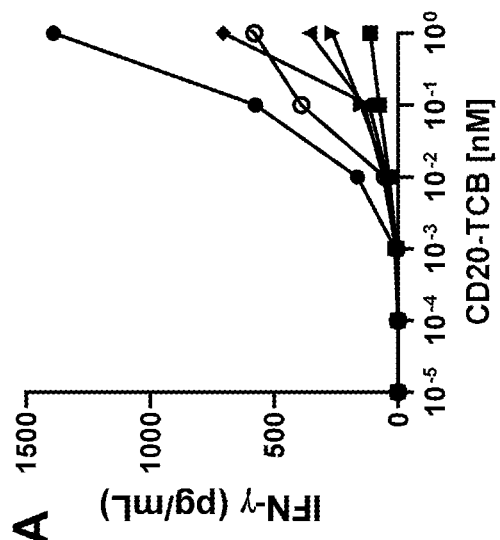
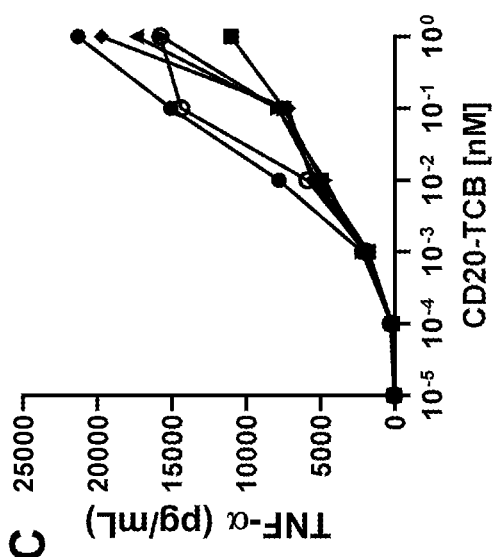

FIG. 53
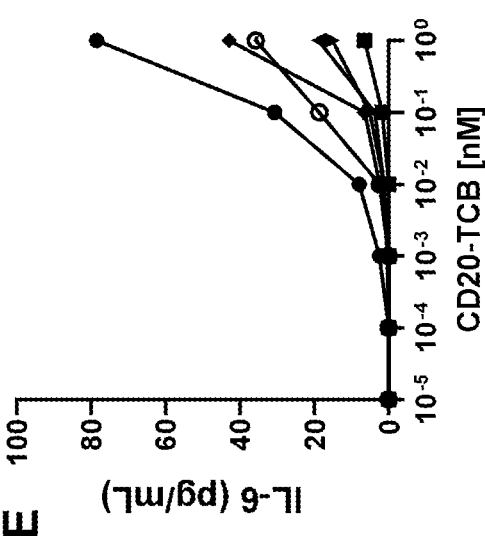
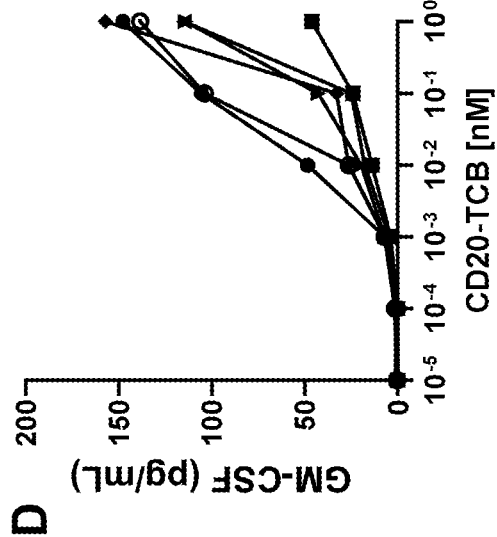
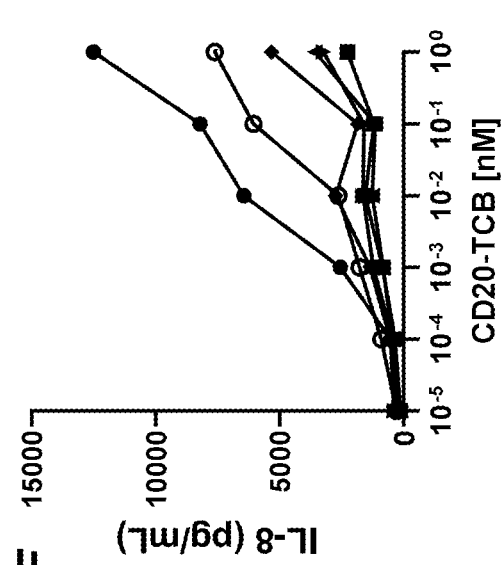

E

D

F baricitinib
ruxolitinib baricitinib ruxolitinib

CD19-TCB
CD19-TCB + 100 nM ruxo
CD19-TCB + 100 nM tofa
CD19-TCB + 100 nM bari

B

A

CD19-TCB

CD19/CD3 + 5 μg/mL aTNF-α

CD19-TCB + 5 μg/mL aIL-6R

CD19-TCB + 100 nM dexa

D

C

FIG. 76
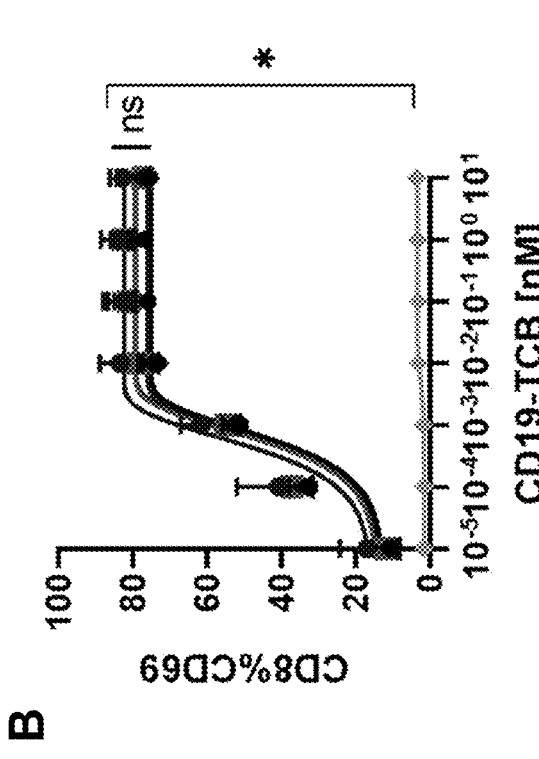
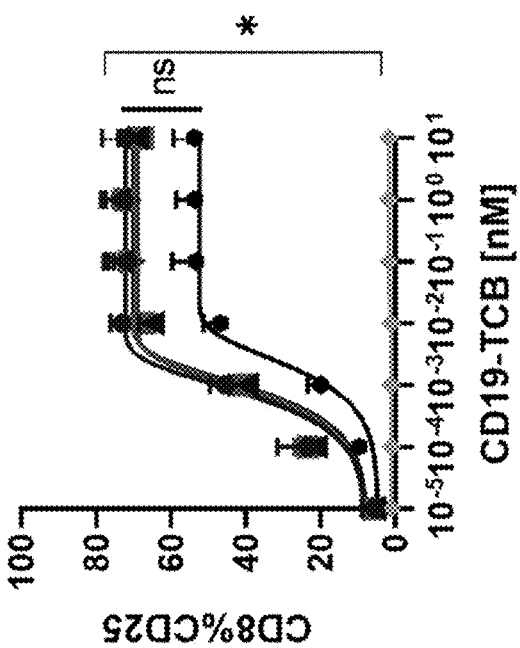
CD19-TCB
CD19/CD3 + 5 μg/mL aTNF-α
CD19-TCB + 5 μg/mL aIL-6R
CD19-TCB + 100 nM dexa

FIG. 79
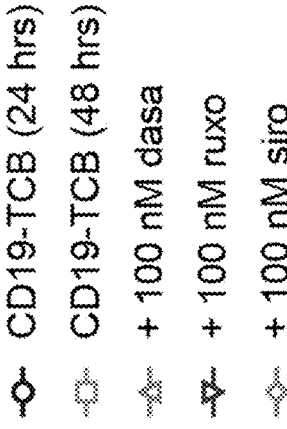
CD19-TCB (24 hrs)
CD19-TCB (48 hrs)
+ 100 nM dasa
+ 100 nM ruxo
+ 100 nM siro
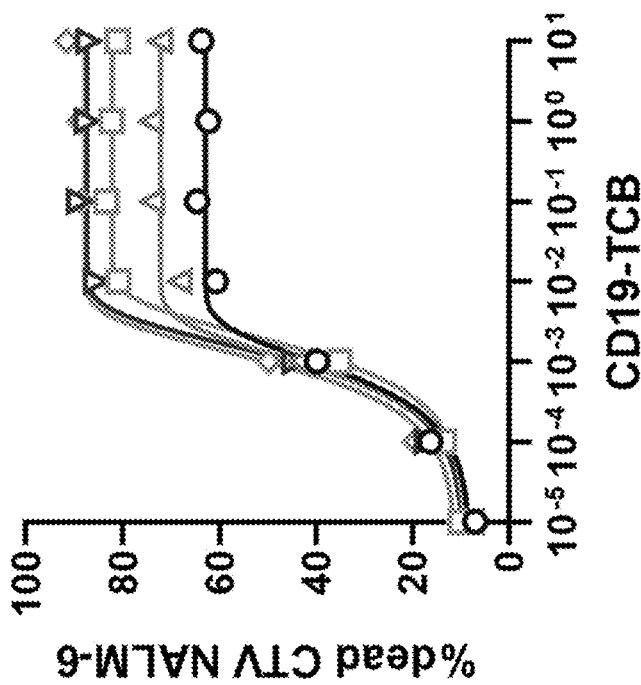

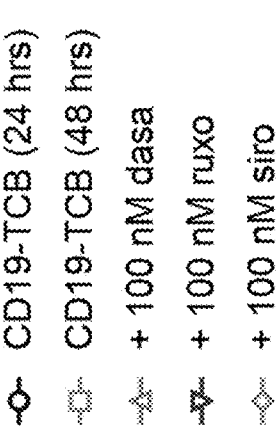
CD19-TCB (24 hrs)
CD19-TCB (48 hrs)
+ 100 nM dasa
+ 100 nM ruxo
+ 100 nM siro
FIG. 80
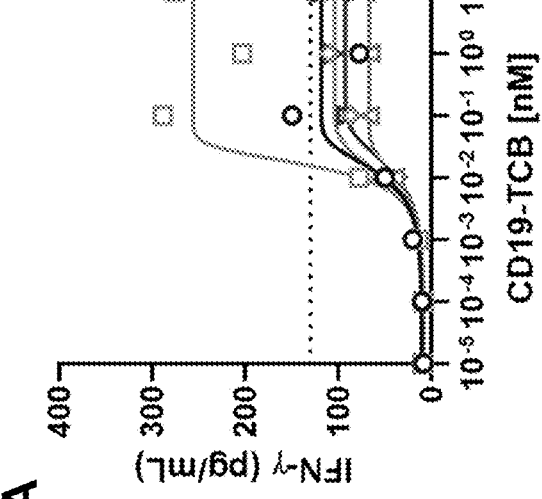
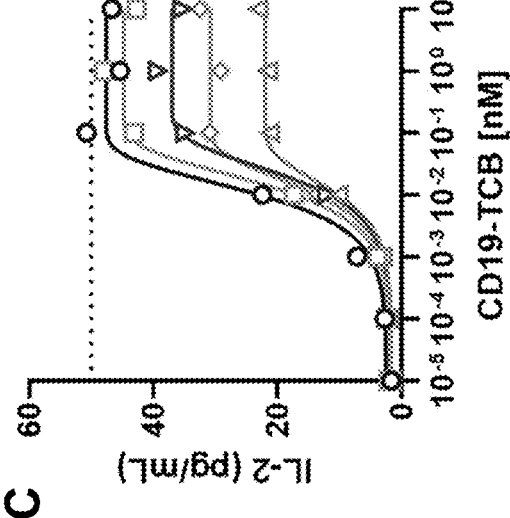

PREVENTION OR MITIGATION OF T-CELL ENGAGING AGENT-RELATED ADVERSE EFFECTS

CROSS REFERENCE TO RELATED APPLICATIONS

This application claims priority to EP patent application Ser. No. 21/187,472.2, filed Jul. 23, 2021, EP patent application Ser. No. 21/172,623.7, filed May 7, 2021, EP patent application Ser. No. 21/155,823.4, filed Feb. 8, 2021, and EP patent application No. 20206567.8, filed Nov. 10, 2020, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Nov. 1, 2021, is named P36507-US_Sequence listing.txt and is 105,560 bytes in size.

FIELD OF THE INVENTION

The present invention relates to the prevention or mitigation of adverse effects related to T cell engaging agents, such as cytokine release syndrome. Specifically, the invention relates to the prevention or mitigation of such side effects using an inhibitor of JAK and/or mTOR.

BACKGROUND

T cell engaging agents such as T cell bispecific antibodies (TCBs) or chimeric antigen receptor (CAR) expressing T cells (CAR-T cells) hold great promise as cancer immunotherapeutics. However, treatment with T cell engaging agent is sometimes associated with safety liabilities due to on-target on-tumor, on-target off-tumor cytotoxic activity and cytokine release. One of the most common adverse effects reported for T cell engaging agents is Cytokine Release Syndrome (CRS). This complex clinical syndrome is characterized by fever, hypotension and respiratory deficiency and associated with the release of pro-inflammatory cytokines such as IL-6, TNF-α, IFN-γ, and IL-10 (see e.g. Shimabukuro-Vomhagen et al., J Immunother Cancer (2018) 6, 56). Approaches to mitigate these life-threatening toxicities are greatly needed. The Src inhibitor dasatinib was identified as a potent candidate for prevention or mitigation of adverse effects of CAR-T cells (Weber et al., Blood Advances (2019) 3, 711-7; Mestermann et al., Sci Transl Med (2019) 11, eaau5907) as well as TCBs (Leclercq et al., J Immunother Cancer (2020) 8 (Suppl 3): A690 (abstract 653)). Dasatinib, however, switches off CAR-T cell functionality as well as TCB-induced T cell functionality entirely, without differentiation between desired and undesired activity of these agents. A way to prevent or mitigate adverse effects of T cell engaging agents while preserving their therapeutic efficacy would be highly desirable. Blockade of individual cytokines such as IL-6 or TNF-α was proposed as strategy for prevention of CRS without affecting TCB-induced T cell activity (Li et al., Sci Transl Med 11, eaax8861 (2019)). Besides anti-IL-6 treatment (e.g. with tocilizumab), glucocorticoids are also used in the management of CRS. Some patients are refractory to these approaches, however, reinforcing the need to develop novel approaches for CRS mitigation.

DESCRIPTION OF THE INVENTION

The present inventors have found that inhibitors of JAK and/or mTOR signaling may be used to mitigate CRS by T cell engaging therapies. mTOR inhibitors such as temsirolimus, sirolimus and everolimus, and JAK inhibitors such as ruxolitinib, were found to potently prevent TCB-induced cytokine release while retaining TCB-mediated target cell killing. The results provide evidence that the mechanisms of TCB-dependent cytokine release and target cell killing can be uncoupled, and suggests mTOR and/or JAK inhibitors as attractive potential superior alternative or complementation to currently used strategies, such as steroids or IL-6/IL-6R blockade, for the mitigation of CRS associated with T cell engaging therapies.

Accordingly, in a first aspect, the present invention provides a T cell engaging agent for use in the treatment of a disease in an individual, wherein said treatment comprises (a) the administration of the T cell engaging agent to the individual, and (b) the administration of an inhibitor of Janus kinase (JAK) and/or mammalian target of rapamycin (mTOR) signaling to the individual.

The invention further provides the use of a T cell engaging agent in the manufacture of a medicament for the treatment of a disease in an individual, wherein said treatment comprises (a) the administration of the T cell engaging agent to the individual, and (b) the administration of an inhibitor of JAK and/or mTOR signaling to the individual.

The invention also provides a method for treatment of a disease in an individual, wherein said method comprises (a) the administration of a T cell engaging agent to the individual, and (b) the administration of an inhibitor of JAK and/or mTOR signaling to the individual.

According to any of the above aspects, the administration of the inhibitor of JAK and/or mTOR signaling may be for the prevention or mitigation of an adverse effect related to the administration of the T cell engaging agent.

In another aspect, the invention provides an inhibitor of JAK and/or mTOR signaling for use in the prevention or mitigation of an adverse effect related to the administration of a T cell engaging agent to an individual.

The invention further provides the use of an inhibitor of JAK and/or mTOR signaling in the manufacture of a medicament for the prevention or mitigation of an adverse effect related to the administration of a T cell engaging agent.

The invention also provides a method for preventing or mitigating an adverse effect related to the administration of a T cell engaging agent to an individual, comprising the administration of an inhibitor of JAK and/or mTOR signaling to the individual.

The T cell engaging agent for use, inhibitor of JAK and/or mTOR signaling for use, uses or methods described above and herein, may incorporate, singly or in combination, any of the features described in the following (unless the context dictates otherwise).

Terms are used herein as generally used in the art, unless otherwise defined herein.

In some aspects, the inhibitor of JAK and/or mTOR signaling is an mTOR inhibitor. In more specific aspects, the inhibitor of JAK and/or mTOR signaling is an mTOR kinase inhibitor, particularly a small molecule mTOR kinase inhibitor.

"mTOR" stands for mammalian target of rapamycin (also known as FK506-binding protein 12-rapamycin complex-associated protein 1 (FRAP1)), and is a serine/threonine-specific protein kinase that belongs to the family of phosphatidylinositol-3 kinase (PI3K) related kinases. It serves as a core component of two distinct protein complexes, mTOR complex 1 (TORC1) and mTOR complex 2 (TORC2), which regulate different cellular processes. Human mTOR is described in UniProt entry P42345 (version 218). mTOR inhibitors are compounds that inhibit mTOR. The most established inhibitors of mTOR are the so-called rapalogs, which are derivatives of rapamycin. Rapalogs include sirolimus, temsirolimus, everolimus and ridaforolimus. A second generation of mTOR inhibitors are ATP-competitive mTOR kinase inhibitors, designed to compete with ATP in the catalytic site of mTOR.

Exemplary mTOR inhibitors that might be useful in the present invention are provided in Table 1 below.

TABLE 1

| mTOR inhibitors. | |
| --- | --- |
| INN | Structure |
| Sirolimus | |
| Everolimus | |

TABLE 1-continued

| mTOR inhibitors. | |
| --- | --- |
| INN | Structure |
| Temsirolimus | |
| Ridaforolimus | |

In some aspects, the mTOR inhibitor is a derivative of rapamycin (also known as a rapalog).

In some aspects, the mTOR inhibitor is selected from the group consisting of sirolimus, temsirolimus, everolimus and ridaforolimus, particularly the group consisting of sirolimus, temsirolimus and everolimus.

In specific aspects, the mTOR inhibitor is sirolimus. In further specific aspects, the mTOR inhibitor is temsirolimus. In yet further specific aspects, the mTOR inhibitor is everolimus.

In some aspects, the inhibitor of JAK and/or mTOR signaling is a JAK inhibitor. In more specific aspects, the inhibitor of JAK and/or mTOR signaling is a JAK kinase inhibitor, particularly a small molecule JAK kinase inhibitor.

"JAK" stands for Janus kinase and refers to a family of intracellular, non-receptor tyrosine kinases that transduce cytokine-mediated signals via the JAK/STAT pathway. JAKs possess two near-identical phosphate-transferring domains, one exhibiting the kinase activity, and the other one negatively regulating the kinase activity of the first. The four JAK family members are JAK1, JAK2, JAK3 and TYK2 (tyrosine kinase 2). In particular aspects herein, JAK is JAK1 and/or JAK2 (JAK1/2). Human JAK1 and JAK2 are described in UniProt entries P23458 (version 221) and P60674 (version 224), respectively. JAK inhibitors (also sometimes referred to as jakinibs) are compounds that inhibit the activity of one or more of the JAK family of enzymes (JAK1, JAK2, JAK3, TYK2), thereby interfering with the the JAK/STAT signaling pathway.

Exemplary JAK inhibitors that might be useful in the present invention are provided in Table 2 below.

TABLE 2

| | | |
|---|---|---|
| JAK inhibitors. | | |
| INN | Main specificity | Structure |
| Ruxolitinib | JAK1, JAK2 | |
| Baricitinib | JAK1, JAK2 | |
| Momelotinib | JAK1, JAK2 | |
| Upadacitinib | JAK1 | |

TABLE 2-continued

| INN | Main specificity | Structure |
|---|---|---|
| Filgotinib | JAK1 | |
| Abrocitinib | JAK1 | |
| Itacitinib | JAK1 | |
| Solcitinib | JAK1 | |
| Oclacitinib | JAK1 | |
| Fedratinib | JAK2 | |

JAK inhibitors.

TABLE 2-continued

JAK inhibitors.

| INN | Main specificity | Structure |
|---|---|---|
| Gandotinib | JAK2 | |
| Lestaurtinib | JAK2 | |
| Pacritinib | JAK2 | |
| Peficitinib | pan-JAK (JAK3) | |
| Tofacitinib | pan-JAK (JAK3) | |

US 12,629,419 B2

13

14

TABLE 2-continued

JAK inhibitors.

| INN | Main specificity | Structure |
|-----|------------------|-----------|
| Decemotinib | JAK3 | |

In some aspects, the JAK inhibitor is a JAK1 and/or JAK2 (JAK1/2) inhibitor. In some aspects, the JAK inhibitor is selected from the group consisting of ruxolitinib, baricitinib, momelotinib, upadacitinib, filgotinib, abrocitinib, itacitinib, solcitinib, oclacitinib, fedratinib, gandotinib, lestaurtinib and pacritinib.

In particular aspects, the JAK inhibitor is a JAK1 and JAK2 inhibitor. In specific such aspects, the JAK inhibitor is selected from the group consisting of ruxolitinib, baricitinib and momelotinib.

In some aspects, the JAK inhibitor is a JAK1 inhibitor. In specific such aspects, the JAK inhibitor is selected from the group consisting of upadacitinib, filgotinib, abrocitinib, itacitinib, solcitinib and oclacitinib.

In some aspects, the JAK inhibitor is a JAK2 inhibitor. In specific such aspects, the JAK inhibitor is selected from the group consisting of fedratinib, gandotinib, lestaurtinib and pacritinib. In a particular such aspect, the JAK inhibitor is fedratinib.

In some aspects, the JAK inhibitor is a pan-JAK inhibitor. In specfic such aspects, the JAK inhibitor is tofacitinib or peficitinib, particularly tofacitinib.

In particular aspects, the JAK inhibitor is ruxolitinib. In further particular aspects, the JAK inhibitor is baricitinib. In some aspects, the JAK inhibitor is tofacitinib. In some aspects, the JAK inhibitor is fedratinib.

In particular aspects, the inhibitor of JAK and/or mTOR signaling is selected from the group consisting of sirolimus, temsirolimus, everolimus and ruxolitinib. In further particular aspects, the inhibitor of JAK and/or mTOR signaling is selected from the group consisting of sirolimus, temsirolimus, everolimus, ruxolitinib and baricitinib.

In some aspects, (administration of) the inhibitor of JAK and/or mTOR signaling causes inhibition of an activity of the T cell engaging agent. In some aspects, (administration of) the inhibitor of JAK and/or mTOR signaling does not cause inhibition of another activity of the T cell engaging agent. In some aspects, (administration of) the inhibitor of JAK and/or mTOR signaling causes inhibition of a first activity of the T cell engaging agent but does not cause inhibition of a second activity of the T cell engaging agent. In some of these aspects, said inhibition is a complete inhibition.

In some aspects, (administration of) the inhibitor of JAK and/or mTOR signaling causes inhibition of a first activity of the T cell engaging agent and inhibition of a second activity of the T cell engaging agent, wherein said inhibition of the first activity is stronger than said inhibition of the second activity. In some aspects, (administration of) the inhibitor of JAK and/or mTOR signaling causes inhibition of a first activity of the T cell engaging agent and inhibition of a second activity of the T cell engaging agent, wherein said inhibition of the first activity is a complete inhibition and said inhibition of the second activity is a partial inhibition.

"Activity" of a T cell engaging agent refers to responses in an individual's body caused by the T cell engaging agent. Such activity may include cellular response(s) of T cells, particularly CD4+ and/or CD8+ T cells, such as proliferation, differentiation, cytokine secretion, cytotoxic effector molecule release, cytotoxic activity, and expression of activation markers, and/or effects on target cells, particularly target cells (e.g. tumor cells) expressing the target cell antigen of the T cell engaging agent, such as lysis of target cells.

In some aspects, (administration of) the inhibitor of JAK and/or mTOR signaling causes inhibition of cytokine secretion by immune cells, particularly T cells (induced by the T cell engaging agent). In some aspects, said cytokine is one or more cytokine selected from the group consisting of IL-6, IFN-γ, IL-10, TNF-α, GM-CSF, MCP-1 and IL-1β. Immune cells may include various immune cell types, such as T cells, macrophages, monocytes, NK cells etc. In some aspects, said T cells are CD8+ T cells or CD4+ cells. In some aspects, said inhibition is a complete inhibition.

In some aspects, (administration of) the inhibitor of JAK and/or mTOR signaling does not cause inhibition of the activation of T cells (induced by the T cell engaging agent). In some aspects, said inhibition is a complete inhibition. In some aspects, (administration of) the inhibitor of JAK and/or mTOR signaling causes inhibition of the activation of T cells (induced by the T cell engaging agent), wherein said inhibition is a partial inhibition.

"Activation of T cells" or "T cell activation" as used herein refers to one or more cellular response of a T lymphocyte, particularly a CD4+ or CD8+ T cell, selected from: proliferation, differentiation, cytotoxic effector molecule release, cytotoxic activity, and expression of activation markers. Suitable assays to measure T cell activation are known in the art and described herein. In particular aspects, T cell activation is the expression of activation markers, particularly expression of CD25 and/or CD69 (optionally as measured by flow cytometry). In particular aspects, T cell activation is determined by measuring expression of CD25 and/or CD69 on the T cell, e.g. by flow cytometry.

In some aspects, (administration of) the inhibitor of JAK and/or mTOR signaling does not cause inhibition of the cytotoxic activity of T cells (induced by the T cell engaging agent). In some aspects, said inhibition is a complete inhibition. In some aspects, (administration of) the inhibitor of JAK and/or mTOR signaling causes inhibition of the cytotoxic activity of T cells (induced by the T cell engaging agent), wherein said inhibition is a partial inhibition.

"Cytotoxic activity" of a T cell refers to the induction of lysis (i.e. killing) of target cells by a T lymphocyte, particularly a CD4+ or CD8+ T cell. Cytotoxic activity typically involves degranulation of the T lymphocyte, associated with the release of cytotoxic effector molecules such as granzyme B and/or perforin from the T lymphocyte.

In some aspects, (administration of) the inhibitor of JAK and/or mTOR signaling causes inhibition of cytokine secretion by T cells (induced by the T cell engaging agent) but does not cause inhibition of the activation and/or the cytotoxic activity of T cells (induced by the T cell engaging agent). In some of these aspects, said inhibition is a complete inhibition.

In some aspects, (administration of) the inhibitor of JAK and/or mTOR signaling causes inhibition of cytokine secretion by T cells (induced by the T cell engaging agent) and inhibition of the activation and/or the cytotoxic activity of T cells (induced by the T cell engaging agent), wherein said inhibition of cytokine secretion is stronger than said inhibition of activation and/or cytotoxic activity. In some aspects, (administration of) the inhibitor of JAK and/or mTOR signaling causes inhibition of cytokine secretion by T cells (induced by the T cell engaging agent) and inhibition of the activation and/or the cytotoxic activity of T cells (induced by the T cell engaging agent), wherein said inhibition of cytokine secretion is a complete inhibition and said inhibition of activation and/or cytotoxic activity is a partial inhibition.

An inhibition herein may be a partial inhibition or a complete inhibition. A complete inhibition is a stronger inhibition than a partial inhibition. A partial inhibition in some aspects is an inhibition by no more than 30%, no more than 40%, no more than 50%, no more than 60%, or no more than 70%. In some aspects, a partial inhibition is an inhibition by no more than 30%. In some aspects, a partial inhibition is an inhibition by no more than 40%. In some aspects, a partial inhibition is an inhibition by no more than 50%. In some aspects, a partial inhibition is an inhibition by no more than 60%. In some aspects, a partial inhibition is an inhibition by no more than 70%. A complete inhibition in some aspects is an inhibition by at least 80%, at least 90%, or 100%. In some aspects, a complete inhibition is an inhibition by at least 80%. In some aspects, a complete inhibition is an inhibition by at least 90%. In some aspects, a complete inhibition is an inhibition by 100%. In some aspects, a partial inhibition is an inhibition by no more than 50%, and a complete inhibition is an inhibition by at least 80%. In some aspects, a complete inhibition is clinically meaningful and/or statistically significant, and/or a partial inhibition is not clinically meaningful and/or statistically significant.

In some aspects, (administration of) the inhibitor of JAK and/or mTOR signaling causes reduction of the serum level of one of more cytokine in the individual. In some aspects, (administration of) the inhibitor of JAK and/or mTOR signaling causes reduction of the secretion of one of more cytokine by immune cells, particularly T cells, in the individual. In some aspects, said one or more cytokine is selected from the group consisting of IL-6, IFN-γ, IL-10, TNF-α, GM-CSF, MCP-1 and IL-1β. Immune cells may include various immune cell types, such as T cells, macrophages, monocytes, NK cells etc.

In some aspects, said reduction is sustained after the inhibitor of JAK and/or mTOR signaling has not been administered (to the individual) for a given amount of time. In some aspects, said amount of time is about 1 hour, 2 hours, 3 hours, 4 hours, 5 hours, 6 hours, 7 hours, 8 hours, 12 hours, 16 hours, 20 hours, 24 hours, 36 hours, 48 hours, 72 hours, or 96 hours. In some aspects, said reduction is sustained after a subsequent administration of the T cell engaging agent. Particularly, said reduction is sustained even after administration of the inhibitor of JAK and/or mTOR signaling is stopped/no further administration of the inhibitor of JAK and/or mTOR signaling is made. Said reduction of the serum level/cytokine secretion is in particular as compared to the serum level/cytokine secretion in an individual (including the same individual) without administration of the inhibitor of JAK and/or mTOR signaling (i.e. in such case the serum level/cytokine secretion is reduced as compared to the serum level/cytokine secretion without/before administration of the inhibitor of JAK and/or mTOR signaling). Said reduction of the serum level/cytokine secretion is in particular as compared to the serum level/cytokine secretion in an individual (including the same individual) with administration (in particular first administration) of the T cell engaging agent but without administration of the inhibitor of JAK and/or mTOR signaling (i.e. in such case the serum level/cytokine secretion is reduced as compared to the serum level/cytokine secretion with/after administration of the T cell engaging agent but without/before administration of the inhibitor of JAK and/or mTOR signaling). Without said reduction, the serum level/cytokine secretion particularly may be elevated/increased in relation to the (administration of) the T cell engaging agent. In some aspects, said reduction is clinically meaningful and/or statistically significant. In some aspects, said reduction is at least 30%, at least 40%, at least 50%, at least 60%, or at least 70%. In some aspects, said reduction is at least 30%. In some aspects, said reduction is at least 40%. In some aspects, said reduction is at least 50%. In some aspects, said reduction is at least 60%. In some aspects, said reduction is at least 70%.

In some aspects, (administration of) the inhibitor of JAK and/or mTOR signaling causes inhibition of an adverse effect related to the administration of the T cell engaging agent. In some aspects, (administration of) the inhibitor of JAK and/or mTOR signaling does not cause inhibition of a desired effect related to the administration of the T cell engaging agent. In some aspects, (administration of) the inhibitor of JAK and/or mTOR signaling causes inhibition of an adverse effect related to the administration of the T cell engaging agent but does not cause inhibition of a desired effect related to the administration of the T cell engaging agent. In some of these aspects, said inhibition is a complete inhibition. In some of these aspects, said inhibition is clinically meaningful and/or statistically significant.

In some aspects, (administration of) the inhibitor of JAK and/or mTOR signaling causes inhibition of an adverse effect related to the administration of the T cell engaging agent and inhibition of a desired effect related to the administration of the T cell engaging agent, wherein said inhibition of the adverse effect is stronger than said inhibition of the desired effect. In some aspects, (administration of) the inhibitor of JAK and/or mTOR signaling causes inhibition of an adverse effect related to the administration of the T cell engaging agent and inhibition of a desired effect related to the administration of the T cell engaging agent, wherein said inhibition of the adverse effect is a complete inhibition and said inhibition of the beneficial effect is a partial inhibition. In some aspects, (administration of) the inhibitor of JAK and/or mTOR signaling causes inhibition of an adverse effect related to the administration of the T cell engaging agent and inhibition of a desired effect related to the administration of the T cell engaging agent, wherein said inhibition of the adverse effect is a clinically meaningful and/or statistically significant inhibition and said inhibition of the beneficial effect is not a clinically meaningful and/or statistically significant inhibition.

A "desired effect" is a beneficial and desired effect resulting from medication in the treatment of an individual, herein particularly with a T cell engaging agent, i.e. a therapeutic or prophylactic effect, such as e.g. killing of tumor cells, reduction or retardation of tumor growth, reduction of tumor volume, reduction or prevention of tumor metastasis, increase of progression-free or overall survival, alleviation of disease symptoms, and the like.

An "adverse effect", which is sometimes also denoted as "side effect" or "adverse event" (especially in clinical studies) is a harmful and undesired effect resulting from medication in the treatment of an individual, herein particularly with a T cell engaging agent.

According to the invention, the adverse effect is related to the administration of the T cell engaging agent. In some aspects, the adverse effect is related to the first administration of the T cell engaging agent. In some aspects, the adverse effect occurs upon the first administration of the T cell engaging agent. In some aspects, the adverse effect occurs predominantly or only upon the first administration of the T cell engaging agent. In some aspects, the adverse effect occurs within 12 hours, 24 hours, 36 hours, 48 hours, 72 hours or 96 hours of the administration, particularly the first administration, of the T cell engaging agent. In some aspects, in particular wherein only a single administration of the T cell engaging is made (in the course of the treatment with the T cell engaging agent), the adverse effect occurs within 3 days, 4 days, 5 days, 6 days, 7 days, 10 days, 14 days or 21 days of the administration of the T cell engaging agent.

In some aspects, said adverse effect is cytokine release syndrome (CRS).

"Cytokine release syndrome" (abbreviated as "CRS") refers to an increase in the levels of cytokines, such tumor necrosis factor alpha (TNF-$\alpha$), interferon gamma (IFN-$\gamma$), interleukin-6 (IL-6), interleukin-10 (IL-10) and others, in the blood of a subject during or shortly after (e.g. within 1 day of) administration of a therapeutic agent (e.g. a T cell engaging agent), resulting in adverse symptoms. CRS is an adverse reaction to therapeutic agent and timely related to administration of the therapeutic agent. It typically occurs during or shortly after an administration of the therapeutic agent, i.e. typically within 24 hours after administration (typically infusion), predominantly at the first administration. In some instances, e.g. after the administration of CAR-T cells, CRS can also occur only later, e.g. several days after administration upon expansion of the CAR-T cells. The incidence and severity typically decrease with subsequent administrations. Symptoms may range from symptomatic discomfort to fatal events, and may include fever, chills, dizziness, hypertension, hypotension, hypoxia, dyspnea, restlessness, sweating, flushing, skin rash, tachycardia, tachypnoea, headache, tumour pain, nausea, vomiting and/or organ failure. CRS may be graded according to the Modified Cytokine Release Syndrome Grading System established by Lee et al., Blood (2014) 124: 188-195 or Lee et al., Biol Blood Marrow Transplant (2019) 25(4): 625-638 (each incorporated herein by reference in its entirety). For a review of CRS see e.g. Shimabukuro-Vomhagen et al., Journal for ImmunoTherapy of Cancer (2018) 6:56 (incorporated herein by reference in its entirety).

In some aspects, said adverse effect is fever, hypotension and/or hypoxia.

In some aspects, said adverse effect is an elevated serum level of one of more cytokine. Said elevated serum level is in particular as compared to the serum level in a healthy individual, and/or the serum level in an individual (including the same individual) without administration of the T cell engaging agent (i.e. in such case the serum level is elevated as compared to the serum level without administration of the T cell engaging agent). In some aspects, said one or more cytokine is selected from the group consisting of IL-6, IFN-$\gamma$, IL-10, TNF-$\alpha$, GM-CSF, MCP-1 and IL-1$\beta$.

In some aspects, administration of the inhibitor of JAK and/or mTOR signaling is upon (clinical) manifestation of the adverse effect (in the individual). Said administration may be, for example, within about 1 hour, 2 hours, 3 hours, 4 hours, 5 hours, 6 hours, 7 hours, 8 hours, 12 hours, 16 hours, 20 hours or 24 hours after manifestation of the adverse effect (i.e. the occurrence clinical symptoms of the side effect, such as fever). In some aspects, administration of the inhibitor of JAK and/or mTOR signaling is in response to the (clinical) manifestation of the adverse effect (in the individual).

In some aspects, administration of the inhibitor of JAK and/or mTOR signaling is before the administration of the T cell engaging agent. In some aspects, administration of the inhibitor of JAK and/or mTOR signaling is concurrent to the administration of the T cell engaging agent. In some aspects, administration of the inhibitor of JAK and/or mTOR signaling is after the administration of the T cell engaging agent. Where administration of the inhibitor of JAK and/or mTOR signaling is before or after the administration of the T cell engaging agent, such administration of the inhibitor of JAK and/or mTOR signaling may be, for example, within about 1 hour, 2 hours, 3 hours, 4 hours, 5 hours, 6 hours, 7 hours, 8 hours, 12 hours, 16 hours, 20 hours or 24 hours before or after, respectively, the administration of the T cell engaging agent. Administration of the inhibitor of JAK and/or mTOR signaling may be intermittently or continuously. In some aspects, administration of the inhibitor of JAK and/or mTOR signaling is oral. In some aspects, administration of the inhibitor of JAK and/or mTOR signaling is parenteral, particularly intravenous.

In some aspects, administration of the inhibitor of JAK and/or mTOR signaling is at a dose sufficient to cause inhibition of an activity of the T cell engaging agent. In some aspects, administration of the inhibitor of JAK and/or mTOR signaling is at a dose insufficient to cause inhibition of another activity of the T cell engaging agent. In some aspects, administration of the inhibitor of JAK and/or mTOR signaling is at a dose sufficient to cause inhibition of a first activity of the T cell engaging agent but insufficient to cause inhibition of a second activity of the T cell engaging agent. In some of these aspects, said inhibition is a complete inhibition.

In some aspects, administration of the inhibitor of JAK and/or mTOR signaling is at a dose sufficient to cause inhibition of cytokine secretion by immune cells, particularly T cells (induced by the T cell engaging agent). In some aspects, said cytokine is one or more cytokine selected from the group consisting of IL-6, IFN-$\gamma$, IL-10, TNF-$\alpha$, GM-CSF, MCP-1 and IL-1$\beta$. Immune cells may include various immune cell types, such as T cells, macrophages, monocytes, NK cells etc. In some aspects, said T cells are CD8+ T cells or CD4+ cells. In some aspects, said inhibition is a complete inhibition.

In some aspects, administration of the inhibitor of JAK and/or mTOR signaling is at a dose insufficient to cause inhibition of the activation of T cells (induced by the T cell engaging agent). In some aspects, said inhibition is a complete inhibition.

In some aspects, administration of the inhibitor of JAK and/or mTOR signaling is at a dose insufficient to cause inhibition of the cytotoxic activity of T cells (induced by the T cell engaging agent). In some aspects, said inhibition is a complete inhibition.

In some aspects, administration of the inhibitor of JAK and/or mTOR signaling is at a dose sufficient to causes inhibition of cytokine secretion by T cells (induced by the T cell engaging agent) but insufficient to cause inhibition of the activation and/or the cytotoxic activity of T cells (induced by the T cell engaging agent). In some of these aspects, said inhibition is a complete inhibition.

In some aspects, administration of the inhibitor of JAK and/or mTOR signaling is at a dose sufficient to cause reduction of the serum level of one of more cytokine in the individual. In some aspects, administration of the inhibitor of JAK and/or mTOR signaling is at a dose sufficient to cause reduction of the secretion of one of more cytokine by immune cells, particularly T cells, in the individual. In some aspects, said one or more cytokine is selected from the group consisting of IL-6, IFN-γ, IL-10, TNF-α, GM-CSF, MCP-1 and IL-1β. Immune cells may include various immune cell types, such as T cells, macrophages, monocytes, NK cells etc.

In some aspects, administration of the inhibitor of JAK and/or mTOR signaling is at a dose sufficient to cause inhibition of an adverse effect related to the administration of the T cell engaging agent. In some aspects, administration of the inhibitor of JAK and/or mTOR signaling is at a dose insufficient to cause inhibition of a desired effect related to the administration of the T cell engaging agent. In some aspects, administration of the inhibitor of JAK and/or mTOR signaling is at a dose sufficient to cause inhibition of an adverse effect related to the administration of the T cell engaging agent but insufficient to cause inhibition of a desired effect related to the administration of the T cell engaging agent. In some of these aspects, said inhibition is a complete inhibition. In some of these aspects, said inhibition is clinically meaningful and/or statistically significant.

In some aspects, administration of the inhibitor of JAK and/or mTOR signaling is at an effective dose.

An "effective amount" or "effective dose" of an agent, e.g. a inhibitor of JAK and/or mTOR signaling or a T cell engaging agent, refers to an amount effective, at dosages and for periods of time necessary, to achieve the desired therapeutic or prophylactic result.

In some aspects, the administration of the inhibitor of JAK and/or mTOR signaling is at a dose equaling a dose strength available for the inhibitor of JAK and/or mTOR signaling. Typically, several dose strengths (i.e. dosage forms such as tablets or capsules with a specific amount of active ingredient) are available for a given inhibitor of JAK and/or mTOR signaling. Dosing the inhibitor of JAK and/or mTOR signaling at such (commercially) available dose strengths will be most convenient. For example, if the inhibitor of JAK and/or mTOR signaling is everolimus, it may preferably be administered at a dose of 2.5 mg, 5 mg, 7.5 mg or 10 mg (administration preferably being oral administration). For example, if the inhibitor of JAK and/or mTOR signaling is sirolimus, it may preferably be administered at a dose of 0.5 mg, 1 mg or 2 mg (administration preferably being oral administration). For example, if the inhibitor of JAK and/or mTOR signaling is ruxolitinib, it may preferably be administered at a dose of 5 mg, 10 mg, 15 mg, 20 mg or 25 mg (administration preferably being oral administration). If the inhibitor of JAK and/or mTOR signaling is temsirolimus, it may be administered for example at a dose of 12.5 mg or 25 mg (administration preferably being intravenous administration, particularly using a solution of 25 mg/ml active ingredient).

In some aspects, administration of the inhibitor of JAK and/or mTOR signaling is daily. In some aspects, administration of the inhibitor of JAK and/or mTOR signaling is once daily. In some aspects, administration of the inhibitor of JAK and/or mTOR signaling is once daily at a dose as mentioned hereinabove. In some aspects, administration of the inhibitor of JAK and/or mTOR signaling is for the period of time during which the adverse effect persists (i.e. administration of the inhibitor of JAK and/or mTOR signaling is from manifestation of the adverse effect until reduction or disappearance of the adverse effect). In some aspects, administration of the inhibitor of JAK and/or mTOR signaling is stopped after the adverse effect is prevented or mitigated. In some aspects, administration of the inhibitor of JAK and/or mTOR signaling is stopped after reduction or disappearance of the adverse effect. Said reduction particularly is clinically meaningful and/or statistically significant. In some aspects, administration of the inhibitor of JAK and/or mTOR signaling is once, twice, three times, four times, five times, six times, seven times, eight times, nine times or ten times, particularly once, twice, three times, four times, five times, six times, seven times, eight times, nine times or ten times in the course of the treatment of the individual with the T cell engaging agent. In some aspects, administration of the inhibitor of JAK and/or mTOR signaling is for 1 day, 2 days, 3 days, 4 days, 5 days, 6 days, 7 days, 8 days, 9 days or 10 days. In some aspects, administration of the inhibitor of JAK and/or mTOR signaling is once daily for 1 day, 2 days, 3 days, 4 days, 5 days, 6 days, 7 days, 8 days, 9 days or 10 days. The administration of the inhibitor of JAK and/or mTOR signaling is generally associated with the administration of the T cell engaging agent. In some aspects, administration of the inhibitor of JAK and/or mTOR signaling is associated with the first administration of the T cell engaging agent.

Said first administration is particularly the first administration of the T cell engaging agent in the course of the treatment of the individual with the T cell engaging agent. In some aspects, administration of the inhibitor of JAK and/or mTOR signaling is concurrent with the first administration of the T cell engaging agent. In some aspects, administration of the inhibitor of JAK and/or mTOR signaling is prior to the first administration of the T cell engaging agent. In some aspects, administration of the inhibitor of JAK and/or mTOR signaling is subsequent to the first administration of the T cell engaging agent. In some aspects, administration of the inhibitor of JAK and/or mTOR signaling is subsequent to the first administration of the T cell engaging agent and prior to a second administration of the T cell engaging agent. Where administration of the inhibitor of JAK and/or mTOR signaling is prior or subsequent to the (first) administration of the T cell engaging agent, such administration of the inhibitor of JAK and/or mTOR signaling may be, for example, within about 1 hour, 2 hours, 3 hours, 4 hours, 5 hours, 6 hours, 7 hours, 8 hours, 12 hours, 16 hours, 20 hours, 24 hours, 48 hours or 72 hours before or after, respectively, the administration of the T cell engaging agent.

In some aspects, the administration of the T cell engaging agent is for a longer period of time than the administration of the inhibitor of JAK and/or mTOR signaling. In some aspects, the administration of the T cell engaging agent continues after the administration of the inhibitor of JAK and/or mTOR signaling is stopped. In some aspects, the administration of the T cell engaging agent is a single administration or a repeated administration. In the course of the treatment of the individual with the T cell engaging agent, the T cell engaging agent may be administered once or several times. For example, treatment of the individual with the T cell engaging agent may comprise multiple treatment cycles which each comprise one or more administrations of the T cell engaging agent. In some aspects, the administration of the T cell engaging agent comprises a first and a second administration.

For use in the present invention, the T cell engaging agent would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In some aspects, the administration of the T cell engaging agent is at an effective dose. For systemic administration, an effective dose can be estimated initially from in vitro assays, such as cell culture assays. A dose can then be formulated in animal models to achieve a circulating concentration range that includes the IC50 as determined in cell culture. Such information can be used to more accurately determine useful doses in humans. Initial dosages can also be estimated from in vivo data, e.g., animal models, using techniques that are well known in the art. Dosage amount and interval may be adjusted individually to provide plasma levels of the T cell engaging agent which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

An effective amount of the T cell engaging agent may be administered for prevention or treatment of disease. The appropriate route of administration and dosage of the T cell engaging agent may be determined based on the type of disease to be treated, the type of the T cell engaging agent, the severity and course of the disease, the clinical condition of the individual, the individual's clinical history and response to the treatment, and the discretion of the attending physician. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

The T cell engaging agent and the inhibitor of JAK and/or mTOR signaling can be administered by any suitable route, and may be administered by the same route of administration or by different routes of administration. In some aspects, the administration of the T cell engaging agent is parenteral, particularly intravenous.

In some aspects, the administration of the T cell engaging agent is the first administration of the T cell engaging agent to the individual, particularly the first administration of the T cell engaging agent in the course of the treatment of the individual with the T cell engaging agent.

In some aspects, (administration of) the T cell engaging agent induces (i.e. causes or increases) the activation of T cells. In some aspects, (administration of) the T cell engaging agent induces cytotoxic activity of T cells. In some aspects, (administration of) the T cell engaging agent induces cytokine secretion by T cells. In some aspects, cytokine is one or more cytokine selected from the group consisting of IL-2, IL-6, IFN-γ, IL-10, TNF-α and GM-CSF. In some aspects, said T cells are CD8+ T cells or CD4+ cells.

In some aspects, administration of the T cell engaging agent results in activation of T cells, particularly cytotoxic T cells, particularly at the site of the cancer (e.g. within a solid tumor cancer). Said activation may comprise proliferation of T cells, differentiation of T cells, cytokine secretion by T cells, cytotoxic effector molecule release from T cells, cytotoxic activity of T cells, and expression of activation markers by T cells. In some aspects, the administration of the T cell engaging agent results in an increase of T cell, particularly cytotoxic T cell, numbers at the site of the cancer (e.g. within a solid tumor cancer).

By "T cell engaging agent" is meant an immunotherapeutic agent that exerts its effect through the activity of T cells, particularly cytotoxic T cells. Such activity of T cells may include cellular response(s) of T cells, particularly CD4+ and/or CD8+ T cells, such as proliferation, differentiation, expression of activation markers, cytokine secretion, cytotoxic effector molecule release and/or cytotoxic activity. T cell engaging agents as contemplated herein typically comprise an antigen binding moiety that enables their binding to a target cell antigen on a target cell such as a tumor cell. Such T cell engaging agents exert effects on their target cell, such as lysis of the target cell, through the activity of T cells. Exemplary T cell engaging agents include T cell bispecific antibodies, chimeric antigen receptor (CAR) expressing T cells (CAR-T cells), and T cell receptor (TCR)-based approaches such as ImmTACs ("Immune mobilising monoclonal T-cell receptors Against Cancer"; bispecific fusion proteins of an engineered TCR and an antibody fragment, capable of binding to a T cell and a target cell) or TCR-modified T cells featuring engineered T cell receptors capable of binding to a specific antigenic determinant on a target cell (TCR-T cells).

In particular aspects of the present invention, the T cell engaging agent is a T cell bispecific antibody.

In other aspects, the T cell engaging agent is a CAR-T cell. In some aspects, the CAR-T cell is a universal CAR-T cell. By "universal" CAR-T cell is meant a CAR-T cell that binds to a target cell antigen through an adaptor molecule, such as an antibody, that binds to the target cell antigen. A universal CAR-T cell expresses a CAR comprising an antigen binding moiety that binds to the adaptor molecule, and the adaptor molecule binds to the target cell antigen. Through different adaptor molecules (binding to different target cell antigens), a universal CAR-T cell can bind to different target cell antigens, without the need for expression of a different CAR for each target cell antigen. The adaptor molecule is a molecule that (i) can be bound by the CAR, and (ii) can bind to a target cell antigen, such as, for example, an antibody that binds to the target cell antigen and comprises an Fc region that can be bound by the CAR. In some aspects, the CAR-T cell expresses a CAR comprising an antigen binding moiety that binds to an antibody Fc region, particularly an IgG Fc region, more particularly an IgG₁ Fc region, and particularly a human Fc region. In some aspects, the CAR-T expresses a CAR comprising an antigen binding moiety that binds to an IgG Fc region, particularly a human IgG₁ Fc region, comprising the amino acid substitution P329G (Kabat EU index numbering). In particular such aspects, the antigen binding moiety is a scFv. In other aspects, the CAR-T expresses a CAR comprising an antigen binding moiety that binds to a wild-type Fc region, particularly a wild-type human IgG₁ Fc region. In particular such aspects, the antigen binding moiety is CD16 or an Fc-binding fragment thereof (for example, the extracellular domain of CD16).

In some aspects, the T cell engaging agent is an ImmTAC. In some aspects, the T cell engaging agent is a TCR-T cell.

In the following, the T cell bispecific antibody that may be used in the present invention is described.

By "T cell bispecific antibody" is meant an antibody that is able to bind, including simultaneously bind, to a T cell (typically via an antigenic determinant expressed on the T cell, such as CD3) and to a target cell (typically via an antigenic determinant expressed on the target cell, such as CEA, CD19, CD20 or HLA-A2/MAGE-A4).

In preferred aspects according to the invention, the T cell bispecific antibody is capable of simultaneous binding to the antigenic determinant on the T cell (i.e. a first antigen such as CD3) and the antigenic determinant on the target cell (i.e. a second antigen such as CEA, CD19, CD20 or HLA-A2/MAGE-A4). In some aspects, the T cell bispecific antibody is capable of crosslinking the T cell and the target cell by simultaneous binding to CD3 and a target cell antigen. In even more preferred aspects, such simultaneous binding results in lysis of the target cell, particularly a target cell antigen (e.g. CEA, CD19, CD20 or HLA-A2/MAGE-A4)-expressing tumor cell. In some aspects, such simultaneous binding results in activation of the T cell. In some aspects, such simultaneous binding results in a cellular response of the T cell, selected from the group of: proliferation, differentiation, cytokine secretion, cytotoxic effector molecule release, cytotoxic activity, and expression of activation markers. In some aspects, binding of the T cell bispecific antibody to CD3 without simultaneous binding to the target cell antigen does not result in T cell activation. In some aspects, the T cell bispecific antibody is capable of re-directing cytotoxic activity of a T cell to a target cell. In preferred aspects, said re-direction is independent of MHC-mediated peptide antigen presentation by the target cell and and/or specificity of the T cell.

The term "bispecific" means that the antibody is able to bind to at least two distinct antigenic determinants. Typically, a bispecific antibody comprises two antigen binding sites, each of which is specific for a different antigenic determinant. In certain aspects, the bispecific antibody is capable of simultaneously binding two antigenic determinants, particularly two antigenic determinants expressed on two distinct cells.

As used herein, the term "antigenic determinant" is synonymous with "antigen" and "epitope", and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM).

As used herein, the term "antigen binding moiety" refers to a polypeptide molecule that binds, including specifically binds, to an antigenic determinant. In some aspects, an antigen binding moiety is able to direct the entity to which it is attached (e.g. a second antigen binding moiety) to a target site, for example to a specific type of tumor cell bearing the antigenic determinant. In further aspects, an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain aspects, the antigen binding moieties may comprise antibody constant regions as further defined herein and known in the art. Useful heavy chain constant regions include any of the five isotypes: $\alpha$, $\delta$, $\epsilon$, $\gamma$, or $\mu$. Useful light chain constant regions include any of the two isotypes: $\kappa$ and $\lambda$.

By "specific binding" is meant that the binding is selective for the antigen and can be discriminated from unwanted or non-specific interactions. The term "bind" or "binding" herein generally refers to "specific binding". The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed e.g. on a BIAcore instrument) (Liljeblad et al., Glyco J 17, 323-329 (2000)), and traditional binding assays (Heeley, Endocr Res 28, 217-229 (2002)). In some aspects, the extent of binding of an antigen binding moiety to an unrelated protein is less than about 10% of the binding of the antigen binding moiety to the antigen as measured, e.g., by SPR. In certain aspects, an antigen binding moiety that binds to the antigen, or an antibody comprising that antigen binding moiety, has a dissociation constant ($K_D$) of $\leq$1 $\mu$M, $\leq$100 nM, $\leq$10 nM, $\leq$1 nM, $\leq$0.1 nM, $\leq$0.01 nM, or $\leq$0.001 nM (e.g. $10^{-8}$ M or less, e.g. from $10^{-8}$ M to $10^{-13}$M, e.g., from $10^{-9}$M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In some aspects, CD3 is human CD3, particularly the epsilon subunit of human CD3 (CD3$\epsilon$). The amino acid sequence of human CD3$\epsilon$ is shown in UniProt (www.uniprot.org) accession no. P07766 (version 144), or NCBI (www.ncbi.nlm.nih.gov/) RefSeq NP_000724.1. See also SEQ ID NO: 1. The amino acid sequence of cynomolgus [*Macaca fascicularis*] CD3$\epsilon$ is shown in NCBI GenBank no. BAB71849.1. See also SEQ ID NO: 2.

A "target cell antigen" as used herein refers to an antigenic determinant presented on the surface of a target cell, for example a cell in a tumor such as a cancer cell or a cell of the tumor stroma (in that case a "tumor cell antigen"). Preferably, the target cell antigen is not CD3, and/or is expressed on a different cell than CD3. In some aspects, the target cell antigen is CEA, particularly human CEA. In some aspects, the target cell antigen is CD20, particularly human CD20. In other aspects, the target cell antigen is HLA-A2/MAGE-A4, particularly human HLA-A2/MAGE-A4. In some aspects, the target cell antigen is CD19, particularly human CD19.

As used herein, the terms "first", "second" or "third" with respect to antigen binding moieties etc., are used for convenience of distinguishing when there is more than one of each type of moiety. Use of these terms is not intended to confer a specific order or orientation of the bispecific antibody unless explicitly so stated.

The term "valent" as used herein denotes the presence of a specified number of antigen binding sites in an antibody. As such, the term "monovalent binding to an antigen" denotes the presence of one (and not more than one) antigen binding site specific for the antigen in the antibody.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

The terms "full length antibody," "intact antibody," and "whole antibody" are used herein interchangeably to refer to an antibody having a structure substantially similar to a native antibody structure.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity. As used herein in connection with variable region sequences, "Kabat numbering" refers to the numbering system set forth by Kabat et al., Sequences of Proteins of Immunological Interest, 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The term "hypervariable region" or "HVR", as used herein, refers to each of the regions of an antibody variable domain which are hypervariable in sequence and which determine antigen binding specificity, for example "complementarity determining regions" ("CDRs"). Generally, antibodies comprise six CDRs; three in the VH (HCDR1, HCDR2, HCDR3), and three in the VL (LCDR1, LCDR2, LCDR3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following order in VH (or VL): FR1-H1(L1)-FR2-H2(L2)-FR3-H3 (L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

A "Fab molecule" refers to a protein consisting of the VH and CH1 domain of the heavy chain (the "Fab heavy chain")

and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetra-meric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some aspects the modification promoting association comprises an amino acid mutation in the Fc domain, specifically an amino acid substitution. In particular aspects, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36, and is publicly available from http://fasta.bioch.virginia.edu/fasta_www2/fastadown.shtml. Alternatively, a public server accessible at http://fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

By "fused" is meant that the components (e.g. a Fab molecule and an Fc domain subunit) are linked by peptide bonds, either directly or via one or more peptide linkers.

In particular aspects, the T cell bispecific antibody binds to CD3 and a target cell antigen. Accordingly, in some aspects, the T cell bispecific antibody comprises an antigen binding moiety that binds to CD3 and an antigen binding moiety that binds to a target cell antigen.

In some aspects, the first and/or the second antigen binding moiety is a Fab molecule. In some aspects, the first antigen binding moiety is a crossover Fab molecule wherein either the variable or the constant regions of the Fab light chain and the Fab heavy chain are exchanged. In such aspects, the second antigen binding moiety preferably is a conventional Fab molecule.

In some aspects wherein the first and the second antigen binding moiety of the T cell bispecific antibody are both Fab molecules, and in one of the antigen binding moieties (particularly the first antigen binding moiety) the variable domains VL and VH of the Fab light chain and the Fab heavy chain are replaced by each other, i) in the constant domain CL of the first antigen binding moiety the amino acid at position 124 is substituted by a positively charged amino acid (numbering according to Kabat), and wherein in the constant domain CH1 of the first antigen binding moiety the amino acid at position 147 or the amino acid at position 213 is substituted by a negatively charged amino acid (numbering according to Kabat EU index); or ii) in the constant domain CL of the second antigen binding moiety the amino acid at position 124 is substituted by a positively charged amino acid (numbering according to Kabat), and wherein in the constant domain CH1 of the second antigen binding moiety the amino acid at position 147 or the amino acid at position 213 is substituted by a negatively charged amino acid (numbering according to Kabat EU index).

The T cell bispecific antibody does not comprise both modifications mentioned under i) and ii). The constant domains CL and CH1 of the antigen binding moiety having the VH/VL exchange are not replaced by each other (i.e. remain unexchanged).

In more specific aspects, i) in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index); or ii) in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In some aspects, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In further aspects, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index).

In preferred aspects, in the constant domain CL of the second antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In some aspects, in the constant domain CL of the second antigen binding moiety the amino acid at position 124 is substituted by lysine (K) (numbering according to Kabat) and the amino acid at position 123 is substituted by lysine (K) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In some aspects, in the constant domain CL of the second antigen binding moiety the amino acid at position 124 is substituted by lysine (K) (numbering according to Kabat) and the amino acid at position 123 is substituted by arginine (R) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In particular aspects, if amino acid substitutions according to the above aspects are made in the constant domain CL and the constant domain CH1 of the second antigen binding moiety, the constant domain CL of the second antigen binding moiety is of kappa isotype.

In some aspects, the first and the second antigen binding moiety are fused to each other, optionally via a peptide linker.

In some aspects, the first and the second antigen binding moiety are each a Fab molecule and either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety.

In some aspects, the T cell bispecific antibody provides monovalent binding to CD3.

In particular aspects, the T cell bispecific antibody comprises a single antigen binding moiety that binds to CD3, and two antigen binding moieties that bind to the target cell antigen. Thus, in some aspects, the T cell bispecific antibody comprises a third antigen binding moiety, particularly a Fab molecule, more particularly a conventional Fab molecule, that binds to the target antigen. The third antigen binding moiety may incorporate, singly or in combination, all of the features described herein in relation to the second antigen binding moiety (e.g. the CDR sequences, variable region sequences, and/or amino acid substitutions in the constant regions). In some aspects, the third antigen moiety is identical to the first antigen binding moiety (e.g. is also a conventional Fab molecule and comprises the same amino acid sequences).

In particular aspects, the T cell bispecific antibody further comprises an Fc domain composed of a first and a second subunit. In some aspects, the Fc domain is an IgG Fc domain. In particular aspects, the Fc domain is an $IgG_1$ Fc domain. In other aspects, the Fc domain is an $IgG_4$ Fc domain. In more specific aspects, the Fc domain is an $IgG_4$ Fc domain comprising an amino acid substitution at position 5228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In further particular aspects, the Fc domain is a human Fc domain. In particularly preferred aspects, the Fc domain is a human $IgG_1$ Fc domain. An exemplary sequence of a human $IgG_1$ Fc region is given in SEQ ID NO: 3.

In some aspects wherein the first, the second and, where present, the third antigen binding moiety are each a Fab molecule, (a) either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and (b) the third antigen binding moiety, where present, is fused at the C-terminus of the Fab heavy chain to the N-terminus of the second subunit of the Fc domain.

In some aspects, the T cell bispecific antibody essentially consists of the first, the second and the third antigen binding moiety (particularly Fab molecule), the Fc domain composed of a first and a second subunit, and optionally one or more peptide linkers.

The components of the T cell bispecific antibody may be fused to each other directly or, preferably, via one or more suitable peptide linkers. Where fusion of a Fab molecule is to the N-terminus of a subunit of the Fc domain, it is typically via an immunoglobulin hinge region.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$, $G_4(SG_4)_n$ or $(G_4S)_nG_5$ peptide linkers. "n" is generally an integer from 1 to 10, typically from 2 to 4. In some aspects, said peptide linker has a length of at least 5 amino acids, in some aspects a length of 5 to 100, in further aspects of 10 to 50 amino acids. In some aspects said peptide linker is $(GxS)_n$ or $(GxS)_nG_m$ with G=glycine, S=serine, and (x=3, n=3, 4, 5 or 6, and m=0, 1, 2 or 3) or (x=4, n=1, 2, 3, 4 or 5 and m=0, 1, 2, 3, 4 or 5), in some aspects x=4 and n=2 or 3, in further aspects x=4 and n=2, in yet further aspects x=4, n=1 and m=5. In some aspects, said peptide linker is $(G_4S)_2$. In other aspects, said peptide linker is $G_4SG_5$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In particular aspects, the Fc domain comprises a modification promoting the association of the first and the second subunit of the Fc domain. The site of most extensive protein-protein interaction between the two subunits of a human IgG Fc domain is in the CH3 domain. Thus, in some aspects, said modification is in the CH3 domain of the Fc domain.

In specific aspects, said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in some aspects, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis.

In specific such aspects, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In further aspects, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numbering according to Kabat EU index). In preferred aspects, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In some aspects, the Fc domain comprises one or more amino acid substitution that reduces binding to an Fc receptor and/or effector function.

In particular aspects, the Fc receptor is an Fcγ receptor. In some aspects, the Fc receptor is a human Fc receptor. In some aspects, the Fc receptor is an activating Fc receptor. In specific aspects, the Fc receptor is an activating human Fcγ receptor, more specifically human FcγRIIIa, FcγRI or FcγRIIa, most specifically human FcγRIIIa. In some aspects, the effector function is one or more selected from the group of complement dependent cytotoxicity (CDC), antibody-dependent cell-mediated cytotoxicity (ADCC), antibody-dependent cellular phagocytosis (ADCP), and cytokine secretion. In particular aspects, the effector function is ADCC.

Typically, the same one or more amino acid substitution is present in each of the two subunits of the Fc domain. In some aspects, the one or more amino acid substitution reduces the binding affinity of the Fc domain to an Fc receptor. In some aspects, the one or more amino acid substitution reduces the binding affinity of the Fc domain to an Fc receptor by at least 2-fold, at least 5-fold, or at least 10-fold.

In some aspects, the Fc domain comprises an amino acid substitution at a position selected from the group of E233, L234, L235, N297, P331 and P329 (numberings according to Kabat EU index). In more specific aspects, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In some such aspects, the Fc domain is an IgG$_1$ Fc domain, particularly a human IgG$_1$ Fc domain. In some aspects, the Fc domain comprises an amino acid substitution at position P329. In more specific aspects, the amino acid substitution is P329A or P329G, particularly P329G (numberings according to Kabat EU index). In some aspects, the Fc domain comprises an amino acid substitution at position P329 and a further amino acid substitution at a position selected from E233, L234, L235, N297 and P331 (numberings according to Kabat EU index). In more specific aspects, the further amino acid substitution is E233P, L234A, L235A, L235E, N297A, N297D or P331S. In particular aspects, the Fc domain comprises amino acid substitutions at positions P329, L234 and L235 (numberings according to Kabat EU index). In more particular aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In some such aspects, the Fc domain is an IgG$_1$ Fc domain, particularly a human IgG$_1$ Fc domain.

In some aspects, the target cell antigen of the T cell bispecific antibody is carcinoembryonic antigen (CEA).

"Carcinoembryonic antigen" or "CEA" (also known as Carcinoembryonic antigen-related cell adhesion molecule 5 (CEACAMS)) refers to any native CEA from any vertebrate source, including mammals such as primates (e.g. humans), non-human primates (e.g. cynomolgus monkeys) and rodents (e.g. mice and rats), unless otherwise indicated. The term encompasses "full-length," unprocessed CEA as well as any form of CEA that results from processing in the cell. The term also encompasses naturally occurring variants of CEA, e.g., splice variants or allelic variants. In some aspects, CEA is human CEA. The amino acid sequence of human CEA is shown in UniProt (www.uniprot.org) accession no. P06731, or NCBI (www.ncbi.nlm.nih.gov/) RefSeq NP_004354.2. In some aspects, CEA is cell membrane-bound CEA. In some aspects, CEA is CEA expressed on the surface of a cell, e.g. a cancer cell.

Useful T cell bispecific antibodies for the present invention that bind to CEA are described e.g. in PCT publication no. WO 2014/131712 (incorporated herein by reference in its entirety).

Is some aspects, the T cell bispecific antibody comprises a first antigen binding moiety that binds to CD3, and a second antigen binding moiety that binds to CEA.

In some aspects, the first antigen binding moiety comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

In some aspects, the second antigen binding moiety comprises a heavy chain variable region comprising the heavy chain CDR (HCDR) 1 of SEQ ID NO: 12, the HCDR2 of SEQ ID NO: 13, and the HCDR3 of SEQ ID NO: 14; and a light chain variable region comprising the light chain CDR (LCDR) 1 of SEQ ID NO: 15, the LCDR2 of SEQ ID NO: 16 and the LCDR3 of SEQ ID NO: 17.

In some aspects, the T cell bispecific antibody comprises (i) a first antigen binding moiety that binds to CD3 and comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9; and (ii) a second antigen binding moiety that binds to CEA and comprises a heavy chain variable region comprising the heavy chain CDR (HCDR) 1 of SEQ ID NO: 12, the HCDR2 of SEQ ID NO: 13, and the HCDR3 of SEQ ID NO: 14; and a light chain variable region comprising the light chain CDR (LCDR) 1 of SEQ ID NO: 15, the LCDR2 of SEQ ID NO: 16 and the LCDR3 of SEQ ID NO: 17.

In some aspects, the first antigen binding moiety comprises a heavy chain variable region sequence that is at least about 95%, 96%, 97%, 98%, 99% or 100% identical to the amino acid sequence of SEQ ID NO: 10 and a light chain variable region sequence that is at least about 95%, 96%, 97%, 98%, 99% or 100% identical to the amino acid sequence of SEQ ID NO: 11. In some aspects, the first antigen binding moiety comprises the heavy chain variable region sequence of SEQ ID NO: 10 and the light chain variable region sequence of SEQ ID NO: 11.

In some aspects, the second antigen binding moiety comprises a heavy chain variable region sequence that is at least about 95%, 96%, 97%, 98%, 99% or 100% identical to the amino acid sequence of SEQ ID NO: 18 and a light chain variable region sequence that is at least about 95%, 96%, 97%, 98%, 99% or 100% identical to the amino acid sequence of SEQ ID NO: 19. In some aspects, the second antigen binding moiety comprises the heavy chain variable region sequence of SEQ ID NO: 18 and the light chain variable region sequence of SEQ ID NO: 19.

In some aspects, the T cell bispecific antibody comprises a third antigen binding moiety that binds to CEA and/or an Fc domain composed of a first and a second subunit, as described herein.

In preferred aspects, the T cell bispecific antibody comprises (i) a first antigen binding moiety that binds to CD3, comprising a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety that bind to CEA, comprising a heavy chain variable region comprising the heavy chain CDR (HCDR) 1 of SEQ ID NO: 12, the HCDR2 of SEQ ID NO: 13, and the HCDR3 of SEQ ID NO: 14; and a light chain variable region comprising the light chain CDR (LCDR) 1 of SEQ ID NO: 15, the LCDR2 of SEQ ID NO: 16 and the LCDR3 of SEQ ID NO: 17, wherein the second and third antigen binding moiety are each a Fab molecule, particularly a conventional Fab molecule;

(iii) an Fc domain composed of a first and a second subunit, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In some aspects, the first antigen binding moiety of the T cell bispecific antibody (that binds to CEA and CD3) comprises a heavy chain variable region sequence that is at least about 95%, 96%, 97%, 98%, 99% or 100% identical to the amino acid sequence of SEQ ID NO: 10 and a light chain variable region sequence that is at least about 95%, 96%, 97%, 98%, 99% or 100% identical to the amino acid sequence of SEQ ID NO: 11. In some aspects, the first antigen binding moiety comprises the heavy chain variable region sequence of SEQ ID NO: 10 and the light chain variable region sequence of SEQ ID NO: 11.

In some aspects, the second and (where present) third antigen binding moiety of the T cell bispecific antibody (that binds to CEA and CD3) comprise a heavy chain variable region sequence that is at least about 95%, 96%, 97%, 98%, 99% or 100% identical to the amino acid sequence of SEQ ID NO: 18 and a light chain variable region sequence that is at least about 95%, 96%, 97%, 98%, 99% or 100% identical to the amino acid sequence of SEQ ID NO: 19. In some aspects, the second and (where present) third antigen binding moiety comprise the heavy chain variable region of SEQ ID NO: 18 and the light chain variable region of SEQ ID NO: 19.

The Fc domain according to the above aspects may incorporate, singly or in combination, all of the features described hereinabove in relation to Fc domains.

In some aspects, the Fc domain of the T cell bispecific antibody (that binds to CEA and CD3) comprises a modification promoting the association of the first and the second subunit of the Fc domain, and/or the Fc domain comprises one or more amino acid substitution that reduces binding to an Fc receptor and/or effector function.

In some aspects, the antigen binding moieties and the Fc region are fused to each other by peptide linkers, particularly by peptide linkers as in SEQ ID NO: 21 and SEQ ID NO: 23.

In some aspects, the T cell bispecific antibody (that binds to CEA and CD3) comprises a polypeptide (particularly two polypeptides) comprising a sequence that is at least 80%, 85%, 90%, 95%, 96%, 97%, 98%, or 99% identical to the sequence of SEQ ID NO: 20, a polypeptide comprising a sequence that is at least 80%, 85%, 90%, 95%, 96%, 97%, 98%, or 99% identical to the sequence of SEQ ID NO: 21, a polypeptide comprising a sequence that is at least 80%, 85%, 90%, 95%, 96%, 97%, 98%, or 99% identical to the sequence of SEQ ID NO: 22, and a polypeptide comprising a sequence that is at least 80%, 85%, 90%, 95%, 96%, 97%, 98%, or 99% identical to the sequence of SEQ ID NO: 23. In some aspects, the T cell bispecific antibody (that binds to CEA and CD3) comprises a polypeptide (particularly two polypeptides) comprising the sequence of SEQ ID NO: 20, a polypeptide comprising the sequence of SEQ ID NO: 21, a polypeptide comprising the sequence of SEQ ID NO: 22, and a polypeptide comprising the sequence of SEQ ID NO: 23.

In preferred aspects, the T cell bispecific antibody is cibisatamab (WHO Drug Information (International Nonproprietary Names for Pharmaceutical Substances), Recommended INN: List 80, 2018, vol. 32, no. 3, p. 438).

In some aspects, the target cell antigen of the T cell bispecific antibody is CD20.

"CD20", also known as "B-lymphocyte antigen B1", refers to any native CD20 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD20 as well as any form of CD20 that results from processing in the cell. The term also encompasses naturally occurring variants of CD20, e.g., splice variants or allelic variants. In some aspects, CD20 is human CD20. Human CD20 is described in UniProt (www.uniprot.org) accession no. P11836 (entry version 200), and an amino acid sequence of human CD20 is also shown in SEQ ID NO: 36.

Useful T cell bispecific antibodies for the present invention that bind to CD20 are described e.g. in PCT publication no. WO 2016/020309 (incorporated herein by reference in its entirety).

In some aspects, the T cell bispecific antibody comprises a first antigen binding moiety that binds to CD3, and a second antigen binding moiety that binds to CD20.

In some aspects, the first antigen binding moiety comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

In some aspects, the second antigen binding moiety comprises a heavy chain variable region comprising the heavy chain CDR (HCDR) 1 of SEQ ID NO: 24, the HCDR2 of SEQ ID NO: 25, and the HCDR3 of SEQ ID NO: 26; and a light chain variable region comprising the light chain CDR (LCDR) 1 of SEQ ID NO: 27, the LCDR2 of SEQ ID NO: 28 and the LCDR3 of SEQ ID NO: 29.

In some aspects, the T cell bispecific antibody comprises (i) a first antigen binding moiety that binds to CD3 and comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9; and (ii) a second antigen binding moiety that binds to CD20 and comprises a heavy chain variable region comprising the heavy chain CDR (HCDR) 1 of SEQ ID NO: 24, the HCDR2 of SEQ ID NO: 25, and the HCDR3 of SEQ ID NO: 26; and a light chain variable region comprising the light chain CDR (LCDR) 1 of SEQ ID NO: 27, the LCDR2 of SEQ ID NO: 28 and the LCDR3 of SEQ ID NO: 29.

In some aspects, the first antigen binding moiety comprises a heavy chain variable region sequence that is at least about 95%, 96%, 97%, 98%, 99% or 100% identical to the amino acid sequence of SEQ ID NO: 10 and a light chain variable region sequence that is at least about 95%, 96%, 97%, 98%, 99% or 100% identical to the amino acid sequence of SEQ ID NO: 11. In some aspects, the first antigen binding moiety comprises the heavy chain variable region sequence of SEQ ID NO: 10 and the light chain variable region sequence of SEQ ID NO: 11.

In some aspects, the second antigen binding moiety comprises a heavy chain variable region sequence that is at least about 95%, 96%, 97%, 98%, 99% or 100% identical to the amino acid sequence of SEQ ID NO: 30 and a light chain variable region sequence that is at least about 95%, 96%, 97%, 98%, 99% or 100% identical to the amino acid sequence of SEQ ID NO: 31. In some aspects, the second antigen binding moiety comprises the heavy chain variable region sequence of SEQ ID NO: 30 and the light chain variable region sequence of SEQ ID NO: 31.

In some aspects, the T cell bispecific antibody comprises a third antigen binding moiety that binds to CD20 and/or an Fc domain composed of a first and a second subunit, as described herein.

In preferred aspects, the T cell bispecific antibody comprises (i) a first antigen binding moiety that binds to CD3, comprising a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9, wherein the first antigen binding moiety is a crossover Fab molecule wherein either the variable or the constant regions, particularly the variable regions, of the Fab light chain and the Fab heavy chain are exchanged;

(ii) a second and a third antigen binding moiety that bind to CD20, comprising a heavy chain variable region comprising the heavy chain CDR (HCDR) 1 of SEQ ID NO: 24, the HCDR2 of SEQ ID NO: 25, and the HCDR3 of SEQ ID NO: 26; and a light chain variable region comprising the light chain CDR (LCDR) 1 of SEQ ID NO: 27, the LCDR2 of SEQ ID NO: 28 and the LCDR3 of SEQ ID NO: 29, wherein the second and third antigen binding moiety are each a Fab molecule, particularly a conventional Fab molecule;

(iii) an Fc domain composed of a first and a second subunit, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In some aspects, the first antigen binding moiety of the T cell bispecific antibody (that binds to CD20 and CD3) is a crossover Fab molecule wherein the variable regions of the Fab light chain and the Fab heavy chain are exchanged, and wherein the second and (where present) third antigen binding moiety of the T cell bispecific antibody is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

Particularly, in the above aspects, in the constant domain CL of the second and the third Fab molecule under (ii) the amino acid at position 124 may be substituted by lysine (K) (numbering according to Kabat) and the amino acid at position 123 may be substituted by lysine (K) or arginine (R), particularly by arginine (R) (numbering according to Kabat), and in the constant domain CH1 of the second and the third Fab molecule under (ii) the amino acid at position 147 may be substituted by glutamic acid (E) (numbering according to Kabat EU index) and the amino acid at position 213 may be substituted by glutamic acid (E) (numbering according to Kabat EU index).

In some aspects, the first antigen binding moiety of the T cell bispecific antibody (that binds to CD20 and CD3) comprises a heavy chain variable region sequence that is at least about 95%, 96%, 97%, 98%, 99% or 100% identical to the amino acid sequence of SEQ ID NO: 10 and a light chain variable region sequence that is at least about 95%, 96%, 97%, 98%, 99% or 100% identical to the amino acid sequence of SEQ ID NO: 11. In some aspects, the first antigen binding moiety comprises the heavy chain variable region sequence of SEQ ID NO: 10 and the light chain variable region sequence of SEQ ID NO: 11.

In some aspects, the second and (where present) third antigen binding moiety of the T cell bispecific antibody (that binds to CD20 and CD3) comprise a heavy chain variable region sequence that is at least about 95%, 96%, 97%, 98%, 99% or 100% identical to the amino acid sequence of SEQ ID NO: 30 and a light chain variable region sequence that is at least about 95%, 96%, 97%, 98%, 99% or 100% identical to the amino acid sequence of SEQ ID NO: 31. In some aspects, the second and (where present) third antigen binding moiety comprise the heavy chain variable region of SEQ ID NO: 30 and the light chain variable region of SEQ ID NO: 31.

The Fc domain according to the above aspects may incorporate, singly or in combination, all of the features described hereinabove in relation to Fc domains.

In some aspects, the Fc domain of the T cell bispecific antibody (that binds to CD20 and CD3) comprises a modification promoting the association of the first and the second subunit of the Fc domain, and/or the Fc domain comprises one or more amino acid substitution that reduces binding to an Fc receptor and/or effector function.

In some aspects, the antigen binding moieties and the Fc region are fused to each other by peptide linkers, particularly by peptide linkers as in SEQ ID NO: 33 and SEQ ID NO: 35.

In some aspects, the T cell bispecific antibody (that binds to CD20 and CD3) comprises a polypeptide (particularly two polypeptides) comprising a sequence that is at least 80%, 85%, 90%, 95%, 96%, 97%, 98%, or 99% identical to the sequence of SEQ ID NO: 32, a polypeptide comprising a sequence that is at least 80%, 85%, 90%, 95%, 96%, 97%, 98%, or 99% identical to the sequence of SEQ ID NO: 33, a polypeptide comprising a sequence that is at least 80%, 85%, 90%, 95%, 96%, 97%, 98%, or 99% identical to the sequence of SEQ ID NO: 34, and a polypeptide comprising a sequence that is at least 80%, 85%, 90%, 95%, 96%, 97%, 98%, or 99% identical to the sequence of SEQ ID NO: 35. In some aspects, the T cell bispecific antibody (that binds to CD20 and CD3) comprises a polypeptide (particularly two polypeptides) comprising the sequence of SEQ ID NO: 32, a polypeptide comprising the sequence of SEQ ID NO: 33, a polypeptide comprising the sequence of SEQ ID NO: 34, and a polypeptide comprising the sequence of SEQ ID NO: 35.

In preferred aspects, the T cell bispecific antibody is glofitamab (WHO Drug Information (International Nonproprietary Names for Pharmaceutical Substances), Recommended INN: List 83, 2020, vol. 34, no. 1, p. 39).

In some aspects, the target cell antigen of the T cell bispecific antibody is HLA-A2/MAGE-A4.

"MAGE-A4" stands for "Melanoma-associated antigen 4", which is a member of the MAGE family of Cancer Testis Antigens (CTAs). The MAGE-A family of proteins encompasses 12 highly homologous genes clustered at Xq26-28 and characterized by the presence of a conserved domain (MAGE Homology Domain, MHD). Human MAGE-A4 is described in UniProt (www.uniprot.org) accession no. P43358 (entry version 163), and an amino acid sequence of human MAGE-A4 is also shown in SEQ ID NO: 57 herein. "MAGE-A4" as used herein, refers to any native MAGE-A4 from any vertebrate source, including mammals such as primates (e.g. humans), non-human primates (e.g. cynomolgus monkeys) and rodents (e.g. mice and rats), unless otherwise indicated. The term encompasses "full-length," unprocessed MAGE-A4 as well as any form of MAGE-A4 that results from processing in the cell. The term also encompasses naturally occurring variants of MAGE-A4, e.g., splice variants or allelic variants. In one aspect, MAGE-A4 is human MAGE-A4, particularly the protein of SEQ ID NO: 57.

By "MAGE-A4$_{p230-239}$" or "p230-239 peptide" is meant the MAGE-A4 derived peptide having the amino acid sequence GVYDGREHTV (SEQ ID NO: 58; position 230-239 of the MAGE-A4 protein of SEQ ID NO: 57).

"HLA-A2", "HLA-A*02", "HLA-A02", or "HLA-A*2" (used interchangeably) refers to a human leukocyte antigen serotype in the HLA-A serotype group. The HLA-A2 protein (encoded by the respective HLA gene) constitutes the a chain of the respective class I MHC (major histocompatibility complex) protein, which further comprises a (32 microglobulin subunit. A specific HLA-A2 protein is HLA-A201 (also referred to as HLA-A0201, HLA-A02.01, or HLA-A*02:01). In specific aspects, the HLA-A2 protein described herein is HLA-A201. An exemplary sequence of human HLA-A2 is given in SEQ ID NO: 59.

"HLA-A2/MAGE-A4" refers to a complex of a HLA-A2 molecule and a MAGE-A4 derived peptide (also referred to herein as a "MAGE-A4 peptide"), specifically the p230-239 peptide ("HLA-A2/MAGE-A4$_{p230-239}$").

Useful T cell bispecific antibodies for the present invention that bind to HLA-A2/MAGE-A4 are described e.g. in PCT application no. PCT/EP2020/086614 (incorporated herein by reference in its entirety).

In some aspects, the T cell bispecific antibody comprises a first antigen binding moiety that binds to CD3, and a second antigen binding moiety that binds to HLA-A2/MAGE-A4, particularly HLA-A2/MAGE-A4$_{p230-239}$.

In some aspects, the first antigen binding moiety comprises a heavy chain variable region comprising the heavy chain CDR (HCDR) 1 of SEQ ID NO: 37, the HCDR2 of SEQ ID NO: 38, and the HCDR3 of SEQ ID NO: 39; and a light chain variable region comprising the light chain CDR (LCDR) 1 of SEQ ID NO: 40, the LCDR2 of SEQ ID NO: 41 and the LCDR3 of SEQ ID NO: 42.

In some aspects, the second antigen binding moiety comprises a heavy chain variable region comprising the heavy chain CDR (HCDR) 1 of SEQ ID NO: 45, the HCDR2 of SEQ ID NO: 46, and the HCDR3 of SEQ ID NO: 47; and a light chain variable region comprising the light chain CDR (LCDR) 1 of SEQ ID NO: 48, the LCDR2 of SEQ ID NO: 49 and the LCDR3 of SEQ ID NO: 50.

In some aspects, the T cell bispecific antibody comprises (i) a first antigen binding moiety that binds to CD3 and comprises a heavy chain variable region comprising the heavy chain CDR (HCDR) 1 of SEQ ID NO: 37, the HCDR2 of SEQ ID NO: 38, and the HCDR3 of SEQ ID NO: 39; and a light chain variable region comprising the light chain CDR (LCDR) 1 of SEQ ID NO: 40, the LCDR2 of SEQ ID NO: 41 and the LCDR3 of SEQ ID NO: 42; and (ii) a second antigen binding moiety that binds to HLA-A2/MAGE-A4 and comprises a heavy chain variable region comprising the heavy chain CDR (HCDR) 1 of SEQ ID NO: 45, the HCDR2 of SEQ ID NO: 46, and the HCDR3 of SEQ ID NO: 47; and a light chain variable region comprising the light chain CDR (LCDR) 1 of SEQ ID NO: 48, the LCDR2 of SEQ ID NO: 49 and the LCDR3 of SEQ ID NO: 50.

In some aspects, the first antigen binding moiety comprises a heavy chain variable region sequence that is at least about 95%, 96%, 97%, 98%, 99% or 100% identical to the amino acid sequence of SEQ ID NO: 43 and a light chain variable region sequence that is at least about 95%, 96%, 97%, 98%, 99% or 100% identical to the amino acid sequence of SEQ ID NO: 44. In some aspects, the first antigen binding moiety comprises the heavy chain variable region sequence of SEQ ID NO: 43 and the light chain variable region sequence of SEQ ID NO: 44.

In some aspects, the second antigen binding moiety comprises a heavy chain variable region sequence that is at least about 95%, 96%, 97%, 98%, 99% or 100% identical to the amino acid sequence of SEQ ID NO: 51 and a light chain variable region sequence that is at least about 95%, 96%, 97%, 98%, 99% or 100% identical to the amino acid sequence of SEQ ID NO: 52. In some aspects, the second antigen binding moiety comprises the heavy chain variable region sequence of SEQ ID NO: 51 and the light chain variable region sequence of SEQ ID NO: 52.

In some aspects, the T cell bispecific antibody comprises a third antigen binding moiety that binds to HLA-A2/MAGE-A4 and/or an Fc domain composed of a first and a second subunit, as described herein.

In preferred aspects, the T cell bispecific antibody comprises (i) a first antigen binding moiety that binds to CD3, comprising a heavy chain variable region comprising the heavy chain CDR (HCDR) 1 of SEQ ID NO: 37, the HCDR2 of SEQ ID NO: 38, and the HCDR3 of SEQ ID NO: 39; and a light chain variable region comprising the light chain CDR (LCDR) 1 of SEQ ID NO: 40, the LCDR2 of SEQ ID NO: 41 and the LCDR3 of SEQ ID NO: 42, wherein the first antigen binding moiety is a crossover Fab molecule wherein either the variable or the constant regions, particularly the variable regions, of the Fab light chain and the Fab heavy chain are exchanged;

(ii) a second and a third antigen binding moiety that bind to HLA-A2/MAGE-A4, comprising a heavy chain variable region comprising the heavy chain CDR (HCDR) 1 of SEQ ID NO: 45, the HCDR2 of SEQ ID NO: 46, and the HCDR3 of SEQ ID NO: 47; and a light chain variable region comprising the light chain CDR (LCDR) 1 of SEQ ID NO: 48, the LCDR2 of SEQ ID NO: 49 and the LCDR3 of SEQ ID NO: 50, wherein the second and third antigen binding moiety are each a Fab molecule, particularly a conventional Fab molecule;

(iii) an Fc domain composed of a first and a second subunit, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In some aspects, the first antigen binding moiety of the T cell bispecific antibody (that binds to HLA-A2/MAGE-A4 and CD3) is a crossover Fab molecule wherein the variable regions of the Fab light chain and the Fab heavy chain are exchanged, and wherein the second and (where present) third antigen binding moiety of the T cell bispecific antibody is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

Particularly, in the above aspects, in the constant domain CL of the second and the third Fab molecule under (ii) the amino acid at position 124 may be substituted by lysine (K) (numbering according to Kabat) and the amino acid at position 123 may be substituted by lysine (K) or arginine (R), particularly by arginine (R) (numbering according to Kabat), and in the constant domain CH1 of the second and the third Fab molecule under (ii) the amino acid at position 147 may be substituted by glutamic acid (E) (numbering according to Kabat EU index) and the amino acid at position 213 may be substituted by glutamic acid (E) (numbering according to Kabat EU index).

In some aspects, the first antigen binding moiety of the T cell bispecific antibody (that binds to HLA-A2/MAGE-A4 and CD3) comprises a heavy chain variable region sequence that is at least about 95%, 96%, 97%, 98%, 99% or 100% identical to the amino acid sequence of SEQ ID NO: 43 and a light chain variable region sequence that is at least about 95%, 96%, 97%, 98%, 99% or 100% identical to the amino acid sequence of SEQ ID NO: 44. In some aspects, the first antigen binding moiety comprises the heavy chain variable region sequence of SEQ ID NO: 43 and the light chain variable region sequence of SEQ ID NO: 44.

In some aspects, the second and (where present) third antigen binding moiety of the T cell bispecific antibody (that binds to HLA-A2/MAGE-A4 and CD3) comprise a heavy chain variable region sequence that is at least about 95%, 96%, 97%, 98%, 99% or 100% identical to the amino acid sequence of SEQ ID NO: 51 and a light chain variable region sequence that is at least about 95%, 96%, 97%, 98%, 99% or 100% identical to the amino acid sequence of SEQ ID NO: 52. In some aspects, the second and (where present) third antigen binding moiety comprise the heavy chain variable region of SEQ ID NO: 51 and the light chain variable region of SEQ ID NO: 52.

The Fc domain according to the above aspects may incorporate, singly or in combination, all of the features described hereinabove in relation to Fc domains.

In some aspects, the Fc domain of the T cell bispecific antibody (that binds to HLA-A2/MAGE-A4 and CD3) comprises a modification promoting the association of the first and the second subunit of the Fc domain, and/or the Fc domain comprises one or more amino acid substitution that reduces binding to an Fc receptor and/or effector function.

In some aspects, the antigen binding moieties and the Fc region are fused to each other by peptide linkers, particularly by peptide linkers as in SEQ ID NO: 54 and SEQ ID NO: 56.

In some aspects, the T cell bispecific antibody (that binds to HLA-A2/MAGE-A4 and CD3) comprises a polypeptide (particularly two polypeptides) comprising a sequence that is at least 80%, 85%, 90%, 95%, 96%, 97%, 98%, or 99% identical to the sequence of SEQ ID NO: 53, a polypeptide comprising a sequence that is at least 80%, 85%, 90%, 95%, 96%, 97%, 98%, or 99% identical to the sequence of SEQ ID NO: 54, a polypeptide comprising a sequence that is at least 80%, 85%, 90%, 95%, 96%, 97%, 98%, or 99% identical to the sequence of SEQ ID NO: 55, and a polypeptide comprising a sequence that is at least 80%, 85%, 90%, 95%, 96%, 97%, 98%, or 99% identical to the sequence of SEQ ID NO: 56. In some aspects, the T cell bispecific antibody (that binds to HLA-A2/MAGE-A4 and CD3) comprises a polypeptide (particularly two polypeptides) comprising the sequence of SEQ ID NO: 53, a polypeptide comprising the sequence of SEQ ID NO: 54, a polypeptide comprising the sequence of SEQ ID NO: 55, and a polypeptide comprising the sequence of SEQ ID NO: 56.

In some aspects, the target cell antigen of the T cell bispecific antibody is CD19.

"CD19" stands for cluster of differentiation 19 (also known as B-lymphocyte antigen CD19 or B-lymphocyte surface antigen B4) and refers to any native CD19 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD19 as well as any form of CD19 that results from processing in the cell. The term also encompasses naturally occurring variants of CD19, e.g., splice variants or allelic variants. In some aspects, CD19 is human CD19. See for the human protein UniProt (www.uniprot.org) accession no. P15391 (version 211), or NCBI (www.ncbi.nlm.nih.gov/) RefSeq NP_001761.3. An exemplary sequence of human CD19 is given in SEQ ID NO: 60.

Useful T cell bispecific antibodies for the present invention that bind to CD19 are described e.g. in EP application nos. 20181056.1 and 20180968.8 (incorporated herein by reference in their entirety).

In some aspects, the T cell bispecific antibody comprises a first antigen binding moiety that binds to CD3, and a second antigen binding moiety that binds to CD19.

In some aspects, the first antigen binding moiety comprises a heavy chain variable region comprising the heavy chain CDR (HCDR) 1 of SEQ ID NO: 61, the HCDR2 of SEQ ID NO: 5, and the HCDR3 of SEQ ID NO: 62; and a light chain variable region comprising the light chain CDR (LCDR) 1 of SEQ ID NO: 7, the LCDR2 of SEQ ID NO: 8 and the LCDR3 of SEQ ID NO: 9.

In other aspects, the first antigen binding moiety comprises a heavy chain variable region comprising the heavy chain CDR (HCDR) 1 of SEQ ID NO: 64, the HCDR2 of SEQ ID NO: 5, and the HCDR3 of SEQ ID NO: 65; and a light chain variable region comprising the light chain CDR (LCDR) 1 of SEQ ID NO: 7, the LCDR2 of SEQ ID NO: 8 and the LCDR3 of SEQ ID NO: 9.

In some aspects, the second antigen binding moiety comprises a heavy chain variable region comprising the heavy chain CDR (HCDR) 1 of SEQ ID NO: 67, the HCDR2 of SEQ ID NO: 68, and the HCDR3 of SEQ ID NO: 69; and a light chain variable region comprising the light chain CDR (LCDR) 1 of SEQ ID NO: 70, the LCDR2 of SEQ ID NO: 71 and the LCDR3 of SEQ ID NO: 72.

In some aspects, the T cell bispecific antibody comprises
(i) a first antigen binding moiety that binds to CD3 and comprises a heavy chain variable region comprising the heavy chain CDR (HCDR) 1 of SEQ ID NO: 61, the HCDR2 of SEQ ID NO: 5, and the HCDR3 of SEQ ID NO: 62, or a heavy chain variable region comprising the HCDR1 of SEQ ID NO: 64, the HCDR2 of SEQ ID NO: 5, and the HCDR3 of SEQ ID NO: 65; and a light chain variable region comprising the light chain CDR (LCDR) 1 of SEQ ID NO: 7, the LCDR2 of SEQ ID NO: 8 and the LCDR3 of SEQ ID NO: 9; and
(ii) a second antigen binding moiety that binds to CD19 and comprises a heavy chain variable region comprising the heavy chain CDR (HCDR) 1 of SEQ ID NO: 67, the HCDR2 of SEQ ID NO: 68, and the HCDR3 of SEQ ID NO: 69; and a light chain variable region comprising the light chain CDR (LCDR) 1 of SEQ ID NO: 70, the LCDR2 of SEQ ID NO: 71 and the LCDR3 of SEQ ID NO: 72.

In some aspects, the first antigen binding moiety comprises a heavy chain variable region sequence that is at least about 95%, 96%, 97%, 98%, 99% or 100% identical to the amino acid sequence of SEQ ID NO: 63 or a heavy chain variable region sequence that is at least about 95%, 96%, 97%, 98%, 99% or 100% identical to the amino acid sequence of SEQ ID NO: 66, and a light chain variable region sequence that is at least about 95%, 96%, 97%, 98%, 99% or 100% identical to the amino acid sequence of SEQ ID NO: 35. In some aspects, the first antigen binding moiety comprises the heavy chain variable region sequence of SEQ ID NO: 63 or the heavy chain variable region sequence of SEQ ID NO: 66, and the light chain variable region sequence of SEQ ID NO: 11.

In some aspects, the second antigen binding moiety comprises a heavy chain variable region sequence that is at least about 95%, 96%, 97%, 98%, 99% or 100% identical to the amino acid sequence of SEQ ID NO: 73 and a light chain variable region sequence that is at least about 95%, 96%, 97%, 98%, 99% or 100% identical to the amino acid sequence of SEQ ID NO: 74. In some aspects, the second antigen binding moiety comprises the heavy chain variable region sequence of SEQ ID NO: 73 and the light chain variable region sequence of SEQ ID NO: 74.

In some aspects, the T cell bispecific antibody comprises a third antigen binding moiety that binds to CD19 and/or an Fc domain composed of a first and a second subunit, as described herein.

In preferred aspects, the T cell bispecific antibody comprises
(i) a first antigen binding moiety that binds to CD3, comprising a heavy chain variable region comprising the heavy chain CDR (HCDR) 1 of SEQ ID NO: 61, the HCDR2 of SEQ ID NO: 5, and the HCDR3 of SEQ ID NO: 62, or a heavy chain variable region comprising the HCDR1 of SEQ ID NO: 64, the HCDR2 of SEQ ID NO: 5, and the HCDR3 of SEQ ID NO: 65; and a light chain variable region comprising the light chain CDR (LCDR) 1 of SEQ ID NO: 7, the LCDR2 of SEQ ID NO: 8 and the LCDR3 of SEQ ID NO: 9, wherein the first antigen binding moiety is a crossover Fab molecule wherein either the variable or the constant regions, particularly the variable regions, of the Fab light chain and the Fab heavy chain are exchanged;

(ii) a second and a third antigen binding moiety that bind to CD19, comprising a heavy chain variable region comprising the heavy chain CDR (HCDR) 1 of SEQ ID NO: 67, the HCDR2 of SEQ ID NO: 68, and the HCDR3 of SEQ ID NO: 69; and a light chain variable region comprising the light chain CDR (LCDR) 1 of SEQ ID NO: 70, the LCDR2 of SEQ ID NO: 71 and the LCDR3 of SEQ ID NO: 72, wherein the second and third antigen binding moiety are each a Fab molecule, particularly a conventional Fab molecule;

(iii) an Fc domain composed of a first and a second subunit, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In some aspects, the first antigen binding moiety of the T cell bispecific antibody (that binds to CD19 and CD3) is a crossover Fab molecule wherein the variable regions of the Fab light chain and the Fab heavy chain are exchanged, and wherein the second and (where present) third antigen binding moiety of the T cell bispecific antibody is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

Particularly, in the above aspects, in the constant domain CL of the second and the third Fab molecule under (ii) the amino acid at position 124 may be substituted by lysine (K) (numbering according to Kabat) and the amino acid at position 123 may be substituted by lysine (K) or arginine (R), particularly by arginine (R) (numbering according to Kabat), and in the constant domain CH1 of the second and the third Fab molecule under (ii) the amino acid at position 147 may be substituted by glutamic acid (E) (numbering according to Kabat EU index) and the amino acid at position 213 may be substituted by glutamic acid (E) (numbering according to Kabat EU index).

In some aspects, the first antigen binding moiety of the T cell bispecific antibody (that binds to CD19 and CD3) comprises a heavy chain variable region sequence that is at least about 95%, 96%, 97%, 98%, 99% or 100% identical to the amino acid sequence of SEQ ID NO: 63 or a heavy chain variable region sequence that is at least about 95%, 96%, 97%, 98%, 99% or 100% identical to the amino acid sequence of SEQ ID NO: 66, and a light chain variable region sequence that is at least about 95%, 96%, 97%, 98%, 99% or 100% identical to the amino acid sequence of SEQ ID NO: 11. In some aspects, the first antigen binding moiety comprises the heavy chain variable region sequence of SEQ ID NO: 63 or the heavy chain variable region sequence of SEQ ID NO: 66, and the light chain variable region sequence of SEQ ID NO: 11.

In some aspects, the second and (where present) third antigen binding moiety of the T cell bispecific antibody (that binds to CD19 and CD3) comprise a heavy chain variable region sequence that is at least about 95%, 96%, 97%, 98%, 99% or 100% identical to the amino acid sequence of SEQ ID NO: 73 and a light chain variable region sequence that is at least about 95%, 96%, 97%, 98%, 99% or 100% identical to the amino acid sequence of SEQ ID NO: 74. In some aspects, the second and (where present) third antigen binding moiety comprise the heavy chain variable region of SEQ ID NO: 73 and the light chain variable region of SEQ ID NO: 74.

The Fc domain according to the above aspects may incorporate, singly or in combination, all of the features described hereinabove in relation to Fc domains.

In some aspects, the Fc domain of the T cell bispecific antibody (that binds to CD19 and CD3) comprises a modification promoting the association of the first and the second subunit of the Fc domain, and/or the Fc domain comprises one or more amino acid substitution that reduces binding to an Fc receptor and/or effector function.

In some aspects, the antigen binding moieties and the Fc region are fused to each other by peptide linkers, particularly by peptide linkers as in SEQ ID NO: 75, SEQ ID NO: 76 and SEQ ID NO: 77.

In some aspects, the T cell bispecific antibody (that binds to CD19 and CD3) comprises a polypeptide (particularly two polypeptides) comprising a sequence that is at least 80%, 85%, 90%, 95%, 96%, 97%, 98%, or 99% identical to the sequence of SEQ ID NO: 78, a polypeptide comprising a sequence that is at least 80%, 85%, 90%, 95%, 96%, 97%, 98%, or 99% identical to the sequence of SEQ ID NO: 75, a polypeptide comprising a sequence that is at least 80%, 85%, 90%, 95%, 96%, 97%, 98%, or 99% identical to the sequence of SEQ ID NO: 77, and a polypeptide comprising a sequence that is at least 80%, 85%, 90%, 95%, 96%, 97%, 98%, or 99% identical to the sequence of SEQ ID NO: 79. In some aspects, the T cell bispecific antibody (that binds to CD19 and CD3) comprises a polypeptide (particularly two polypeptides) comprising the sequence of SEQ ID NO: 78, a polypeptide comprising the sequence of SEQ ID NO: 75, a polypeptide comprising the sequence of SEQ ID NO: 77, and a polypeptide comprising the sequence of SEQ ID NO: 79.

In other aspects, the T cell bispecific antibody (that binds to CD19 and CD3) comprises a polypeptide (particularly two polypeptides) comprising a sequence that is at least 80%, 85%, 90%, 95%, 96%, 97%, 98%, or 99% identical to the sequence of SEQ ID NO: 78, a polypeptide comprising a sequence that is at least 80%, 85%, 90%, 95%, 96%, 97%, 98%, or 99% identical to the sequence of SEQ ID NO: 76, a polypeptide comprising a sequence that is at least 80%, 85%, 90%, 95%, 96%, 97%, 98%, or 99% identical to the sequence of SEQ ID NO: 77, and a polypeptide comprising a sequence that is at least 80%, 85%, 90%, 95%, 96%, 97%, 98%, or 99% identical to the sequence of SEQ ID NO: 80. In some aspects, the T cell bispecific antibody (that binds to CD19 and CD3) comprises a polypeptide (particularly two polypeptides) comprising the sequence of SEQ ID NO: 78, a polypeptide comprising the sequence of SEQ ID NO: 76, a polypeptide comprising the sequence of SEQ ID NO: 77, and a polypeptide comprising the sequence of SEQ ID NO: 80.

In some aspects, the disease (to be treated by the T cell engaging agent) is cancer.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "cancer" refers to the physiological condition in mammals that is typically characterized by unregulated cell proliferation. Examples of cancer include but are not limited to, carcinoma, lymphoma, blastoma, sarcoma and leukemia. More non-limiting examples of cancers include haematological cancer such as leukemia, bladder cancer, brain cancer, head and neck cancer, pancreatic cancer, biliary cancer, thyroid cancer, lung cancer, breast cancer, ovarian cancer, uterine cancer, cervical cancer, endometrial cancer, esophageal cancer, colon cancer, colorectal cancer, rectal cancer, gastric cancer, prostate cancer, skin cancer, squamous cell carcinoma, sarcoma, bone cancer, and kidney cancer. Other cell proliferation disorders include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases.

In some aspects, the cancer is a cancer expressing the target cell antigen of the T cell engaging agent (e.g. the T cell bispecific antibody).

In some aspects, the cancer is a carcinoembryonic antigen (CEA)-expressing cancer (in particular in aspects, wherein the target cell antigen of the T cell engaging agent, e.g. T cell bispecific antibody, is CEA). By "CEA-positive cancer" or "CEA-expressing cancer" is meant a cancer characterized by expression or overexpression of CEA on cancer cells. The expression of CEA may be determined for example by an immunohistochemistry (IHC) or flow cytometric assay. In some aspects, the cancer expresses CEA. In some aspects, the cancer expresses CEA in at least 20%, preferably at least 50% or at least 80% of tumor cells as determined by immunohistochemistry (IHC) using an antibody specific for CEA.

In some aspects, the cancer is colon cancer, lung cancer, ovarian cancer, gastric cancer, bladder cancer, pancreatic cancer, endometrial cancer, breast cancer, kidney cancer, esophageal cancer, prostate cancer, or other cancers described herein.

In particular aspects, the cancer is a cancer selected from the group consisting of colorectal cancer, lung cancer, pancreatic cancer, breast cancer, and gastric cancer. In preferred aspects, the cancer is colorectal cancer (CRC). In some aspects, the colorectal cancer is metastatic colorectal cancer (mCRC). In some aspects, the colorectal cancer is microsatellite-stable (MSS) colorectal cancer. In some aspects, the colorectal cancer is microsatellite-stable metastatic colorectal cancer (MSS mCRC).

In some aspects, the cancer is a CD20-expressing cancer (in particular in aspects, wherein the target cell antigen of the T cell engaging agent, e.g. T cell bispecific antibody, is CD20). By "CD20-positive cancer" or "CD20-expressing cancer" is meant a cancer characterized by expression or overexpression of CD20 in cancer cells. The expression of CD20 may be determined for example by quantitative real-time PCR (measuring CD20 mRNA levels), flow cytometry, immunohistochemistry (IHC) or western blot assays. In some aspects, the cancer expresses CD20. In some aspects, the cancer expresses CD20 in at least 20%, preferably at least 50% or at least 80% of tumor cells as determined by immunohistochemistry (IHC) using an antibody specific for CD20.

In some aspects, the cancer is a B-cell cancer, particularly a CD20-positive B-cell cancer. In some aspects, the cancer is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) or Hodgkin lymphoma (HL). In particular aspects, the cancer is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL) and marginal zone lymphoma (MZL). In more particular aspects, the cancer is NHL, particularly relapsed/refractory (r/r) NHL. In some aspects, the cancer is DLBCL. In some aspects, the cancer is FL. In some aspects, the cancer is MCL. In some aspects, the cancer is MZL.

In some aspects, the cancer is a MAGE-A4-expressing cancer (in particular in aspects, wherein the target cell antigen of the T cell engaging agent, e.g. T cell bispecific antibody, is HLA-A2/MAGE-A4). By "MAGE-A4-positive cancer" or "MAGE-A4-expressing cancer" is meant a cancer characterized by expression or overexpression of MAGE-A4 in cancer cells.

In some aspects, the cancer is a cancer selected from the group consisting of lung cancer, head and neck cancer, bladder cancer, esophageal cancer, skin cancer, gastric cancer and ovarian cancer.

In some aspects, the cancer is a CD19-expressing cancer (in particular in aspects, wherein the target cell antigen of the T cell engaging agent, e.g. T cell bispecific antibody, is CD19). By "CD19-positive cancer" or "CD19-expressing cancer" is meant a cancer characterized by expression or overexpression of CD19 in cancer cells. The expression of CD19 may be determined for example by quantitative real-time PCR (measuring CD19 mRNA levels), flow cytometry, immunohistochemistry (IHC) or western blot assays. In some aspects, the cancer expresses CD19. In some aspects, the cancer expresses CD19 in at least 20%, preferably at least 50% or at least 80% of tumor cells as determined by immunohistochemistry (IHC) using an antibody specific for CD19.

In some aspects, the cancer is a B-cell cancer, particularly a CD19-positive B-cell cancer. In some aspects, the cancer is a B-cell lymphoma or a B-cell leukemia. In some aspects, the cancer is non-Hodgkin lymphoma (NHL), acute lymphoblastic leukemia (ALL) or chronic lymphocytic leukemia (CLL).

In some aspects, the cancer is treatable by the T cell engaging agent. In some aspects, the T cell engaging agent is indicated for the treatment of the cancer.

In some aspects, the cancer is a solid tumor cancer. By a "solid tumor cancer" is meant a malignancy that forms a discrete tumor mass (including also tumor metastasis) located at specific location in the patient's body, such as sarcomas or carcinomas (as opposed to e.g. blood cancers such as leukemia, which generally do not form solid tumors). Non-limiting examples of solid tumor cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, skin cancer, squamous cell carcinoma, bone cancer, liver cancer and kidney cancer. Other solid tumor cancers that are contemplated in the context of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, muscles, spleen, thoracic region, and urogenital system. Also included are pre-cancerous conditions or lesions and cancer metastases.

In some aspects wherein the target cell antigen of the T cell engaging agent, e.g. T cell bispecific antibody, is CD19, the disease (to be treated by the T cell bispecific antibody) is an autoimmune disease. In specific aspects, the autoimmune disease is lupus, in particular systemic lupus erythematosus (SLE) or lupus nephritis (LN).

An "individual" or "subject" herein is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain aspects, the individual or subject is a human. In some aspects, the individual has a disease, particularly a disease treatable or to be treated by the T cell engaging agent. In some aspects, the individual has cancer, particularly a cancer treatable or to be treated by the T cell engaging agent. In particular, an individual herein is any single human subject eligible for treatment who is experiencing or has experienced one or more signs, symptoms, or other indicators of cancer. In some aspects, the individual has cancer or has been diagnosed with cancer, in particular any of the cancers described hereinabove. In some aspects, the individual has locally advanced or metastatic cancer or has been diagnosed with locally advanced or metastatic cancer. The individual may have been previously treated with a T cell engaging agent (e.g. a T cell bispecific antibody) or another drug, or not so treated. In particular aspects, the patient has not been previously treated with a T cell engaging agent (e.g. a T cell bispecific antibody). The patient may have been treated with a therapy comprising one or more drugs other than T cell engaging agent (e.g. other than a T cell bispecific antibody) before the T cell engaging agent therapy is commenced.

In some aspects, the individual has an elevated serum level of one of more cytokine. In some aspects, said elevated serum level is related to the administration of the T cell engaging agent to the individual. Said elevated serum level is in particular as compared to the serum level in a healthy individual, and/or the serum level in an individual (including the same individual) without administration of the T cell engaging agent (i.e. in such case the serum level is elevated as compared to the serum level without administration of the T cell engaging agent). In some aspects, said one or more cytokine is selected from the group consisting of IL-6, IFN-γ, IL-10, TNF-α, GM-CSF, MCP-1 and IL-1β.

A cytokine according to any of the aspects of the invention may be one or more cytokine selected from the group consisting of interleukin (IL)-6, interferon (IFN)-γ, IL-10, tumor necrosis factor (TNF)-α, granulocyte-macrophage colony-stimulating factor (GM-CSF), monocyte chemoattractant protein (MCP)-1, IL-1β, IL-8, IL-4 and IL-2. In some aspects, the cytokine is one or more cytokine selected from the group consisting of IL-6, IFN-γ, IL-10, TNF-α, GM-CSF, MCP-1 and IL-1β. In some aspects, the cytokine is one or more cytokine selected from the group consisting of IL-6, IFN-γ, IL-10, TNF-α and GM-CSF. In some aspects, the cytokine is one or more cytokine selected from the group consisting of IL-6, IFN-γ, IL-10 and TNF-α. In some aspects, the cytokine is one or more cytokine selected from the group consisting of IL-6, IFN-γ and IL-10. In some aspects, the cytokine is IL-6. In some aspects, the cytokine is IFN-γ. In some aspects, the cytokine is IL-10. In some aspects, the cytokine is TNF-α. In some aspects, the cytokine is GM-CSF. In some aspects, the cytokine is MCP-1. In some aspects, the cytokine is IL-1β. In some aspects, the cytokine is IL-8. In some aspects, the cytokine is IL-4. In some aspects, the cytokine is IL-2.

Preferably, a T cell according to any of the aspects of the invention is a cytotoxic T cell. In some aspects, the T cell is a CD4$^+$ or a CD8$^+$ T cell. In some aspects, the T cell is a CD8$^+$ T cell. In some aspects, the T cell is a CD4$^+$ T cell.

In some aspects, the treatment with or administration of the T cell engaging agent may result in a response in the individual. In some aspects, the response may be a complete response. In some aspects, the response may be a sustained response after cessation of the treatment. In some aspects, the response may be a complete response that is sustained after cessation of the treatment. In other aspects, the response may be a partial response. In some aspects, the response may be a partial response that is sustained after cessation of the treatment. In some aspects, the treatment with or administration of the T cell engaging agent and the inhibitor of JAK and/or mTOR signaling may improve the response as compared to treatment with or administration of the T cell engaging agent alone (i.e. without the inhibitor of JAK and/or mTOR signaling). In some aspects, the treatment or administration of the T cell engaging agent and the inhibitor of JAK and/or mTOR signaling may increase response rates in a patient population, as compared to a corresponding patient population treated with the T cell engaging agent alone (i.e. without the inhibitor of JAK and/or mTOR signaling).

The T cell engaging agent may be used alone or together with other agents in a therapy. For instance, a T cell engaging agent may be co-administered with at least one additional therapeutic agent. In certain aspects, an additional therapeutic agent is an anti-cancer agent, e.g. a chemotherapeutic agent, an inhibitor of tumor cell proliferation, or an activator of tumor cell apoptosis.

The inhibitor of JAK and/or mTOR signaling may be used alone or together with one or more other agents for the prevention of mitigation of an adverse effect, particularly CRS, related to the administration of the T cell engaging agent. The inhibitor of JAK and/or mTOR signaling may for example be used together with an IL-6R antagonist (e.g. tocilizumab), a steroid (e.g. a corticosteroid such as methylprednisolone or dexamethasone) or a TNF-α antagonist (e.g. etanercept).

Amino Acid Sequences

| | Sequence | SEQ ID NO |
|---|---|---|
| Human CD3 | MQSGTHWRVLGLCLLSVGVW GQDGNEEMGGITQTPYKVSI SGTTVILTCPQYPGSEILWQ HNDRNIGGDEDDKNIGSDED HLSLKEFSELEQSGYYVCYP RGSKPEDANFYLYLRARVCE NCMEMDVMSVATIVIVDICI TGGLLLLVYYWSKNRKAKAK PVTRGAGAGGRQRGQNKERP PPVPNPDYEPIRKGQRDLYS GLNQRRI | 1 |
| Cynomolgus CD3 | MQSGTRWRVLGLCLLSIGVW GQDGNEEMGGSITQTPYQVSI SGTTVILTCSQHLGSEAQWQ HNGKNKEDSGDRLFLPEFSE MEQSGYYVCYPRGSNPEDAS HHLYLKARVCENCMEMDVMA VATIVIVDICITLGLLLLVY YWSKNRKAKAKPVTRGAGAG GRQRGQNKERPPPVPNPDYE PIRRGQQDLYSGLNQRRI | 2 |
| hIgG1 Fc region | DKTHTCPPCPAPELLGGPSV FLFPPKPKDTLMISRTPEVT CVVVDVSHEDPEVKFNWYVD GVEVHNAKTKPREEQYNSTY RVVSVLTVLHQDWLNGKEYK CKVSNRALPAPIEKTISKAK GQPREPQVYTLPPSRDELTK NQVSLTCLVKGFYPSDIAVE WESNGQPENNYKTTPPVLDS DGSFFLYSKLTVDKSRWQQG NVFSCSVMHEALHNHYTQKS LSLSP | 3 |
| CD3 HCDR1 | TYAMN | 4 |
| CD3 HCDR2 | RIRSKYNNYATYYADSVKG | 5 |
| CD3 HCDR3 | HGNFGNSYVSWFAY | 6 |
| CD3 LCDR1 | GSSTGAVTTSNYAN | 7 |
| CD3 LCDR2 | GTNKRAP | 8 |
| CD3 LCDR3 | ALWYSNLWV | 9 |
| CD3 VH | EVQLLESGGGLVQPGGSLRL SCAASGFTFSTYAMNWVRQA PGKGLEWVSRIRSKYNNYAT YYADSVKGRFTISRDDSKNT LYLQMNSLRAEDTAVYYCVR HGNFGNSYVSWFAYWGQGTL VTVSS | 10 |
| CD3 VL | QAVVTQEPSLTVSPGGTVTL TCGSSTGAVTTSNYANWVQE KPGQAFRGLIGGTNKRAPGT PARFSGSLLGGKAALTLSGA QPEDEAEYYCALWYSNLWVF GGGTRLTVL | 11 |
| CEA HCDR1 | EFGMN | 12 |
| CEA HCDR2 | WINTKTGEATYVEEFKG | 13 |
| CEA HCDR3 | WDFAYYVEAMDY | 14 |
| CEA LCDR1 | KASAAVGTYVA | 15 |
| CEA LCDR2 | SASYRKR | 16 |
| CEA LCDR3 | HQYYTYPLFT | 17 |

-continued

Amino Acid Sequences

| | Sequence | SEQ ID NO |
|---|---|---|
| CEA VH | QVQLVQSGAEVKKPGASVKV SCKASGYTFTEFGMNWVRQA PGQGLEWMGWINTKTGEATY VEEFKGRVTFTTDTSTSTAY MELRSLRSDDTAVYYCARWD FAYYVEAMDYWGQGTTVTVS S | 18 |
| CEA VL | DIQMTQSPSSLSASVGDRVT ITCKASAAVGTYVAWYQQKP GKAPKLLIYSASYRKRGVPS RFSGSGSGTDFTLTISSLQP EDFATYYCHQYYTYPLFTFG QGTKLEIK | 19 |
| CEA VL-CL | DIQMTQSPSSLSASVGDRVT ITCKASAAVGTYVAWYQQKP GKAPKLLIYSASYRKRGVPS RFSGSGSGTDFTLTISSLQP EDFATYYCHQYYTYPLFTFG QGTKLEIKRTVAAPSVFIFP PSDEQLKSGTASVVCLLNNF YPREAKVQWKVDNALQSGNS QESVTEQDSKDSTYSLSSTL TLSKADYEKHKVYACEVTHQ GLSSPVTKSFNRGEC | 20 |
| CEA VH-CH1-Fc(hole, PGLALA) | QVQLVQSGAEVKKPGASVKV SCKASGYTFTEFGMNWVRQA PGQGLEWMGWINTKTGEATY VEEFKGRVTFTTDTSTSTAY MELRSLRSDDTAVYYCARWD FAYYVEAMDYWGQGTTVTVS SASTKGPSVFPLAPSSKSTS GGTAALGCLVKDYFPEPVTV SWNSGALTSGVHTFPAVLQS SGLYSLSSVVTVPSSSLGTQ TYICNVNHKPSNTKVDKKVE PKSCDKTHTCPPCPAPEAAG GPSVFLFPPKPKDTLMISRT PEVTCVVVDVSHEDPEVKFN WYVDGVEVHNAKTKPREEQY NSTYRVVSVLTVLHQDWLNG KEYKCKVSNKALGAPIEKTI SKAKGQPREPQVCTLPPSRD ELTKNQVSLSCAVKGFYPSD IAVEWESNGQPENNYKTTPP VLDSDGSFFLVSKLTVDKSR WQQGNVFSCSVMHEALHNHY TQKSLSLSPGK | 21 |
| CD3 VL-CH1 | QAVVTQEPSLTVSPGGTVTL TCGSSTGAVTTSNYANWVQE KPGQAFRGLIGGTNKRAPGT PARFSGSLLGGKAALTLSGA QPEDEAEYYCALWYSNLWVF GGGTKLTVLSSASTKGPSVF PLAPSSKSTSGGTAALGCLV KDYFPEPVTVSWNSGALTSG VHTFPAVLQSSGLYSLSSVV TVPSSSLGTQTYICNVNHKP SNTKVDKKVEPKSC | 22 |
| CEA VH-CH1-CD3 VH-CL-Fc(knob, PGLALA) | QVQLVQSGAEVKKPGASVKV SCKASGYTFTEFGMNWVRQA PGQGLEWMGWINTKTGEATY VEEFKGRVTFTTDTSTSTAY MELRSLRSDDTAVYYCARWD FAYYVEAMDYWGQGTTVTVS SASTKGPSVFPLAPSSKSTS GGTAALGCLVKDYFPEPVTV SWNSGALTSGVHTFPAVLQS SGLYSLSSVVTVPSSSLGTQ | 23 |

-continued

-continued

Amino Acid Sequences

| | Sequence | SEQ ID NO |
|---|---|---|
| | TYICNVNHKPSNTKVDKKVE PKSCDGGGGSGGGGSEVQLL ESGGGLVQPGGSLRLSCAAS GFTFSTYAMNWVRQAPGKGL EWVSRIRSKYNNYATYYADS VKGRFTISRDDSKNTLYLQM NSLRAEDTAVYYCVRHGNFG NSYVSWFAYWGQGTLVTVSS ASVAAPSVFIFPPSDEQLKS GTASVVCLLNNFYPREAKVQ WKVDNALQSGNSQESVTEQD SKDSTYSLSSTLTLSKADYE KHKVYACEVTHQGLSSPVTK SFNRGECDKTHTCPPCPAPE AAGGPSVFLFPPKPKDTLMI SRTPEVTCVVVDVSHEDPEV KFNWYVDGVEVHNAKTKPRE EQYNSTYRVVSVLTVLHQDW LNGKEYKCKVSNKALGAPIE KTISKAKGQPREPQVYTLPP CRDELTKNQVSLWCLVKGFY PSDIAVEWESNGQPENNYKT TPPVLDSDGSFFLYSKLTVD KSRWQQGNVFSCSVMHEALH NHYTQKSLSLSPGK | |
| CD20 HCDR1 | YSWIN | 24 |
| CD20 HCDR2 | RIFPGDGDTDYNGKFKG | 25 |
| CD20 HCDR3 | NVFDGYWLVY | 26 |
| CD20 LCDR1 | RSSKSLLHSNGITYLY | 27 |
| CD20 LCDR2 | QMSNLVS | 28 |
| CD20 LCDR3 | AQNLELPYT | 29 |
| CD20 VH | QVQLVQSGAEVKKPGSSVKV SCKASGYAFSYSWINWVRQA PGQGLEWMGRIFPGDGDTDY NGKFKGRVTITADKSTSTAY MELSSLRSEDTAVYYCARNV FDGYWLVYWGQGTLVTVSS | 30 |
| CD20 VL | DIVMTQTPLSLPVTPGEPAS ISCRSSKSLLHSNGITYLYW YLQKPGQSPQLLIYQMSNLV SGVPDRFSGSGSGTDFTLKI SRVEAEDVGVYYCAQNLELP YTFGGGTKVEIK | 31 |
| CD20 VL-CL(RK) | DIVMTQTPLSLPVTPGEPAS ISCRSSKSLLHSNGITYLYW YLQKPGQSPQLLIYQMSNLV SGVPDRFSGSGSGTDFTLKI SRVEAEDVGVYYCAQNLELP YTFGGGTKVEIKRTVAAPSV FIFPPSDRKLKSGTASVVCL LNNFYPREAKVQWKVDNALQ SGNSQESVTEQDSKDSTYSL SSTLTLSKADYEKHKVYACE VTHQGLSSPVTKSFNRGEC | 32 |
| CD20 VH-CH1(EE)-Fc(hole, PGLALA) | QVQLVQSGAEVKKPGSSVKV SCKASGYAFSYSWINWVRQA PGQGLEWMGRIFPGDGDTDY NGKFKGRVTITADKSTSTAY MELSSLRSEDTAVYYCARNV FDGYWLVYWGQGTLVTVSSA STKGPSVFPLAPSSKSTSGG TAALGCLVEDYFPEPVTVSW NSGALTSGVHTFPAVLQSSG | 33 |

| | Sequence | SEQ ID NO |
|---|---|---|
| | LYSLSSVVTVPSSSLGTQTY ICNVNHKPSNTKVDEKVEPK SCDKTHTCPPCPAPEAAGGP SVFLFPPKPKDTLMISRTPE VTCVVVDVSHEDPEVKFNWY VDGVEVHNAKTKPREEQYNS TYRVVSVLTVLHQDWLNGKE YKCKVSNKALGAPIEKTISK AKGQPREPQVCTLPPSRDEL TKNQVSLSCAVKGFYPSDIA VEWESNGQPENNYKTTPPVL DSDGSFFLVSKLTVDKSRWQ QGNVFSCSVMHEALHNHYTQ KSLSLSP | |
| CD3 VH-CL | EVQLLESGGGLVQPGGSLRL SCAASGFTFSTYAMNWVRQA PGKGLEWVSRIRSKYNNYAT YYADSVKGRFTISRDDSKNT LYLQMNSLRAEDTAVYYCVR HGNFGNSYVSWFAYWGQGTL VTVSSASVAAPSVFIFPPSD EQLKSGTASVVCLLNNFYPR EAKVQWKVDNALQSGNSQES VTEQDSKDSTYSLSSTLTLS KADYEKHKVYACEVTHQGLS SPVTKSFNRGEC | 34 |
| CD20 VH-CH1(EE)-CD3 VL-CH1-Fc(knob, PGLALA) | QVQLVQSGAEVKKPGSSVKV SCKASGYAFSYSWINWVRQA PGQGLEWMGRIFPGDGDTDY NGKFKGRVTITADKSTSTAY MELSSLRSEDTAVYYCARNV FDGYWLVYWGQGTLVTVSSA STKGPSVFPLAPSSKSTSG GTAALGCLVEDYFPEPVTV SWNSGALTSGVHTFPAVLQS SGLYSLSSVVTVPSSSLGTQ TYICNVNHKPSNTKVDEKVE PKSCDGGGGSGGGGSQAVVT QEPSLTVSPGGTVTLTCGSS TGAVTTSNYANWVQEKPGQA FRGLIGGTNKRAPGTPARFS GSLLGGKAALTLSGAQPEDE AEYYCALWYSNLWVFGGGTK LTVLSSASTKGPSVFPLAPS SKSTSGGTAALGCLVKDYFP EPVTVSWNSGALTSGVHTFP AVLQSSGLYSLSSVVTVPSS SLGTQTYICNVNHKPSNTKV DKKVEPKSCDKTHTCPPCPA PEAAGGPSVFLFPPKPKDTL MISRTPEVTCVVVDVSHEDP EVKFNWYVDGVEVHNAKTKP REEQYNSTYRVVSVLTVLHQ DWLNGKEYKCKVSNKALGAP IEKTISKAKGQPREPQVYTL PPCRDELTKNQVSLWCLVKG FYPSDIAVEWESNGQPENNY KTTPPVLDSDGSFFLYSKLT VDKSRWQQGNVFSCSVMHEA LHNHYTQKSLSLSP | 35 |
| Human CD20 | MTTPRNSVNGTFPAEPMKGP IAMQSGPKPLFRRMSSLVGP TQSFFMRESKTLGAVQIMNG LFHIALGGLLMIPAGIYAPI CVTVWYPLWGGIMYIISGSL LAATEKNSRKCLVKGKMIMN SLSLFAAISGMILSIMDILN IKISHFLKMESLNFIRAHTP YINIYNCEPANPSEKNSPST QYCYSIQSLFLGILSVMLIF | 36 |

-continued

| | Amino Acid Sequences | |
|---|---|---|
| | Sequence | SEQ ID NO |
| | AFFQELVIAGIVENEWKRTC SRPKSNIVLLSAEEKKEQTI EIKEEVVGLTETSSQPKNEE DIEIIPIQEEEEEETETNFP EPPQDQESSPIENDSSP | |
| CD3 HCDR1 | GYTMN | 37 |
| CD3 HCDR2 | LINPYKGVSTYNQKFKD | 38 |
| CD3 HCDR3 | SGYYGDSDWYFDV | 39 |
| CD3 LCDR1 | RASQDIRNYLN | 40 |
| CD3 LCDR2 | YTSRLES | 41 |
| CD3 LCDR3 | QQGNTLPWT | 42 |
| CD3 VH | EVQLVESGGGLVQPGGSLRL SCAASGYSFTGYTMNWVRQA PGKGLEWVALINPYKGVSTY NQKFKDRFTISVDKSKNTA YLQMNSLRAEDTAVYYCARS GYYGDSDWYFDVWGQGTLVT VSS | 43 |
| CD3 VL | DIQMTQSPSSLSASVGDRVT ITCRASQDIRNYLNWYQQKP GKAPKLLIYYTSRLESGVPS RFSGSGSGTDYTLTISSLQP EDFATYYCQQGNTLPWTFGQ GTKVEIK | 44 |
| MAGE-A4 HCDR1 | KAMS | 45 |
| MAGE-A4 HCDR2 | SISPSGGSTYYNDNVLG | 46 |
| MAGE-A4 HCDR3 | DVGFFDE | 47 |
| MAGE-A4 LCDR1 | RASQSISSYLA | 48 |
| MAGE-A4 LCDR2 | DASIRDI | 49 |
| MAGE-A4 LCDR3 | QQYSSYPYT | 50 |
| MAGE-A4 VH | AQLVESGGGLVQPGGSLRLS CAASAYFSFKAMSWVRQAPG KGLEWVGSISPSGGSTYYND NVLGRFTISRDNSKNTLYLQ MNSLRAEDTAVYYCAKDVGF FDEWGQGTLVTVSS | 51 |
| MAGE-A4 VL | DIQMTQSPSSLSASVGDRVT ITCRASQSISSYLAWYQQKP GKAPKLLIYDASIRDIGVPS RFSGSGSGTDFTLTISSLQP EDFATYYCQQYSSYPYTFGQ GTKLEIK | 52 |
| MAGE-A4 VL-CL(RK) | DIQMTQSPSSLSASVGDRVT ITCRASQSISSYLAWYQQKP GKAPKLLIYDASIRDIGVPS RFSGSGSGTDFTLTISSLQP EDFATYYCQQYSSYPYTFGQ GTKLEIKRTVAAPSVFIFPP SDRKLKSGTASVVCLLNNFY PREAKVQWKVDNALQSGNSQ | 53 |

-continued

| | Amino Acid Sequences | |
|---|---|---|
| | Sequence | SEQ ID NO |
| | ESVTEQDSKDSTYSLSSTLT LSKADYEKHKVYACEVTHQG LSSPVTKSFNRGEC | |
| MAGE-A4 VH-CH1(EE)- Fc(hole, PGLALA) | AQLVFSGGGLVQPGGSLRLS CAASAYFSFKAMSWNRQAPG KGLEWVGSISPSGGSTYYND NVLGRFTISRDNSKNTLYLQ MNSLRAEDTAVYYCAKDVGF FDEWGQGTLVTVSSASTKGP SVFPLAPSSKSTSGGTAALG CLVEDYFPEPVTVSWNSGAL TSGVHTFPAVLQSSGLYSLS SVVTVPSSSLGTQTYICNVN HKPSNTKVDEKVEPKSCDKT HTCPPCPAPEAAGGPSVFLF PPKPKDTLMISRTPEVTCVV VDVSHEDPEVKFNWYVDGVE VHNAKTKPREEYNSTYRVV SVLTVLHQDWLNGKEYKCKV SNKALGAPIEKTISKAKGQP REPQVCTLPPSRDELTKNQV SLSCAVKGFYPSDIAVEWES NGQPENNYKTTPPVLDSDGS FFLVSKLTVDKSRWQQGNVF SCSVMHEALHNHYTQKSLSL SP | 54 |
| CD3 VH-CL | EVQLVESGGGLVQPGGSLRL SCAASGYSFTGYTMNWVRQA PGKGLEWVALINPYKGVSTY NQKFKDRFTISVDKSKNTAY LQMNSLRAEDTAVYYCARSG YYGDSDWYFDVWGQGTLVTV SSASVAAPSVFIFPPSDEQL KSGTASVVCLLNNFYPREAK VQWKVDNALQSGNSQESVTE QDSKDSTYSLSSTLTLSKAD YEKHKVYACEVTHQGLSSPV TKSFNRGEC | 55 |
| MAGE-A4 VH-CH1(EE)- CD3 VL-CH1- Fc(knob, PGLALA) | AQLVESGGGLVQPGGSLRLS CAASAYFSFKAMSWVRQAPG KGLEWVGSISPSGGSTYYND NVLGRFTISRDNSKNTLYLQ MNSLRAEDTAVYYCAKDVGF FDEWGQGTLVTVSSASTKGP SVFPLAPSSKSTSGGTAALG CLVEDYFPEPVTVSWNSGAL TSGVHTFPAVLQSSGLYSLS SVVTVPSSSLGTQTYICNVN HKPSNTKVDEKVEPKSCDGG GGSGGGGSDIQMTQSPSSLS ASVGDRVTITCRASQDIRNY LNWYQQKPGKAPKLLIYYTS RLESGVPSRFSGSGSGTDYT LTISSLQPEDFATYYCQQGN TLPWTFGQGTKVEIKSSAST KGPSVFPLAPSSKSTSGGTA ALGCLVKDYFPEPVTVSWNS GALTSGVHTFPAVLQSSGLY SLSSVVTVPSSSLGTQTYIC NVNHKPSNTKVDKKVEPKSC DKTHTCPPCPAPEAAGGPSV FLFPPKPKDTLMISRTPEVT CVVVDVSHEDPEVKFNWYVD GVEVHNAKTKPREEYNSTY RVVSVLTVLHQDWLNGKEYK CKVSNKALGAPIEKTISKAK GQPREPQVYTLPPCRDELTK NQVSLWCLVKGFYPSDIAVE WESNGQPENNYKTTPPVLDS DGSFFLYSKLTVDKSRWQQG | 56 |

-continued

| | Amino Acid Sequences | |
|---|---|---|
| | Sequence | SEQ ID NO |
| | NVFSCSVMHEALHNHYTQKS LSLSP | |
| Human MAGE-A4 | MSSEQKSQHCKPEEGVEAQE EALGLVGAQAPTTEEQEAAV SSSSPLVPGTLEEVPAAESA GPPQSPQGASALPTTISFTC WRQPNEGSSSQEEEGPSTSP DAESLFREALSNKVDELAHF LLRKYRAKELVTKAEMLERV IKNYKRCFPVIFGKASESLK MIFGIDVKEVDPASNTYTLV TCLGLSYDGLLGNNQIFPKT GLLIIVLGTIAMEGDSASEE EIWEELGVMGVYDGREHTVY GEPRKLLTQDWVQENYLEYR QVPGSNPARYEFLWGPRALA ETSYVKVLEHVVRVNARVRI AYPSLREAALLEEEEGV | 57 |
| p230-239 peptide | GVYDGREHTV | 58 |
| HLA-A2 | GSHSMRYFFTSVSRPGRGEP RFIAVGYVDDTQFVRFDSDA ASQRMEPRAPWIEQEGPEYW DGETRKVKAHSQTHRVDLGT LRGYYNQSEAGSHTVQRMYG CDVGSDWRFLRGYHQYAYDG KDYIALKEDLRSWTAADMAA QTTKHKWEAAHVAEQLRAYL EGTCVEWLRRYLENGKETLQ RTDAPKTHMTHHAVSDHEAT LRCWALSFYPAEITLTWQRD GEDQTQDTELVETRPAGDGT FQKWAAVVVPSGQEQRYTCH VQHEGLPKPLTLRWE | 59 |
| Human CD19 | MPPPRLLFFLLFLTPMEVRP EEPLVVKVEEGDNAVLQCLK GTSDGPTQQLTWSRESPLKP FLKLSLGLPGLGIHMRPLAI WLFIFNVSQQMGGFYLCQPG PPSEKAWQPGWTVNVEGSGE LFRWNVSDLGGLGCGLKNRS SEGPSSPSGKLMSPKLYVWA KDRPEIWEGEPPCLPPRDSL NQSLSQDLTMAPGSTLWLSC GVPPDSVSRGPLSWTHVHPK GPKSLLSLELKDDRPARDMW VMETGLLLPRATAQDAGKYY CHRGNLTMSFHLEITARPVL WHWLLRTGGWKVSAVTLAYL IFCLCSLVGILHLQRALVLR RKRKRMTDPTRRFFKVTPPP GSGPQNQYGNVLSLPTPTSG LGRAQRWAAGLGGTAPSYGN PSSDVQADGALGSRSPPGVG PEEEEGEGYEEPDSEEDSEF YENDSNLGQDQLSQDGSGYE NPEDEPLGPEDEDSFSNAES YENEDEELTQPVARTMDFLS PHGSAWDPSREATSLGSQSY EDMRGILYAAPQLRSIRGQP GPNHEEDADSYENMDNPDGP DPAWGGGGRMGTWSTR | 60 |
| CD3 HCDR1 | SYAMN | 61 |
| CD3 HCDR3 | HTTFPSSYVSYYGY | 62 |
| CD3 VH | EVQLLESGGGLVQPGGSLRL SCAASGFQFSSYAMNWVRQA | 63 |

-continued

| | Amino Acid Sequences | |
|---|---|---|
| | Sequence | SEQ ID NO |
| | PGKGLEWVSRIRSKYNNYAT YYADSVKGRFTISRDDSKNT LYLQMNSLRAEDTAVYYCVR HTTFPSSYVSYYGYWGQGTL VTVSS | |
| CD3 HCDR1 | SYAMN | 64 |
| CD3 HCDR3 | ASNFPASYVSYFAY | 65 |
| CD3 VH | EVQLLESGGGLVQPGGSLRL SCAASGFTFSSYAMNWVRQA PGKGLEWVSRIRSKYNNYAT YYADSVKGRFTISRDDSKNT LYLQMNSLRAEDTAVYYCVR ASNFPASYVSYFAYWGQGTL VTVSS | 66 |
| CD19 HCDR1 | DYIMH | 67 |
| CD19 HCDR2 | YINPYNDGSKYTEKFQG | 68 |
| CD19 HCDR3 | GTYYYGPQLFDY | 69 |
| CD19 LCDR1 | KSSQSLETSTGTTYLN | 70 |
| CD19 LCDR2 | RVSKRFS | 71 |
| CD19 LCDR3 | LQLLEDPYT | 72 |
| CD19 VH | QVQLVQSGAEVKKPGASVKV SCKASGYTFTDYIMHWVRQA PGQGLEWMGYINPYNDGSKY TEKFQGRVTMTSDTSISTAY MELSRLRSDDTAVYYCARGT YYYGPQLFDYWGQGTTVTVS S | 73 |
| CD19VL | DIVMTQTPLSLSVTPGQPAS ISCKSSQSLETSTGTTYLNW YLQKPGQSPQLLIYRVSKRF SGVPDRFSGSGSGTDFTLKI SRVEAEDVGVYYCLQLLEDP YTFGQGTKLEIK | 74 |
| CD19 VH-CH1(EE)-CD3 VL-CH1-Fc (knob, PGLALA) | QVQLVQSGAEVKKPGASVKV SCKASGYTFTDYIMHWVRQA PGQGLEWMGYINPYNDGSKY TEKFQGRVTMTSDTSISTAY MELSRLRSDDTAVYYCARGT YYYGPQLFDYWGQGTTVTVS SASTKGPSVFPLAPSSKSTS GGTAALGCLVEDYFPEPVTV SWNSGALTSGVHTFPAVLQS SGLYSLSSVVTVPSSSLGTQ TYICNVNHKPSNTKVDEKVE PKSCDGGGSGGGGSQAVVT QEPSLTVSGGTVTLTCGSS TGAVTTSNYANWVQEKPGQA FRGLIGGTNKRAPGTPARFS GSLLGGKAALTLSGAQPEDE AEYYCALWYSNLWVFGGGTK LTVLSSASTKGPSVFPLAPS SKSTSGGTAALGCLVKDYFP EPVTVSWNSGALTSGVHTFP AVLQSSGLYSLSSVVTVPSS SLGTQTYICNVNHKPSNTKV DKKVEPKSCDKTHTCPPCPA PEAAGGPSVFLFPPKPKDTL MISRTPEVTCVVVDVSHEDP EVKFNWYVDGVEVHNAKTKP REEQYNSTYRVVSVLTVLHQ DWLNGKEYKCKVSNKALGAP | 75 |

-continued        -continued

| | Amino Acid Sequences | |
|---|---|---|
| | Sequence | SEQ ID NO |
| | IEKTISKAKGQPREPQVYTL PPCRDELTKNQVSLWCLVKG FYPSDIAVEWESNGQPENNY KTTPPVLDSDGSFFLYSKLT VDKSRWQQGNVFSCSVMHEA LHNHYTQKSLSLSP | |
| CD19VH-CH1(EE)-CD3 VL-CH1-Fc (knob, PGLALA) | QVQLVQSGAEVKKPGASVKV SCKASGYTFTDYIMHWVRQA PGQGLEWMGYINPYNDGSKY TEKFQGRVTMTSDTSISTAY MELSRLRSDDTAVYYCARGT YYYGPQLFDYWGQGTTVTVS SASTKGPSVFPLAPSSKSTS GGTAALGCLVEDYFPEPVTV SWNSGALTSGVHTFPAVLQS SGLYSLSSVVTVPSSSLGTQ TYICNVNHKPSNTKVDEKV EPKSCDGGGGSGGGGGQAV VTQEPSLTVSPGGTVTLTCG SSTGAVTTSNYANWVQEKPG QAFRGLIGGTNKRAPGTPAR FSGSLLGGKAALTLSGAQPE DEAEYYCALWYSNLWVFGGG TKLTVLSSASTKGPSVFPLA PSSKSTSGGTAALGCLVKDY FPEPVTVSWNSGALTSGVHT FPAVLQSSGLYSLSSVVTVP SSSLGTQTYICNVNHKPSNT KVDKKVEPKSCDKTHTCPPC PAPEAAGGPSVFLFPPKPKD TLMISRTPEVTCVVVDVSHE DPEVKFNWYVDGVEVHNAKT KPREEQYNSTYRVVSVLTVL HQDWLNGKEYKCKVSNKALG APIEKTISKAKGQPREPQVY TLPPCRDELTKNQVSLWCLV KGFYPSDIAVEWESNGQPEN NYKTTPPVLDSDGSFFLYSK LTVDKSRWQQGNVFSCSVMH EALHNHYTQKSLSLSP | 76 |
| CD19 VH-CH1(EE)-Fc (hole, PGLALA) | QVQLVQSGAEVKKPGASVKV SCKASGYTFTDYIMHWVRQA PGQGLEWMGYINPYNDGSKY TEKFQGRVTMTSDTSISTAY MELSRLRSDDTAVYYCARGT YYYGPQLFDYWGQGTTVTVS SASTKGPSVFPLAPSSKSTS GGTAALGCLVEDYFPEPVTV SWNSGALTSGVHTFPAVLQS SGLYSLSSVVTVPSSSLGTQ TYICNVNHKPSNTKVDEKVE PKSCDKTHTCPPCPAPEAAG GPSVFLFPPKPKDTLMISRT PEVTCVVVDVSHEDPEVKFN WYVDGVEVHNAKTKPREEQY NSTYRVVSVLTVLHQDWLNG KEYKCKVSNKALGAPIEKTI SKAKGQPREPQVCTLPPSRD ELTKNQVSLSCAVKGFYPSD IAVEWESNGQPENNYKTTPP VLDSDGSFFLVSKLTVDKSR WQQGNVFSCSVMHEALHNHY TQKSLSLSP | 77 |
| CD19 VL-CL(RK) | DIVMTQTPLSLSVTPGQPAS ISCKSSQSLETSTGTTYLNW YLQKPGQSPQLLIYRVSKRF SGVPDRFSGSGSGTDFTLKI SRVEAEDVGVYYCLQLLEDP YTFGQGTKLEIKRTVAAPSV FIFPPSDRKLKSGTASVVCL | 78 |

| | Amino Acid Sequences | |
|---|---|---|
| | Sequence | SEQ ID NO |
| | LNNFYPREAKVQWKVDNALQ SGNSQESVTEQDSKDSTYSL SSTLTLSKADYEKHKVYACE VTHQGLSSPVTKSFNRGEC | |
| CD3 VH-CL | EVQLLESGGGLVQPGGSLRL SCAASGFQFSSYAMNWVRQA PGKGLEWVSRIRSKYNNYAT YYADSVKGRFTISRDDSKNT LYLQMNSLRAEDTAVYYCVR HTTFPSSYVSYYGYWGQGTL VTVSSASVAAPSVFIFPPSD EQLKSGTASVVCLLNNFYPR EAKVQWKVDNALQSGNSQES VTEQDSKDSTYSLSSTLTLS KADYEKHKVYACEVTHQGLS SPVTKSFNRGEC | 79 |
| CD3 VH-CL | EVQLLESGGGLVQPGGSLRL SCAASGFTFSSYAMNWVRQA PGKGLEWVSRIRSKYNNYAT YYADSVKGRFTFSRDDSKNT LYLQMNSLRAEDTAVYYCVR ASNFPASYVSYFAYWGQGTL VTVSSASVAAPSVFIFPPSD EQLKSGTASVVCLLNNFYPR EAKVQWKVDNALQSGNSQES VTEQDSKDSTTSLSSTLTLS KADYEKHKVYACEVTHQGLS SPVTKSFNRGEC | 80 |

BRIEF DESCRIPTION OF THE DRAWINGS

FIG. 4. Effect of escalating concentrations of everolimus (A), sirolimus (B) and temsirolimus (C) on PBMC viability at 72 h in the assay described in FIG. 1. Technical replicates were pooled and viability of PBMCs was measured by flow cytometry using a Live/Dead™ Fixable Aqua Dead Cell Stain. 1 representative donor.

Figure 6:
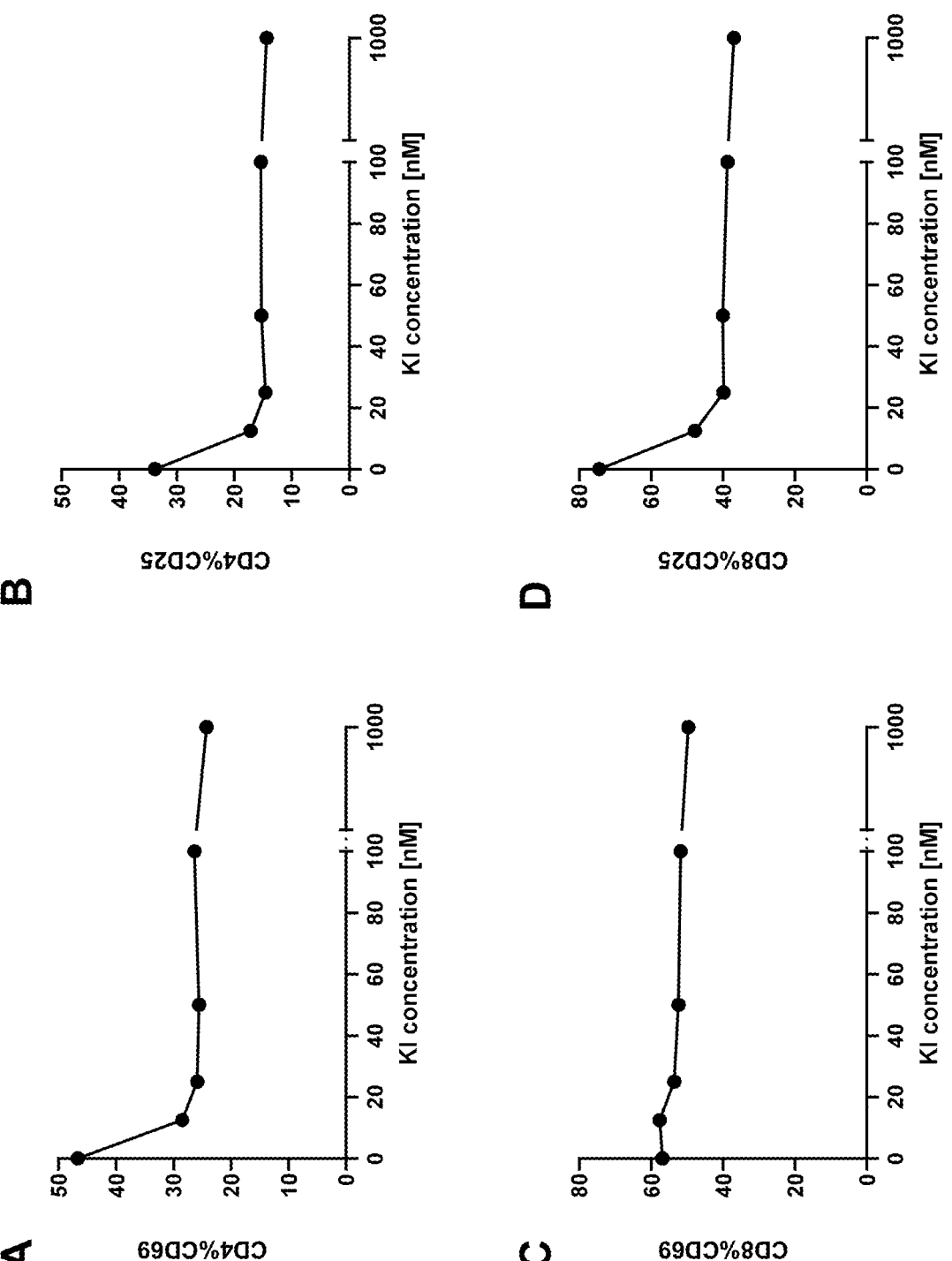

FIG. 6. Effect of escalating concentrations of sirolimus on CD69 expression on CD4+(A) and CD8+(C) T cells and on CD25 expression on CD4+(B) and CD8+(D) T cells at 72 h after treatment with 10 nM CEA-TCB in the assay of FIG. 1. Technical replicates were pooled and expression of CD69 and CD25 on CD4+ and CD8+ T cells was measured by flow cytometry at 72 h. 1 representative donor.

Figure 7:
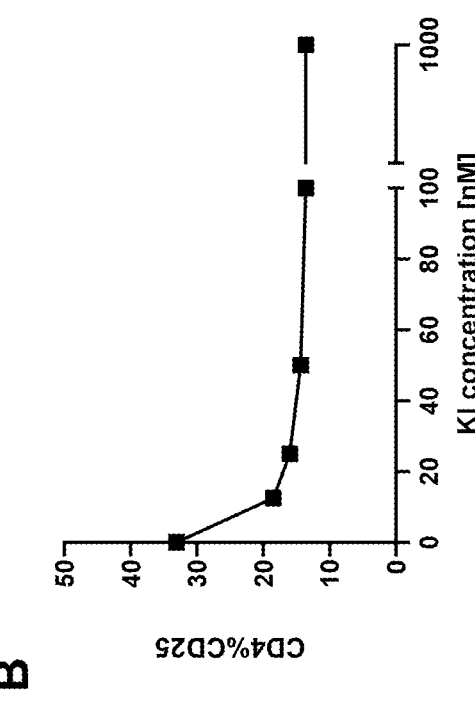
Figure 7:
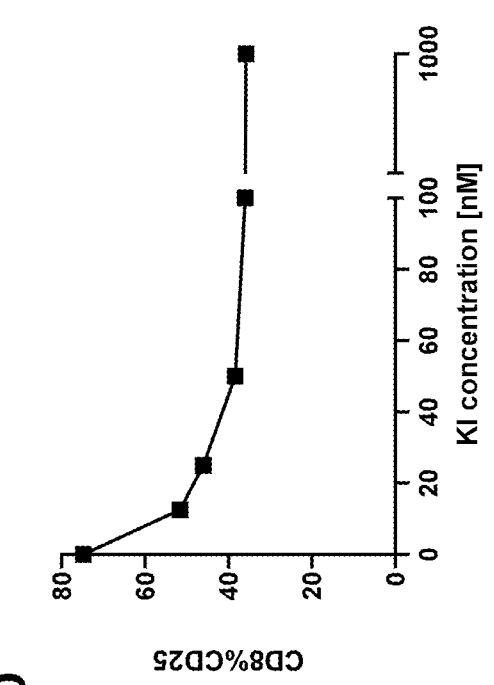
Figure 7:
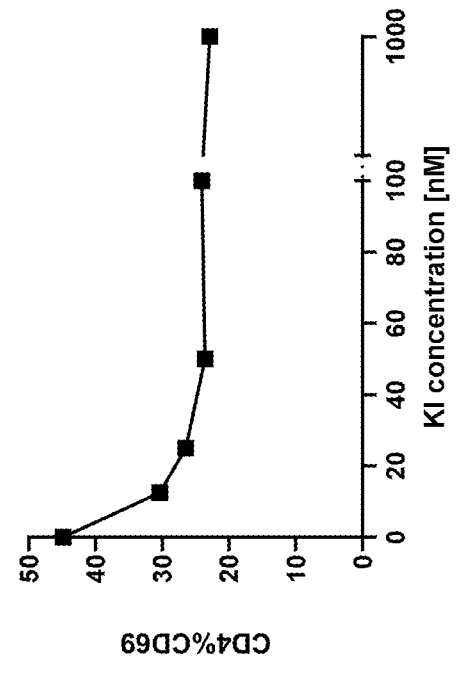
Figure 7:
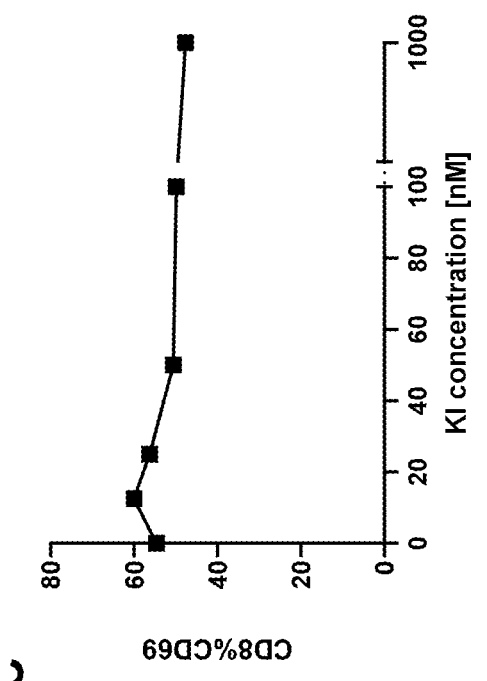

FIG. 7. Effect of escalating concentrations of temsirolimus on CD69 expression on CD4+(A) and CD8+(C) T cells and on CD25 expression on CD4+(B) and CD8+(D) T cells at 72 h after treatment with 10 nM CEA-TCB in the assay of FIG. 1. Technical replicates were pooled and expression of CD69 and CD25 on CD4+ and CD8+ T cells was measured by flow cytometry at 72 h. 1 representative donor.

Figure 8:
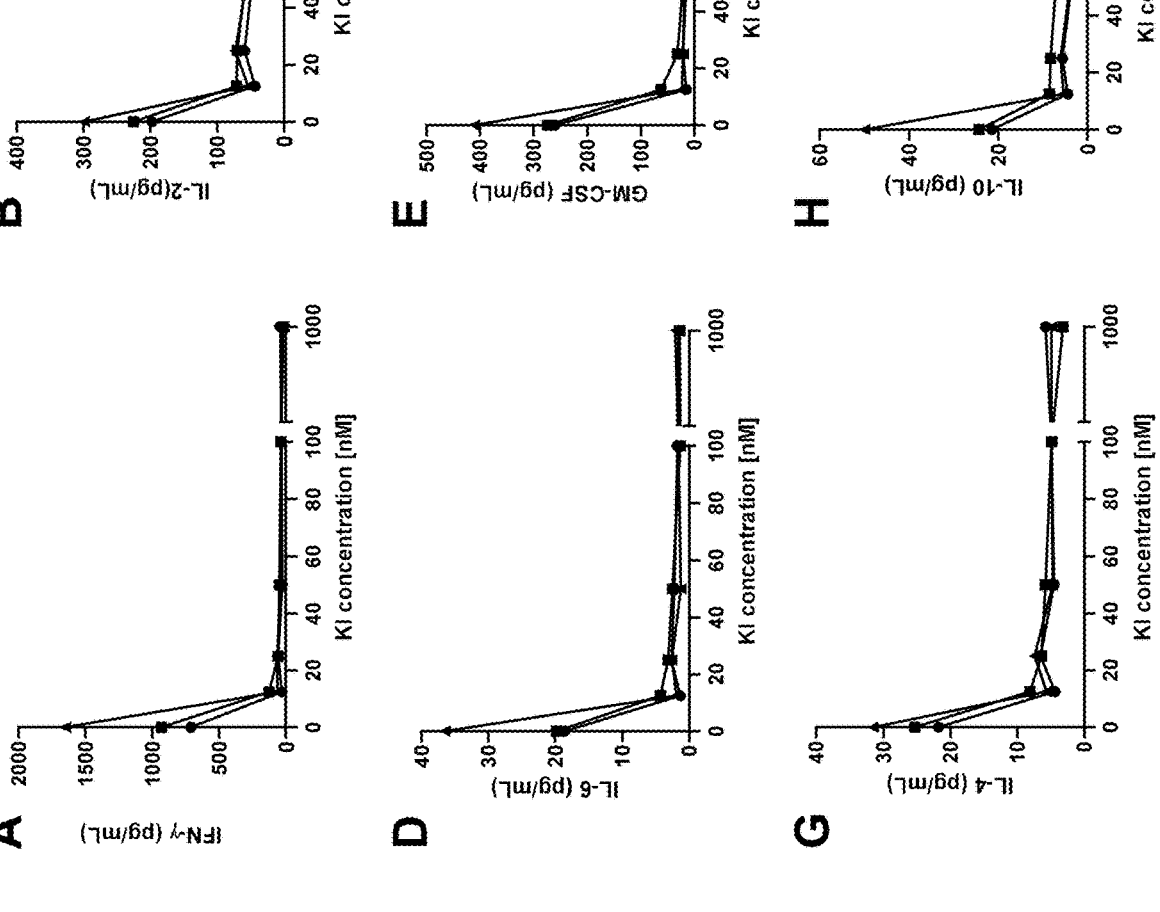

FIG. 8. Effect of escalating concentrations of sirolimus, everolimus, and temsirolimus on cytokine release (IFN-$\gamma$ (A), IL-2 (B), TNF-$\alpha$ (C), IL-6 (D), GM-CSF (E), IL-8 (F), IL-4 (G), IL-10 (H), MCP-1 (I)) measured at 72 h after treatment with 10 nM CEA-TCB in the assay of FIG. 1. Supernatants from technical replicates were pooled and cytokines were analyzed by Luminex. 1 representative donor.

Figure 9:
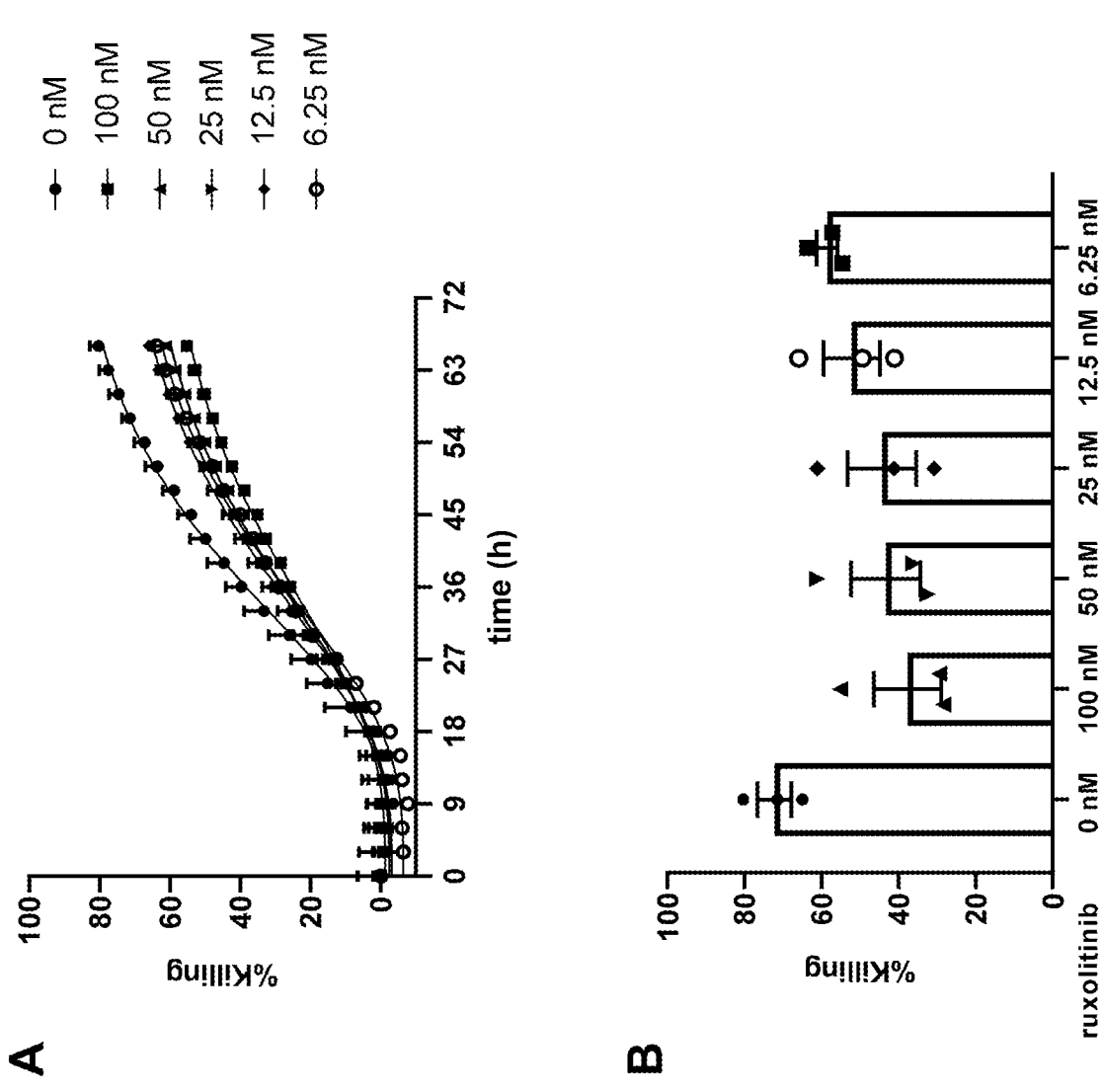

FIG. 9. (A) Real-time killing of MKN45 NLR cells by 10 nM CEA-TCB in the presence of ruxolitinib concentrations ranging from 0 nM to 100 nM in the assay of FIG. 1. (B) Effect of escalating concentrations of ruxolitinib on target cell killing measured at 69 h after treatment with 10 nM CEA-TCB in the assay of FIG. 1. % Killing was measured by normalizing total red area with values at t=0 hour and target cells+PBMCs+ruxolitinib control wells for each time point. Means of technical replicates+SEM for one representative donor (A). Mean of n=3 donors+/−SD.

Figure 10:
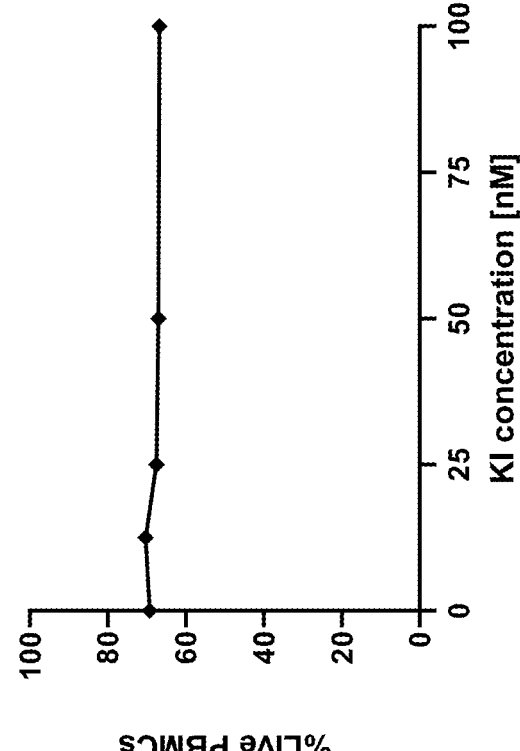

FIG. 10. Effect of escalating concentrations of ruxolitinib on PBMC viability at 69 h in the assay of FIG. 1. Technical replicates were pooled and viability of PBMCs was measured by flow cytometry using a Live/Dead™ Fixable Aqua Dead Cell Stain. 1 representative donor.

Figure 11:
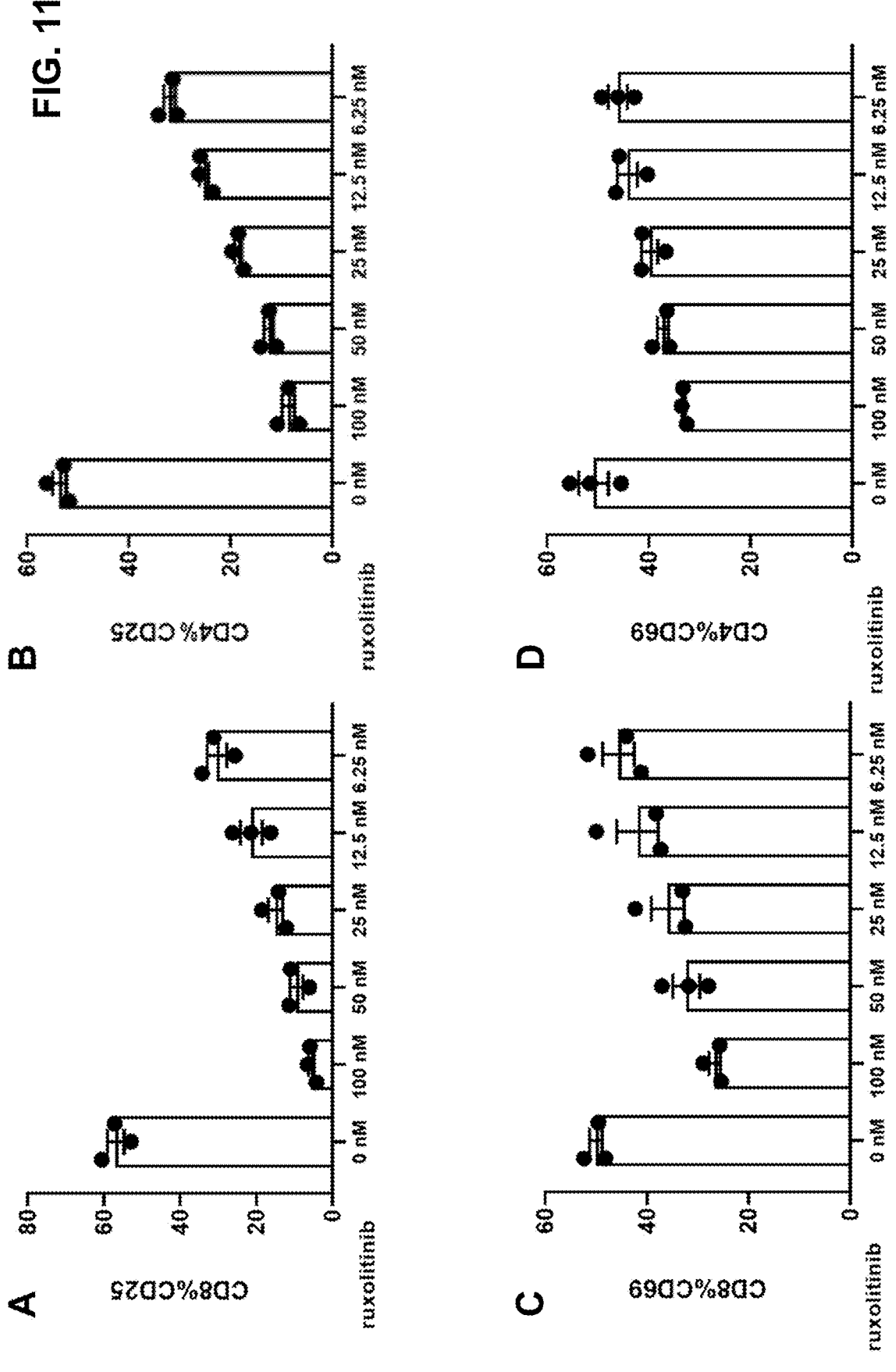

FIG. 11. Effect of escalating concentrations of ruxolitinib on CD25 expression on CD8+(A) and CD4+(B) T cells and on CD69 expression on CD8+(C) and CD4+(D) T cells at 69 h, after treatment with 10 nM CEA-TCB in the assay of FIG. 1. Technical replicates were pooled and the expression of CD25 and CD69 on CD4+ and CD8+ T cells was measured by flow cytometry at 69 h. Mean of n=3 donors+/−SD.

Figure 12:
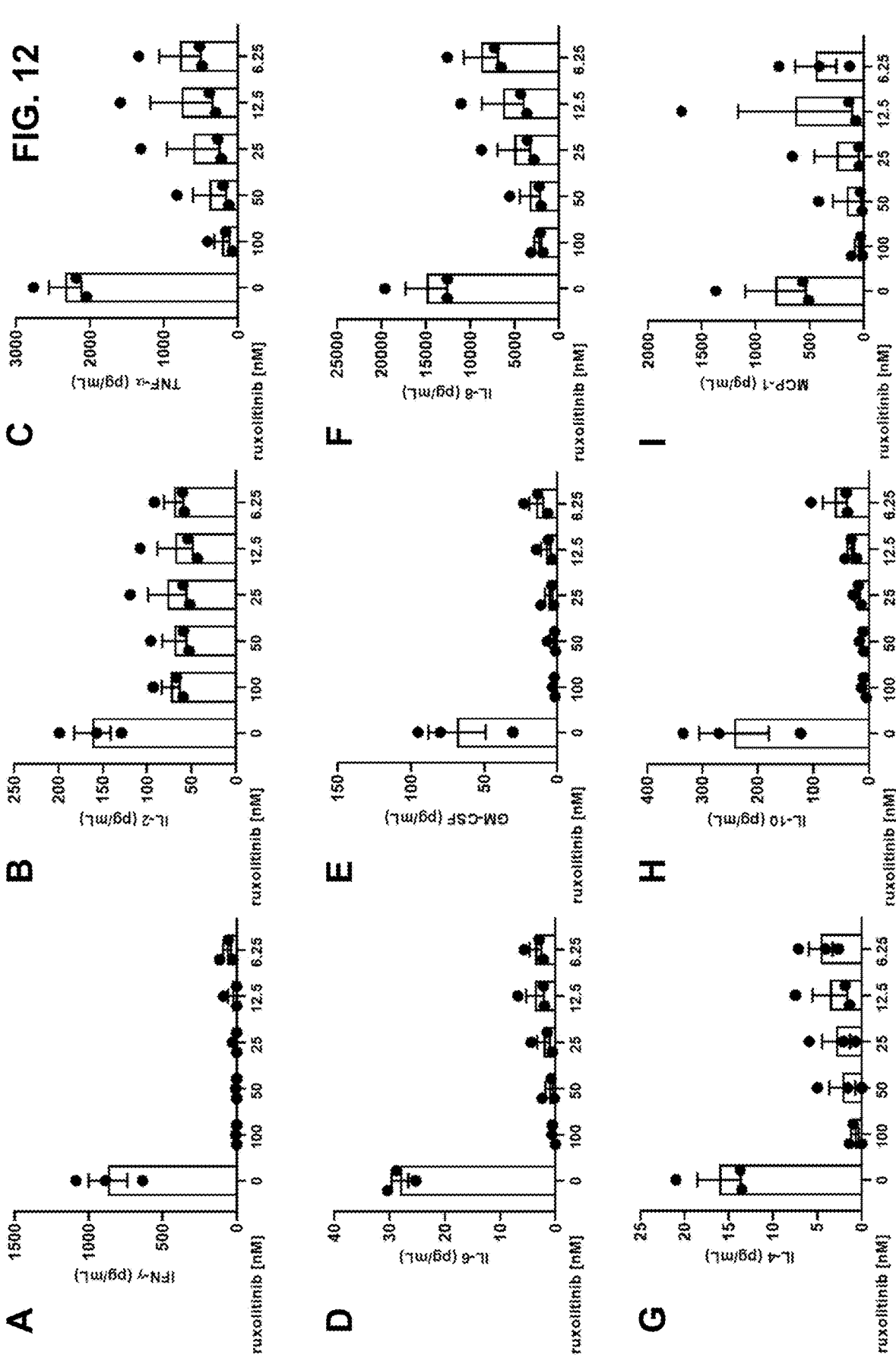

FIG. 12. Effect of escalating concentrations of ruxolitinib on cytokine release (IFN-$\gamma$ (A), IL-2 (B), TNF-$\alpha$ (C), IL-6 (D), GM-CSF (E), IL-8 (F), IL-4 (G), IL-10 (H), MCP-1 (I)) induced by 10 nM CEA-TCB at 69 h in the assay of FIG. 1. Supernatants from technical replicates were pooled at 69 h and cytokines were analyzed by Luminex. Mean of n=3 donors+/−SD.

Figure 13:
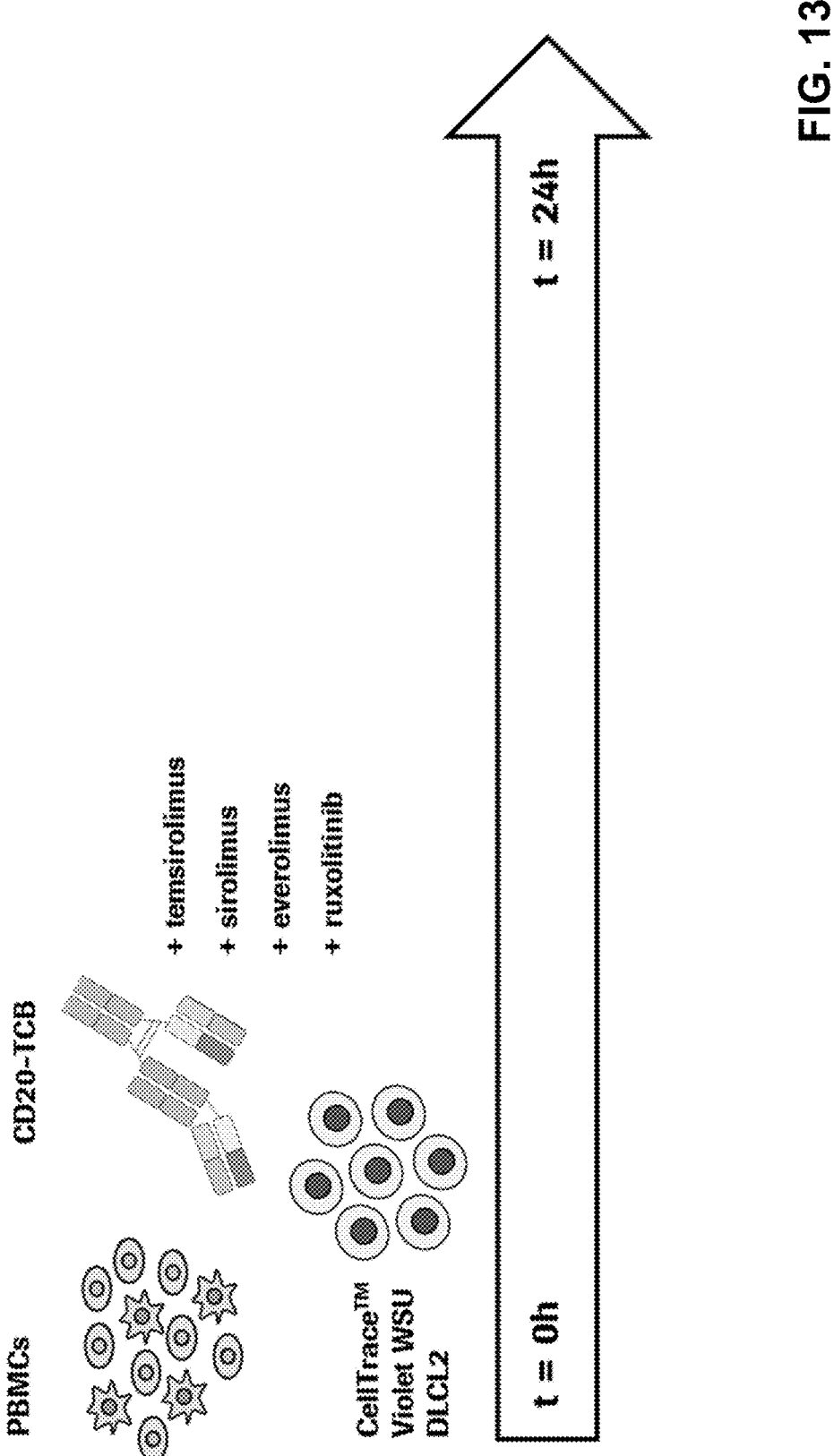

FIG. 13. In vitro killing assay set-up. Cell Trace™ Violet (CTV) labelled WSU DLCL2 tumor cells were co-cultured together with PBMCs [E:T=200'000:20'000], CD20-TCB and in the presence of escalating doses of ruxolitinib, temsirolimus, sirolimus and everolimus ranging from 0 nM to 1000 nM.

Figure 14:
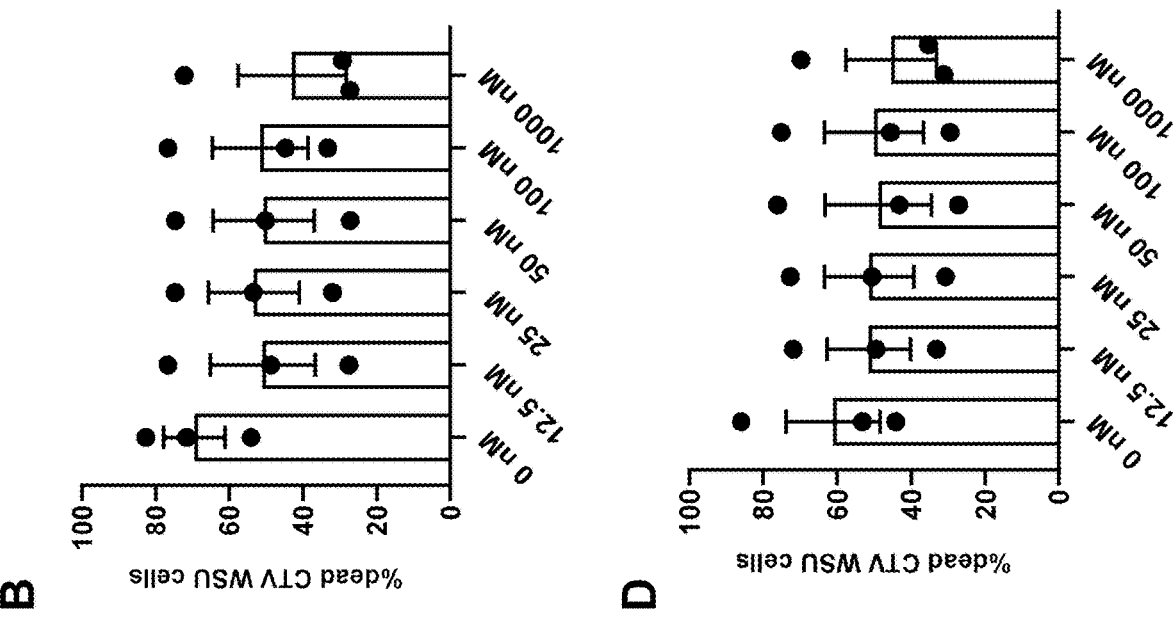
Figure 14:
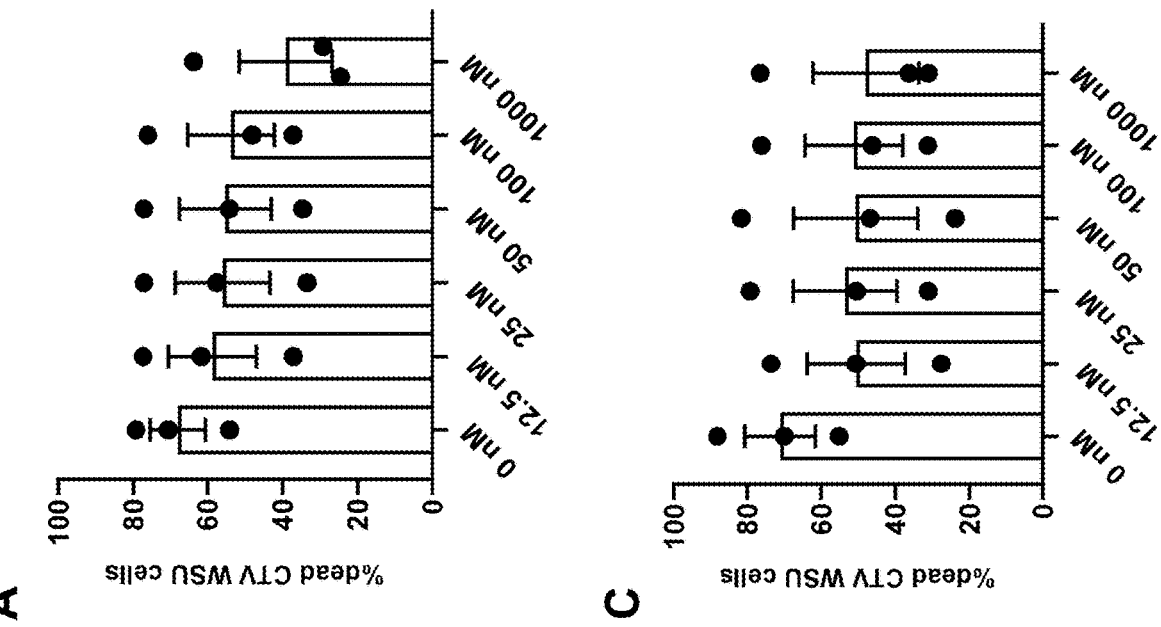

FIG. 14. Effect of escalating concentrations of ruxolitinib (A), temsirolimus (B), sirolimus (C) and everolimus (D) on CTV WSU DLCL2 tumor cell killing in the assay of FIG. 13 for 1 nM CD20-TCB. At 24 hours, the tumor cells and PBMCs from technical replicates were pooled and stained with a LIVE/DEAD™ Near-IR dead cell dye to allow exclusion of dead CTV labelled WSU DLCL2 tumor cells by flow cytometry. Mean of n=3 donors+/−SEM.

Figure 15:
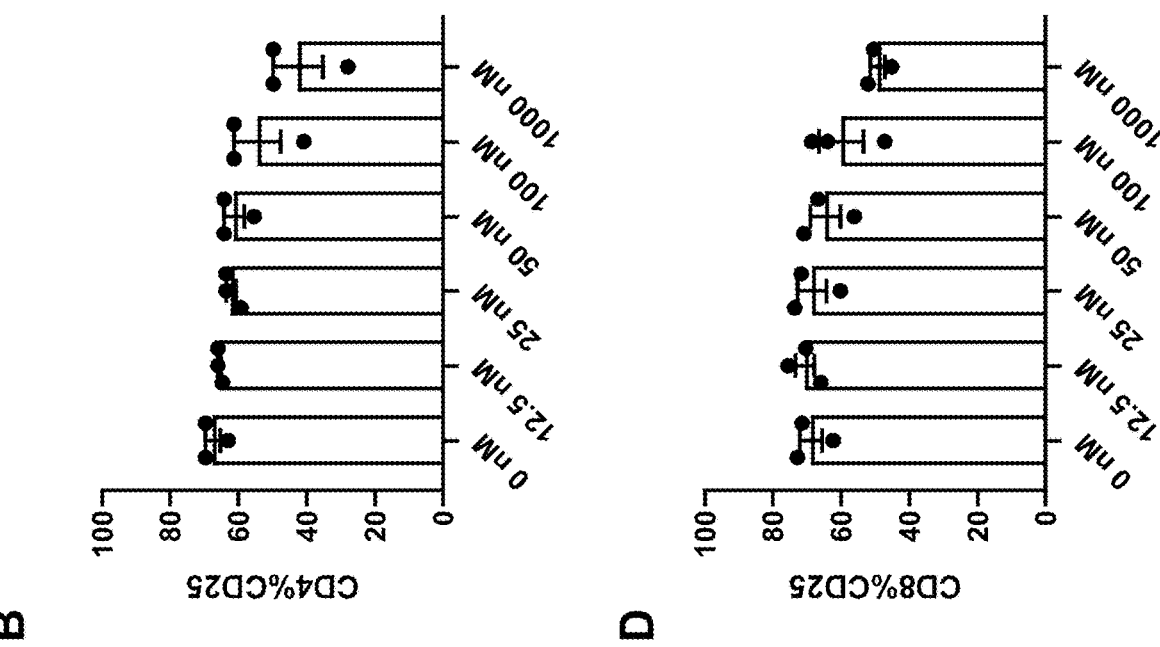
Figure 15:
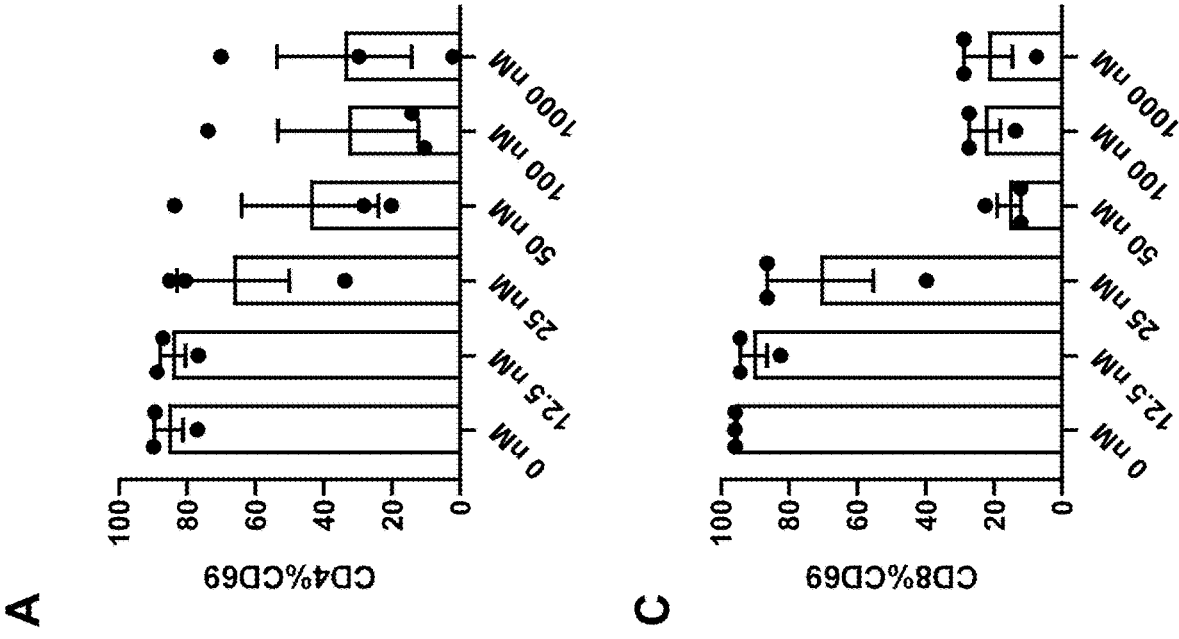

FIG. 15. Effect of escalating concentrations of ruxolitinib on CD25 expression on CD4+(B) and CD8+(D) T cells as well as CD69 expression on CD4+(A) and CD8+(C) T cells in the assay of FIG. 13 for 1 nM CD20-TCB. At 24 hours, the tumor cells and PBMCs from technical replicates were pooled and expression of CD69 and CD25 on CD4+ and CD8+ T cells was measured by flow cytometry. Mean of n=3 donors+/−SEM.

Figure 16:
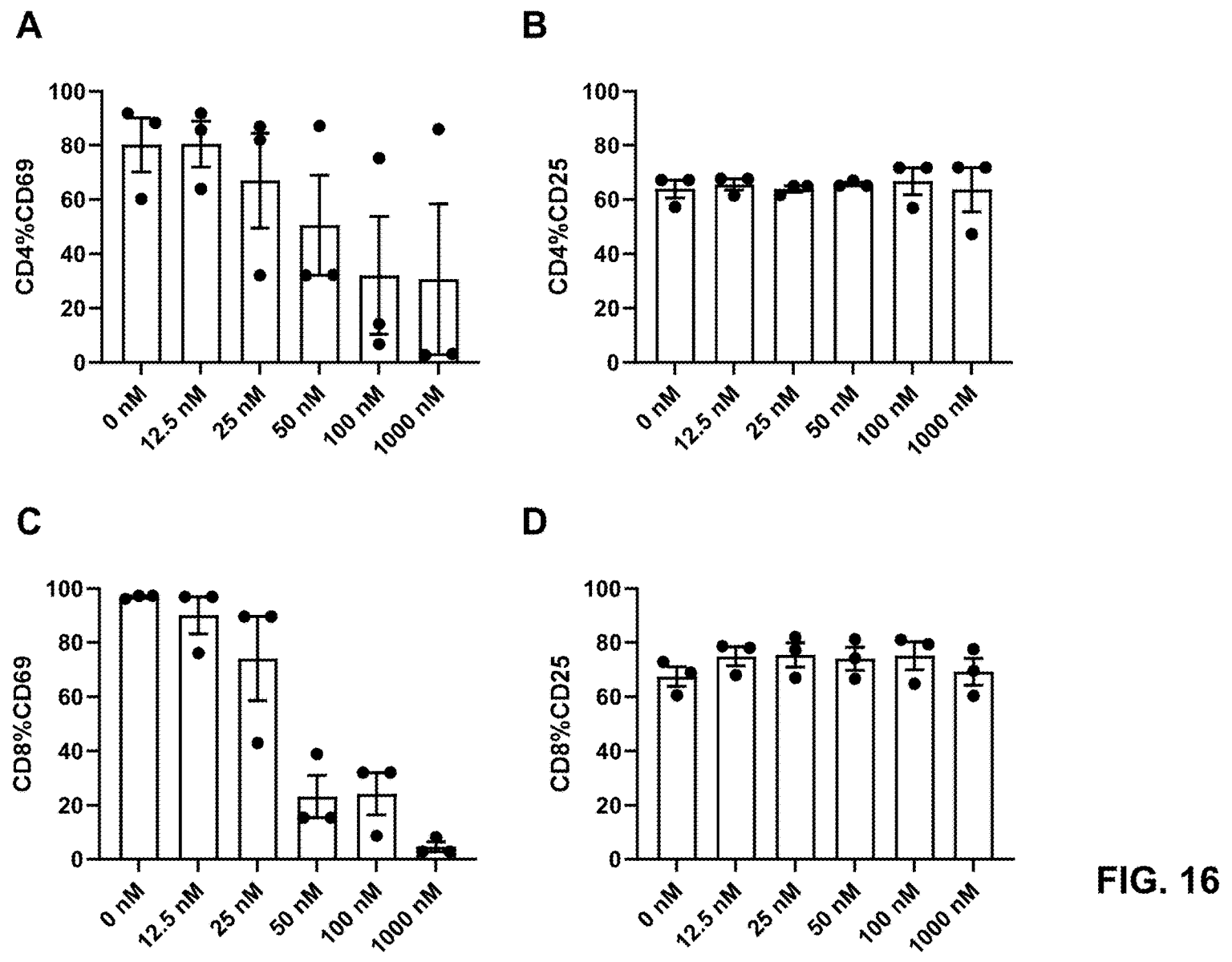

FIG. 16. Effect of escalating concentrations of temsirolimus on CD25 expression on CD4+(B) and CD8+(D) T cells as well as CD69 expression on CD4+(A) and CD8+(C) T cells in the assay of FIG. 13 for 1 nM CD20-TCB. At 24 hours, the tumor cells and PBMCs from technical replicates were pooled and expression of CD69 and CD25 on CD4+ and CD8+ T cells was measured by flow cytometry. Mean of n=3 donors+/−SEM.

Figure 17:
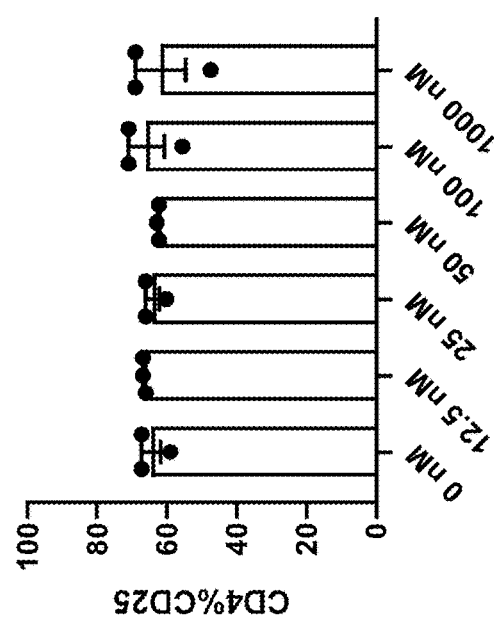
Figure 17:
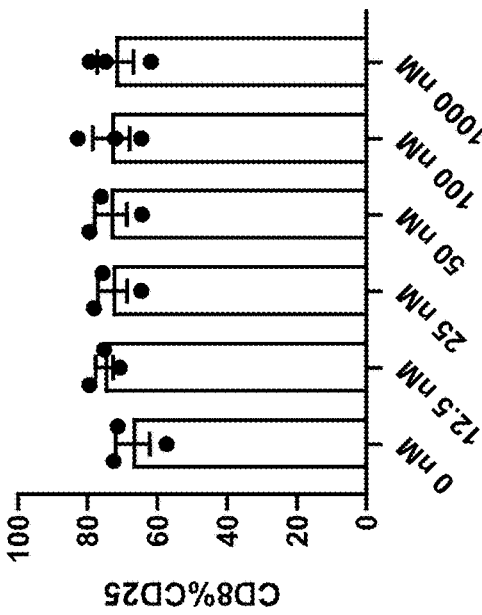
Figure 17:
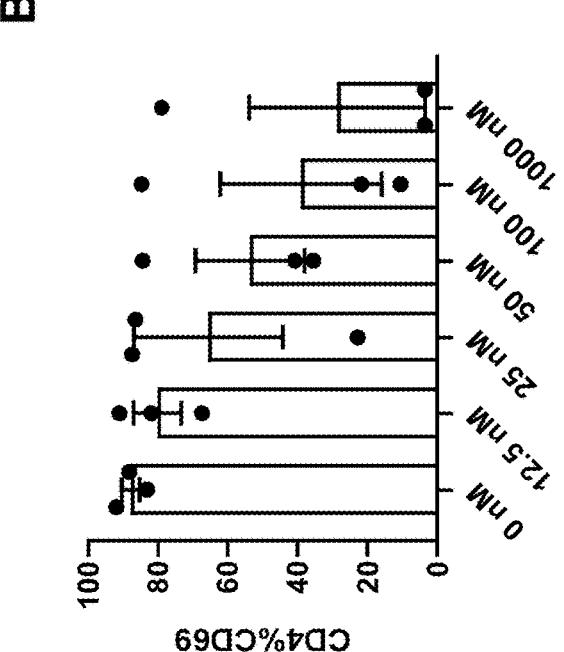
Figure 17:
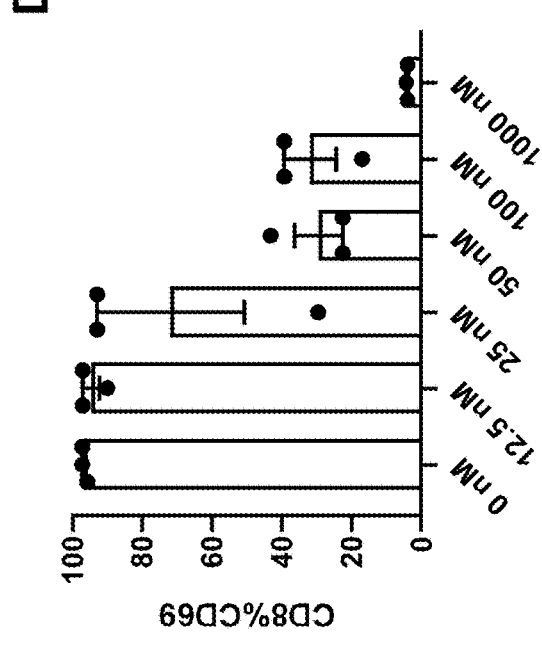

FIG. 17. Effect of escalating concentrations of sirolimus on CD25 expression on CD4+(B) and CD8+(D) T cells as well as CD69 expression on CD4+(A) and CD8+(C) T cells in the assay of FIG. 13 for 1 nM CD20-TCB. At 24 hours, the tumor cells and PBMCs from technical replicates were pooled and expression of CD69 and CD25 on CD4+ and CD8+ T cells was measured by flow cytometry. Mean of n=3 donors+/−SEM.

Figure 18:
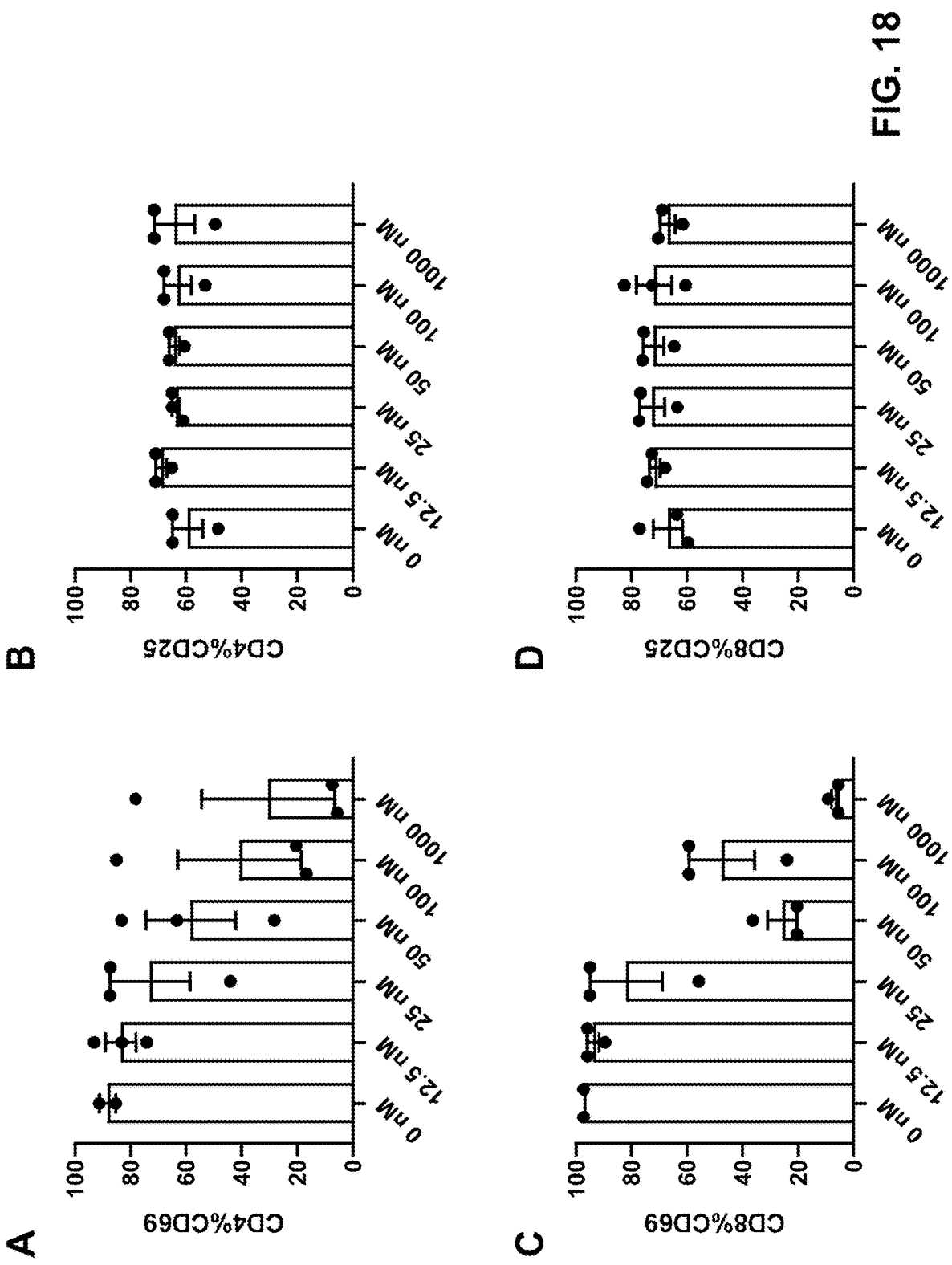

FIG. 18. Effect of escalating concentrations of everolimus on CD25 expression on CD4+(B) and CD8+(D) T cells as well as CD69 expression on CD4+(A) and CD8+(C) T cells in the assay of FIG. 13 for 1 nM CD20-TCB. At 24 hours, the tumor cells and PBMCs from technical replicates were pooled and expression of CD69 and CD25 on CD4+ and CD8+ T cells was measured by flow cytometry. Mean of n=3 donors+/−SEM.

Figure 19:
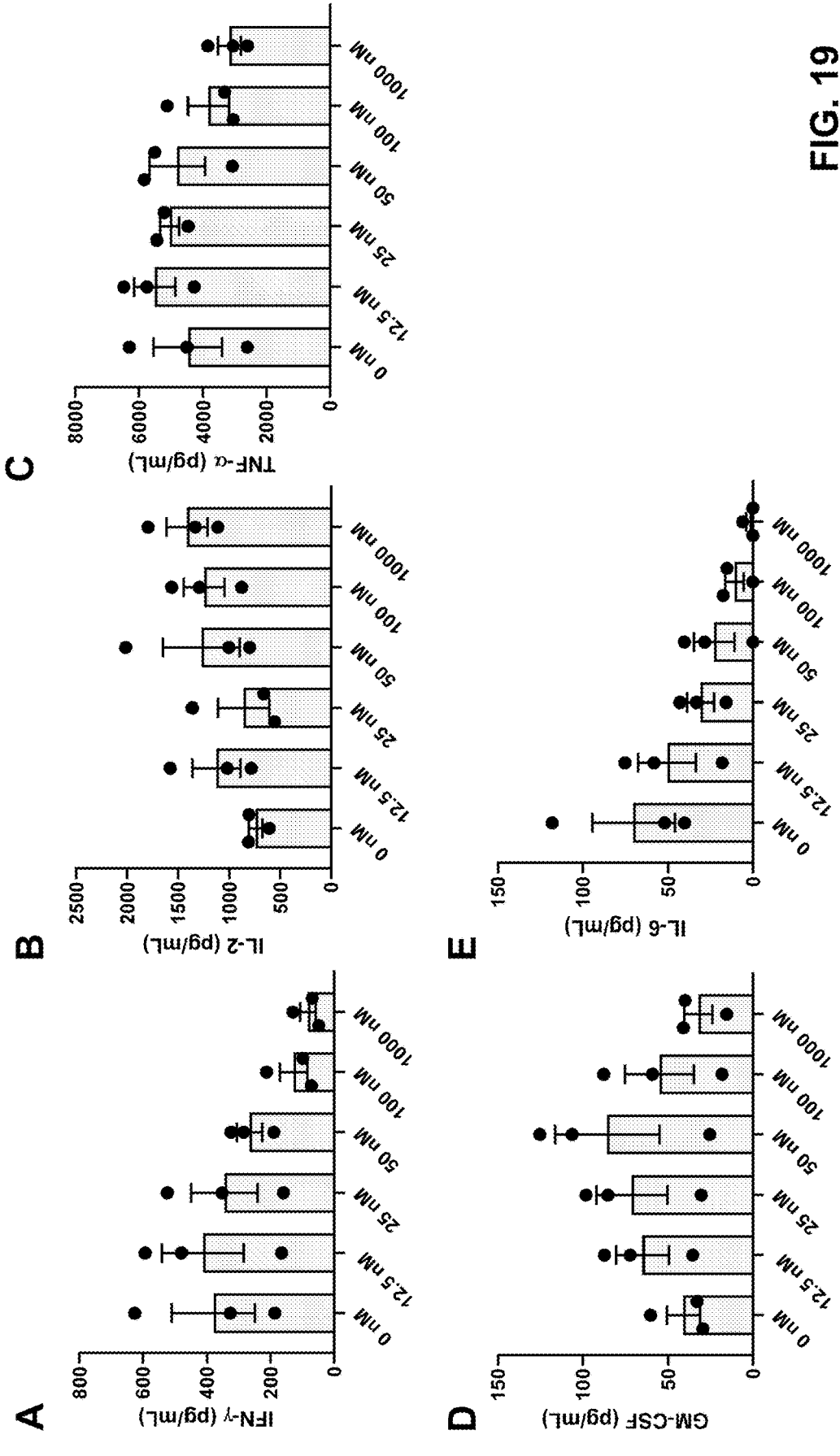

FIG. 19. Effect of escalating concentrations of ruxolitinib on IFN-$\gamma$ (A), IL-2 (B), TNF-$\alpha$ (C), GM-CSF (D) and IL-6 (E) release in the assay of FIG. 13 for 1 nM CD20-TCB. At 24 hours, the supernatants from technical replicates were pooled and cytokines were analyzed by Luminex. Mean of n=3 donors+/−SEM.

Figure 20:
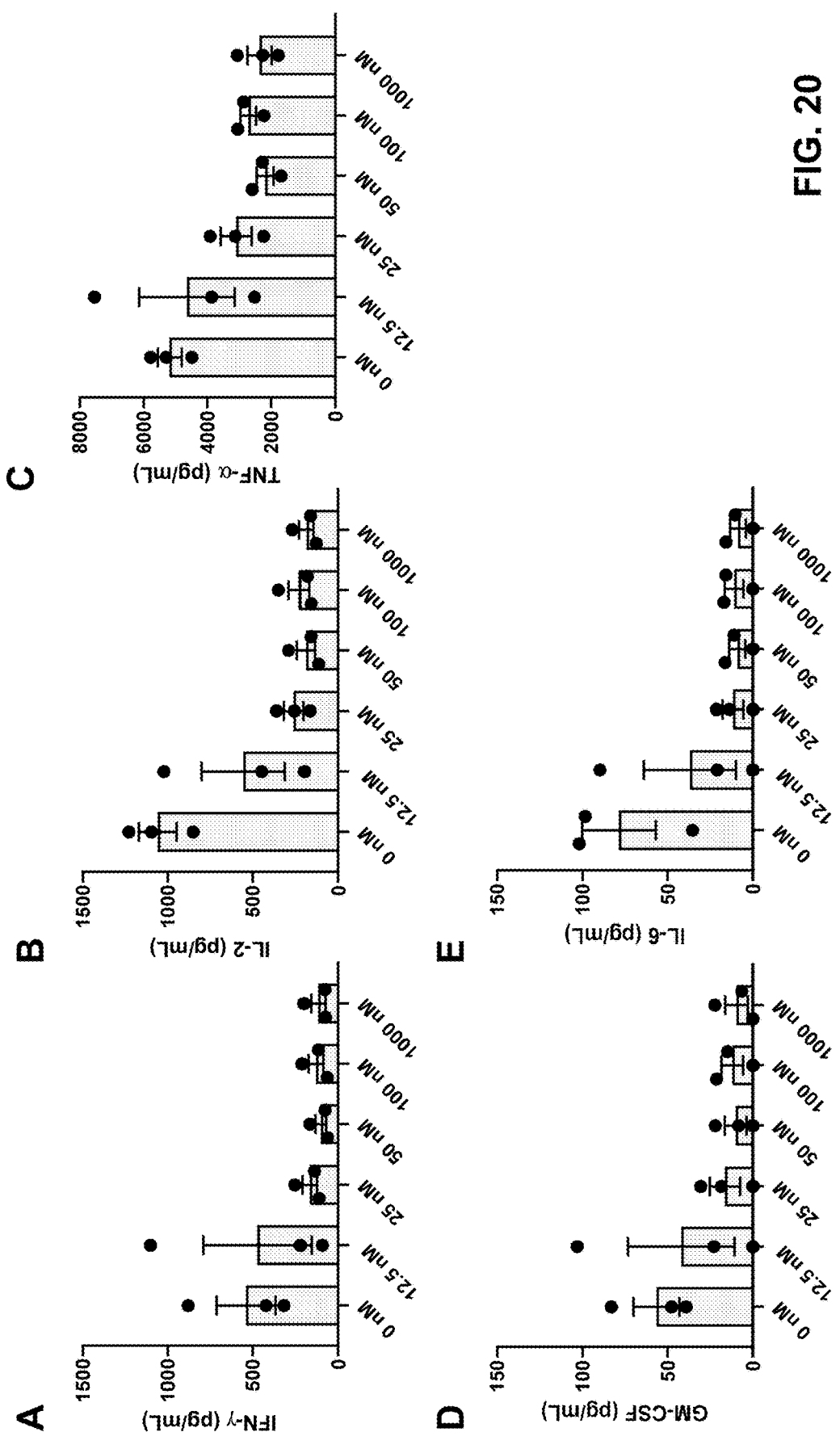

FIG. 20. Effect of escalating concentrations of temsirolimus on IFN-$\gamma$ (A), IL-2 (B), TNF-$\alpha$ (C), GM-CSF (D) and IL-6 (E) release in the assay of FIG. 13 for 1 nM CD20-TCB. At 24 hours, the supernatants from technical replicates were pooled and cytokines were analyzed by Luminex. Mean of n=3 donors+/−SEM.

Figure 21:
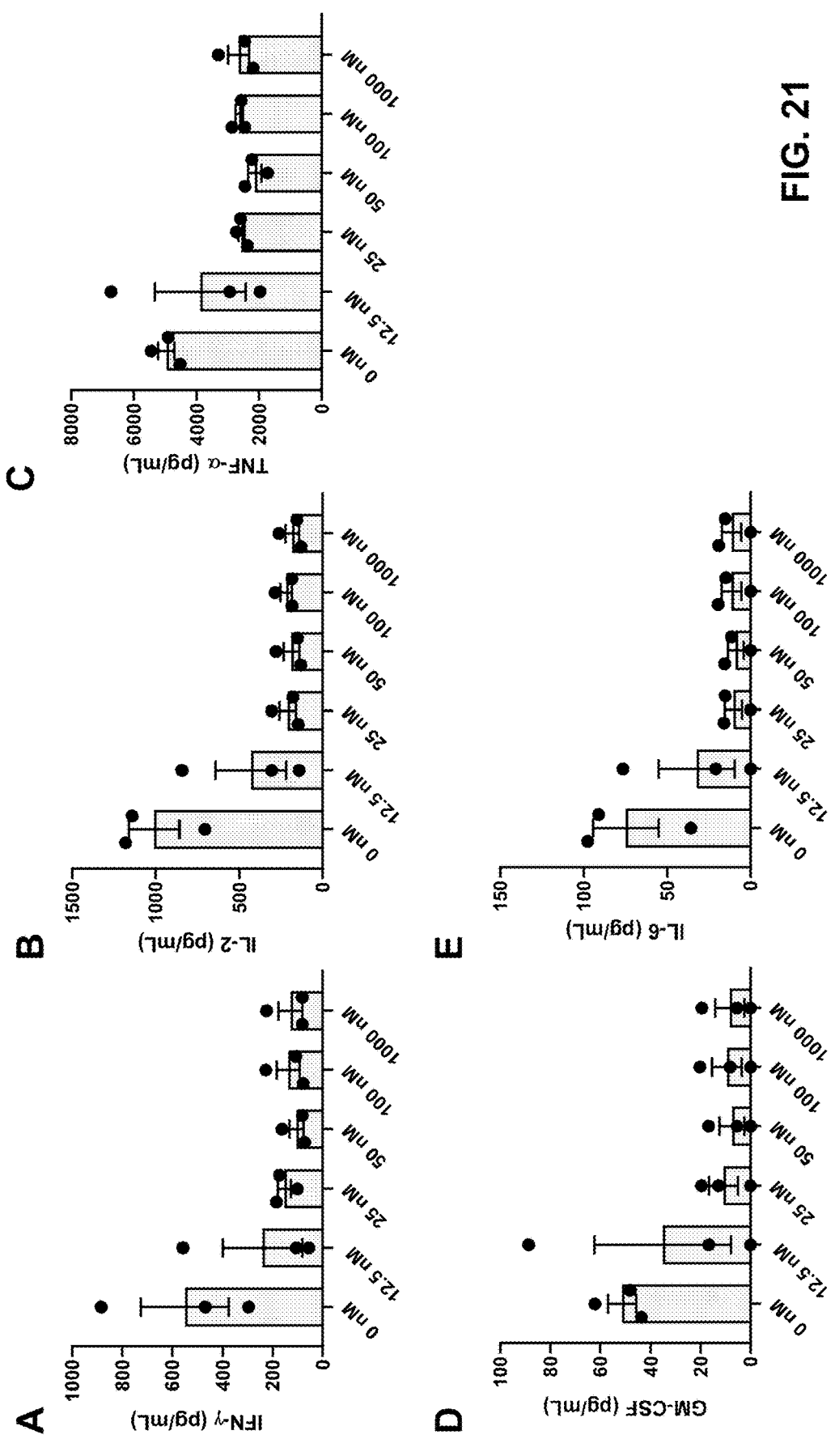

FIG. 21. Effect of escalating concentrations of sirolimus on IFN-$\gamma$ (A), IL-2 (B), TNF-$\alpha$ (C), GM-CSF (D) and IL-6 (E) release in the assay of FIG. 13 for 1 nM CD20-TCB. At 24 hours, the supernatants from technical replicates were pooled and cytokines were analyzed by Luminex. Mean of n=3 donors+/−SEM.

Figure 22:
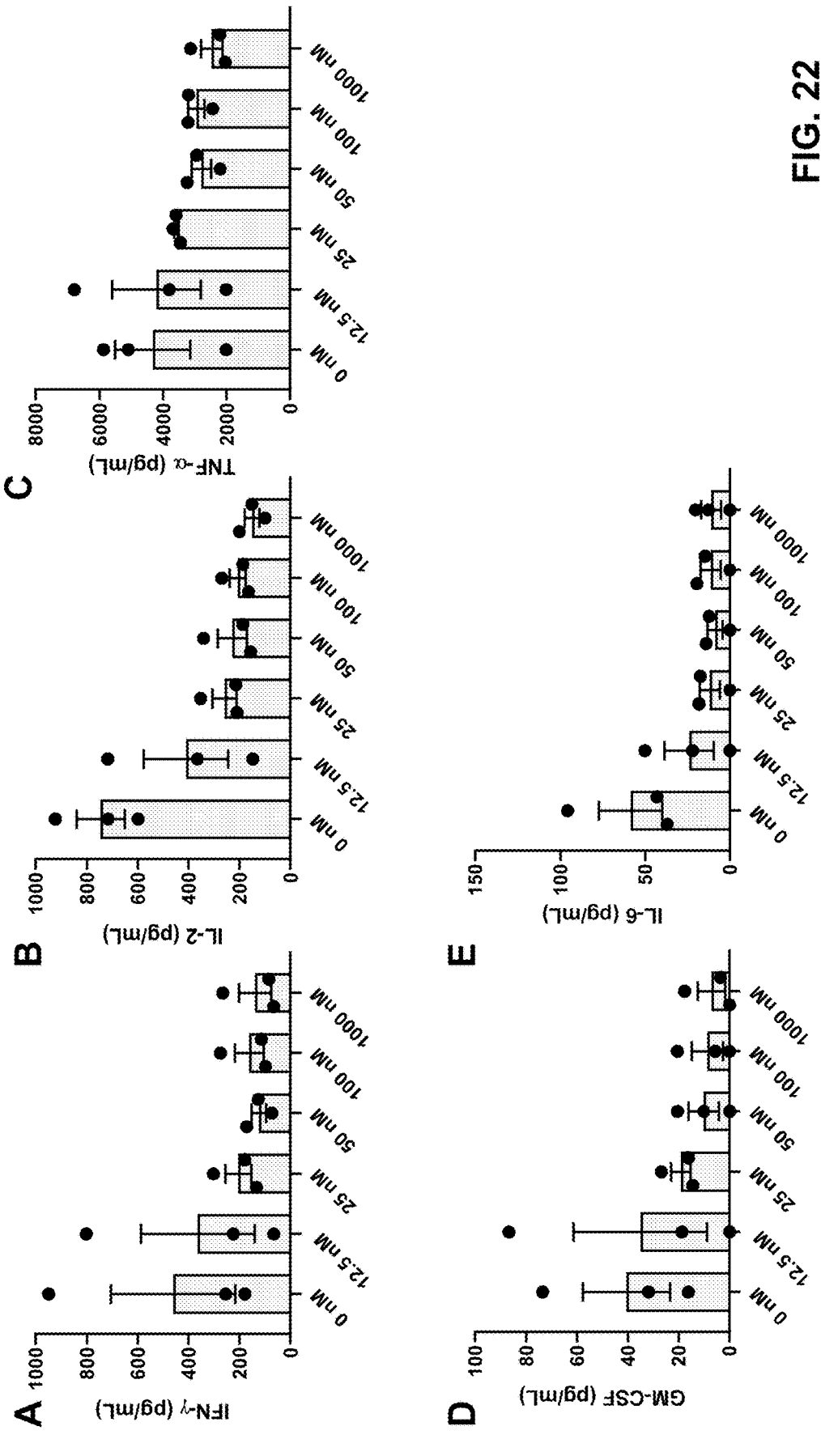

FIG. 22. Effect of escalating concentrations of everolimus on IFN-$\gamma$ (A), IL-2 (B), TNF-$\alpha$ (C), GM-CSF (D) and IL-6 (E) release in the assay of FIG. 13 for 1 nM CD20-TCB. At 24 hours, the supernatants from technical replicates were pooled and cytokines were analyzed by Luminex. Mean of n=3 donors+/−SEM.

Figure 23:
Figure 23:
Figure 23:
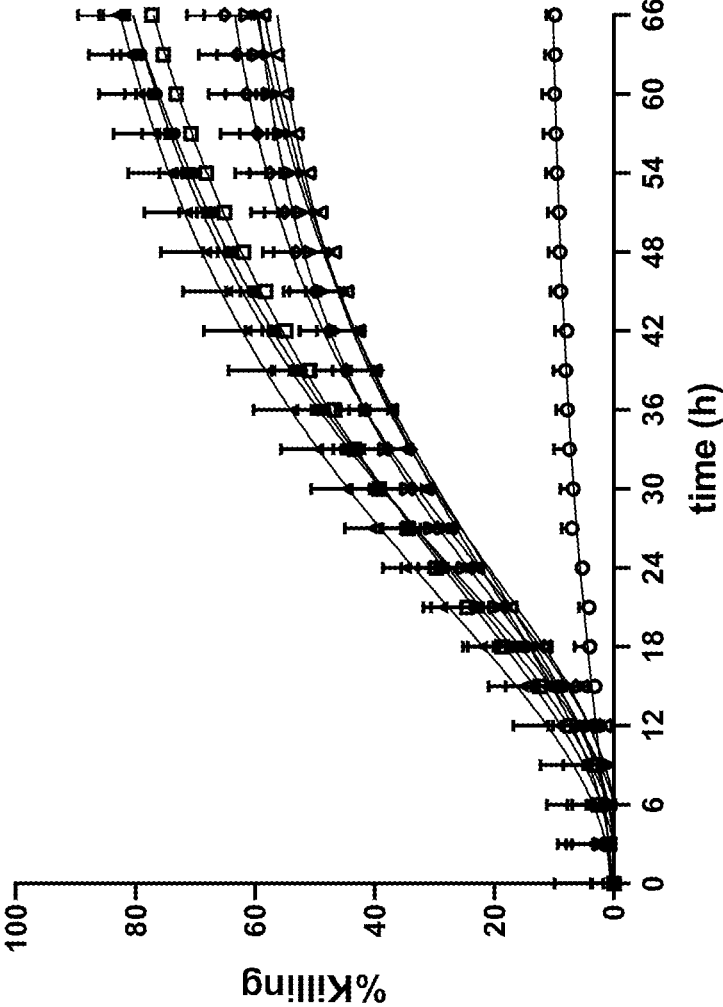

FIG. 23. Real-time killing of MKN45 NLR cells by 10 nM CEA-TCB in the presence of 5 μg/mL anti-TNF-$\alpha$ antibody (aTNF-$\alpha$; Biolegend #502922 (antibody Mab11)), 5 μg/mL anti-IL-6R antibody (aIL-6R; Roche in-house), 1 μM dexamethasone (dexa), 0.1 μM dexamethasone, 50 nM dasatinib (dasa), 50 nM ruxolitinib (ruxo), 50 nM temsirolimus (temsi), 40 nM sirolimus (siro), 50 nM everolimus (evero) in the assay of FIG. 1. % Killing was measured by normalizing total red area with values at t=0 hour and target cells+PBMCs+ corresponding coumpound control wells for each time point. Means of technical replicates+SD for 1 representative donor.

Figure 24:
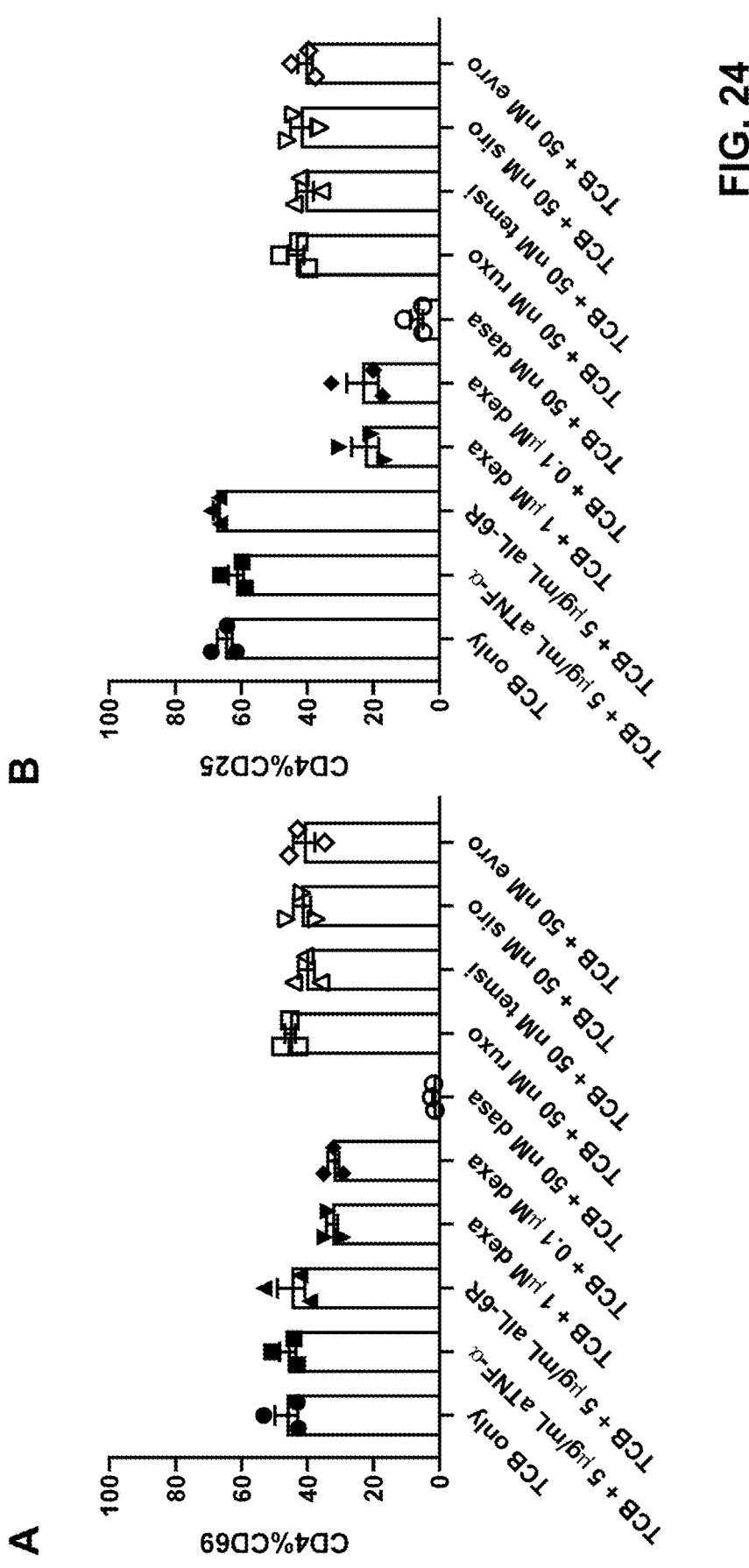

FIG. 24. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD69 (A) and CD25 (B) expression on CD4+ T cells induced by 10 nM CEA-TCB in the assay of FIG. 1. Technical replicates were pooled and expression of CD69 and CD25 on CD4+ T cells was measured by flow cytometry at 66 h. Mean of n=3 donors+/−SD FIG. 25. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD69 (A) and CD25 (B) expression on CD8+ T cells induced by 10 nM CEA-TCB in the assay of FIG. 1. Technical replicates were pooled and expression of CD69 and CD25 on CD8+ T cells was measured by flow cytometry at 66 h. Mean of n=3 donors+/−SD.

Figure 26:
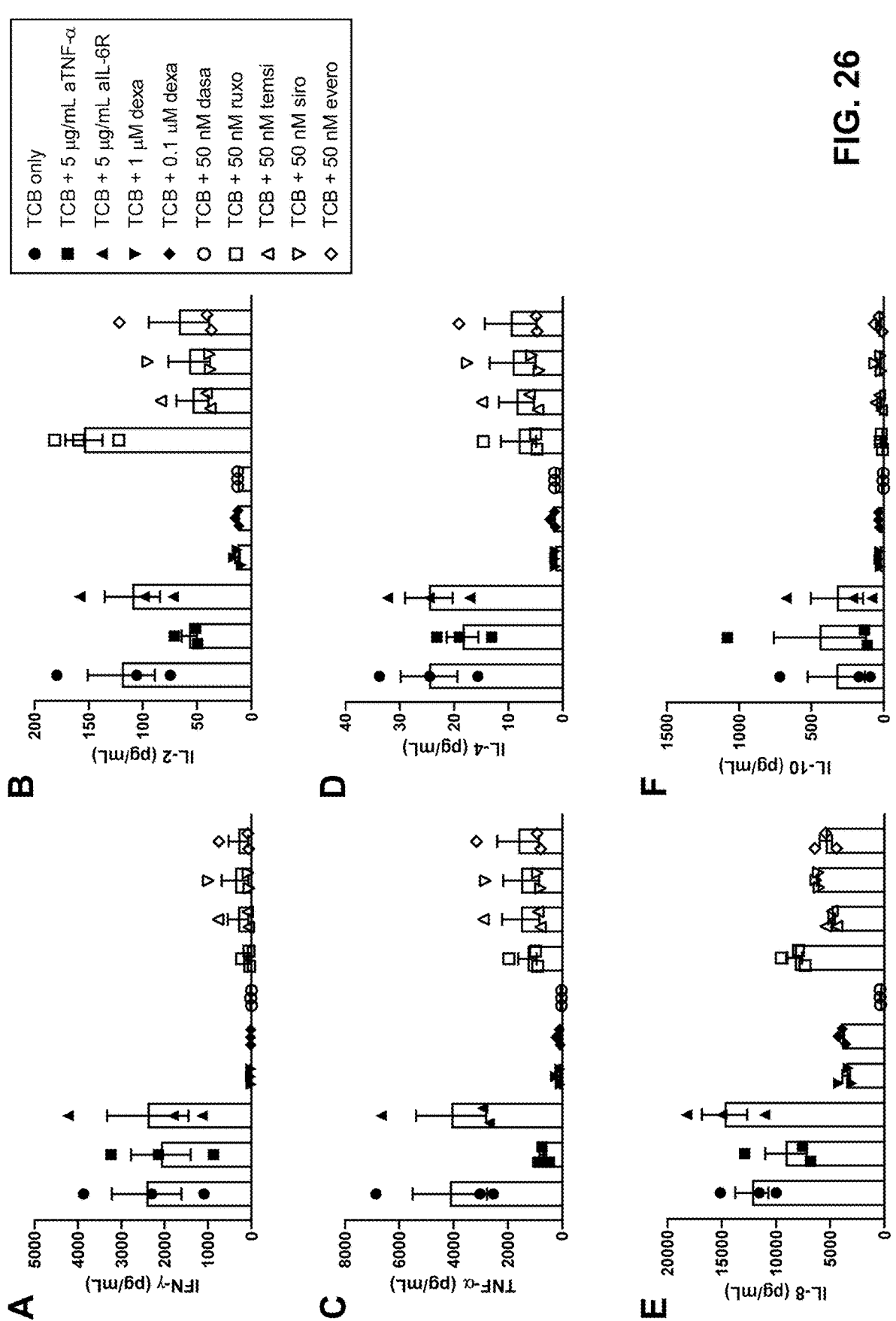
Figure 26:
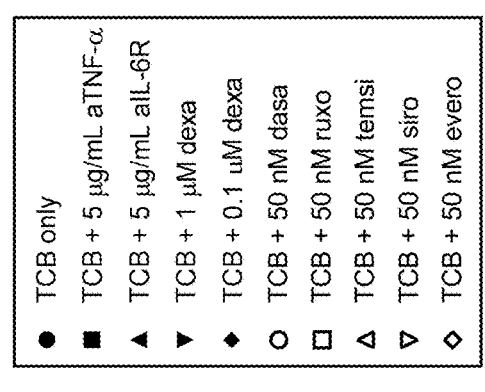
Figure 26:
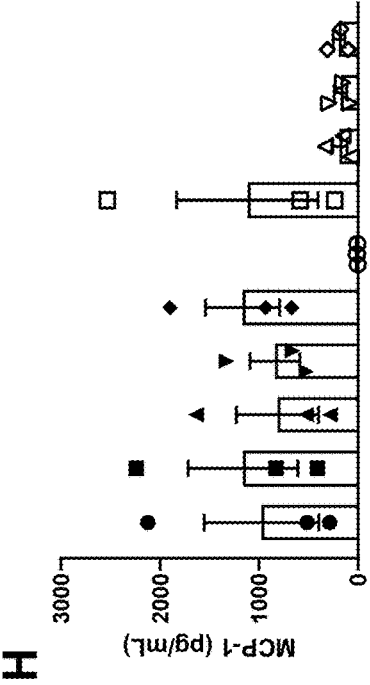
Figure 26:
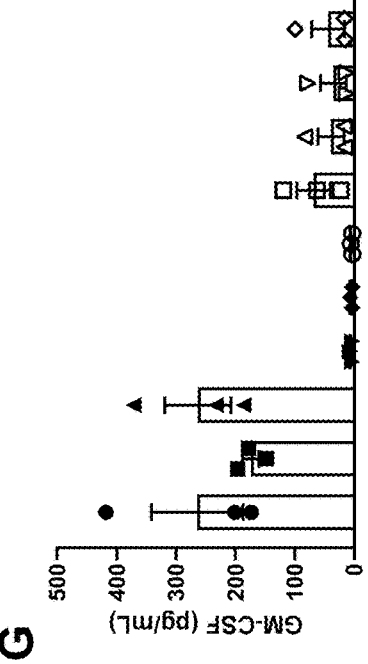

FIG. 26. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on cytokine release (IFN-γ (A), IL-2 (B), TNF-α (C), IL-4 (D), IL-8 (E), IL-10 (F), GM-CSF (G), MCP-1 (H)) induced by 10 nM CEA-TCB in the assay of FIG. 1. Supernatants from technical replicates were pooled at 66 h and cytokines were analyzed by Luminex. Mean of n=3 donors+/−SD.

Figure 27:
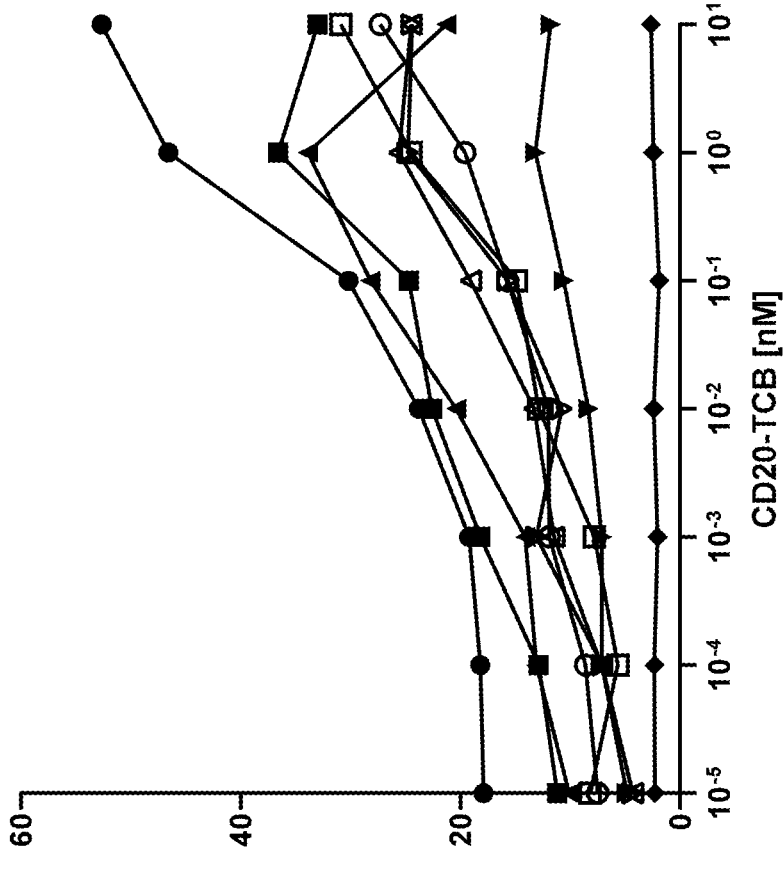

FIG. 27. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD20-TCB-induced B cell killing. WSU target cells were co-cultured with PBMCs (E:T=200 000:20 000), escalating CD20-TCB concentrations and corresponding compound. Technical replicates were pooled at 24 h and CD19+ B cells were measured by flow cytometry. Dead B cells were excluded from CD19+ B cells using Live/Dead™ Fixable Aqua Dead Cell Stain. 1 representative donor.

Figure 28:
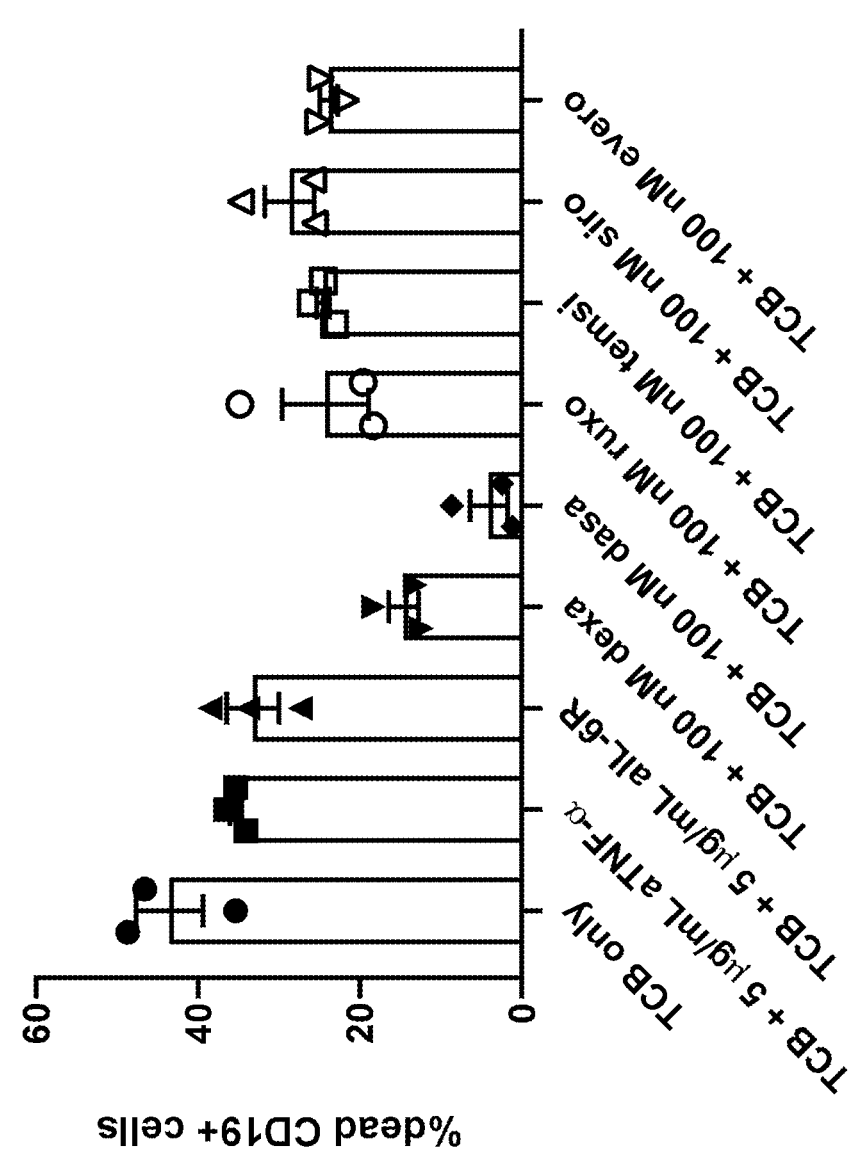

FIG. 28. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD20-TCB-induced B cell killing. WSU target cells were co-cultured with PBMCs (E:T=200 000:20 000), 1 nM CD20-TCB and corresponding compound. Technical replicates were pooled at 24 h and CD19+ B cells were measured by flow cytometry. Dead B cells were excluded from CD19+ B cells using Live/Dead™ Fixable Aqua Dead Cell Stain. Mean of n=3 donors+/−SD.

FIG. 29. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD20-TCB-induced T cell activation. WSU target cells were co-cultured with PBMCs (E:T=200 000:20 000), escalating CD20-TCB concentrations and corresponding compound. Technical replicates were pooled at 24 h and expression of CD69 on CD4+(A) and CD8+(C) T cells and CD25 on CD4+(B) and CD8+(D) T cells was measured by flow cytometry. 1 representative donor.

FIG. 30. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD69 (A) and CD25 (B) expression on CD4+ T cells. WSU target cells were co-cultured with PBMCs (E:T=200 000:20 000), 1 nM CD20-TCB and corresponding compound. Technical replicates were pooled at 24 h and expression of CD69 and CD25 on CD4+ T cells was measured by flow cytometry. Mean of n=3 donors+/−SD.

Figure 31:
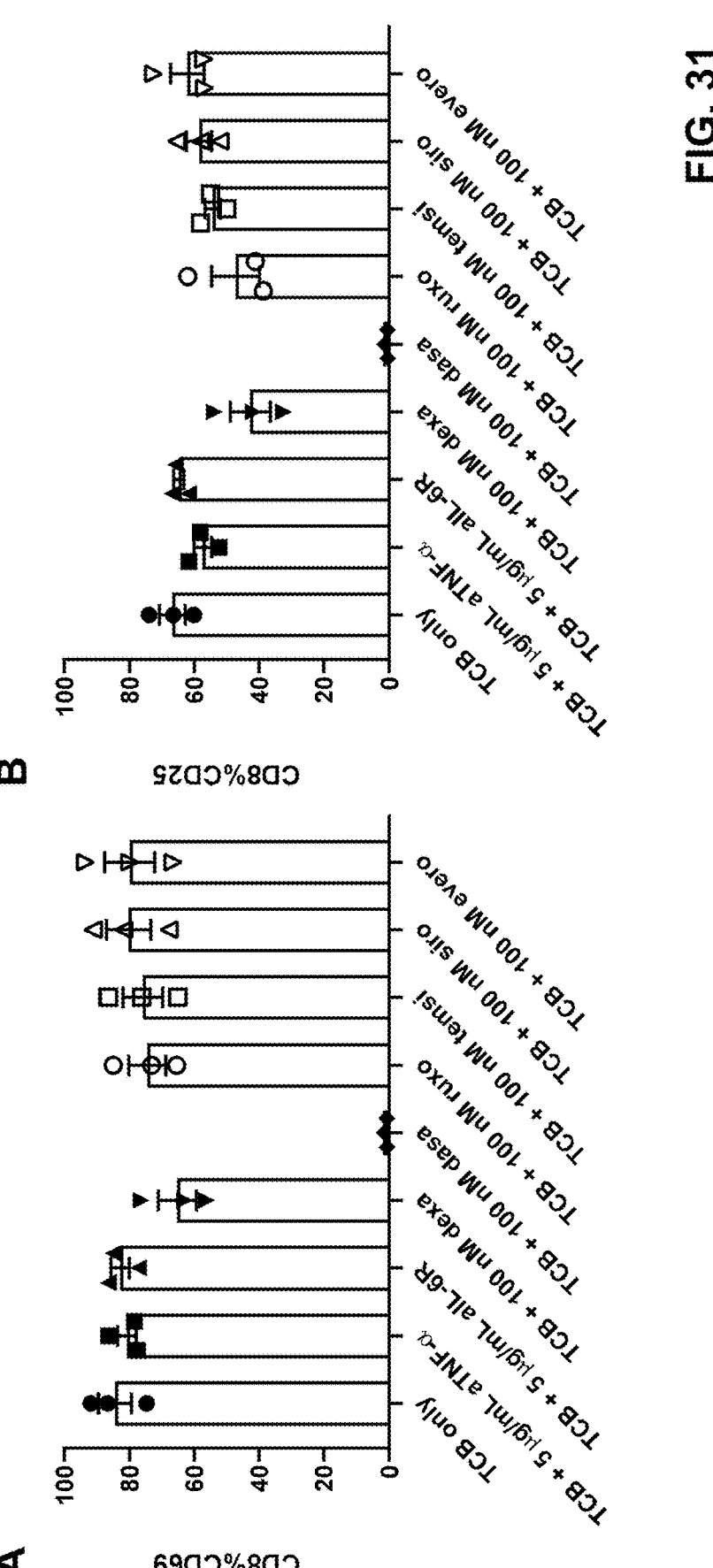

FIG. 31. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD69 (A) and CD25 (B) expression on CD8+ T cells. WSU target cells were co-cultured with PBMCs (E:T=200 000:20 000), 1 nM CD20-TCB and corresponding compound. Technical replicates were pooled at 24 h and expression of CD69 and CD25 on CD8+ T cells was measured by flow cytometry. Mean of n=3 donors+/−SD.

Figure 32:
Figure 32:
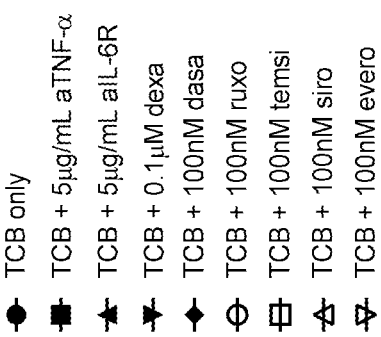

FIG. 32. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD20-TCB-induced cytokine release (TNF-α (A), IFN-γ (B), IL-2 (C), IL-113 (D), IL-6 (E), IL-4 (F), IL-10 (G), GM-CSF (H)). WSU target cells were co-cultured with PBMCs (E:T=200 000:20 000), escalating CD20-TCB concentrations and corresponding compound. Supernatant from technical replicates were pooled at 24 h and cytokines were analyzed by Luminex. 1 representative donor.

Figure 33:
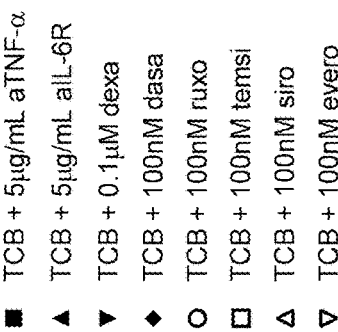
Figure 33:
Figure 33:
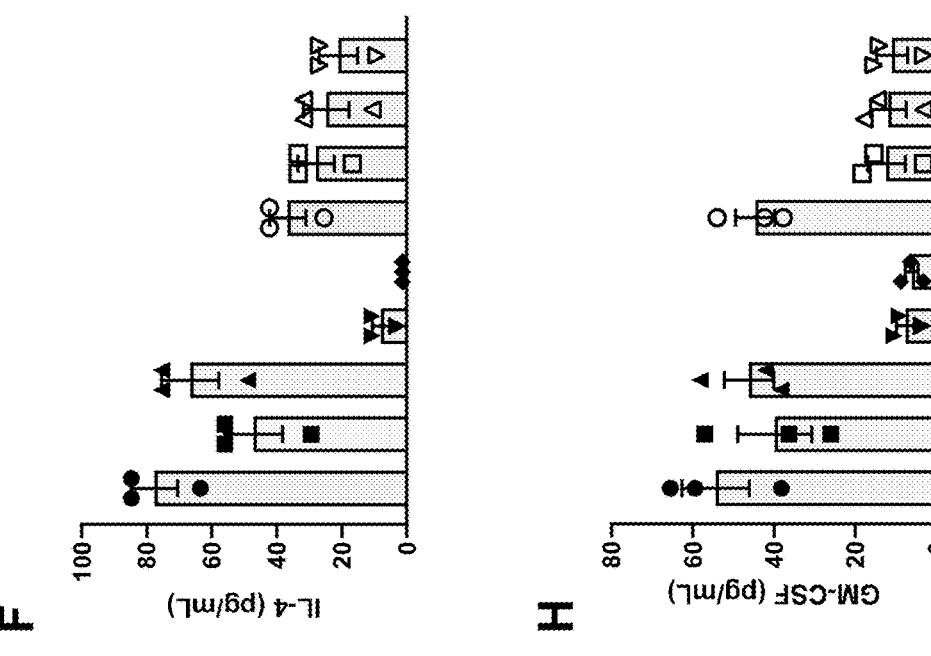
Figure 33:
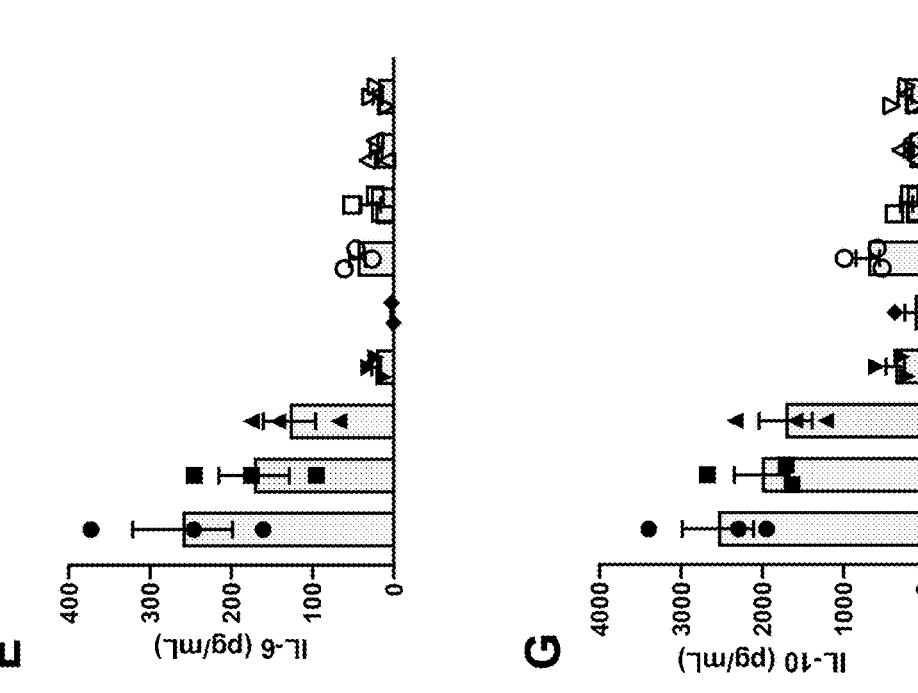

FIG. 33. Effect of anti-TNF-α antibody (aTNF-α), anti-IL-6R antibody (aIL-6R), dexamethasone (dexa), dasatinib (dasa), ruxolitinib (ruxo), temsirolimus (temsi), sirolimus (siro), everolimus (evero) on CD20-TCB-induced cytokine release (TNF-α (A), IFN-γ (B), IL-2 (C), IL-1β IL-6 (E), IL-4 (F), IL-10 (G), GM-CSF (H)). WSU target cells were co-cultured with PBMCs (E:T=200 000:20 000), 1 nM CD20-TCB and corresponding compound. Supernatant from technical replicates were pooled at 24 h and cytokines were analyzed by Luminex. Mean of n=3 donors+/−SD.

Figure 34:
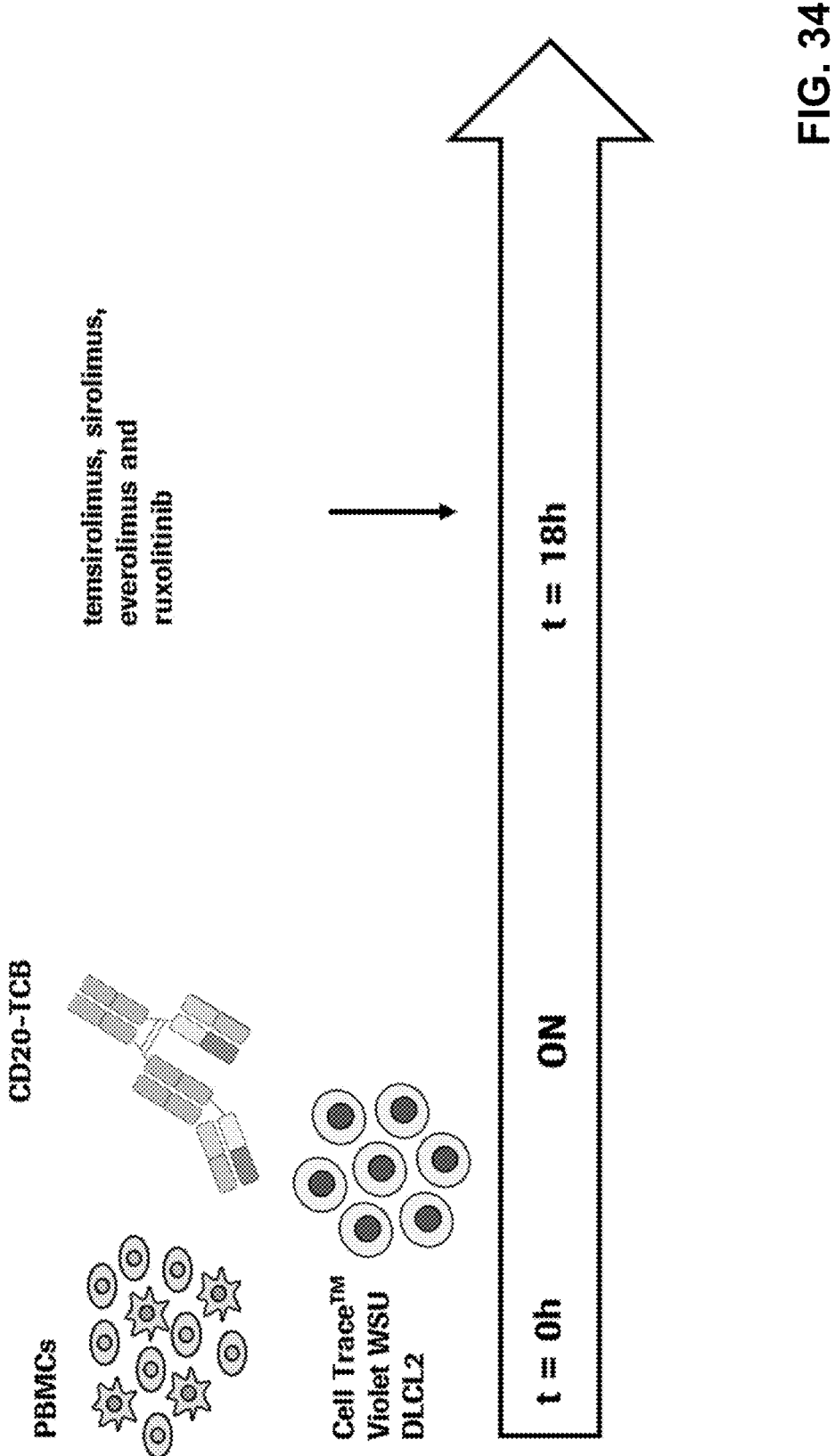

FIG. 34. In vitro killing assay set-up. Cell Trace™ Violet (CTV) labelled WSU DLCL2 tumor cells were co-cultured together with PBMCs [E:T=200'000:20'000] and stimulated with CD20-TCB for 18 h. At 18 h, 100 nM ruxolitinib, 100 nM temsirolimus, 100 nM sirolimus or 100 nM everolimus was added in the system.

Figure 35:
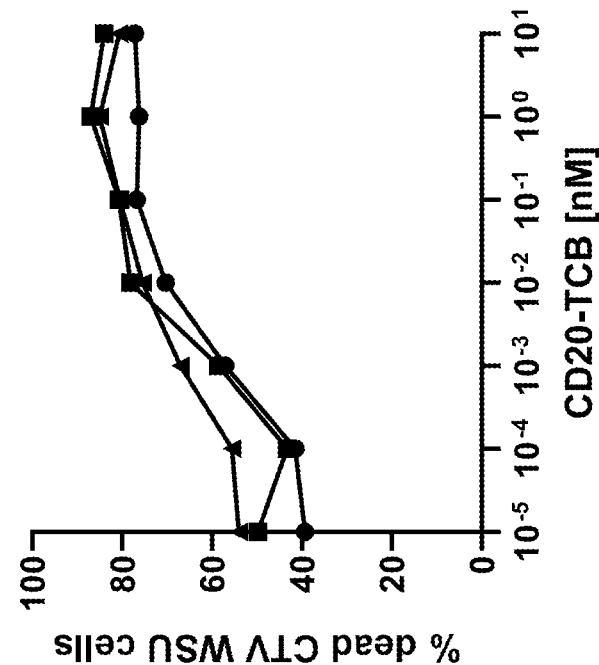

FIG. 35. CTV labelled WSU DLCL2 target cell killing at 18 h in the assay of FIG. 34 before the addition of ruxolitinib, temsirolimus, sirolimus and everolimus for 3 representative donors (D1-D3). At 18 hours, the tumor cells and PBMCs from technical replicates were pooled and stained with a LIVE/DEAD™ Near-IR dead cell dye to allow exclusion of dead CTV labelled WSU DLCL2 tumor cells by flow cytometry.

Figure 36:
Figure 36:
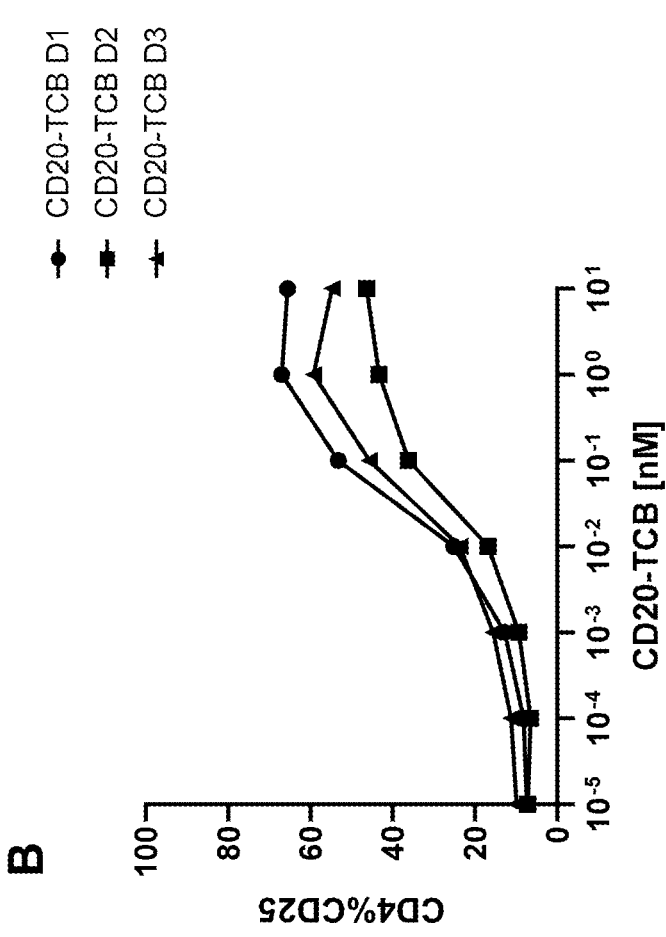
Figure 36:
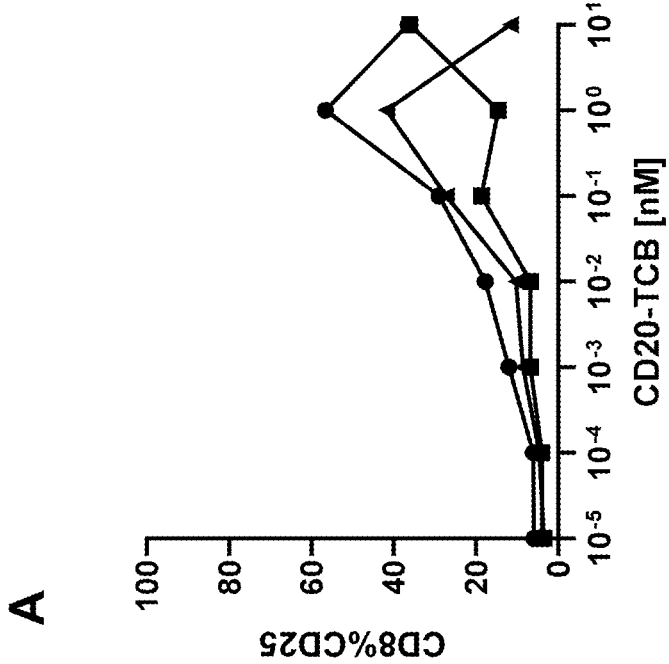

FIG. 36. CD25 expression on CD8+(A) and CD4+(B) T cells at 18 h in the assay of FIG. 34 before the addition of ruxolitinib, temsirolimus, sirolimus and everolimus for 3 representative donors (D1-D3). At 18 hours, the technical replicates were pooled and expression of CD25 was measured on CD4+ and CD8+ T cells by flow cytometry.

Figure 37:
Figure 37:
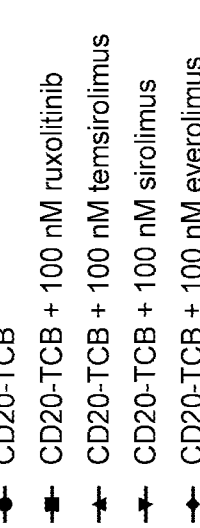
Figure 37:
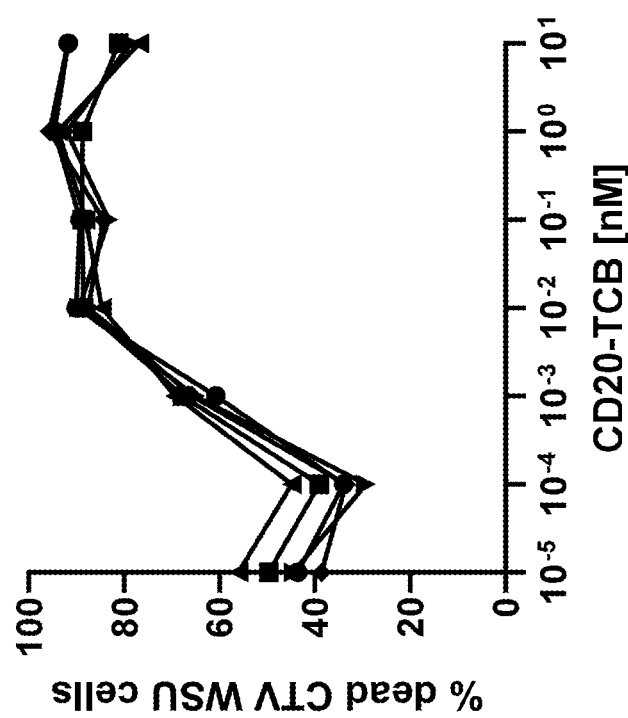

FIG. 37. CTV labelled WSU DLCL2 target cell killing at 44 h in the assay of FIG. 34 after the addition of ruxolitinib, temsirolimus, sirolimus and everolimus. At 44 hours, the tumor cells and PBMCs from technical replicates were pooled and stained with a LIVE/DEAD™ Near-IR dead cell dye to allow exclusion of dead CTV labelled WSU DLCL2 tumor cells by flow cytometry. 1 representative donor.

Figure 38:
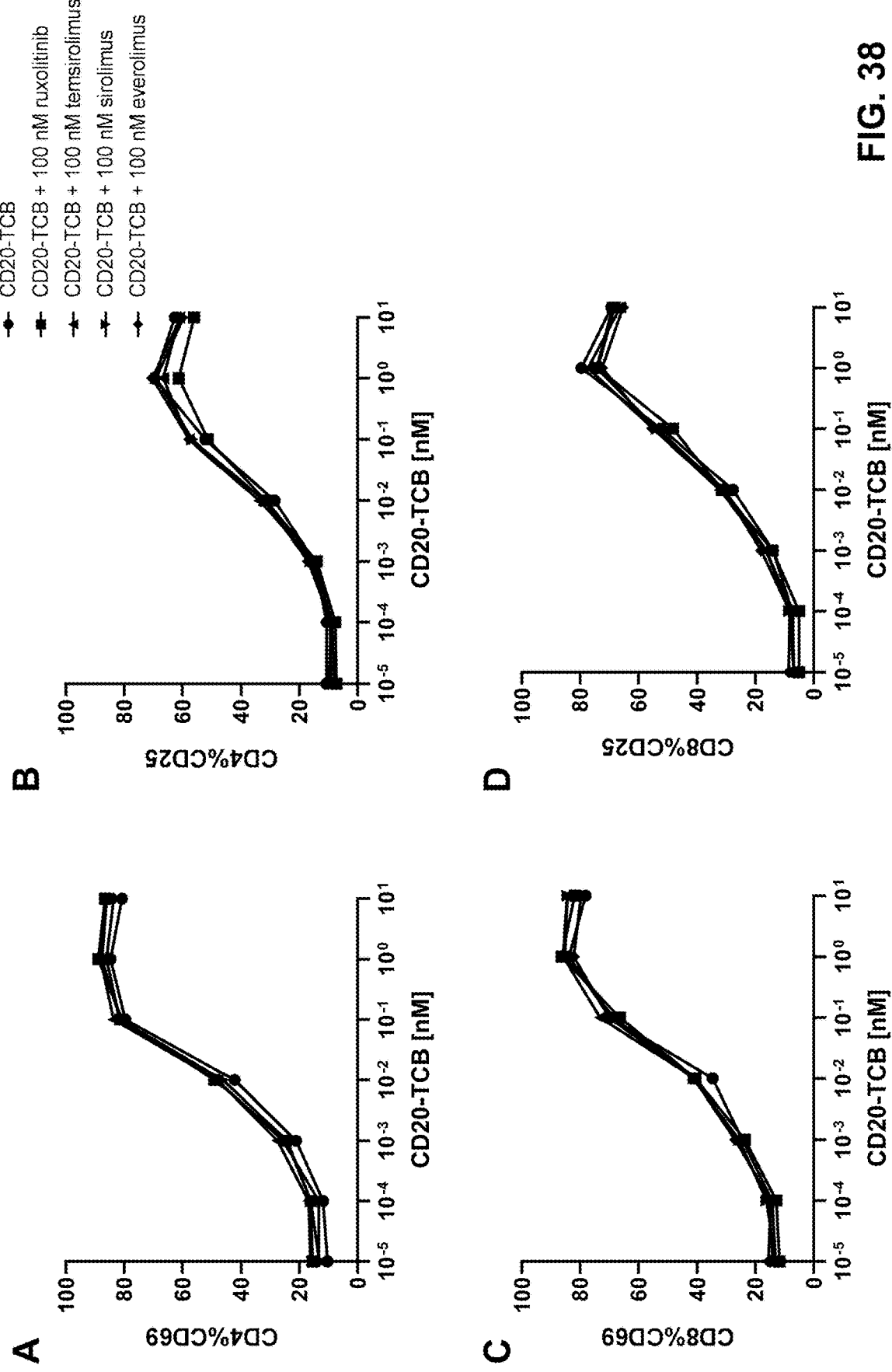

FIG. 38. Expression of CD25 expression on CD4+(B) and CD8+(D) T cells and CD69 expression on CD4+(A) and CD8+(C) T cells after the addition of ruxolitinib, temsirolimus, sirolimus and everolimus in the assay of FIG. 34. At 44 hours, the tumor cells and PBMCs from technical replicates were pooled and expression of CD25 and CD69 on CD4+ and CD8+ T cells was measured by flow cytometry. 1 representative donor.

Figure 39:
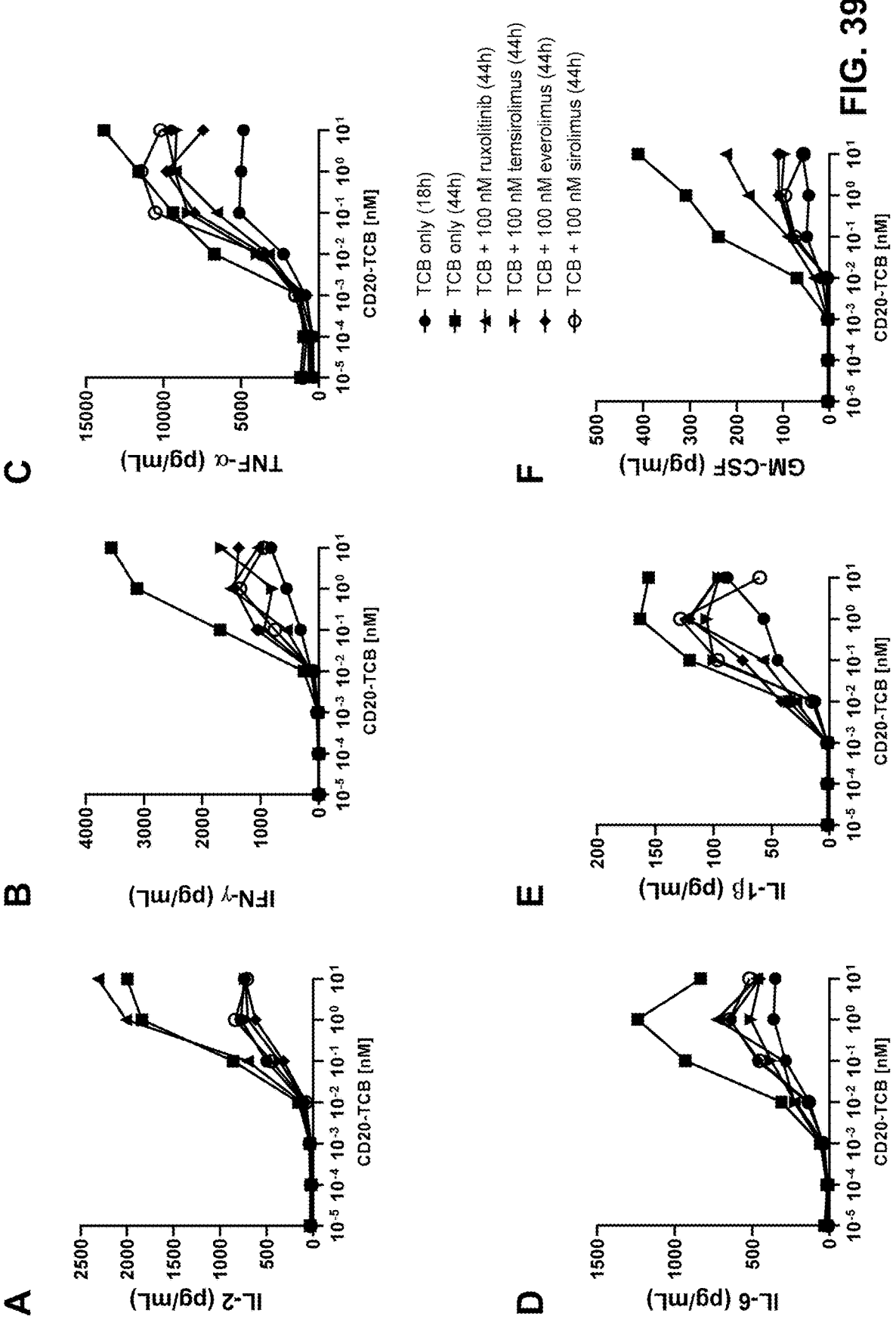

FIG. 39. IL-2 (A), IFN-γ (B), TNF-α (C), IL-6 (D), IL-1β (E), GM-CSF (F) levels before (18 h) and after (44 h) addition of ruxolitinib, temsirolimus, sirolimus and everolimus in the assay of FIG. 34. At 18 hours and 44 hours, the supernatants from technical replicates were pooled and cytokines were analyzed by Luminex. 1 representative donor.

Figure 40:
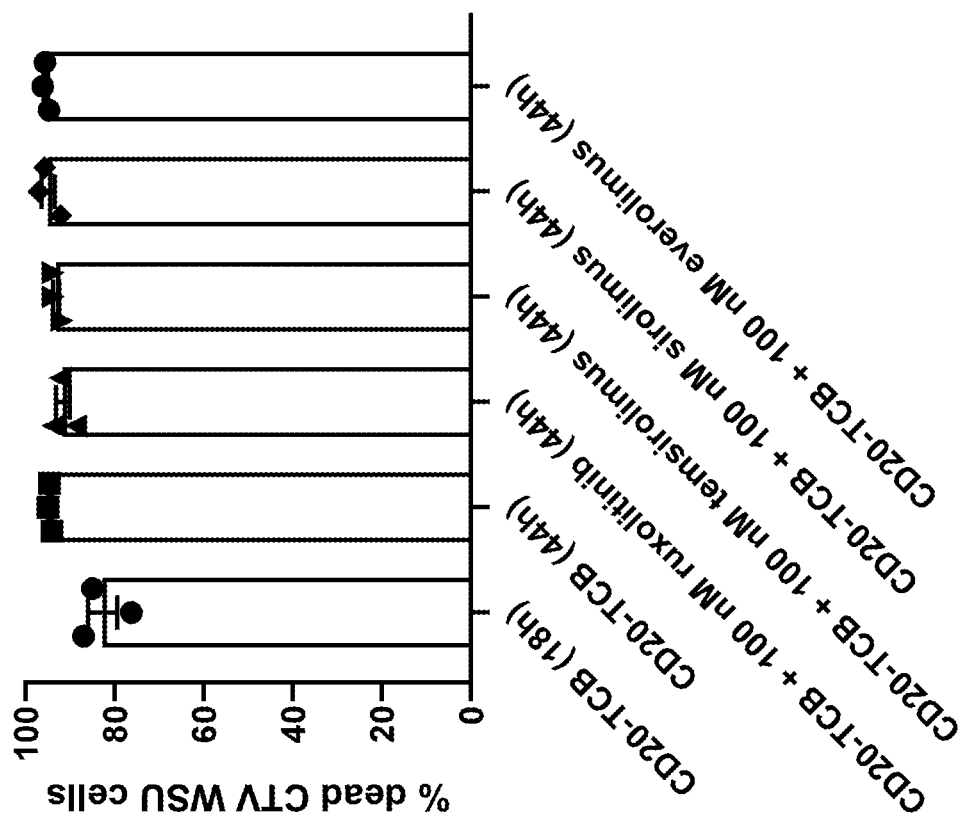

FIG. 40. CTV labelled WSU DLCL2 target cell killing before (18 h) and after (44 h) addition of ruxolitinib, temsirolimus, sirolimus and everolimus for 1 nM CD20-TCB in the assay of FIG. 34. At 18 hours and 44 hours, the tumor cells and PBMCs from technical replicates were pooled and stained with a LIVE/DEAD™ Near-IR dead cell dye to allow exclusion of dead CTV labelled WSU DLCL2 tumor cells by flow cytometry. Mean of n=3 donors+/−SEM.

Figure 41:
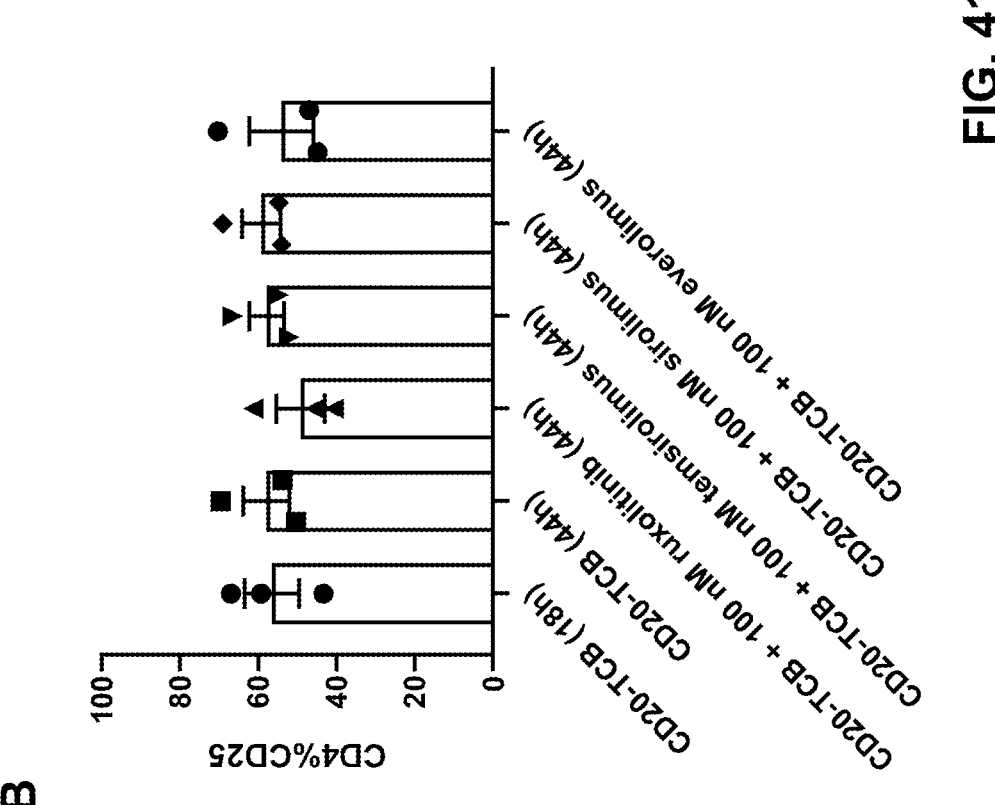
Figure 41:
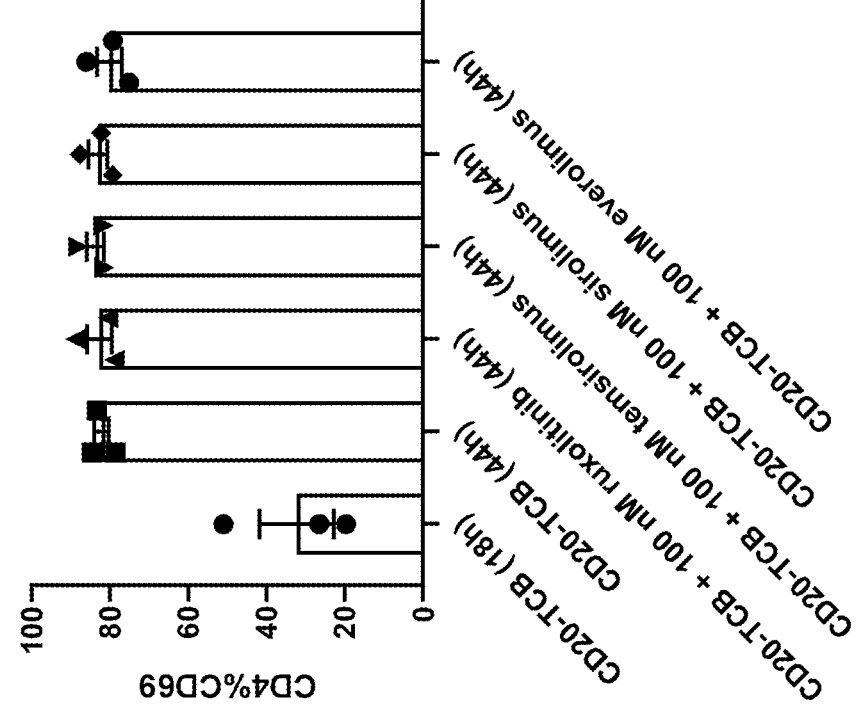

FIG. 41. Expression of CD69 (A) and CD25 (B) on CD4+ T cells before (18 h) and after (44 h) the addition of ruxolitinib, temsirolimus, sirolimus and everolimus for 1 nM CD20-TCB in the assay of FIG. 34. At 18 hours and 44 hours, the tumor cells and PBMCs from technical replicates were pooled and expression of CD25 and CD69 on CD4+ T cells was measured by flow cytometry. Mean of n=3 donors+/−SEM.

Figure 42:
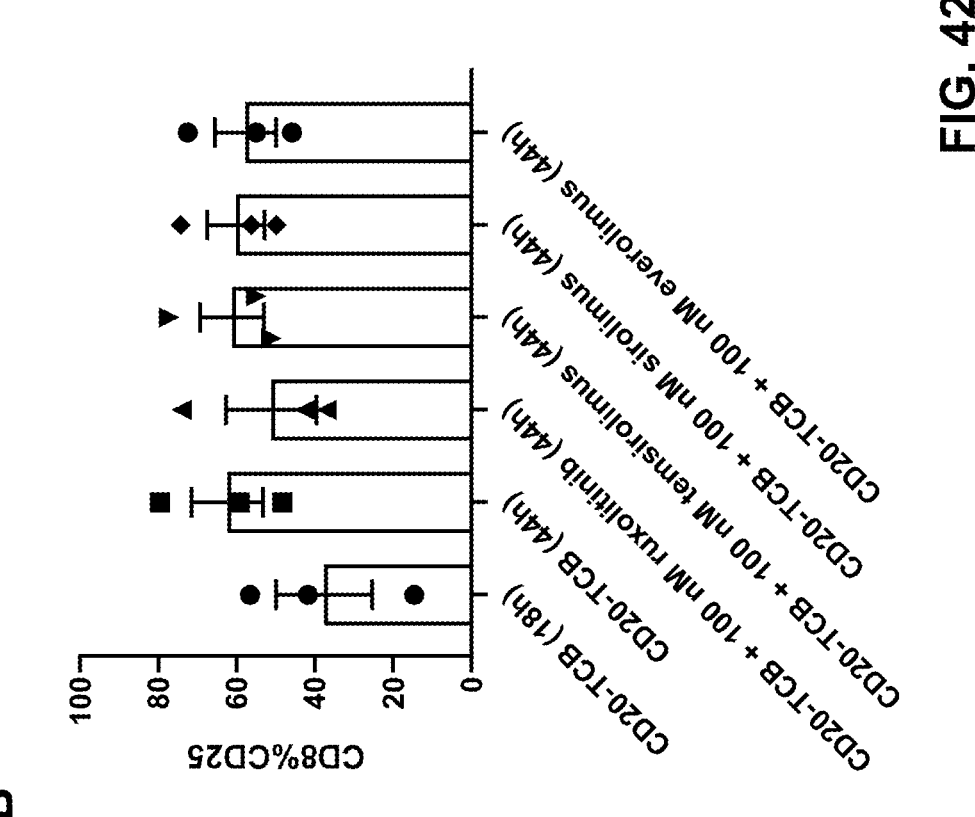
Figure 42:
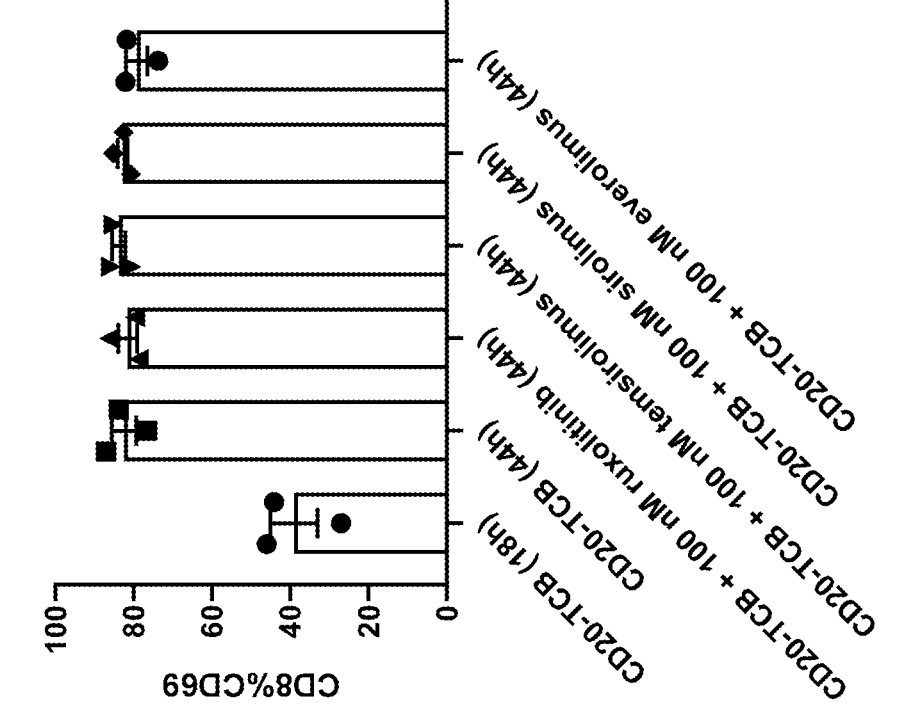

FIG. 42. Expression of CD69 (A) and CD25 (B) on CD8+ T cells before (18 h) and after (44 h) the addition of ruxolitinib, temsirolimus, sirolimus and everolimus for 1 nM CD20-TCB in the assay of FIG. 34. At 18 hours and 44 hours, the tumor cells and PBMCs from technical replicates were pooled and expression of CD25 and CD69 on CD8+ T cells was measured by flow cytometry. Mean of n=3 donors+/−SEM.

Figure 43:
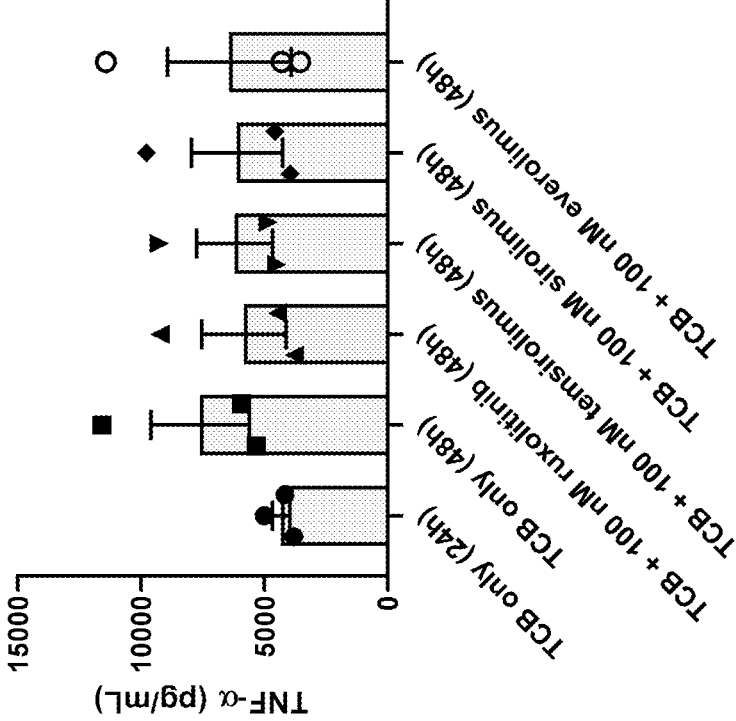
Figure 43:
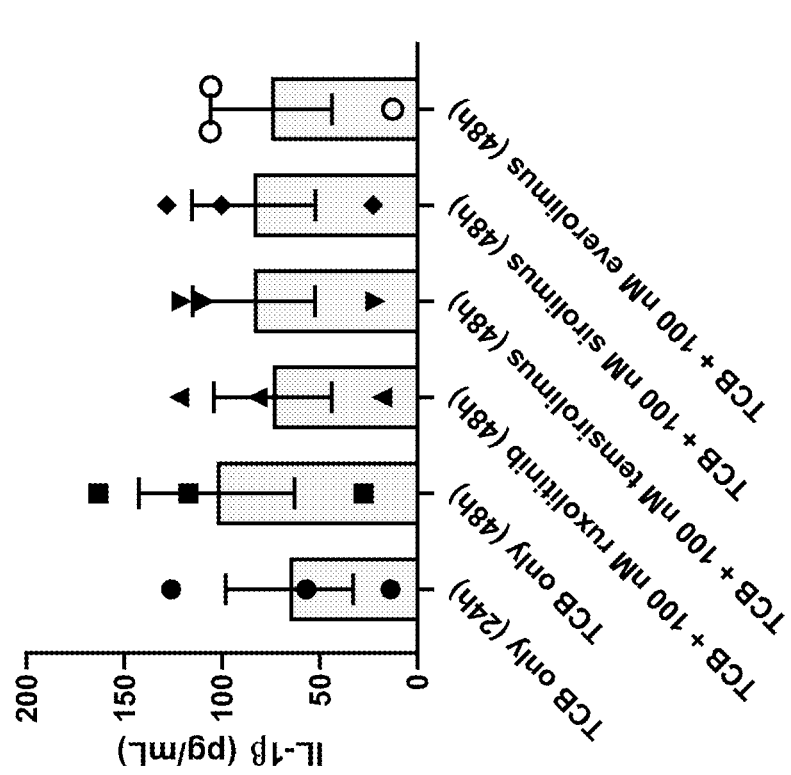
Figure 43:
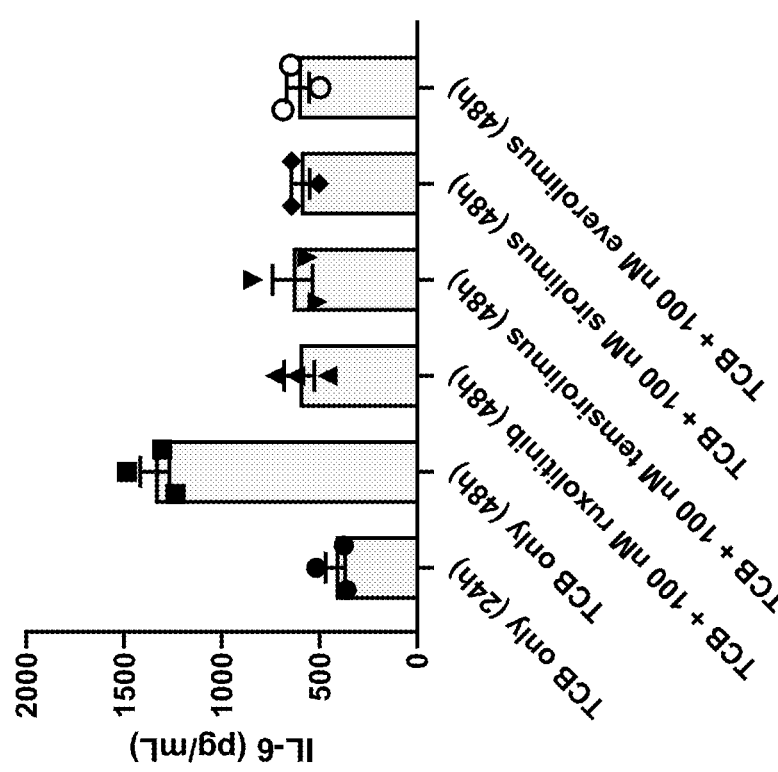

FIG. 43. IFN-γ (A), IL-2 (B), TNF-α (C), IL-6 (D) and IL-1β (E) levels before (18 h) and after (44 h) addition of ruxolitinib, temsirolimus, sirolimus and everolimus for 1 nM CD20-TCB in the assay of FIG. 34. At 18 hours and 44 hours, the supernatants from technical replicates were pooled and cytokines were analyzed by Luminex. Mean of n=3 donors+/−SEM.

Figure 44:
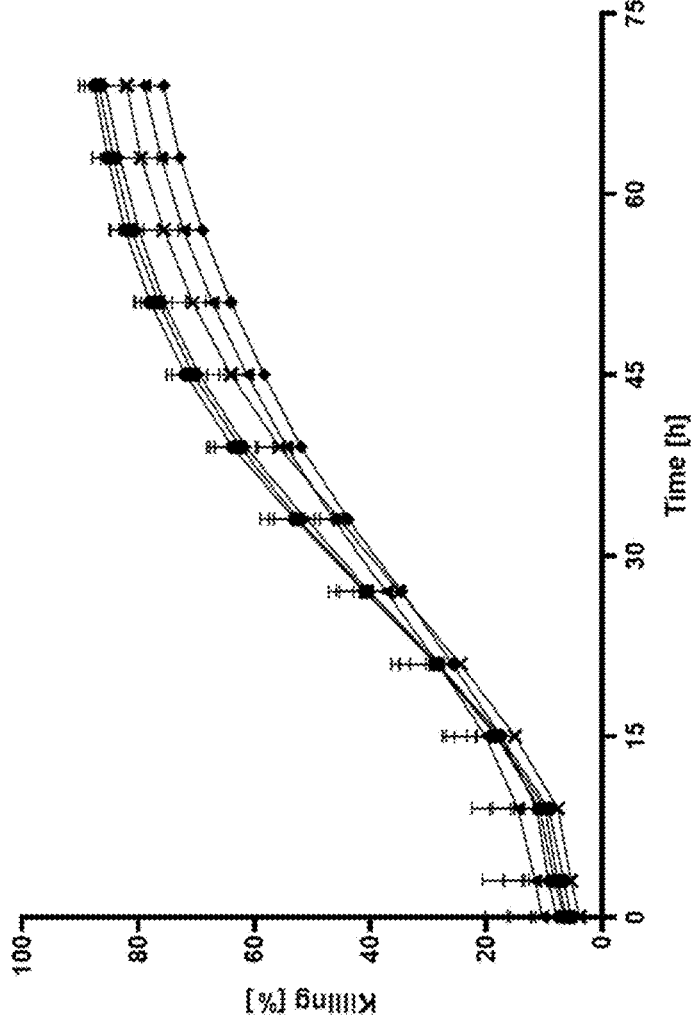

FIG. 44. Real time killing of A375 NucLightRed (NLR) cells by 8 nM MAGEA4-TCB in the presence of escalating concentrations of ruxolitinib ranging from 0 nM to 1000 nM. A375 NLR target cells were co-cultured with MAGEA4-TCB (8 nM), ruxolitinib and PBMCs, E:T=50 000 PBMCs: 5000 target cells. The killing was followed using an Incucyte® (1 scan every 3 hours, zoom 10×, phase and red 400 ms acquisition time). % Killing was measured by normalizing total red area with values at t=0 hour and target cells+PBMCs+ruxolitinib control wells for each time point. Means of technical replicates+SD for 1 representative donor.

Figure 45:
Figure 45:
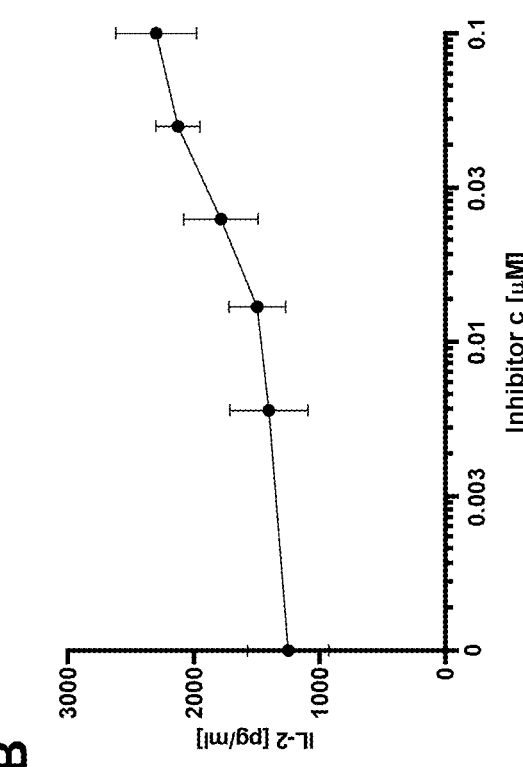
Figure 45:
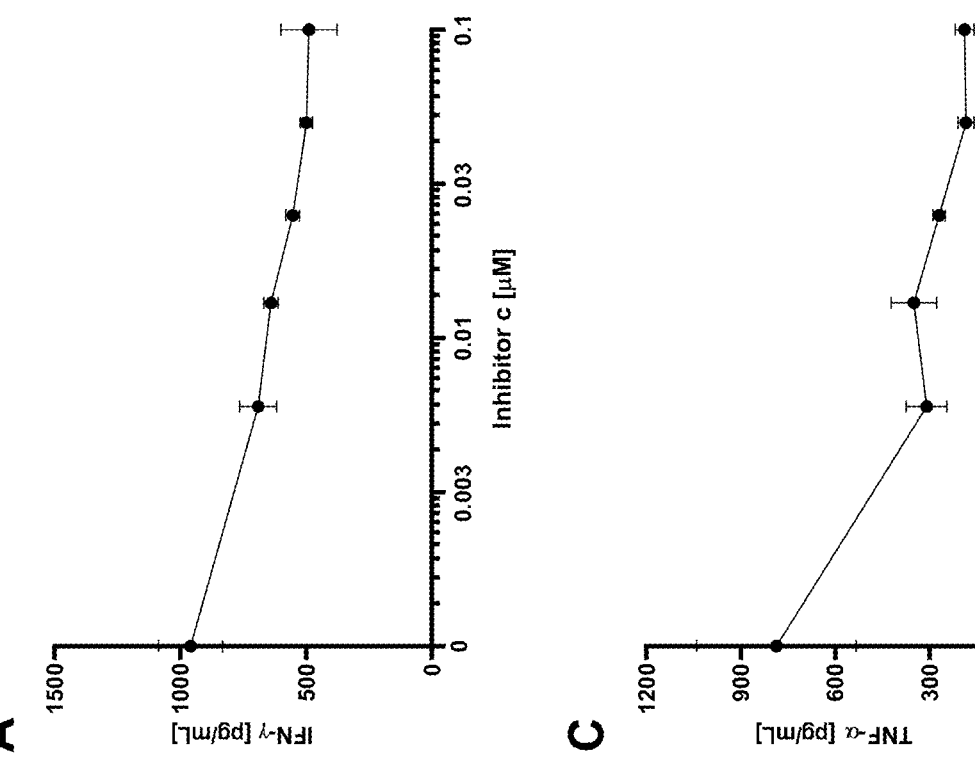
Figure 45:
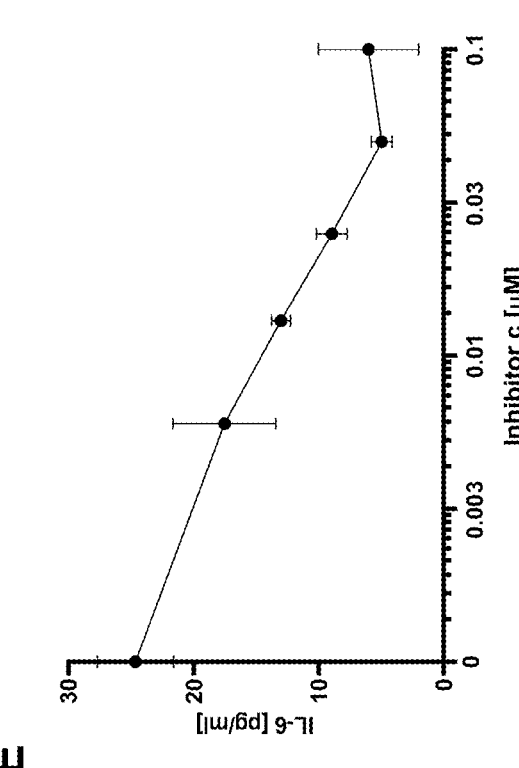
Figure 45:
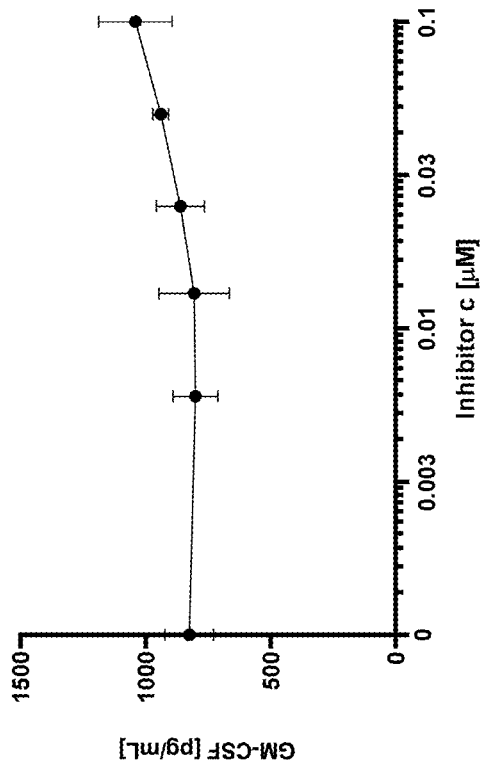
Figure 45:
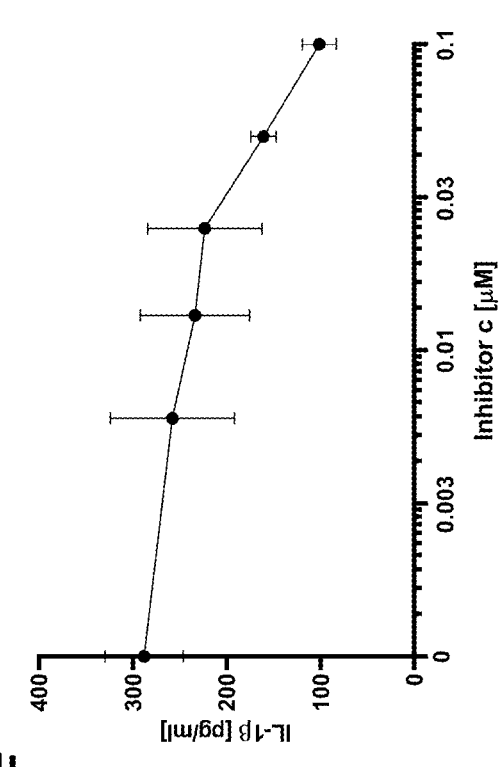
Figure 45:
Figure 45:
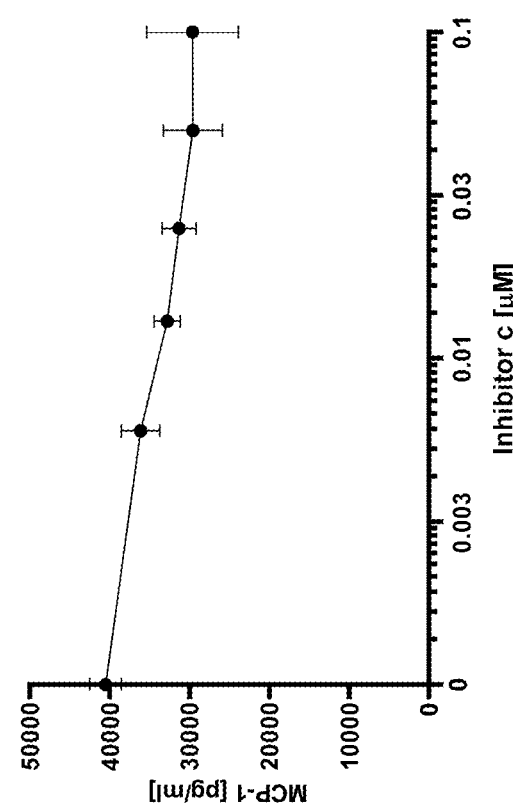
Figure 45:
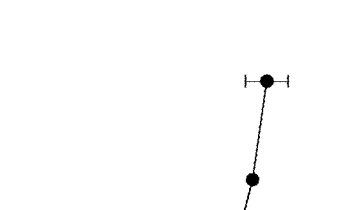
Figure 45:
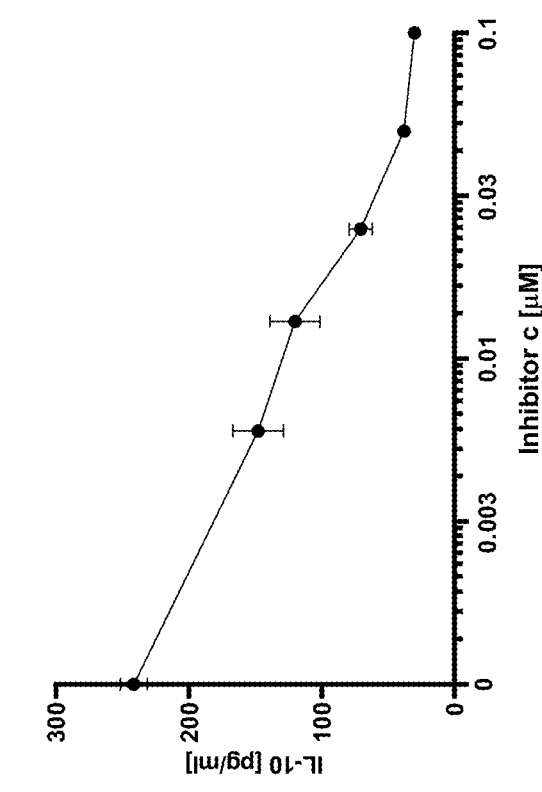
Figure 45:
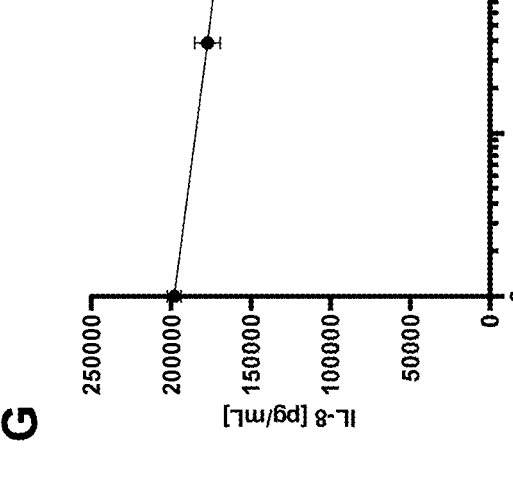

FIG. 45. Effect of escalating concentrations (c) of ruxolitinib on IFN-γ (A), IL-2 (B), TNF-α (C), GM-CSF (D), IL-6 (E), IL-1β (F), IL-8 (G), MCP-1 (H) and IL-10 (I) levels induced by 8 nM MAGEA4-TCB. At 72 hours, the supernatants were collected and cytokines were analyzed by cytometric bead array (CBA). Mean of technical replicates+/−SD for 1 representative donor.

Figure 46:

FIG. 46. Real time killing of A375 NucLightRed (NLR) cells by 8 nM MAGEA4-TCB in the presence of escalating concentrations of sirolimus (A), temsirolimus (B) and everolimus (C) ranging from 0 nM to 1000 nM. A375 NLR target cells were co-cultured with 8 nM MAGEA4-TCB, mTOR inhibitors and PBMCs, E:T=50 000 PBMCs: 5000 target cells. The killing was followed using anIncucyte® (1 scan every 3 hours, zoom 10×, phase and red 400 ms acquisition time). % Killing was measured by normalizing total red area with values at t=0 hour and target cells+PBMCs+mTOR inhibitors control wells for each time point. Means of technical replicates +SEM for 1 representative donor.

Figure 47:
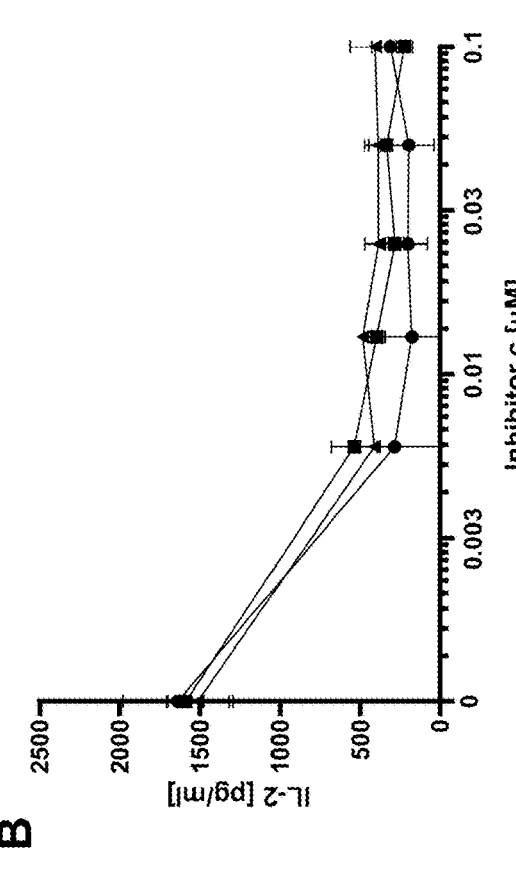
Figure 47:
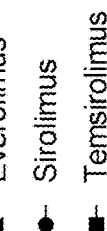
Figure 47:
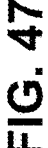
Figure 47:
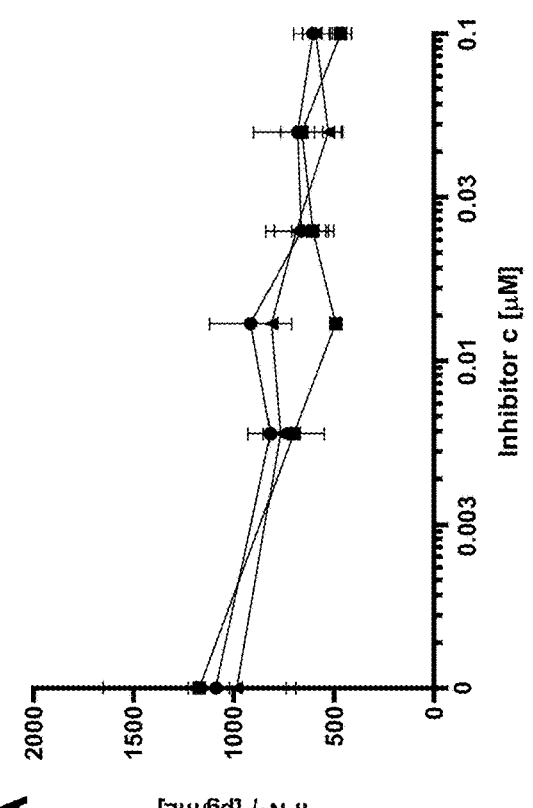
Figure 47:
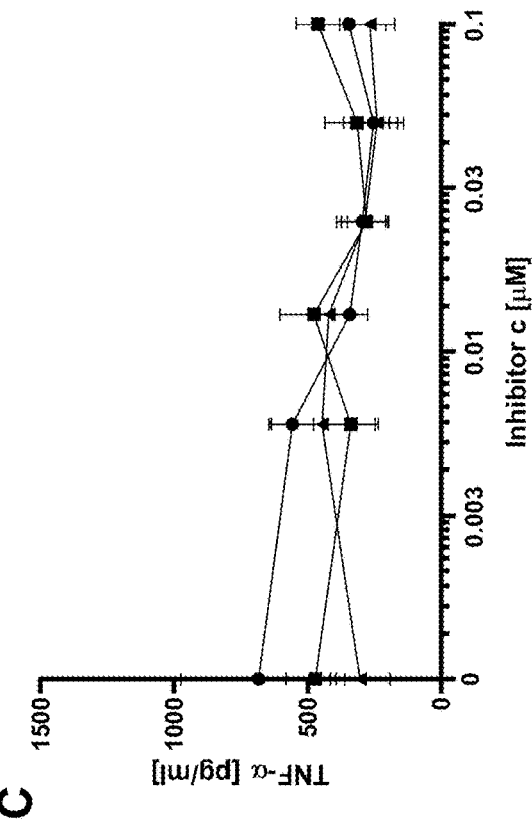
Figure 47:
Figure 47:
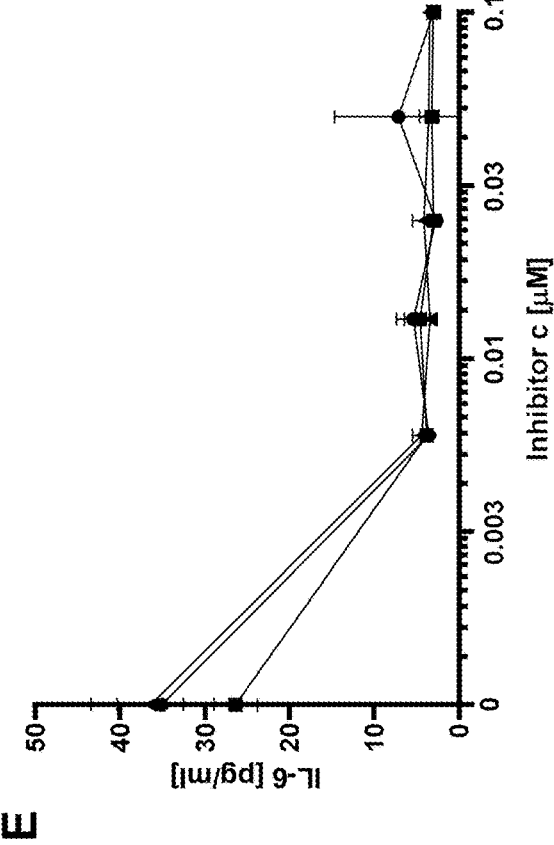
Figure 47:
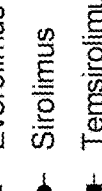
Figure 47:
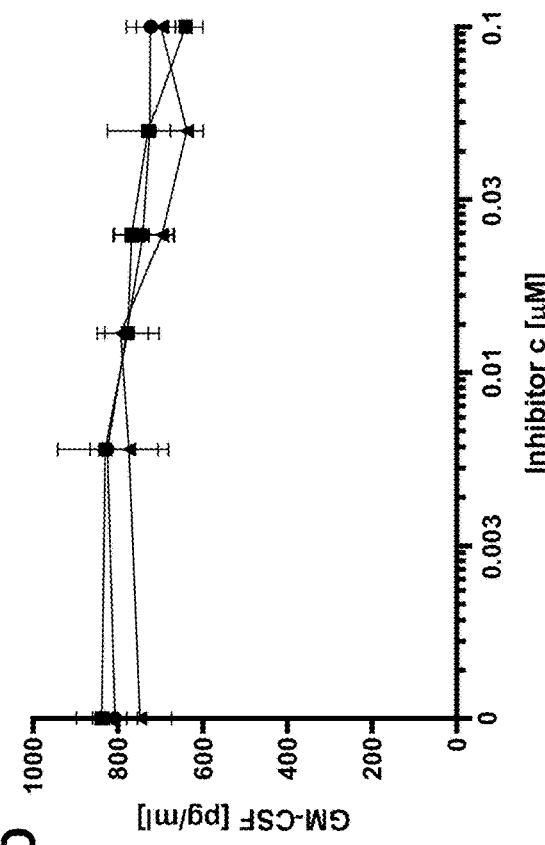
Figure 47:
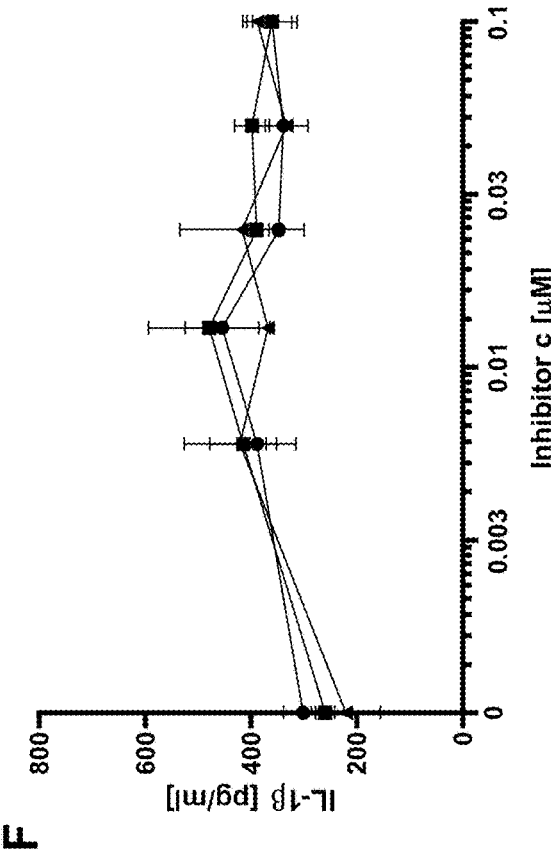
Figure 47:
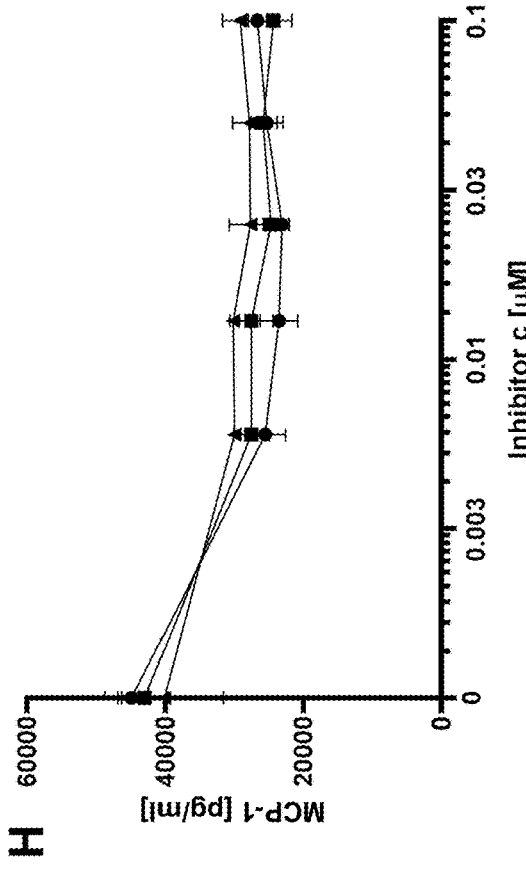
Figure 47:
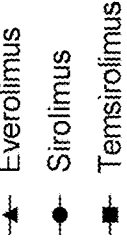
Figure 47:
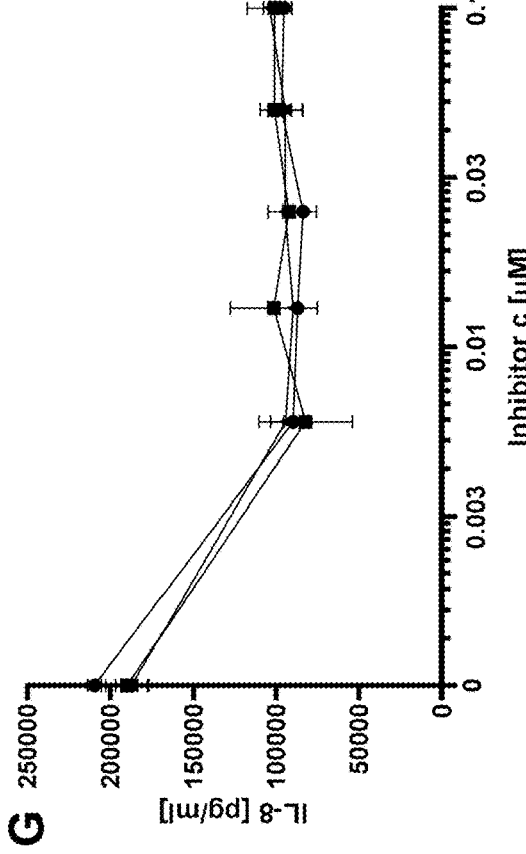
Figure 47:
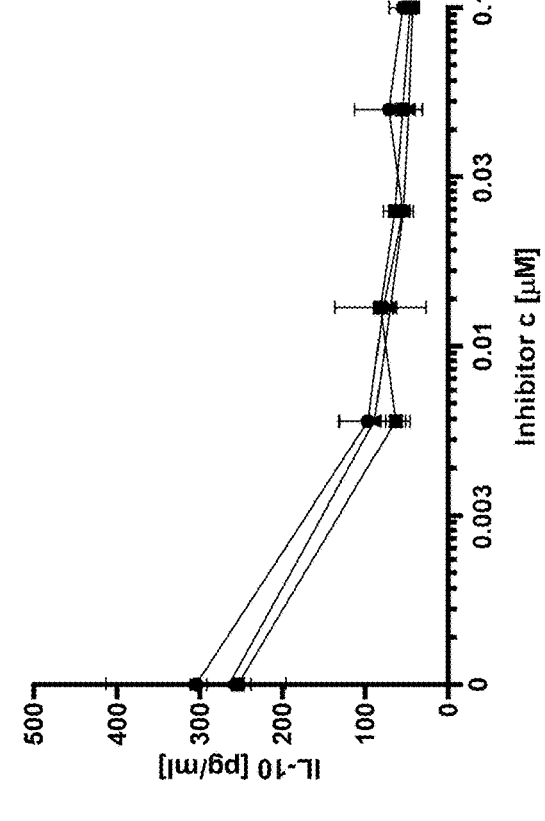

FIG. 47. Effect of escalating concentrations (c) of sirolimus, temsirolimus and everolimus on IFN-γ (A), IL-2 (B), TNF-α (C), GM-CSF (D), IL-6 (E), IL-1β (F), IL-8 (G), MCP-1 (H) and IL-10 (I) levels induced by 8 nM MAGEA4-TCB. At 72 hours, the supernatants were collected and cytokines were analyzed by CBA. Mean of technical replicates+/−SD for 1 representative donor.

Figure 48:
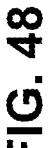
Figure 48:
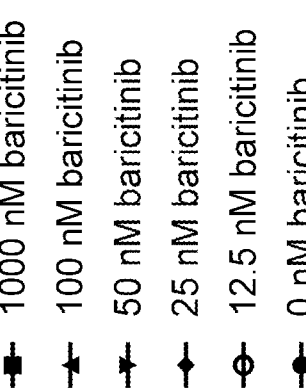
Figure 48:
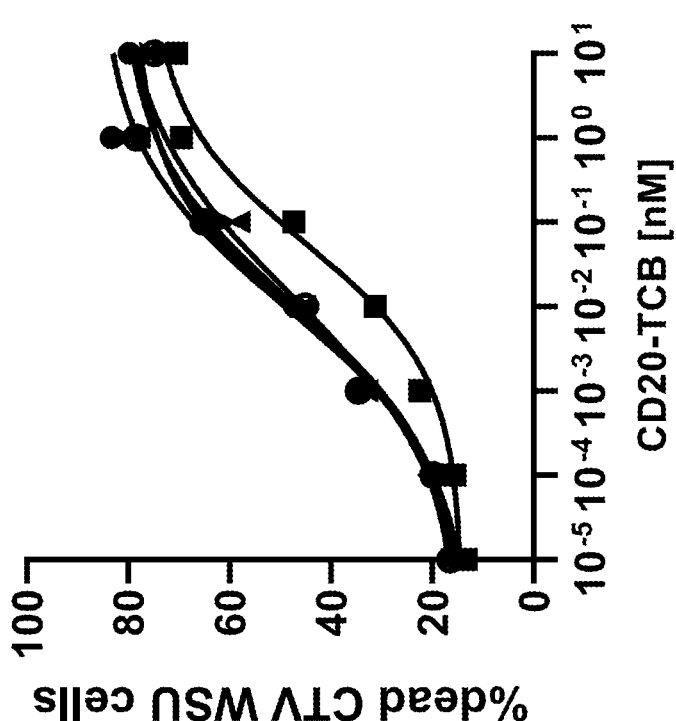

FIG. 48. Effect of escalating concentrations of baricitinib on CTV labelled WSU DLCL2 target cell killing induced by CD20-TCB. At 24 hours, the tumor cells and PBMCs from technical replicates were pooled and stained with a LIVE/DEAD™ Near-IR dye to allow exclusion of dead CTV labelled WSU DLCL2 tumor cells by flow cytometry. 1 representative donor.

Figure 49:
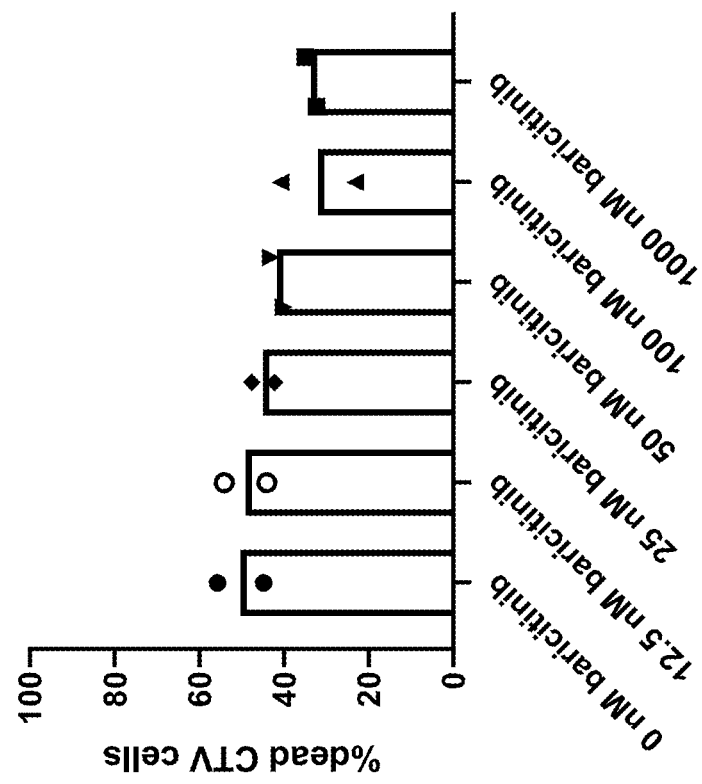

FIG. 49. Effect of escalating concentrations of baricitinib on CTV labelled WSU DLCL2 target cell killing induced by 1 nM CD20-TCB. At 24 hours, the tumor cells and PBMCs from technical replicates were pooled and stained with a LIVE/DEAD™ Near-IR dye to allow exclusion of dead CTV labelled WSU DLCL2 tumor cells by flow cytometry. Mean of n=2 donors.

FIG. 50. Effect of escalating concentrations of baricitinib on CD69 on CD4+(A) and CD8+(B) T cells and CD25 expression on CD4+(C) and CD8+(D) T cells induced by CD20-TCB. At 24 hours, the technical replicates were pooled and the expression of CD69 and CD25 was measured on CD4+ and CD8+ T cells by flow cytometry. 1 representative donor.

Figure 51:
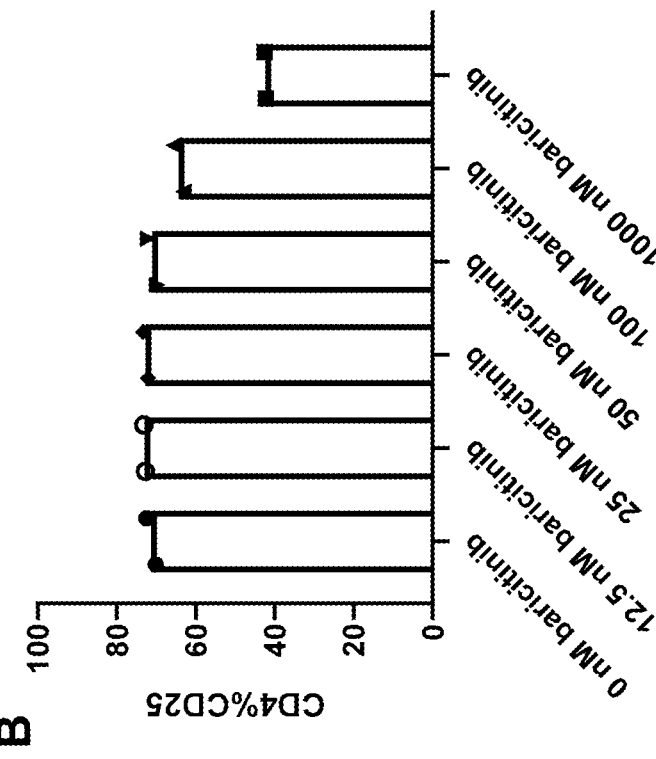
Figure 51:
Figure 51:
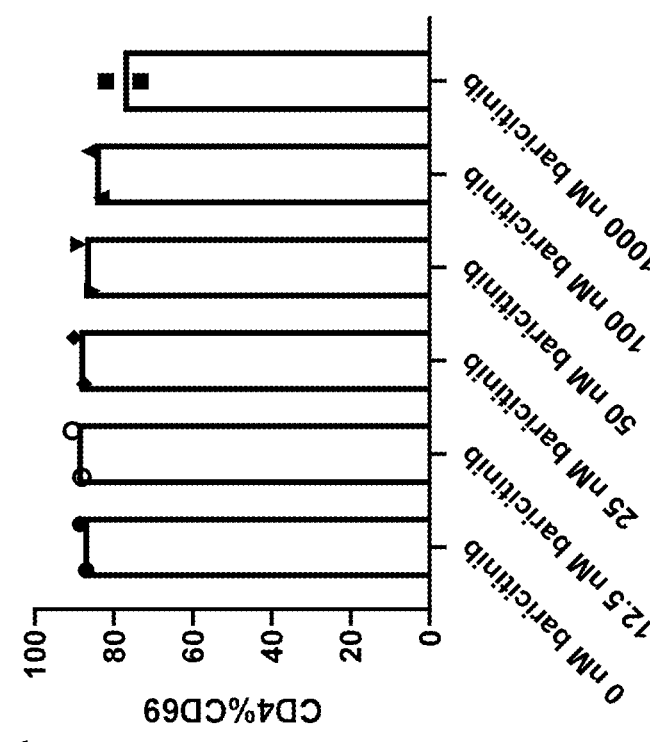

FIG. 51. Effect of escalating concentrations of baricitinib on CD69 (A) and CD25 (B) expression on CD4+ T cells for 1 nM CD20-TCB. At 24 hours, the technical replicates were pooled and the expression of CD69 and CD25 was measured on CD4+ T cells by flow cytometry. Mean of n=2 donors.

FIG. 52. Effect of escalating concentrations of baricitinib on CD69 (A) and CD25 (B) expression on CD8+ T cells for 1 nM CD20-TCB. At 24 hours, the technical replicates were pooled and expression of CD69 and CD25 was measured on CD8+ T cells by flow cytometry. Mean of n=2 donors.

FIG. 53. Effect of escalating concentrations of baricitinib on IFN-γ (A), IL-2 (B), TNF-α (C), GM-CSF (D), IL-6 (E), IL-8 (F) levels in a killing assay for a dose-response of CD20-TCB. At 24 hours, the supematants from technical replicates were pooled and cytokines were analyzed by Luminex. 1 representative donor.

Figure 54:
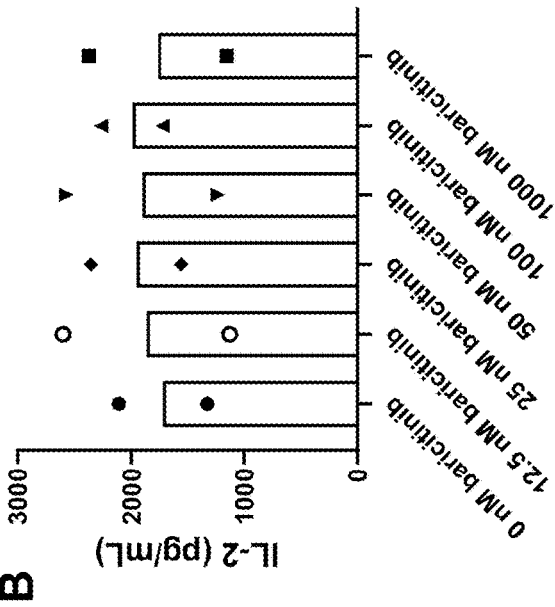
Figure 54:
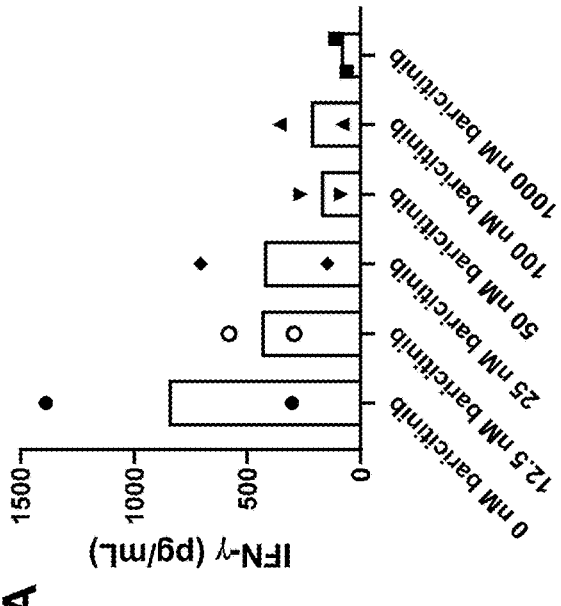
Figure 54:
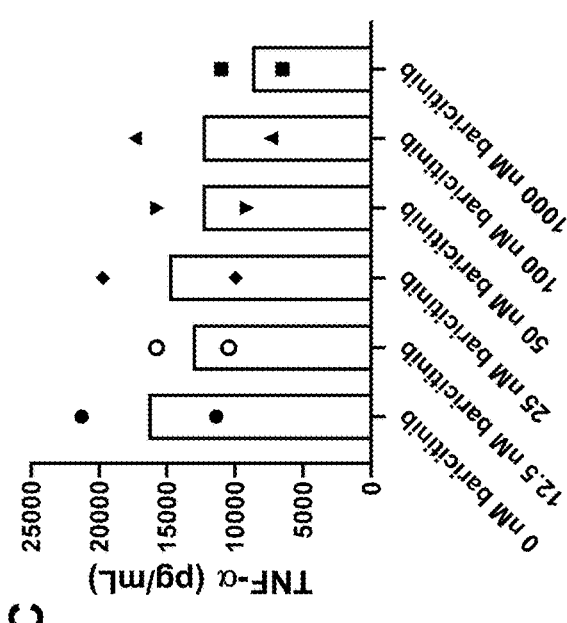
Figure 54:
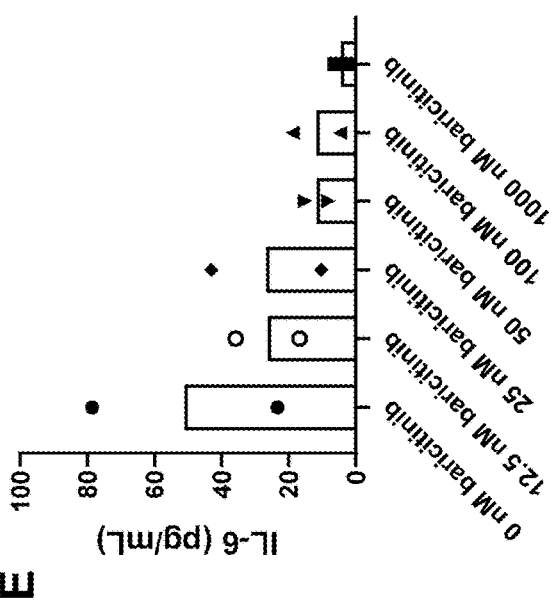
Figure 54:
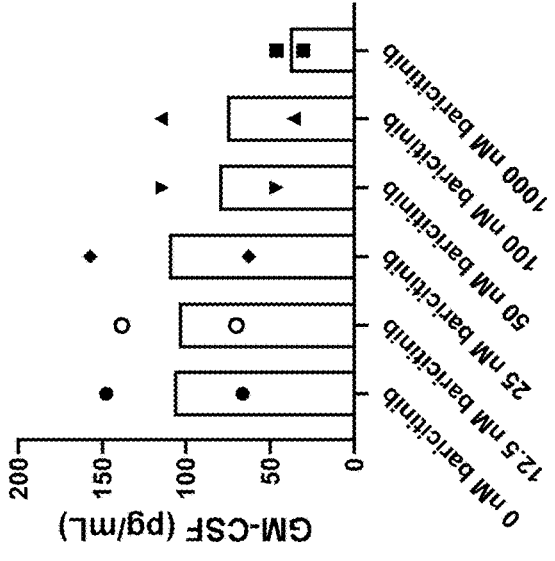
Figure 54:
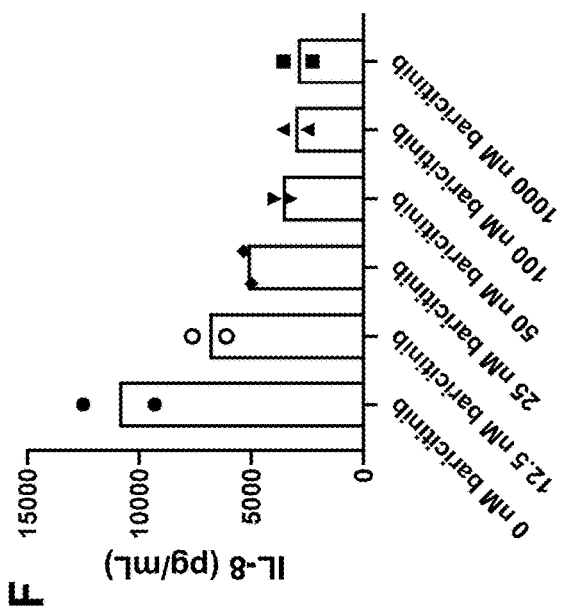

FIG. 54. Effect of escalating concentrations of baricitinib on IFN-γ (A), IL-2 (B), TNF-α (C), GM-CSF (D), IL-6 (E), IL-8 (F) levels for 1 nM CD20-TCB. At 24 hours, the supematants from technical replicates were pooled and cytokines were analyzed by Luminex. Mean of n=2 donors.

Figure 55:
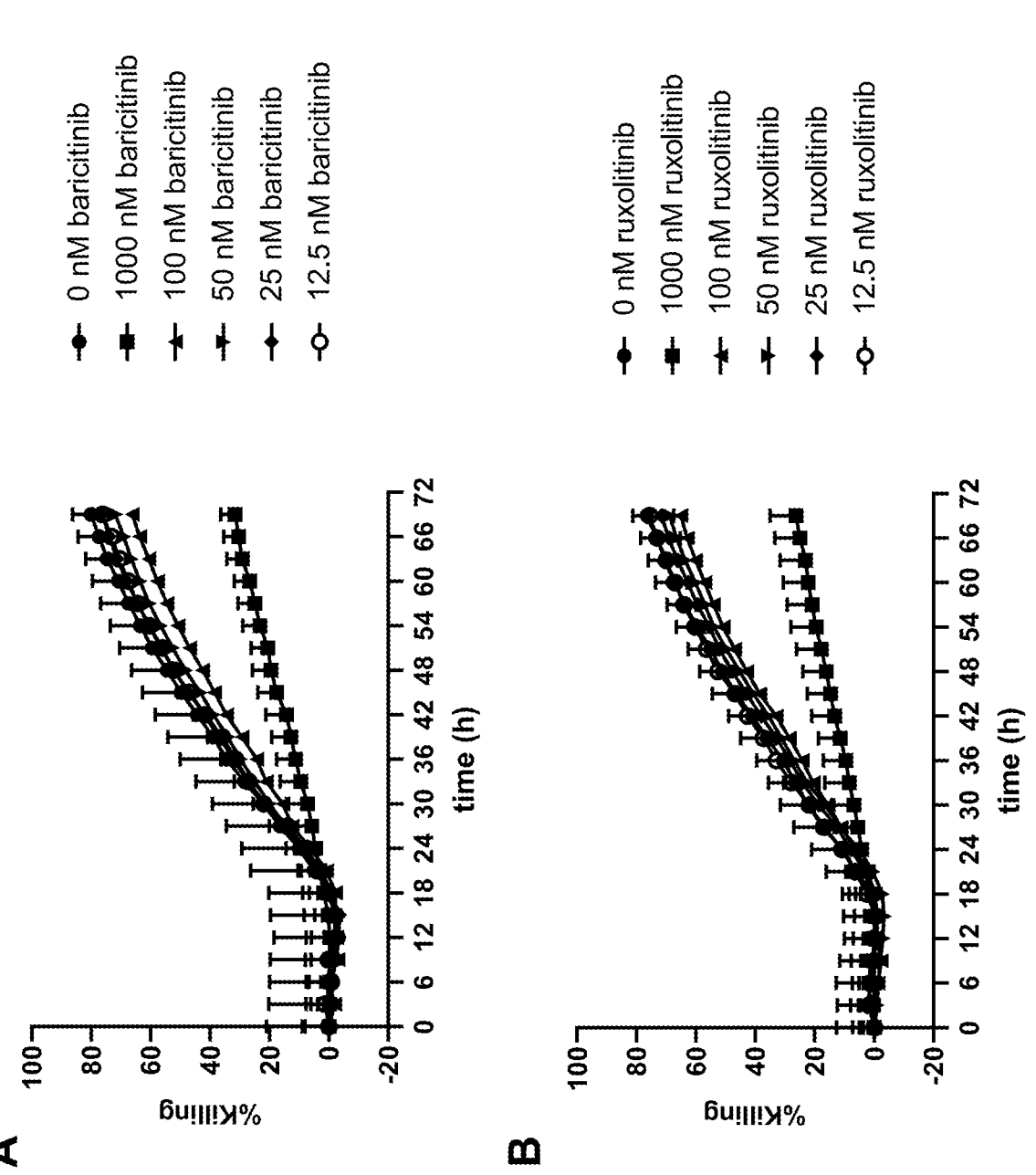

FIG. 55. Real-time killing of MKN45 NLR cells by 1 nM CEA-TCB in the presence of baricitinib (A) and ruxolitinib (B) concentrations ranging from 0 nM to 1000 nM. MKN45 NLR target cells were co-cultured with PBMCs (E:T=50 000 PBMCs:5000 target cells) in medium supplemented with 1 nM CEA-TCB and the JAK inhibitors. The killing was followed using an Incucyte® (1 scan every 3 hours, zoom 10×, phase and red 400 ms acquisition time). % Killing was measured by normalizing total red area with values at t=0 hour and target cells+PBMCs+ruxolitinib or baricitinib control wells for each time point. Means of technical replicates+SEM for 1 representative donor.

Figure 56:
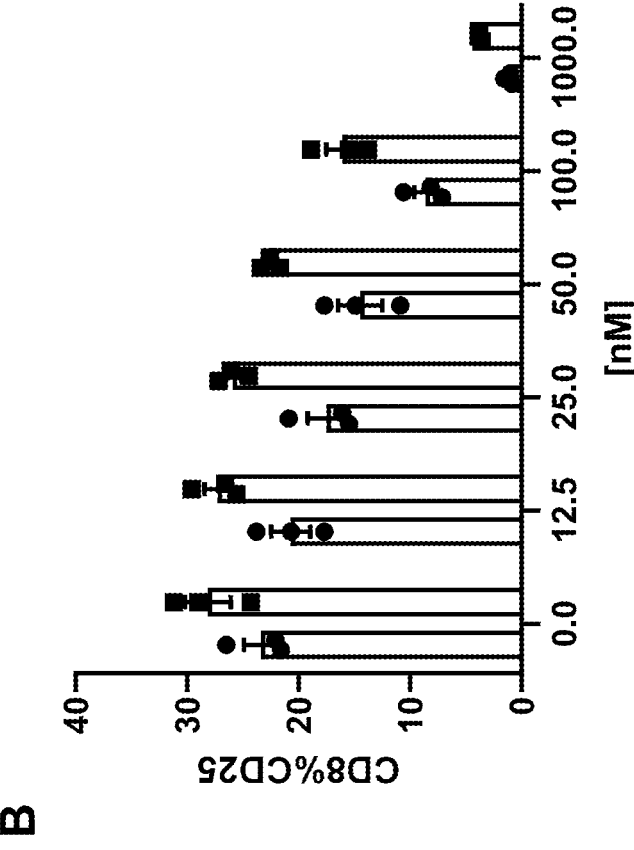
Figure 56:
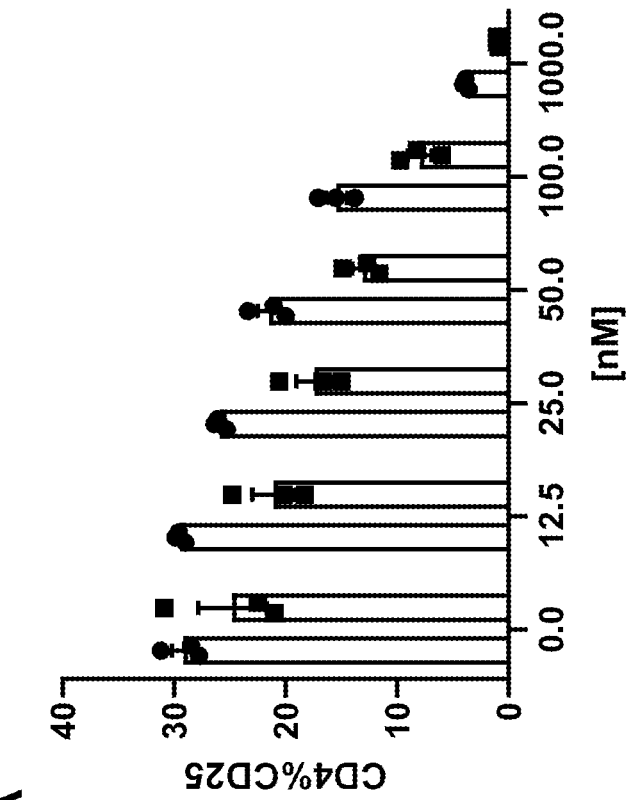

FIG. 56. Effect of escalating concentrations of baricitinib vs. ruxolitinib on CD25 expression on CD4+(A) and CD8+ (B) T cells at 72 hours, after treatment with 10 nM CEA-TCB. Technical replicates were pooled and the expression of CD25 on CD4+ and CD8+ T cells was measured by flow cytometry at 69 hours. Mean of n=3 donors+/−SD.

Figure 57:
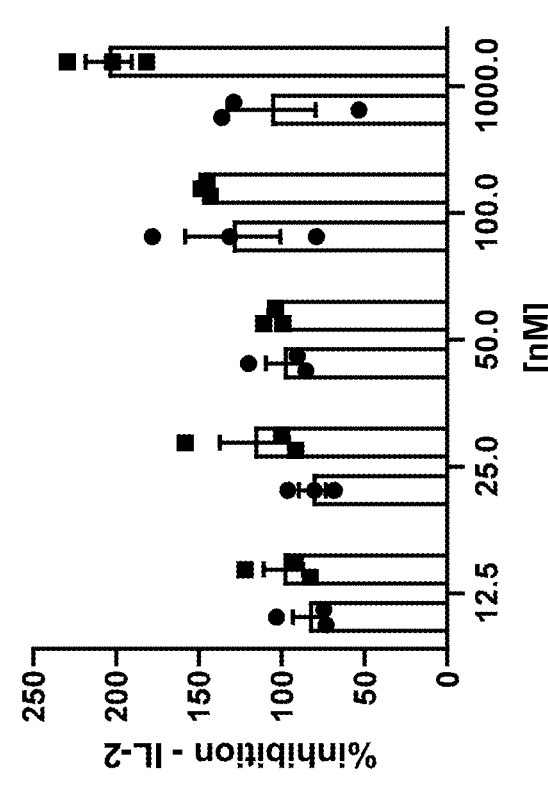
Figure 57:
Figure 57:
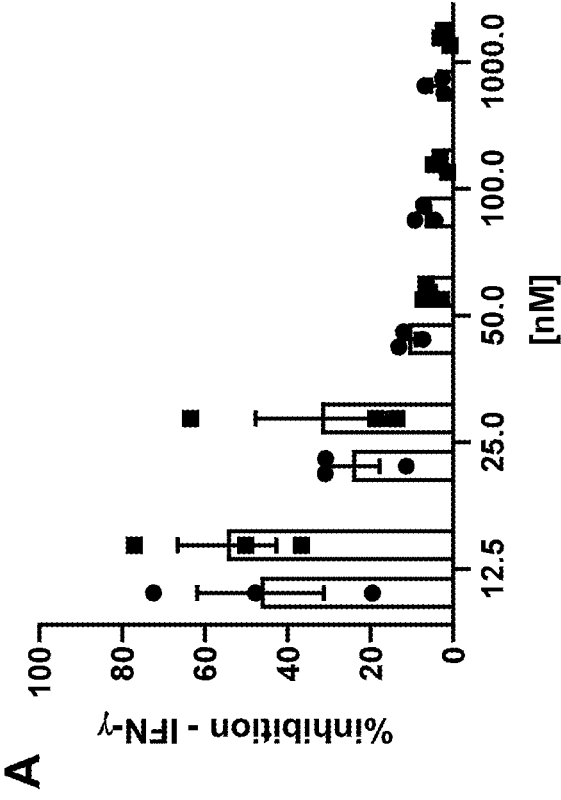
Figure 57:
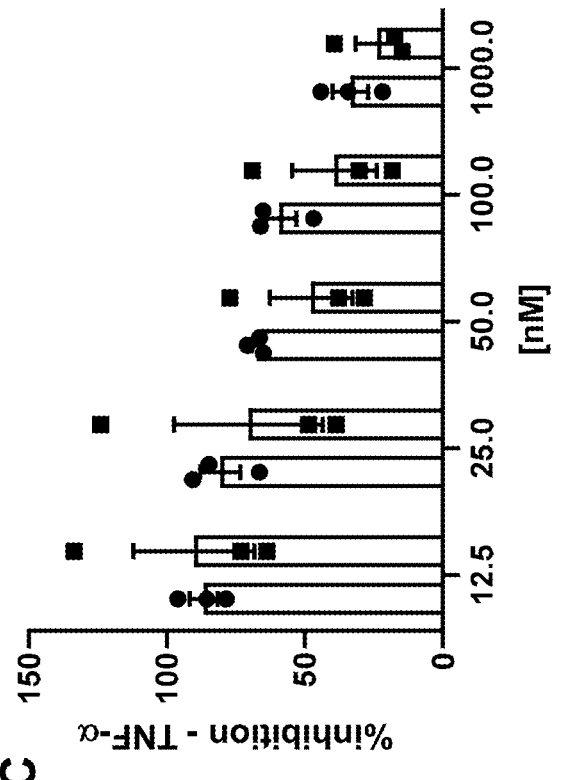
Figure 57:
Figure 57:
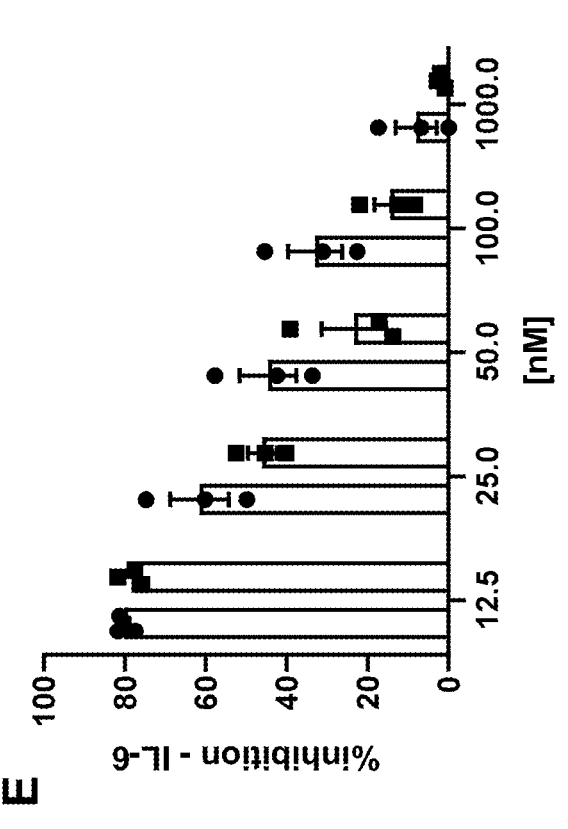
Figure 57:
Figure 57:
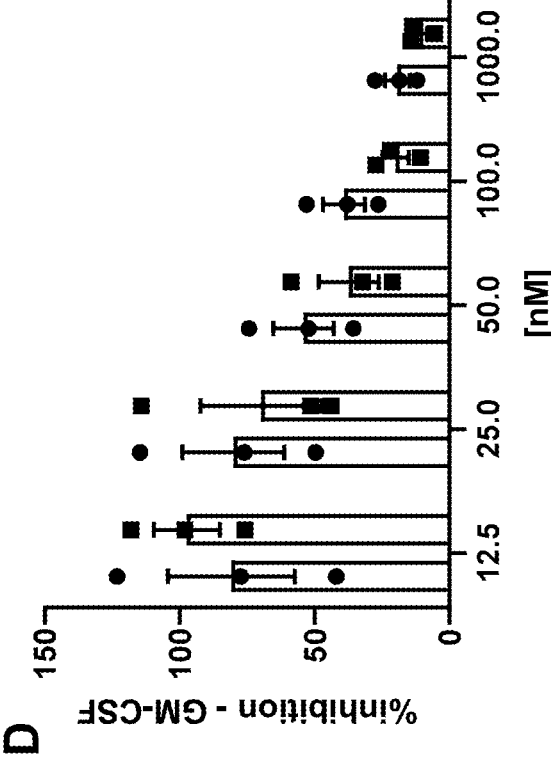
Figure 57:
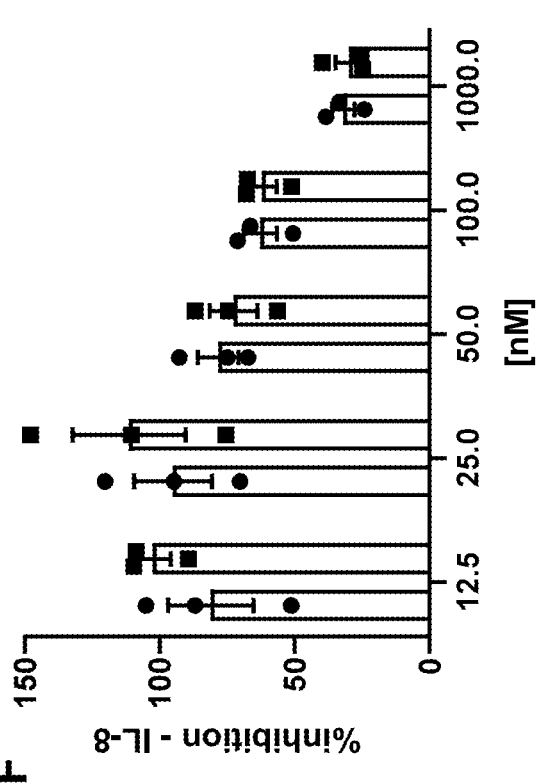

FIG. 57. Effect of escalating concentrations of baricitinib vs. ruxolitinib on IFN-γ (A), IL-2 (B), TNF-α (C), GM-CSF (D), IL-6 (E), IL-8 (F) release after treatment with 10 nM CEA-TCB. At 24 hours, the supematants from technical replicates were pooled and cytokines were analyzed by Luminex. % inhibition was calculated by normalizing the cytokines levels for each kinase inhibitor concentration to the condition where no kinase inhibitor was added. Mean of n=3 donors+/−SEM.

Figure 58:
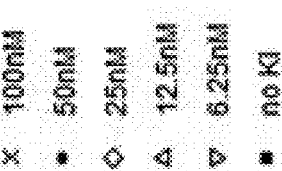
Figure 58:
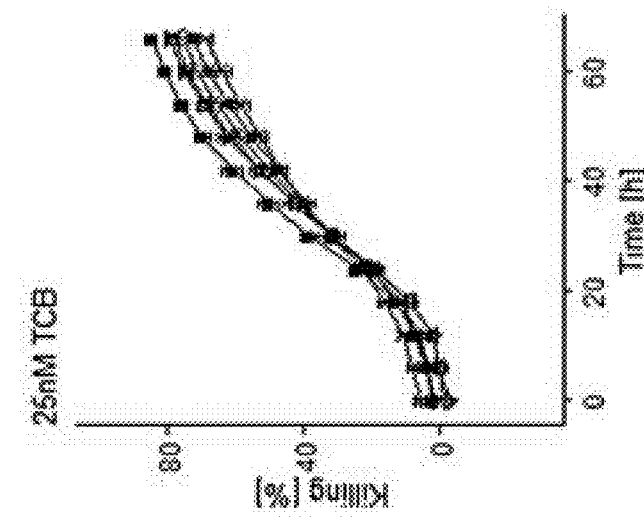
Figure 58:
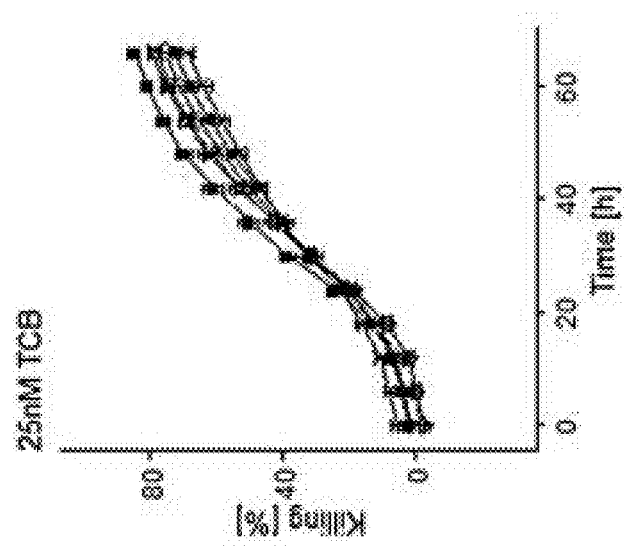

FIG. 58. Real time killing of A375 NucLightRed (NLR) cells by 25 nM MAGEA4-TCB in the presence of escalating concentrations of baricitinib (A) and ruxolitinib (B) ranging from 0 nM to 100 nM. A375 NLR target cells were co-cultured with PBMCs (E:T=50 000 PBMCs: 5000 target cells) in medium supplemented with 25 nM MAGEA4-TCB and the JAK inhibitors. The killing was followed using an Incucyte® (1 scan every 3 hours, zoom 10×, phase and red 400 ms acquisition time). Killing [%] was measured by normalizing total red area with values at t=0 hour and target cells+PBMCs+JAK inhibitors control wells for each time point. Means of technical replicates+/−SD for 1 representative donor.

Figure 59:
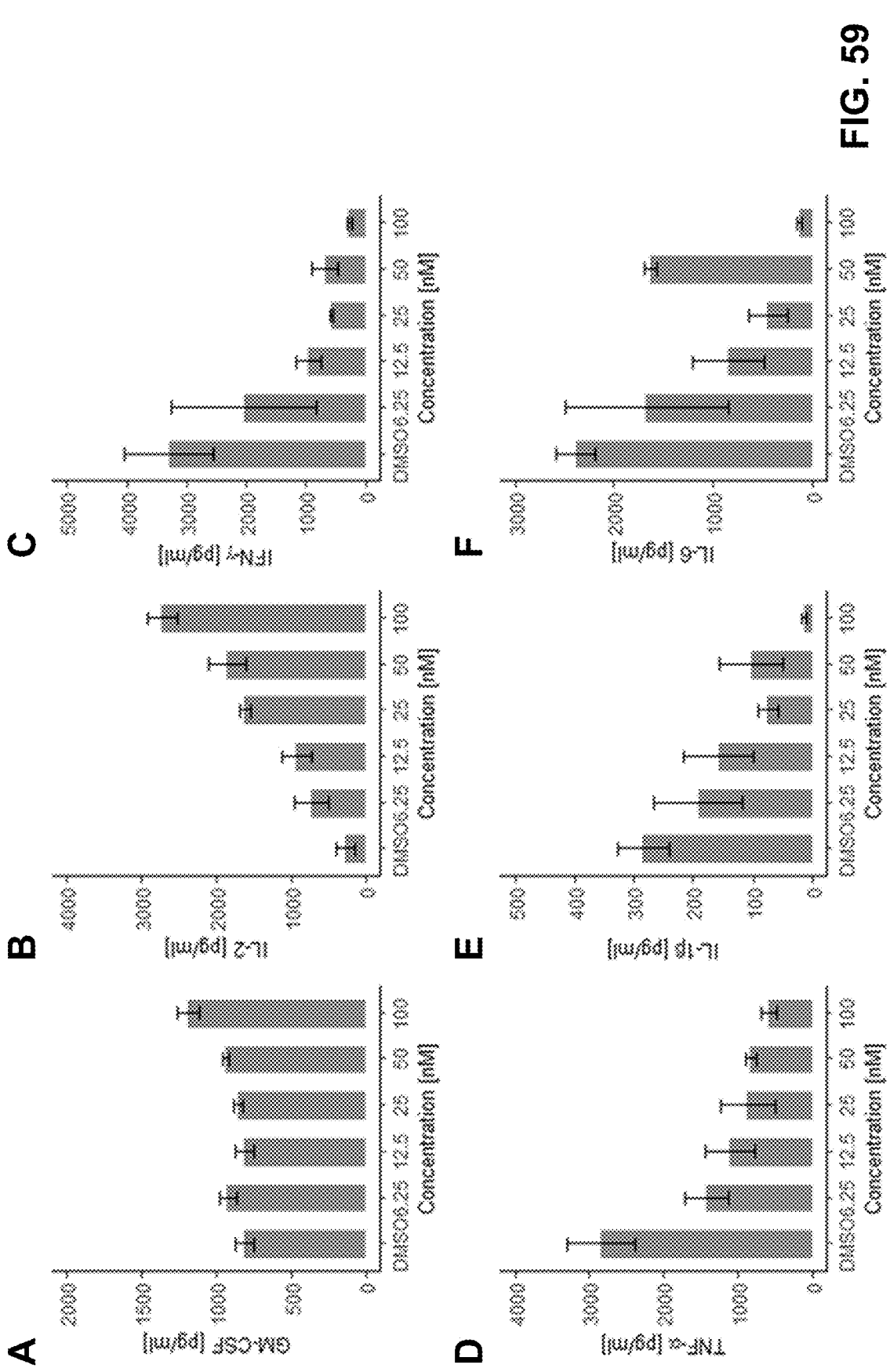

FIG. 59. Effect of escalating concentrations (0-100 nM) of baricitinib on GM-CSF (A), IL-2 (B), IFN-γ (C), TNF-α (D), IL-1β (E) and IL-6 (F) levels induced by 25 nM MAGEA4-TCB. At 69 hours, the supematants were collected and cytokines were analyzed by CBA. Mean of technical replicates+/−SD for 1 representative donor.

Figure 60:
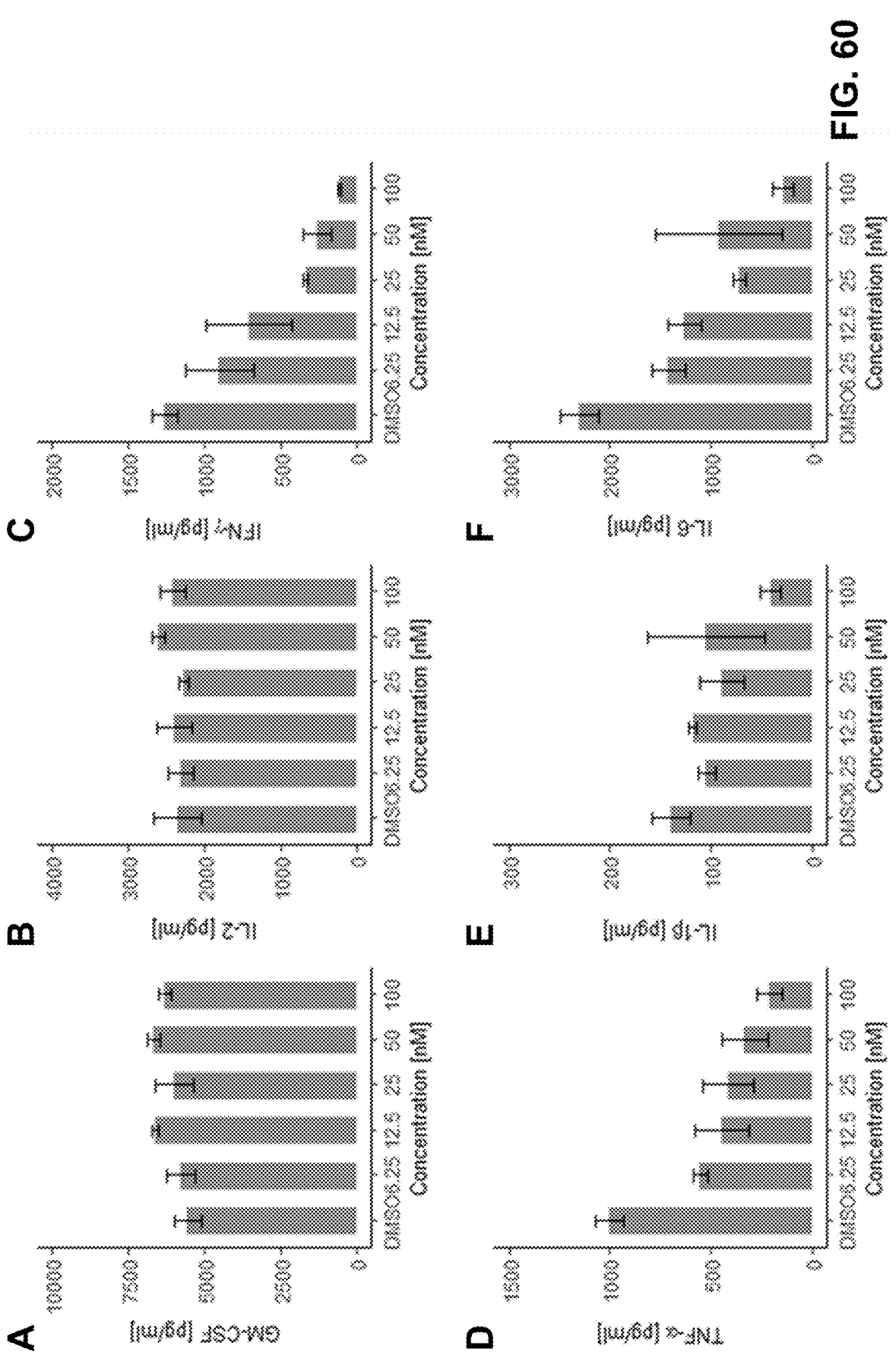

FIG. 60. Effect of escalating concentrations (0-100 nM) of ruxolitinib on GM-CSF (A), IL-2 (B), IFN-γ (C), TNF-α (D), IL-1β (E) and IL-6 (F) levels induced by 25 nM MAGEA4-TCB. At 69 hours, the supematants were collected and cytokines were analyzed by CBA. Mean of technical replicates+/−SD for 1 representative donor.

Figure 61:
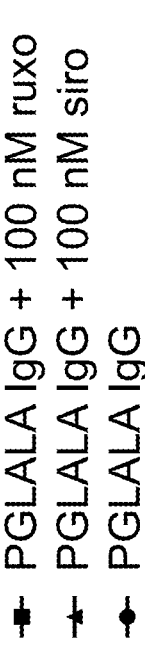
Figure 61:
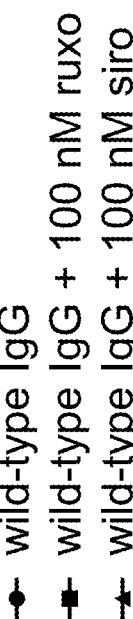
Figure 61:
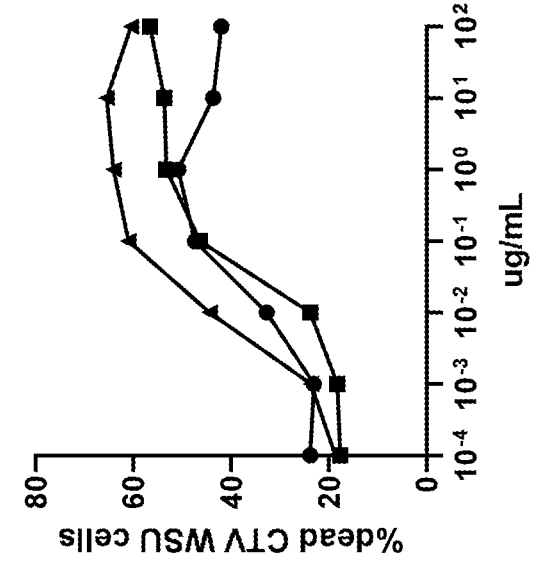
Figure 61:
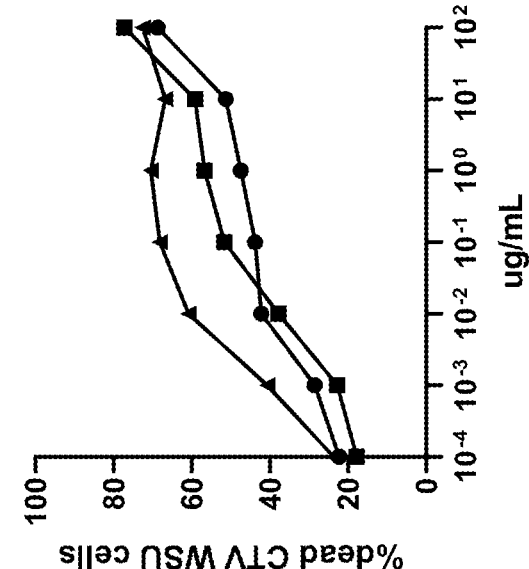

FIG. 61. CTV labelled WSU tumor cell killing by PGLALA CAR-T cells (A) and CD16 CAR-T cells (B) in the presence and absence of 100 nM ruxolitinib or 100 nM sirolimus. PGLALA CAR-T cells and CD16 CAR-T cells were co-cultured together with CTV labelled WSU tumor cells (E:T=10:1) and escalating concentrations of anti-CD20 IgG with either PGLALA-Fc (for PGLALA CAR-T cells) or wild-type Fc (for CD16 CAR-T cells) in the presence and absence of 100 nM ruxolitinib (ruxo) or 100 nM sirolimus (siro). At 24 hours, the technical replicates were pooled and stained with a LIVE/DEAD™ Near-IR dye to allow exclusion of dead CTV labelled WSU DLCL2 tumor cells by flow cytometry. 1 representative donor.

Figure 62:
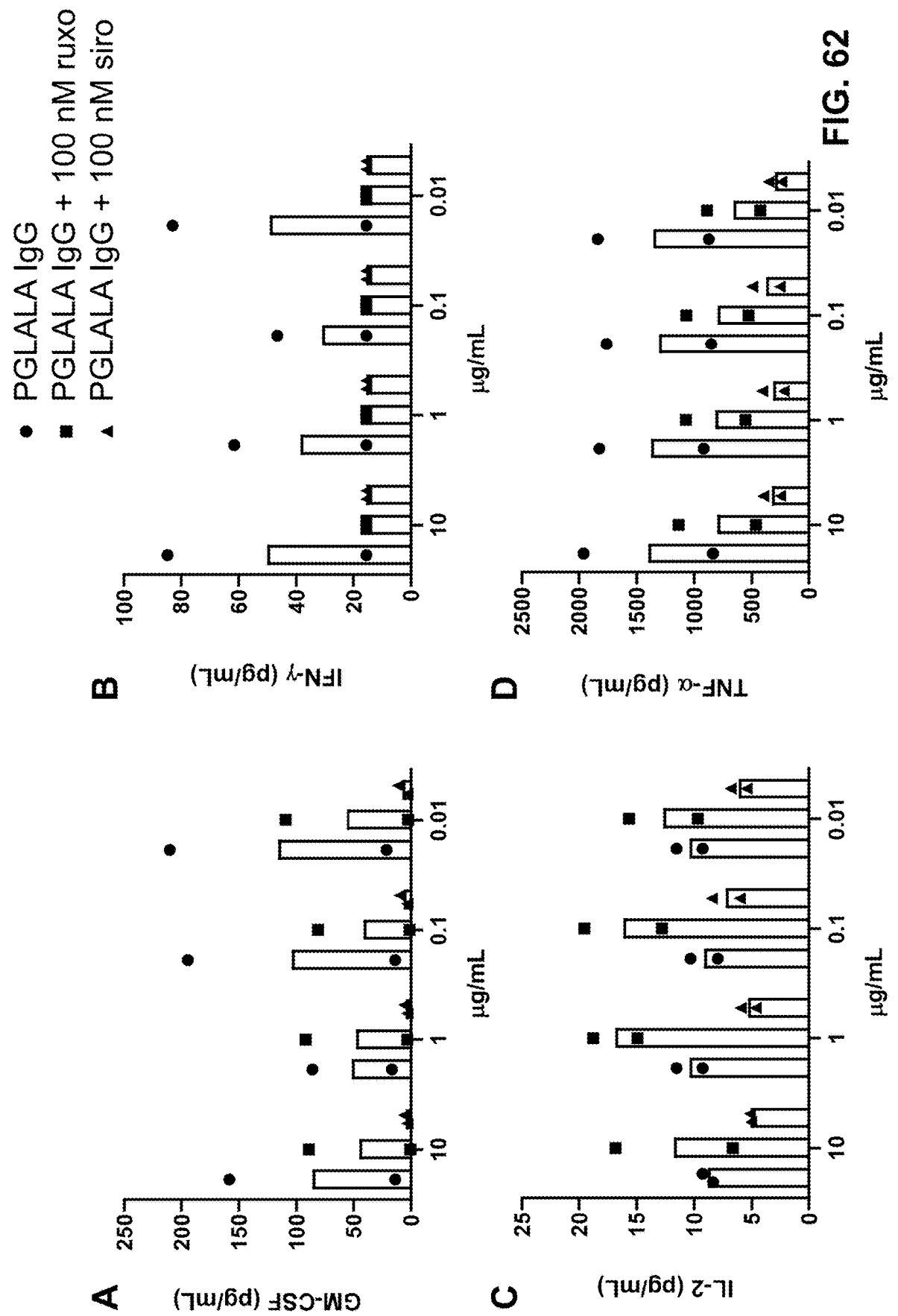

FIG. 62. Effect of 100 nM ruxolitinib and 100 nM sirolimus on GM-CSF (A), IFN-γ (B), IL-2 (C) and TNF-α (D) induced by PGLALA CAR-T cells. PGLALA CAR-T cells were co-cultured together with CTV labelled WSU tumor cells (E:T=10:1) and escalating concentrations of PGLALA-Fc anti-CD20 IgG in the presence and absence of 100 nM ruxolitinib (ruxo) or 100 nM sirolimus (siro) respectively. At 24 hours, the supernatants from technical replicates were pooled and cytokines were analyzed by Luminex. Mean of n=2 donors.

Figure 63:
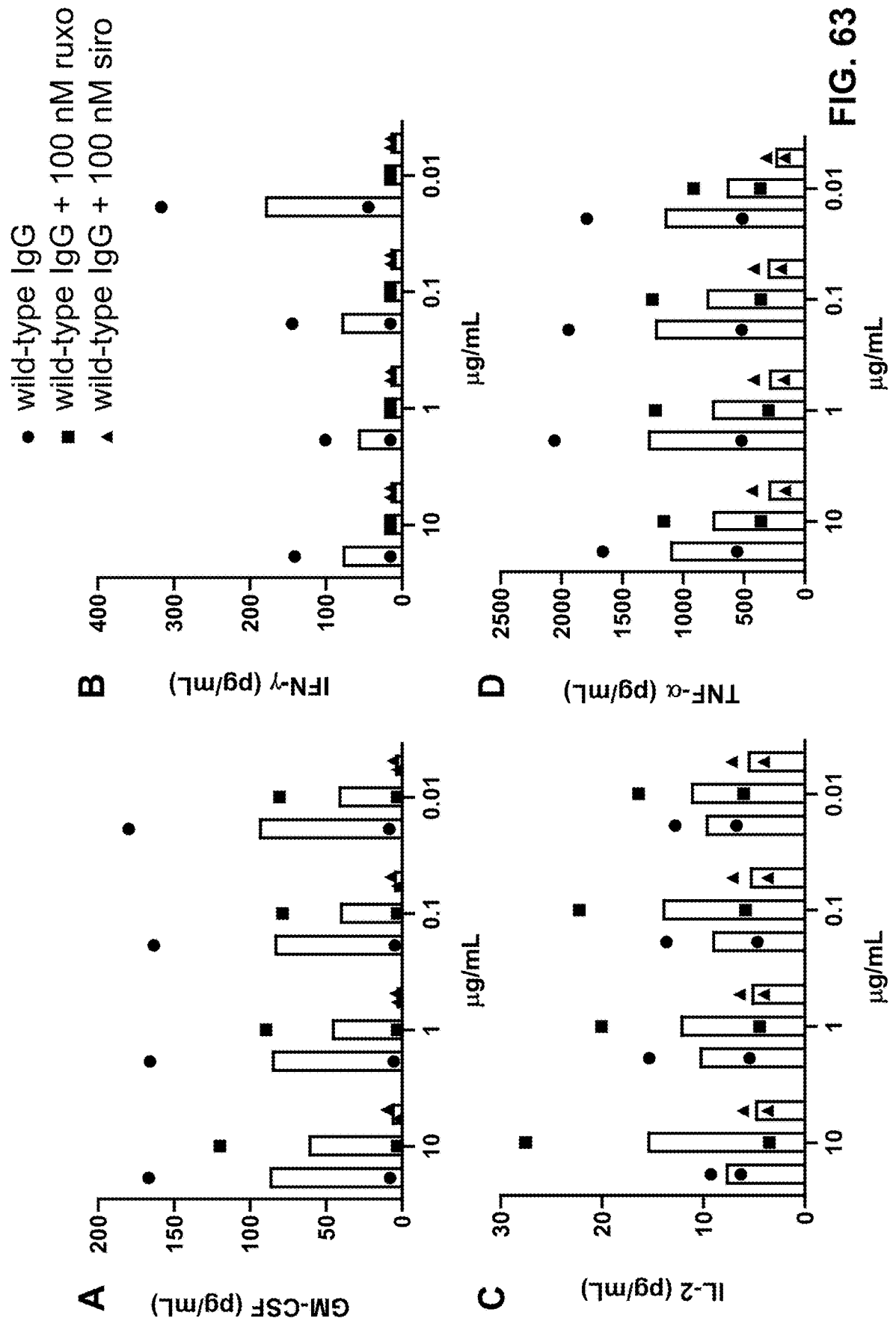

FIG. 63. Effect of 100 nM ruxolitinib and 100 nM sirolimus on GM-CSF (A), IFN-γ (B), IL-2 (C) and TNF-α (D) induced by CD16 CAR-T cells. CD16 CAR-T cells were co-cultured together with CTV labelled WSU tumor cells (E:T=10:1) and escalating concentrations of wild-type Fc anti-CD20 IgG in the presence and absence of 100 nM ruxolitinib (ruxo) or 100 nM sirolimus (siro). At 24 hours, the supernatants from technical replicates were pooled and cytokines were analyzed by Luminex. Mean of n=2 donors.

Figure 64:
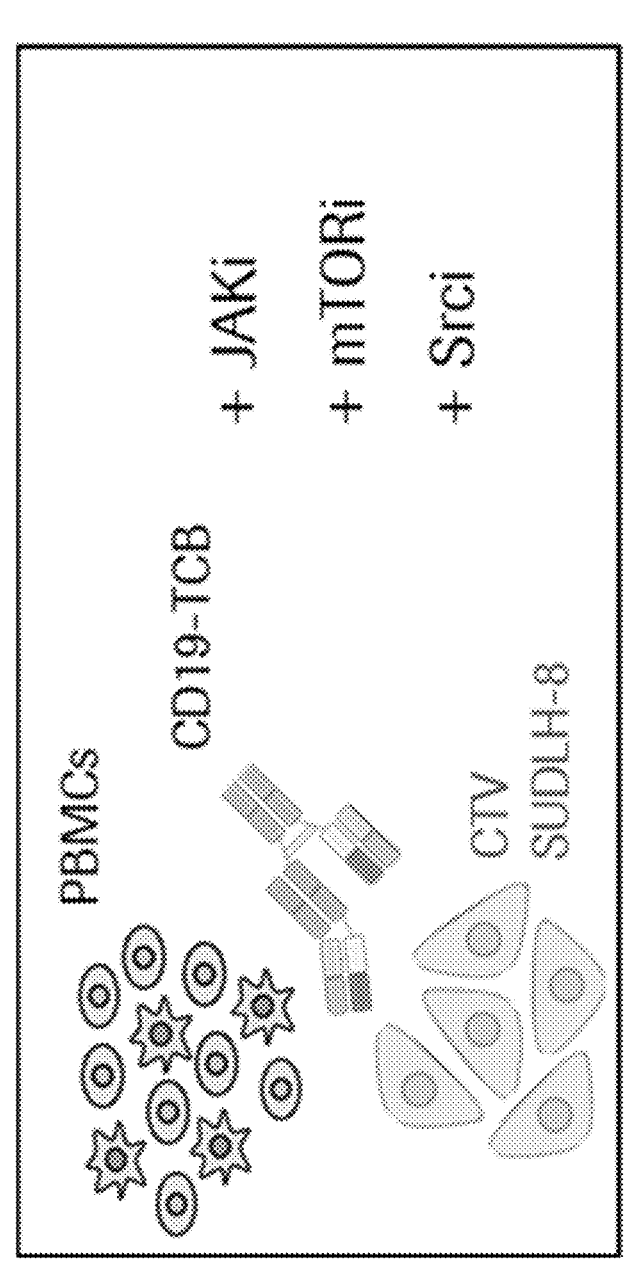

FIG. 64. In vitro killing assay set-up. PBMCs were co-cultured with CellTrace™ Violet (CTV) labelled SUDLH-8 tumor cells (E:T=10:1) in the presence of escalating concentrations of CD19-TCB in media supplemented with the different kinase inhibitors (100 nM) for 24 hrs.

Figure 65:
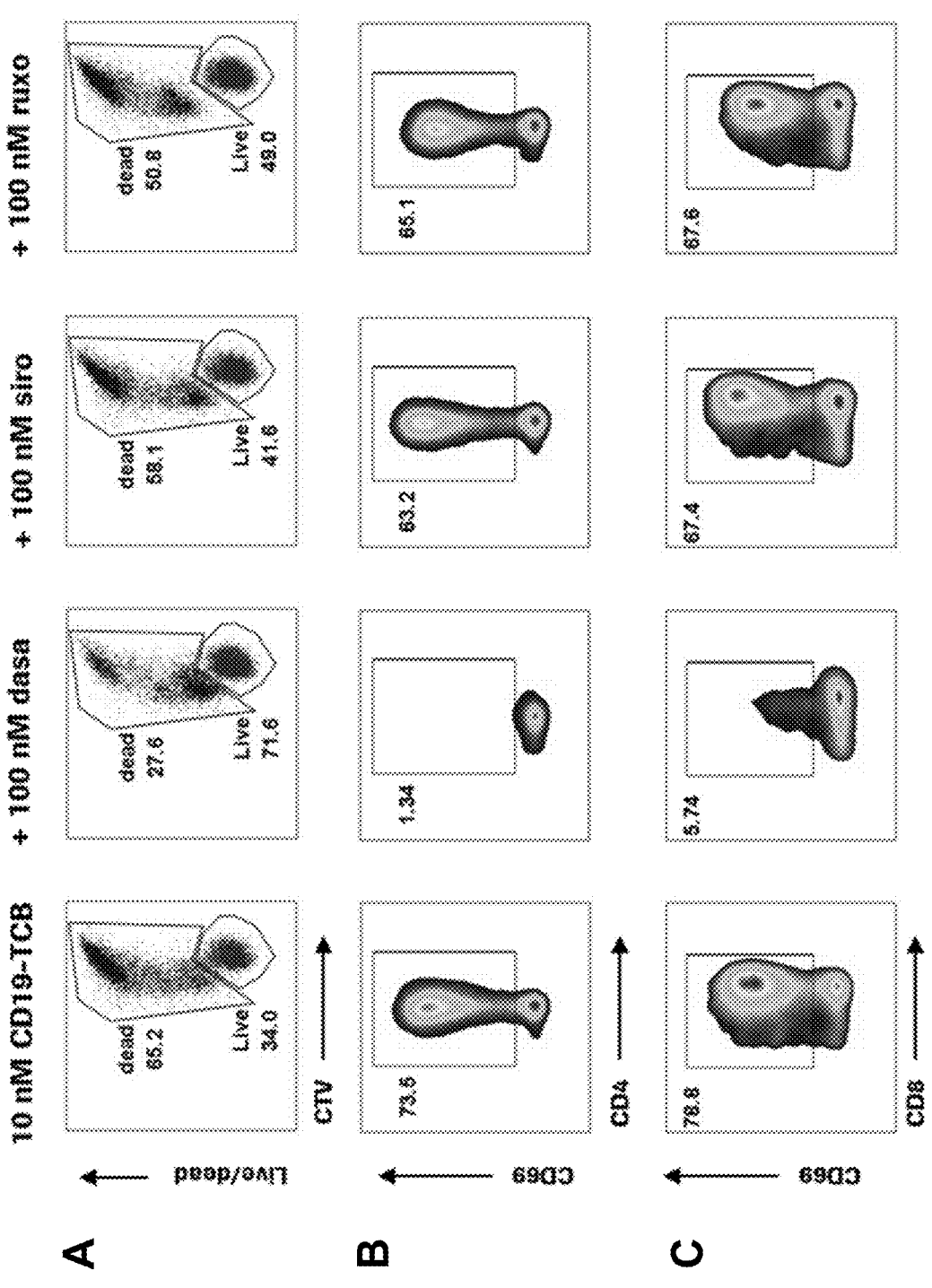
Figure 65:
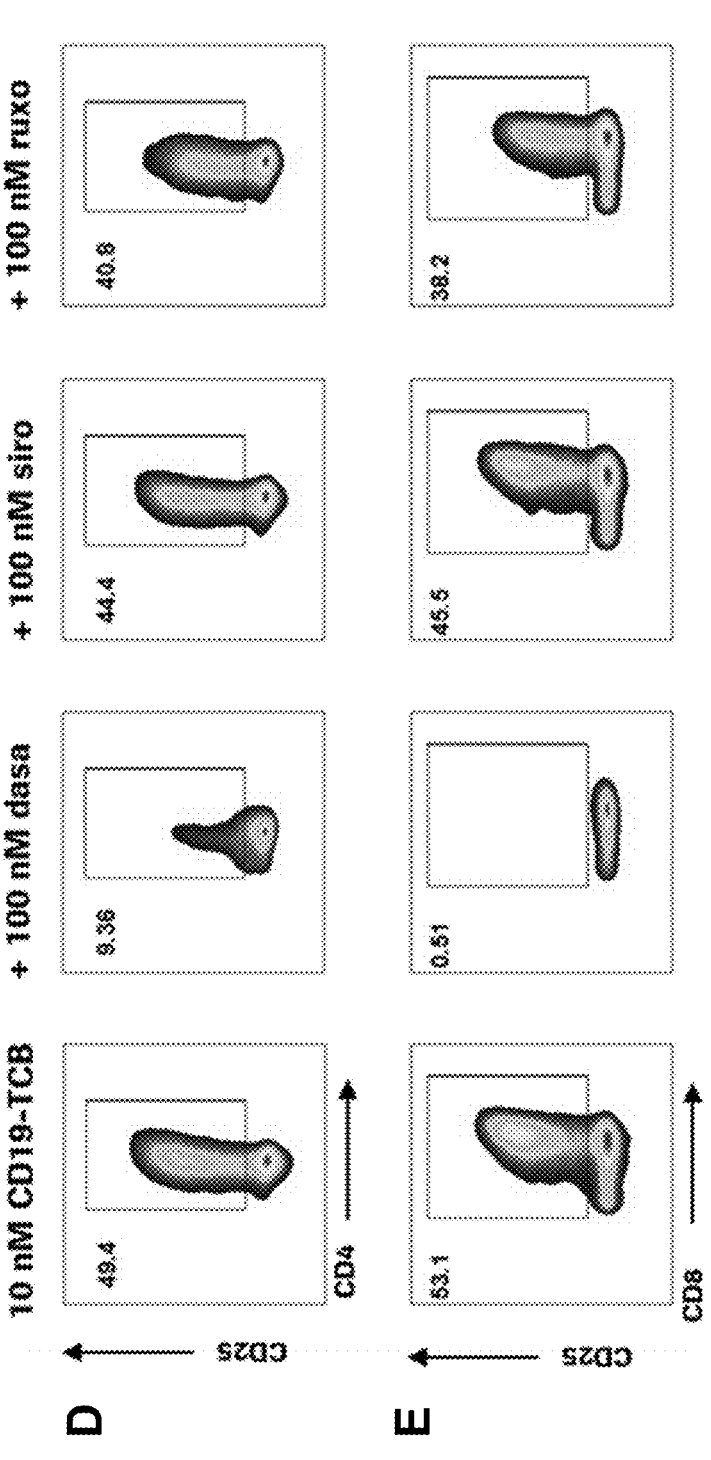

FIG. 65. Effect of 100 nM dasatinib (Src inhibitor), sirolimus (mTOR inhibitor) and ruxolitinib (JAK1/2 inhibitor) on CD19-TCB-induced SUDLH-8 killing (A) and T cell activation (B, C, D, E) in the assay of FIG. 64 (24 hrs). Representative flow cytometry plots of dead CTV labelled SUDLH-8 cells (A) excluded from live cells using a Live/Dead stain, and of CD69 expression on CD4+(B) and CD8+(C) T cells, and CD25 expression on CD4+(D) and CD8+(E) T cells. 1 representative donor out of 3, 10 nM CD19-TCB.

Figure 66:
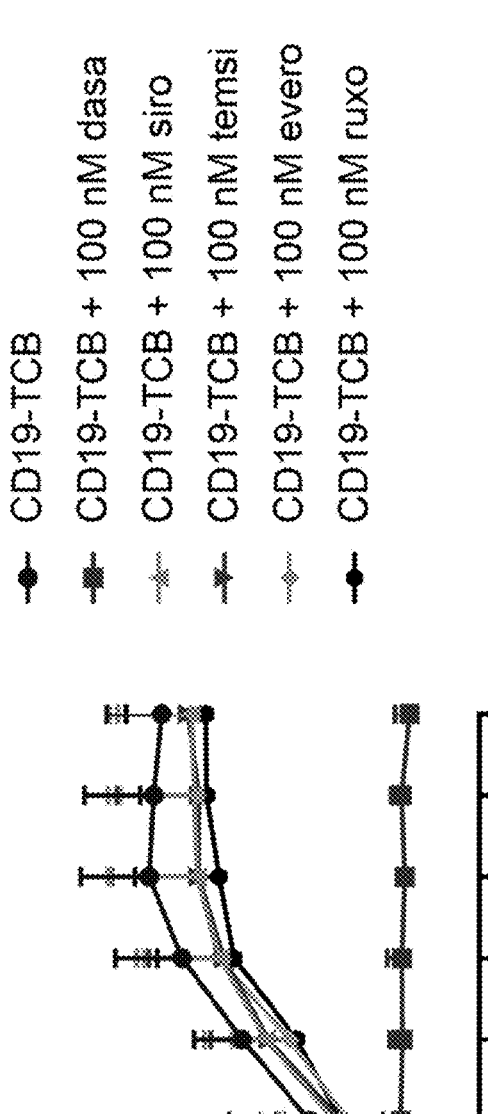

FIG. 66. Effect of 100 nM dasatinib (dasa), 100 nM sirolimus (siro), 100 nM temsirolimus (temsi), 100 nM everolimus (evero) and 100 nM ruxolitinib (ruxo) on CD19-TCB-dependent killing of CTV labelled SUDLH-8 cells in the assay of FIG. 64. The killing of CTV labelled SUDLH-8 cells was measured by flow cytometry at 24 hrs using a Live/Dead stain allowing for exclusion of dead cells. Mean of n=3 donors+standard deviation (SD).

Figure 67:
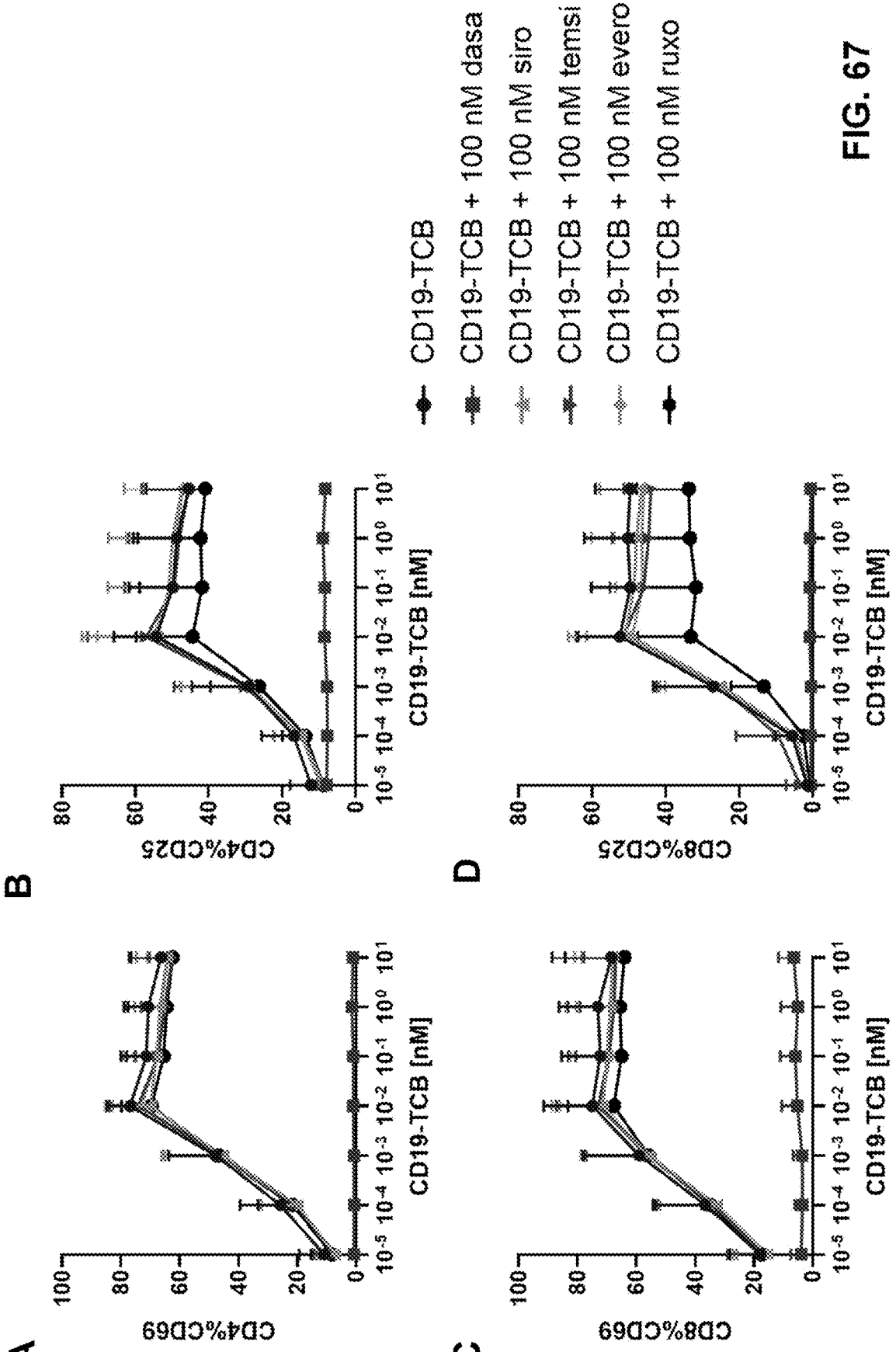

FIG. 67. Effect of 100 nM dasatinib (dasa), 100 nM sirolimus (siro), 100 nM temsirolimus (temsi), 100 nM everolimus (evero) and 100 nM ruxolitinib (ruxo) on CD19-TCB-dependent T cell activation in the assay of FIG. 64. The expression of CD69 and CD25 on CD4+(A, B) and CD8+(C, D) T cells was measured by flow cytometry at 24 hrs. Mean of n=3 donors+SD.

Figure 68:
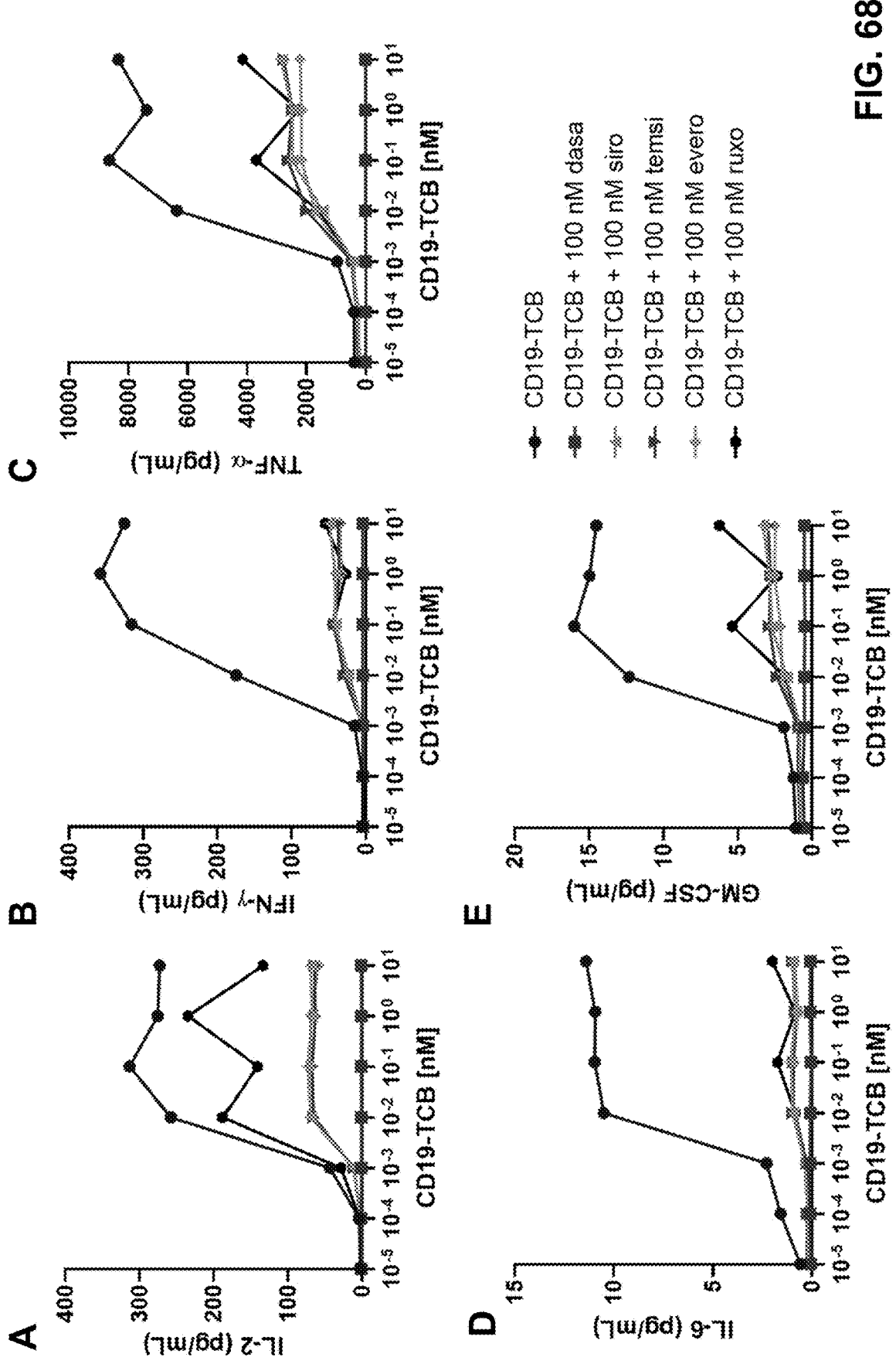

FIG. 68. Effect of 100 nM dasatinib (dasa), 100 nM sirolimus (siro), 100 nM temsirolimus (temsi), 100 nM everolimus (evero) and 100 nM ruxolitinib (ruxo) on CD19-TCB-dependent cytokine release in the assay of FIG. 64. The levels of IL-2 (A), IFN-γ (B), TNF-α (C), IL-6 (D) and GM-CSF (E) were measured in the supernatants by Luminex (24 hrs). 1 representative donor out of 3.

Figure 69:
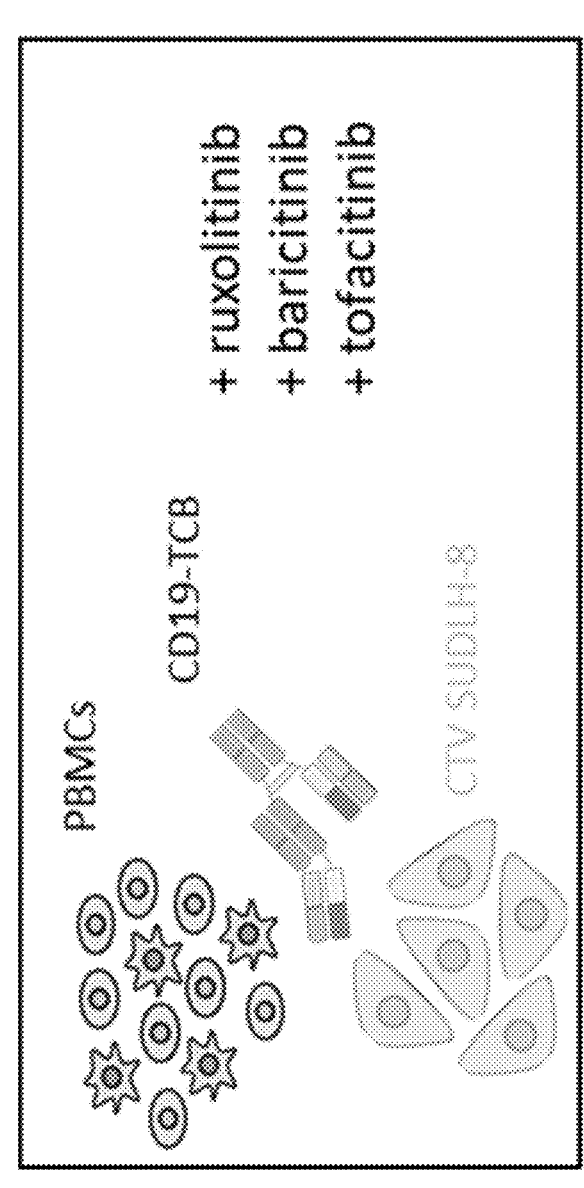

FIG. 69. In vitro killing assay set-up. PBMCs were co-cultured with CTV labelled SUDLH-8 cells (E:T=10:1) in the presence of escalating concentrations of CD19-TCB in media supplemented with the different JAK inhibitors (100 nM) for 24 hrs.

Figure 70:
Figure 70:
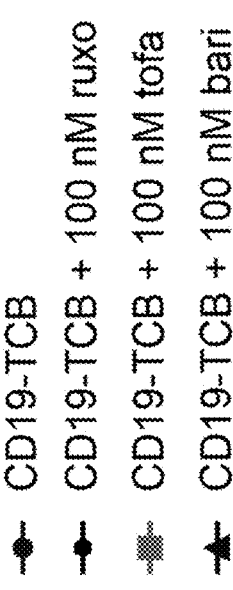
Figure 70:
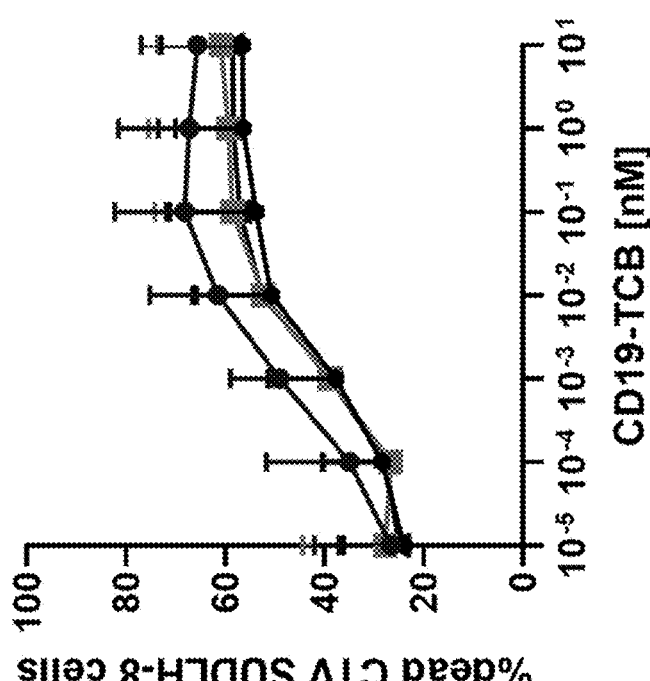

FIG. 70. Effect of 100 nM ruxolitinib (ruxo), 100 nM baricitinib (bari) and 100 nM tofacitinib (tofa) on CD19-TCB-dependent killing of CTV labelled SUDLH-8 cells in the assay of FIG. 69. The killing of CTV labelled SUDLH-8 cells was measured by flow cytometry at 24 hrs using a Live/Dead stain allowing for exclusion of dead cells. Mean of n=3 donors+SD.

Figure 71:
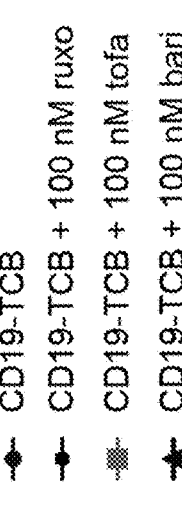
Figure 71:
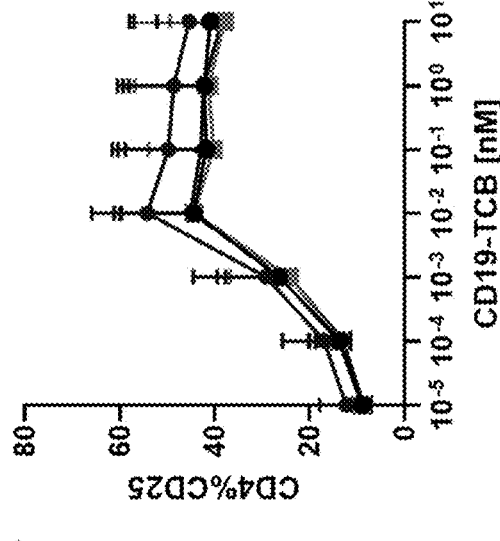
Figure 71:
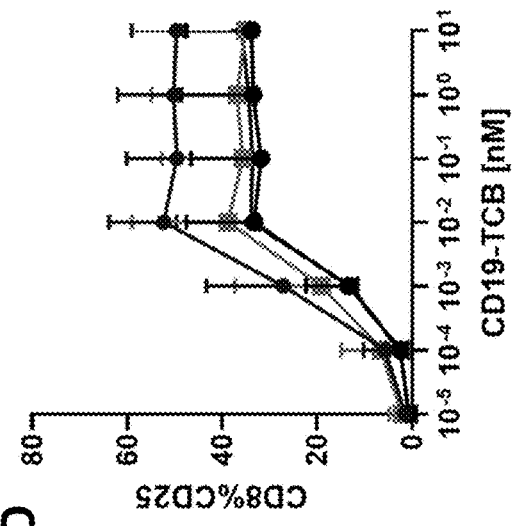
Figure 71:
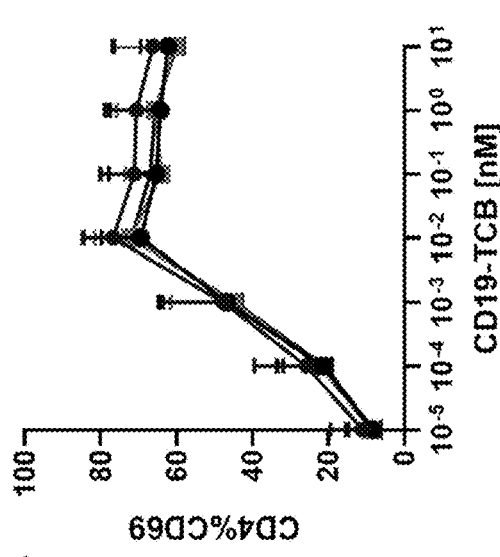
Figure 71:
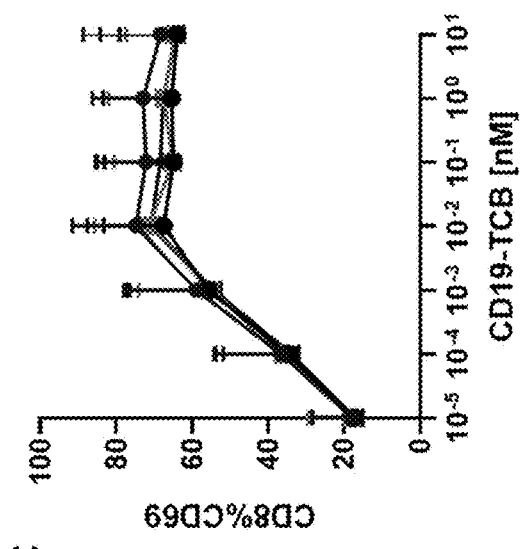

FIG. 71. Effect of 100 nM ruxolitinib (ruxo), 100 nM baricitinib (ban) and 100 nM tofacitinib (tofa) on CD19-TCB-dependent T cell activation in the assay of FIG. 69. The expression of CD69 and CD25 on CD4+(A, B) and CD8+(C, D) T cells was measured by flow cytometry at 24 hrs. Mean of n=3 donors+SD.

Figure 72:
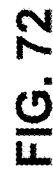
Figure 72:
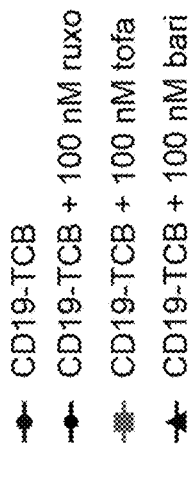
Figure 72:
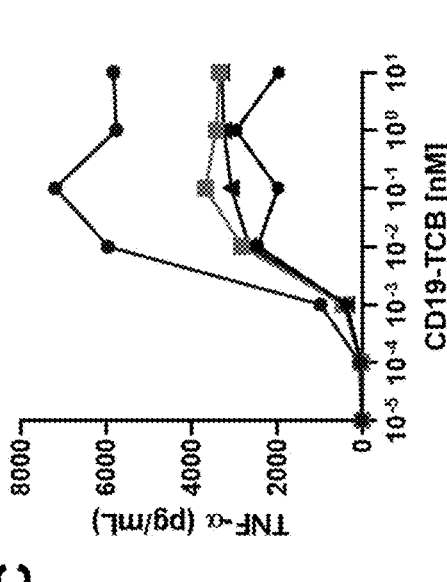
Figure 72:
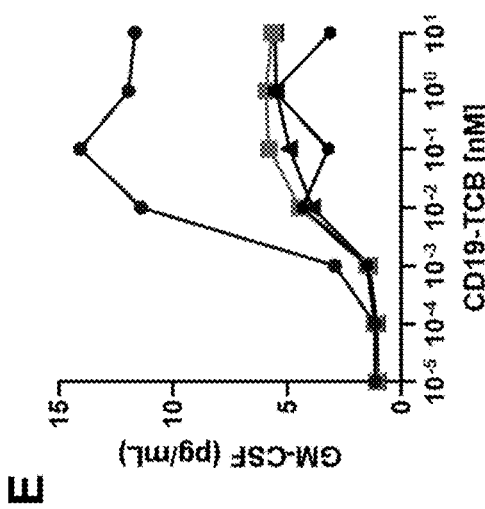
Figure 72:
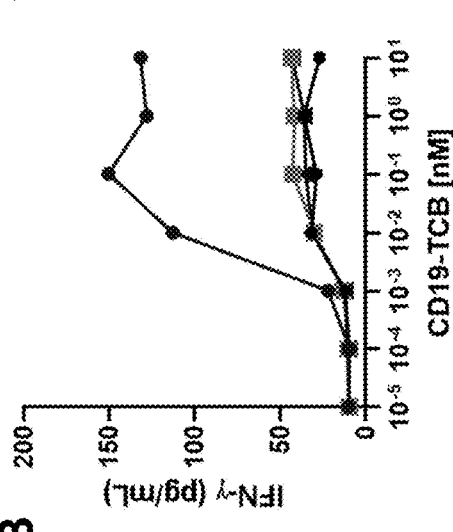
Figure 72:
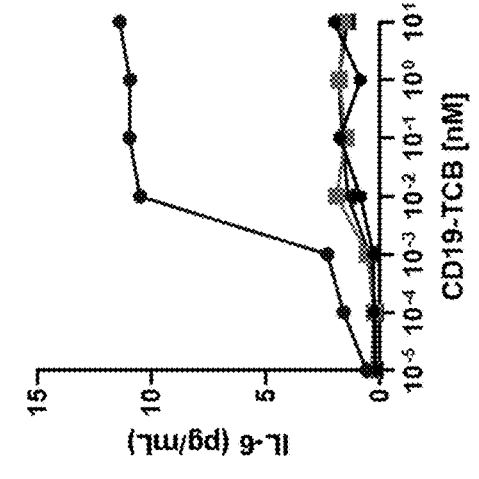
Figure 72:
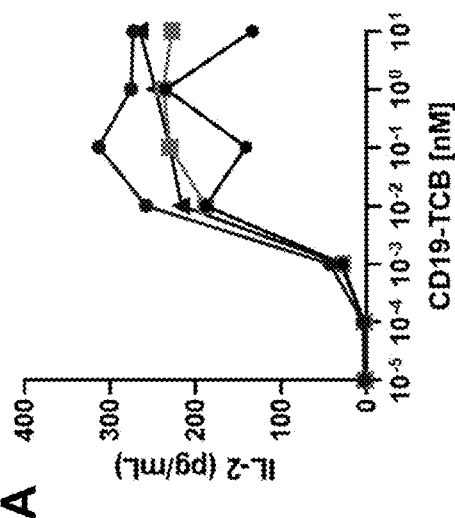

FIG. 72. Effect of 100 nM ruxolitinib (ruxo), 100 nM baricitinib (ban) and 100 nM tofacitinib (tofa) on CD19-TCB-dependent cytokine release in the assay of FIG. 69. The levels of IL-2 (A), IFN-γ (B), TNF-α (C), IL-6 (D) and GM-CSF (E) were measured in the supernatants by Luminex (24 hrs). 1 representative donor out of 3.

Figure 73:
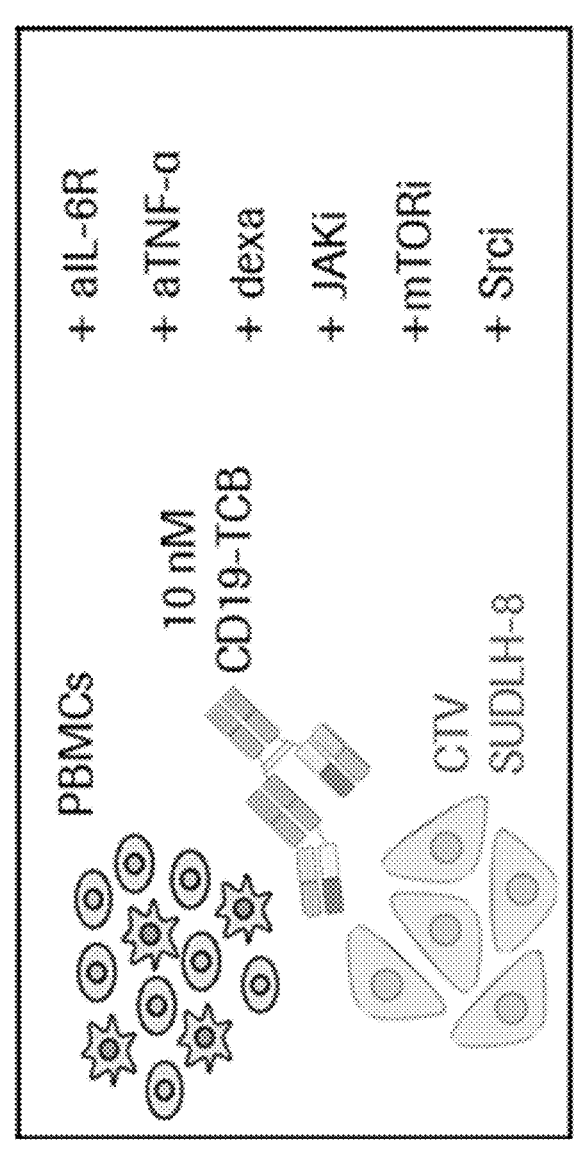

FIG. 73. In vitro killing assay set-up. PBMCs were co-cultured with CTV labelled SUDLH-8 cells (E:T=10:1) in the presence of escalating concentrations of CD19-TCB in media supplemented with the different kinase inhibitors (100 nM), dexamethasone (100 nM), 5 µg/mL anti-TNF-α antibody (aTNF-α) or 5 µg/mL anti-IL-6R antibody (aIL-6R) for 24 hrs.

Figure 74:
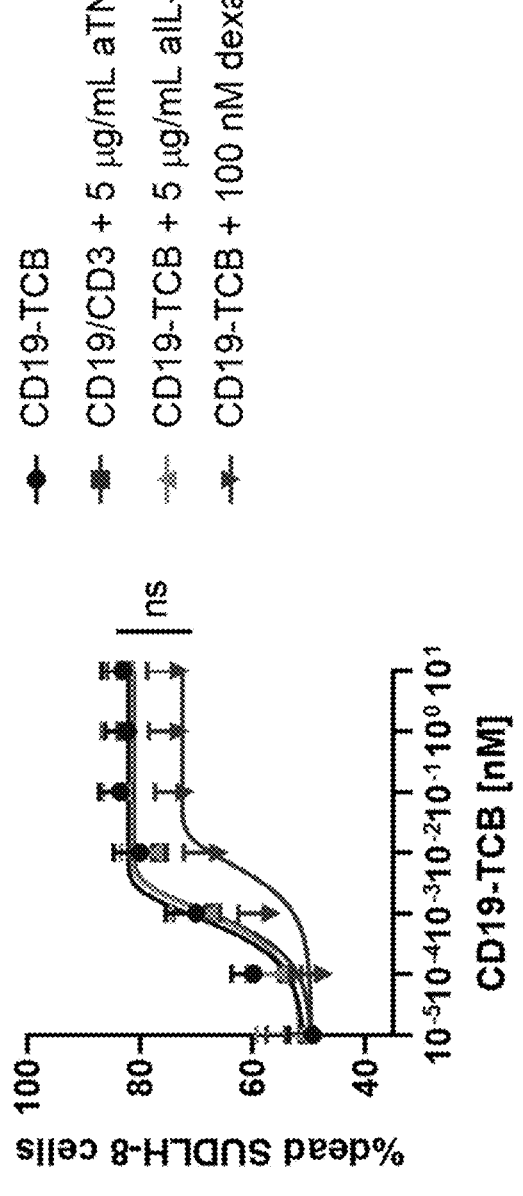
Figure 74:
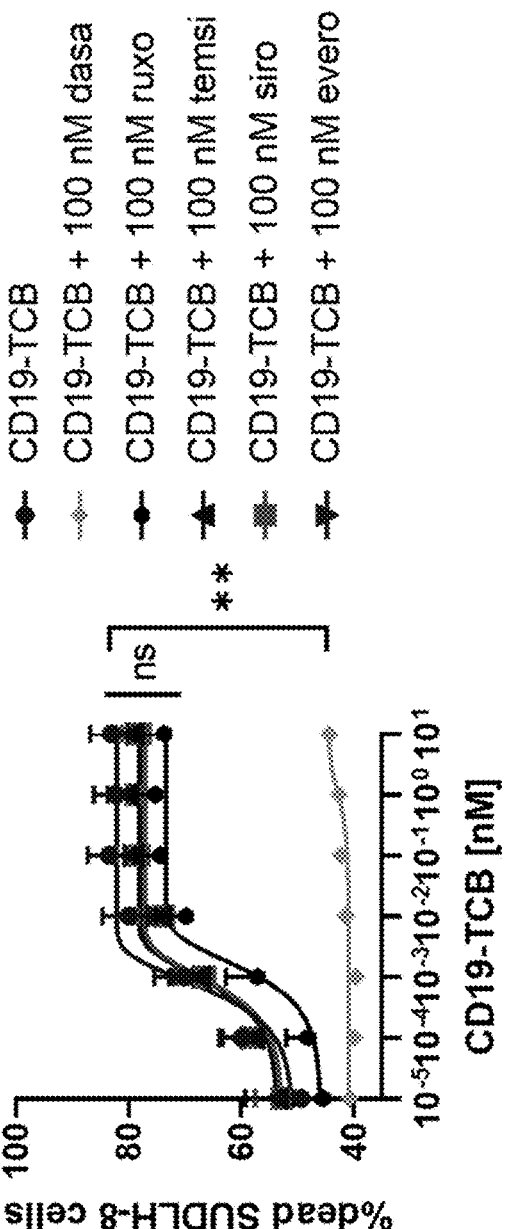

FIG. 74. Effect of 100 nM dexamethasone (dexa), 5 µg/mL anti-TNF-α antibody (aTNF-α) or 5 µg/mL anti-IL-6R antibody (aIL-6R) (A), or 100 nM dasatinib (dasa), 100 nM sirolimus (siro), 100 nM temsirolimus (temsi), 100 nM everolimus (evero) or 100 nM ruxolitinib (ruxo) (B), on CD19-TCB-dependent killing of CTV labelled SUDLH-8 cells in the assay of FIG. 73. The killing of CTV labelled SUDLH-8 cells was measured by flow cytometry at 24 hrs using a Live/Dead stain allowing for exclusion of dead cells. Mean of n=3 donors+SD with *p≤0.0332, **p≤0.0021 by 1 way ANOVA (Friedman test).

Figure 75:
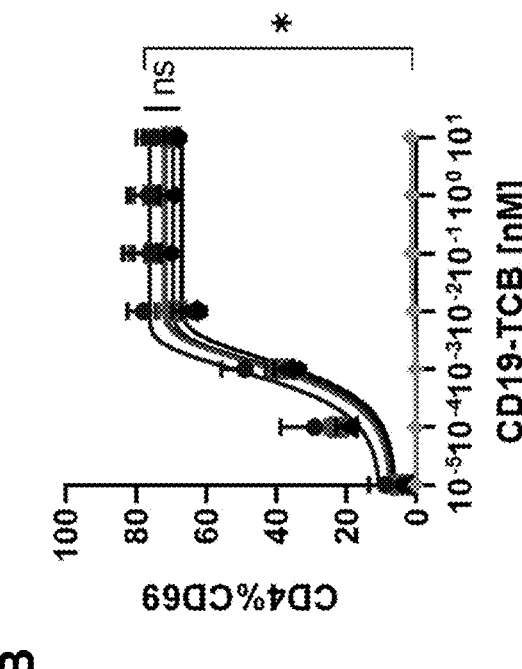
Figure 75:
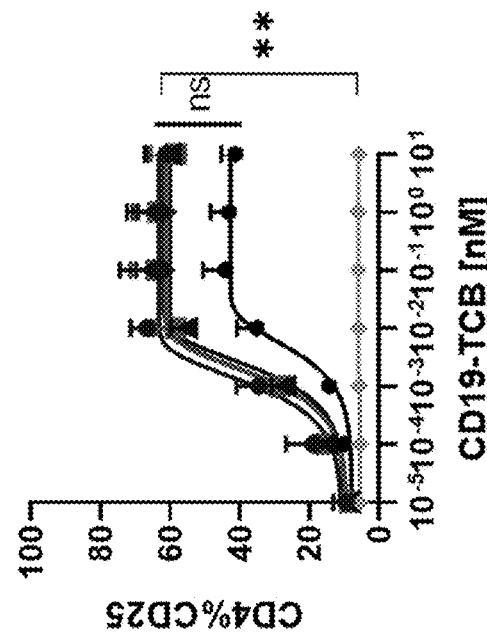
Figure 75:
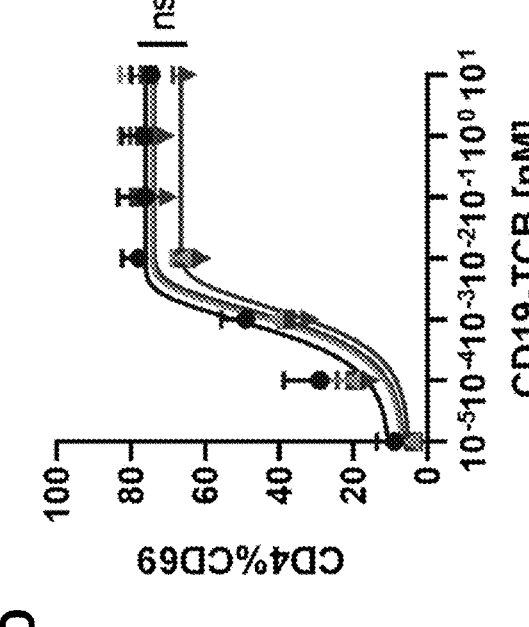
Figure 75:
Figure 75:
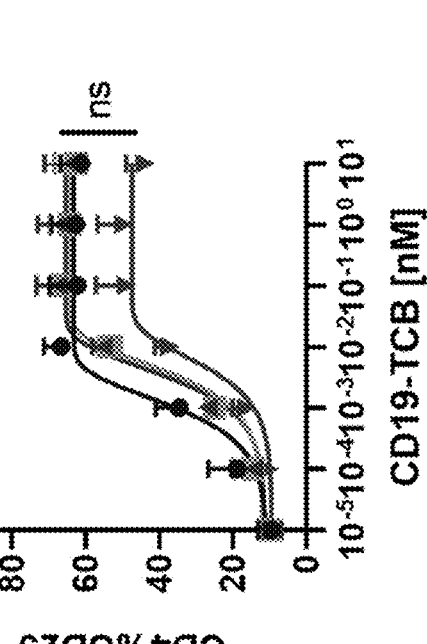

FIG. 75. Effect of 100 nM dexamethasone (dexa), 5 µg/mL anti-TNF-α antibody (aTNF-α) or 5 µg/mL anti-IL-6R antibody (aIL-6R) (A, B) or 100 nM dasatinib (dasa), 100 nM sirolimus (siro), 100 nM temsirolimus (temsi), 100 nM everolimus (evero) or 100 nM ruxolitinib (ruxo) (C, D) on CD19-TCB-dependent T cell activation in the assay of FIG. 73. The expression of CD25 (A, C) and CD69 (B, D) on CD4+ T cells was measured by flow cytometry at 24 hrs. Mean of n=3 donors +SD with *p≤0.0332, **p<0.0021 by 1 way ANOVA (Friedman test).

Figure 76:
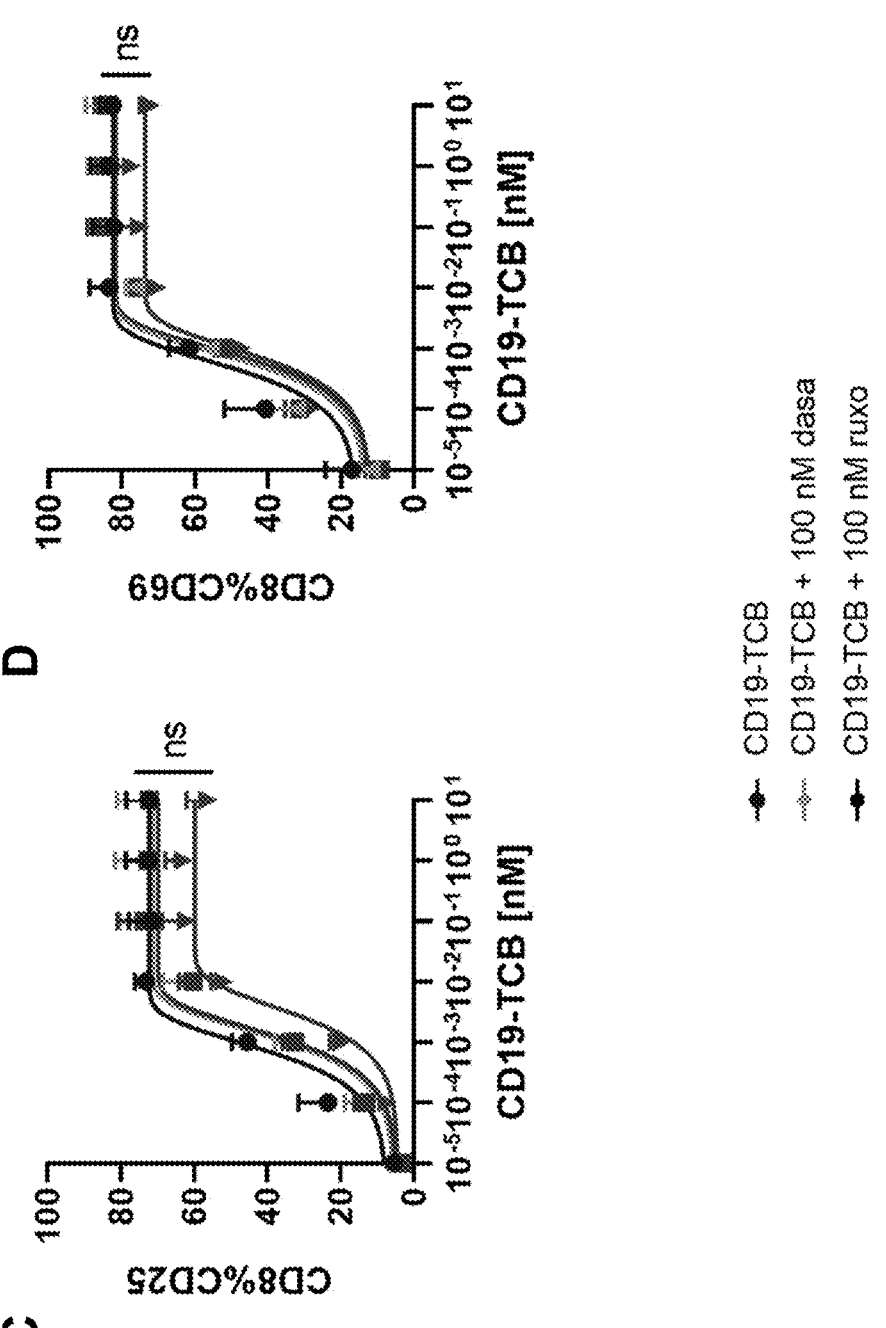

FIG. 76. Effect of 100 nM dexamethasone (dexa), 5 µg/mL anti-TNF-α antibody (aTNF-α) or 5 µg/mL anti-IL-6R antibody (aIL-6R) (A, B), or 100 nM dasatinib (dasa), 100 nM sirolimus (siro), 100 nM temsirolimus (temsi), 100 nM everolimus (evero) or 100 nM ruxolitinib (ruxo) (C, D), on CD19-TCB-dependent T cell activation in the assay of FIG. 73. The expression of CD25 (A, C) and CD69 (B, D) on CD8+ T cells was measured by flow cytometry at 24 hrs. Mean of n=3 donors +SD with *p≤0.0332, **p<0.0021 by 1 way ANOVA (Friedman test).

Figure 77:
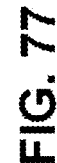
Figure 77:
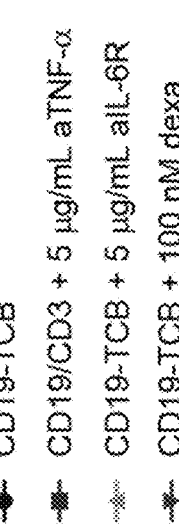
Figure 77:
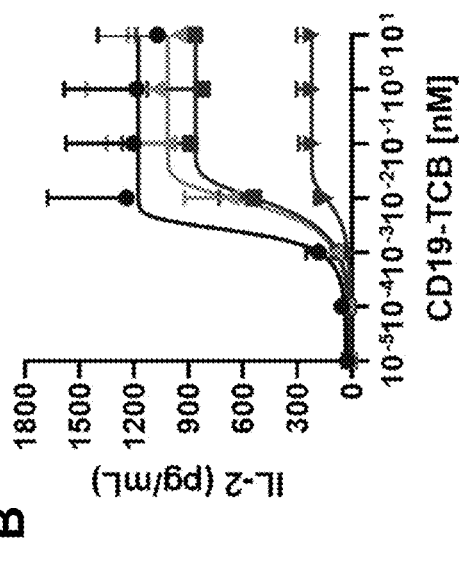
Figure 77:
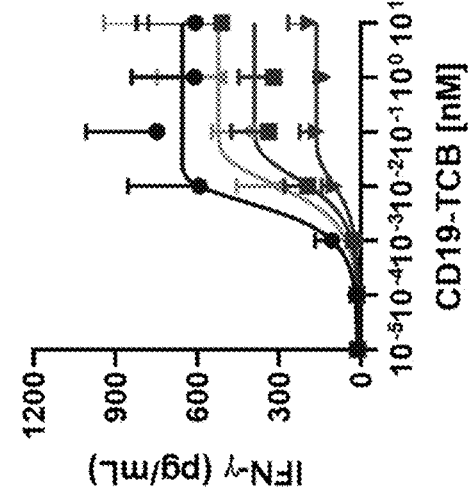
Figure 77:
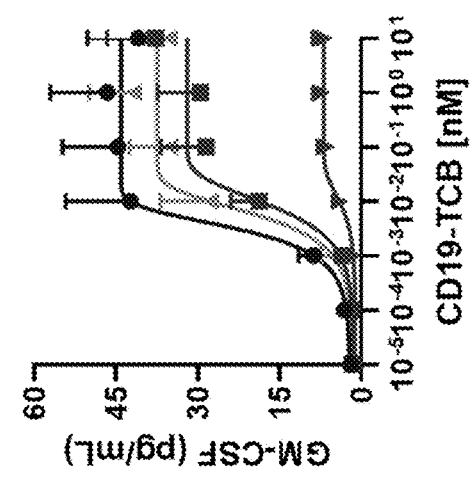
Figure 77:
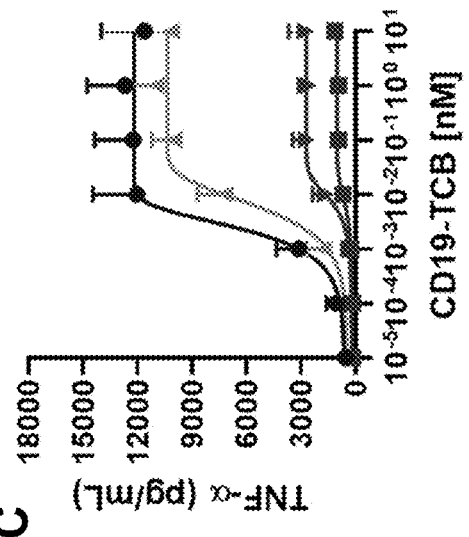
Figure 77:
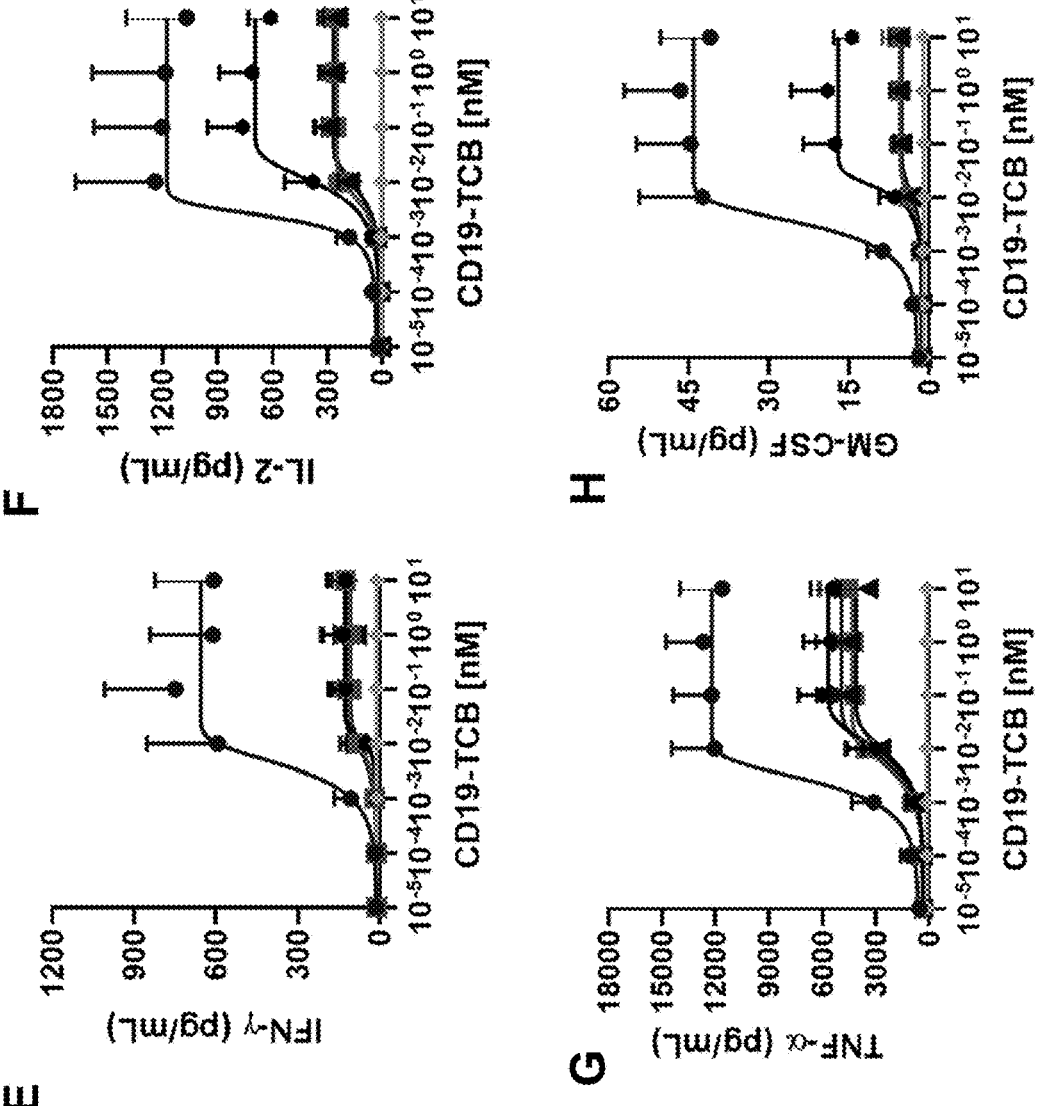

FIG. 77. Effect of 100 nM dexamethasone (dexa), 5 µg/mL anti-TNF-α antibody (aTNF-α) or 5 µg/mL anti-IL-6R antibody (aIL-6R) (A-D), or 100 nM dasatinib (dasa), 100 nM sirolimus (siro), 100 nM temsirolimus (temsi), 100 nM everolimus (evero) or 100 nM ruxolitinib (ruxo) (E-H), on CD19-TCB-dependent cytokine release in the assay of FIG. 73. The levels of IFN-γ (A, E), IL-2 (B, F), TNF-α (C, G) and GM-CSF (D, H) were measured in the supernatants by Luminex (24 hrs). Mean of n=3 donors+standard error of mean (SEM).

Figure 78:

FIG. 78. In vitro killing assay set-up. PBMCs were co-cultured with CTV labelled NALM-6 cells (E:T=10:1) in the presence of escalating concentrations of CD19-TCB for 24 hrs. At 24 hrs, the culture medium was supplemented with 100 nM dasatinib, 100 nM sirolimus or 100 nM ruxolitinib.

FIG. 79. Effect of 100 nM dasatinib (dasa), 100 nM sirolimus (siro), 100 nM ruxolitinib (ruxo) on CD19-TCB-induced tumor cell killing when added in the system after 24 hrs of activation in the assay of FIG. 78. The killing of CTV labelled NALM-6 cells was measured by flow cytometry at 24 hrs and 48 hrs using a Live/Dead stain allowing exclusion of dead cells. 1 representative donor out of 2.

FIG. 80. Effect of 100 nM dasatinib (dasa), 100 nM sirolimus (siro), 100 nM ruxolitinib (ruxo) on CD19-TCB-induced cytokine release when added in the system after 24 hrs of activation in the assay of FIG. 78. The levels of IFN-γ

(A), TNF-α (B), IL-2 (C) and IL-6 (D) were measured in the supernatants by Luminex (24 hrs and 48 hrs). 1 representative donor out of 2.

Figure 81:
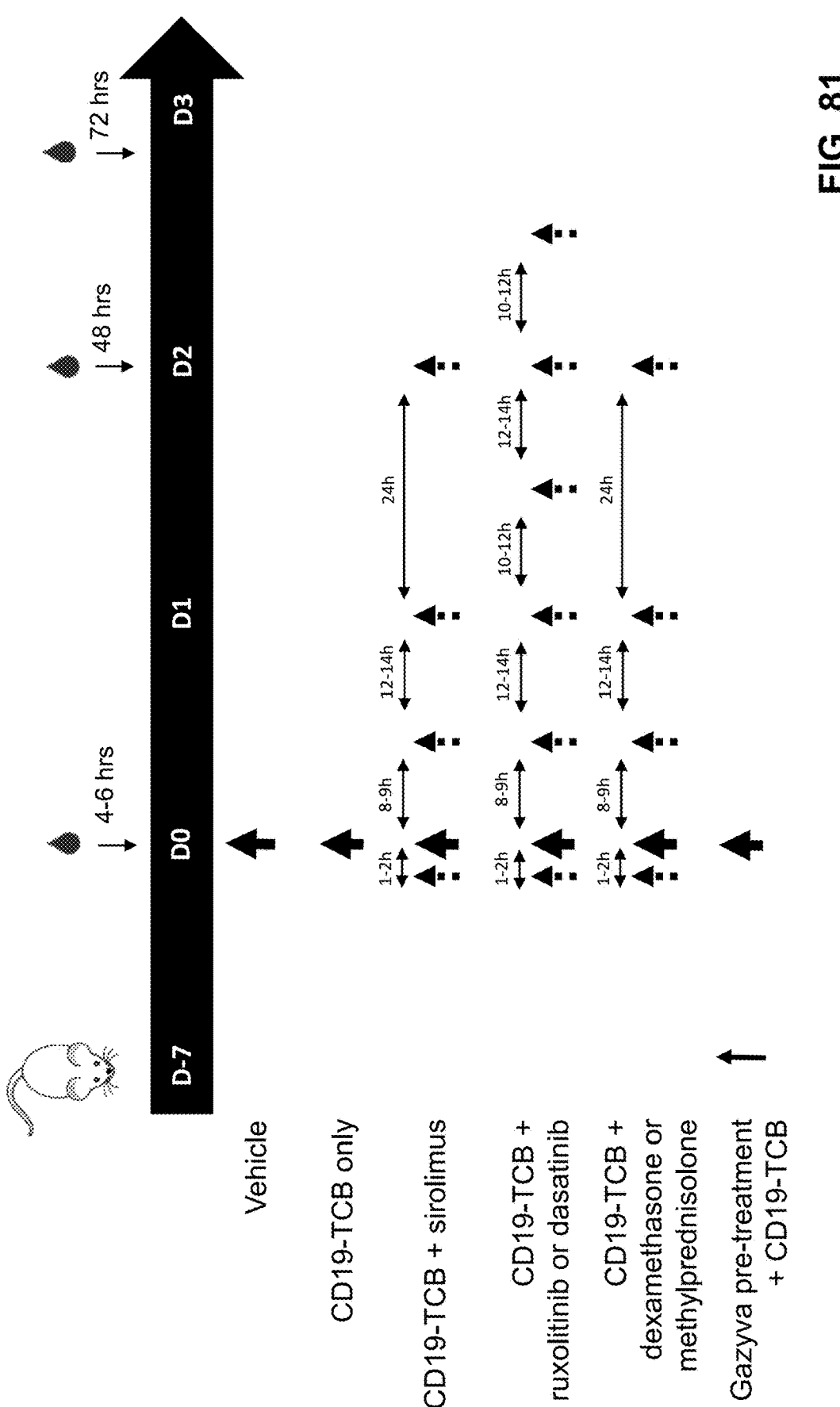

FIG. 81. In vivo experiment timelines and dosing schedule. Humanized NSG mice were co-treated with 0.5 mg/kg CD19-TCB (i.v.) and (i) 6×50 mg/kg dasatinib (p.o.), (ii) 6×30 mg/kg ruxolitinib (p.o), (iii) 4×5 mg/kg sirolimus (p.o.), (iv) 2×1 mg/kg, 1×0.5 mg/kg and 1×0.25 mg/kg dexamethasone (p.o), or (v) 2×10 mg/kg, 1×5 mg/kg, 1×2.5 mg/kg methylprednisolone (p.o.), or pre-treated with 30 mg/kg obinutuzumab (Gazyva®) (GpT) (i.v.) and then treated with 0.5 mg/kg CD19-TCB (i.v.).

Figure 82:
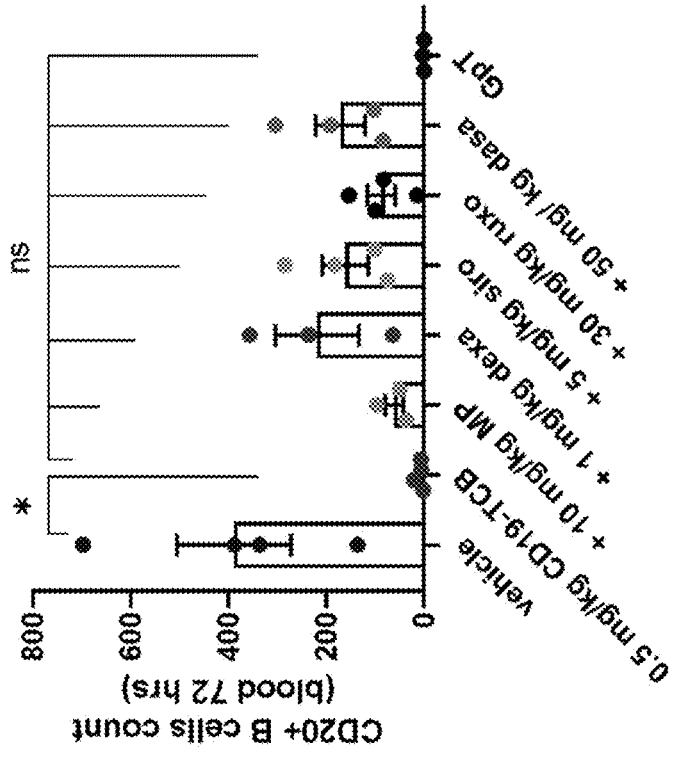
Figure 82:
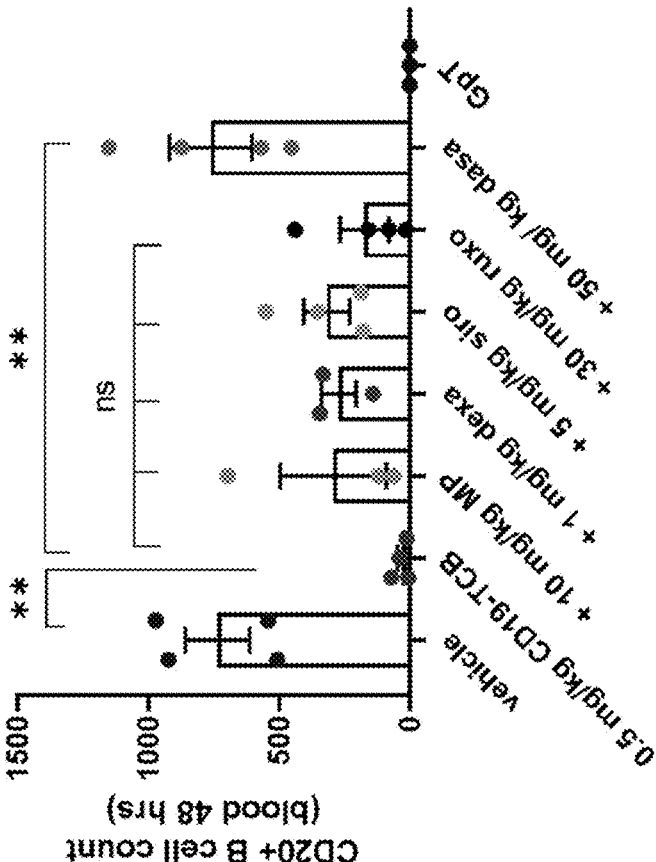

FIG. 82. Effect of obinutuzumab (Gazyva®) pre-treatment (GpT), ruxolitinib (ruxo), dasatinib (dasa), sirolimus (siro), dexamethasone (dexa) and methylprednisolone (MP) on CD19-TCB induced B cell depletion in the experiment described in FIG. 81. CD20+ B cell count was measured by flow cytometry in blood collected 48 hrs (A) and 72 hrs (B) post-treatment with CD19-TCB. Mean of n=4 mice or n=3 mice (dexa, MP and GpT)+/−SEM with *p≤0.0332, **p≤0.0021 by 1 way ANOVA (Kruskal wallis test).

Figure 83:
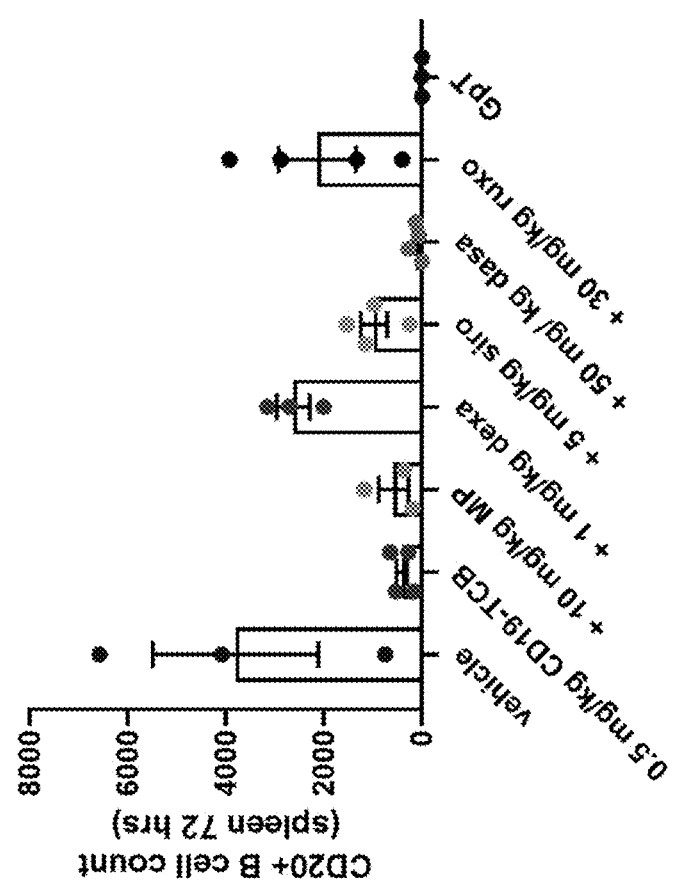

FIG. 83. Effect of obinutuzumab (Gazyva®) pre-treatment (GpT), ruxolitinib (ruxo), dasatinib (dasa), sirolimus (siro), dexamethasone (dexa) and methylprednisolone (MP) on CD19-TCB induced B cell depletion in the experiment described in FIG. 81. CD20+ B cell count was measured by flow cytometry in spleen collected at termination, 72 hrs post-treatment with CD19-TCB. Mean of n=4 mice or n=3 mice (vehicle, dexa, MP and GpT)+/−SEM.

Figure 84:
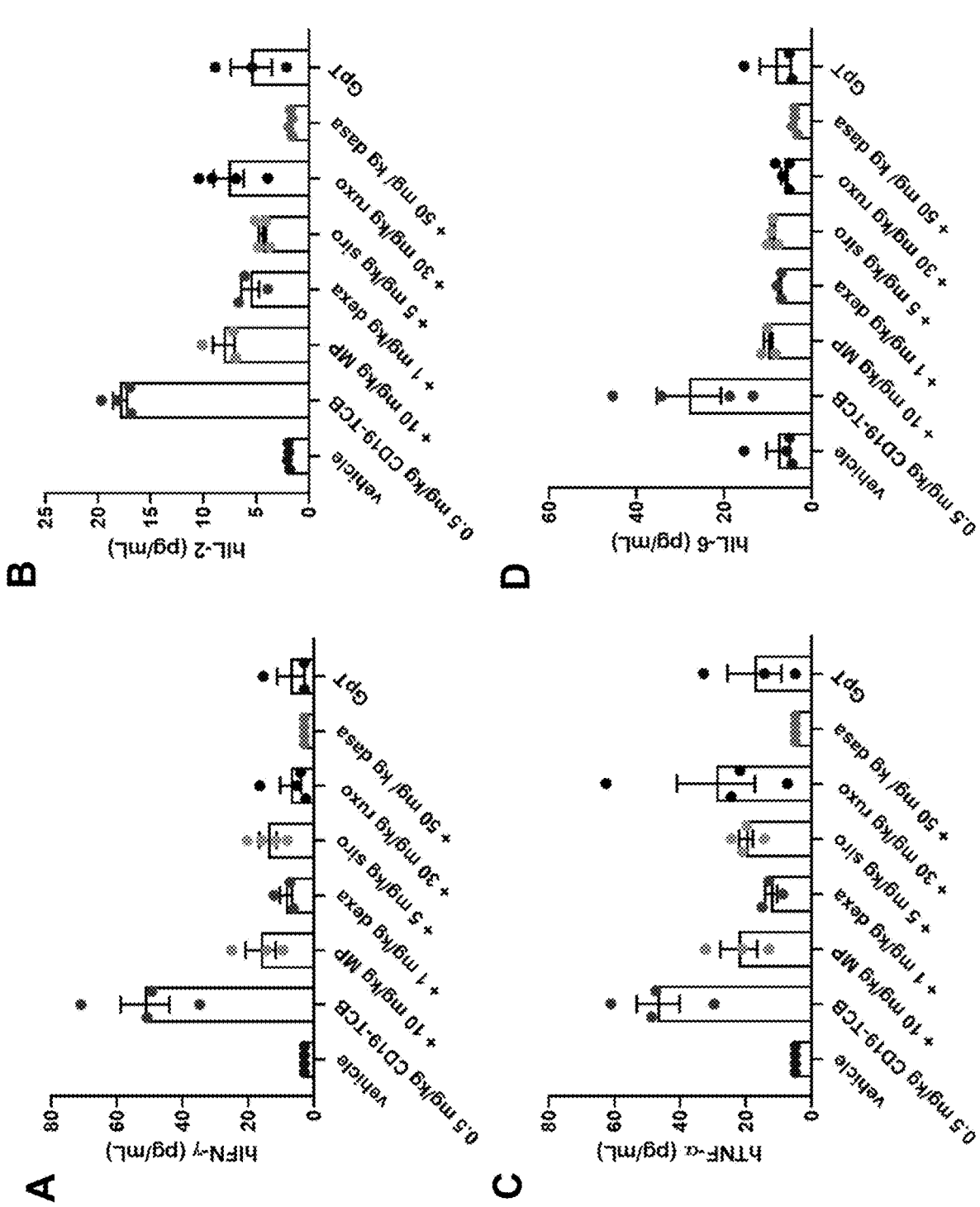

FIG. 84. Effect of obinutuzumab (Gazyva®) pre-treatment (GpT), ruxolitinib (ruxo), dasatinib (dasa), sirolimus (siro), dexamethasone (dexa) and methylprednisolone (MP) on CD19-TCB induced cytokine release in the experiment described in FIG. 81. The levels of human IFN-γ (hIFN-γ) (A), human IL-2 (hIL-2) (B), human TNF-α (hTNF-α) (C), human IL-6 (hIL-6) (D) were measured by Luminex in serum collected 6 hrs post-treatment with CD19-TCB. Mean of n=4 mice or n=3 mice (dexa, MP and GpT)+/−SEM.

Figure 85:
Figure 85:
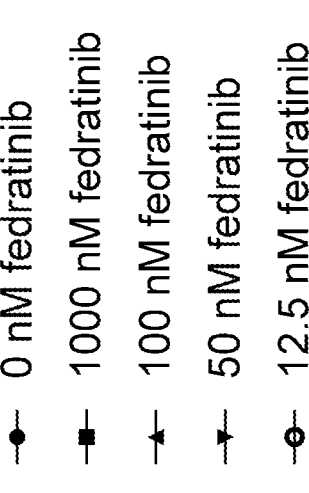
Figure 85:
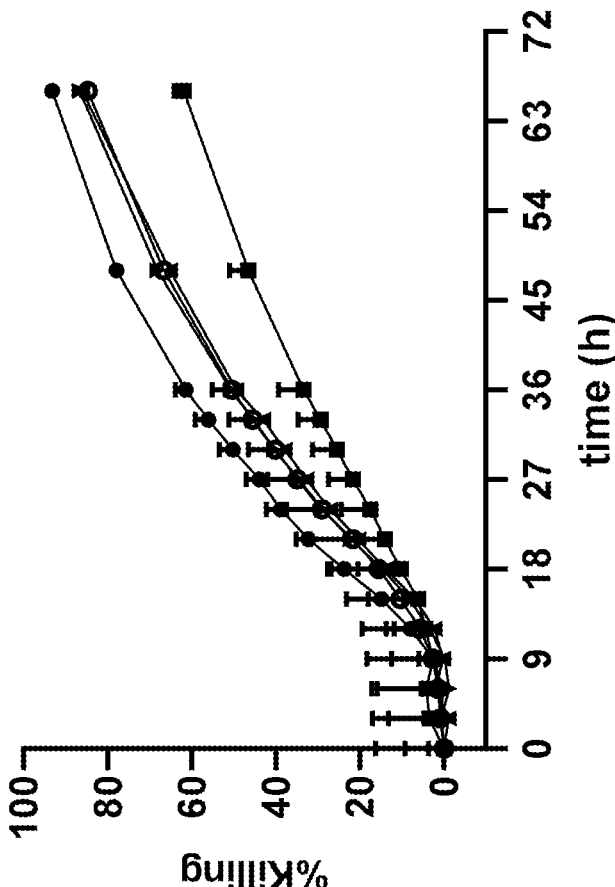

FIG. 85. Real time killing of MKN45 NucLightRed (NLR) cells by 10 nM CEA-TCB in the presence of escalating concentrations of fedratinib ranging from 0 nM to 1000 nM. MKN45 NLR target cells were co-cultured with PBMCs (E:T=50 000 PBMCs: 5000 target cells) in medium supplemented with 10 nM CEA-TCB and fedratinib. The killing was followed using an Incucyte® (1 scan every 3 hours, zoom 10×, phase and red 400 ms acquisition time). Killing [%] was measured by normalizing total red area with values at t=0 hour and target cells+PBMCs+fedratinib control wells for each time point. Means of technical replicates+/−SEM for 1 donor.

Figure 86:
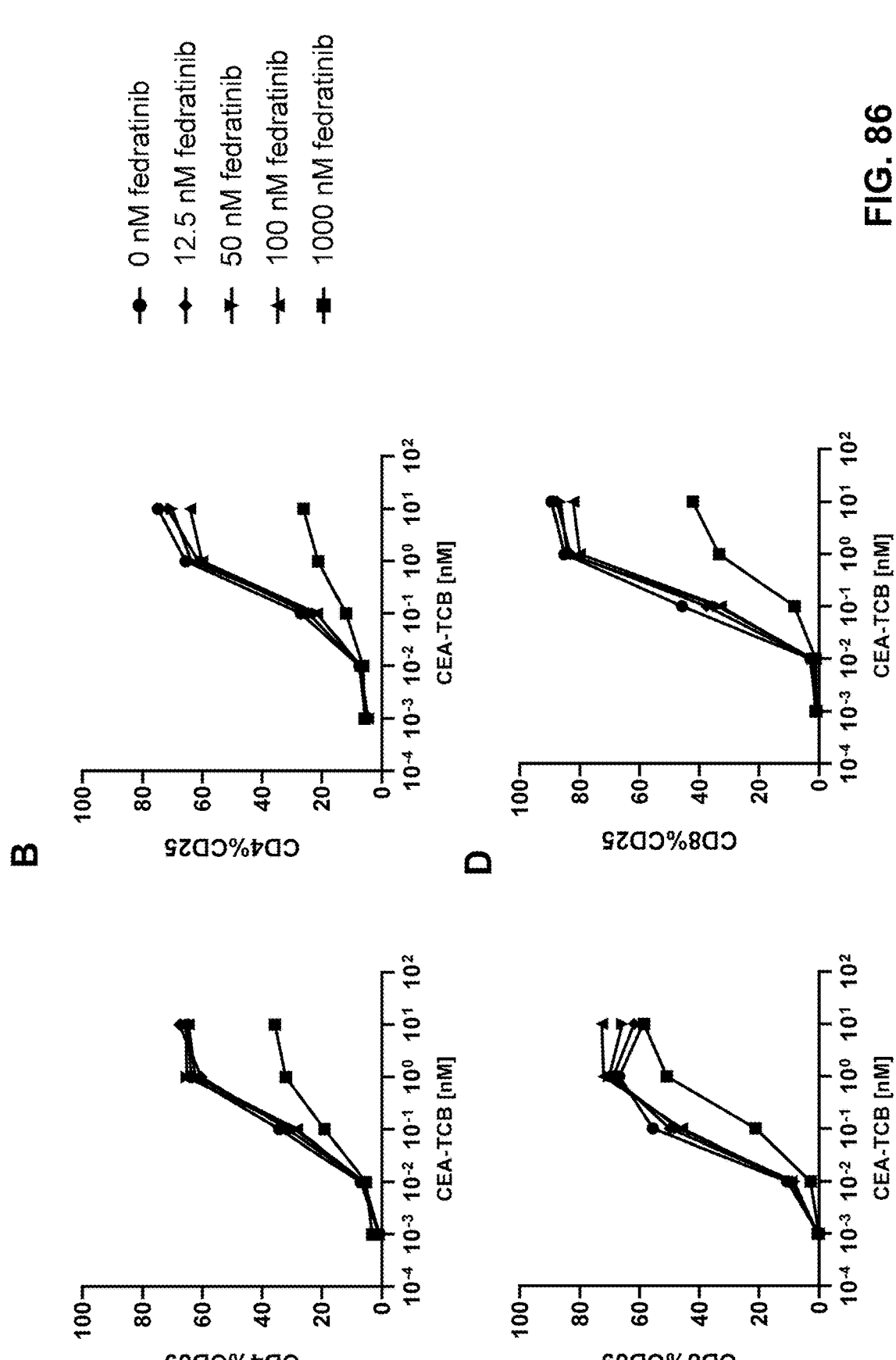

FIG. 86. Effect of escalating concentrations of fedratinib (0-1000 nM) on CD25 (B, D) and CD69 (A, C) expression on CD4+(A, B) and CD8+(C, D) T cells at 72 hours, after treatment with 10 nM CEA-TCB. Technical replicates were pooled and the expression of CD25 on CD4+ and CD8+ T cells was measured by flow cytometry at 72 hours. 1 donor.

Figure 87:
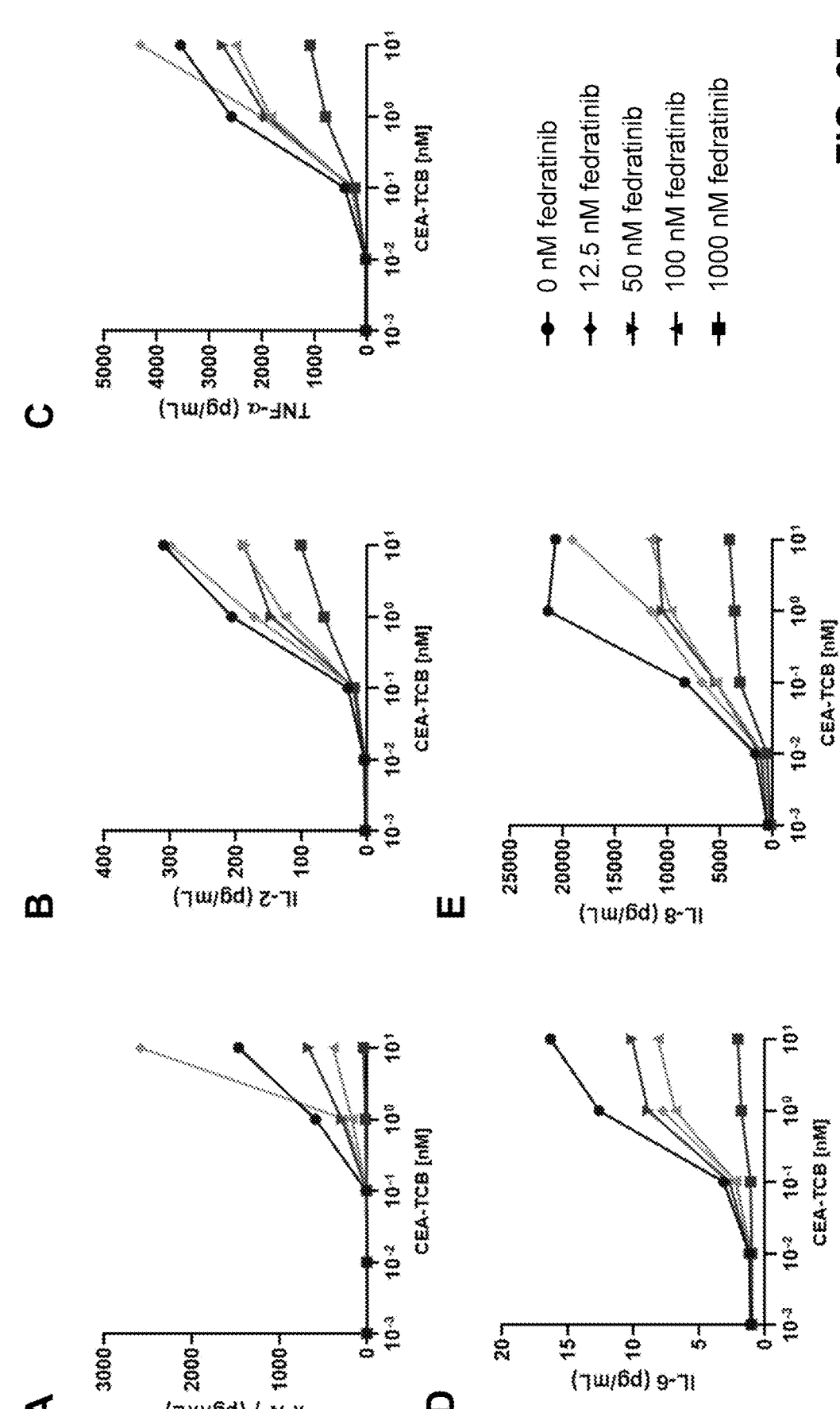

FIG. 87. Effect of escalating concentrations (0-1000 nM) of fedratinib on IFN-γ (A), IL-2 (B), TNF-α (C), IL-6 (D) and IL-8 (E) levels induced by 10 nM CEA-TCB. At 72 hours, the supernatants from technical replicates were pooled and the cytokine levels were analyzed by Luminex. 1 donor.

Figure 88:
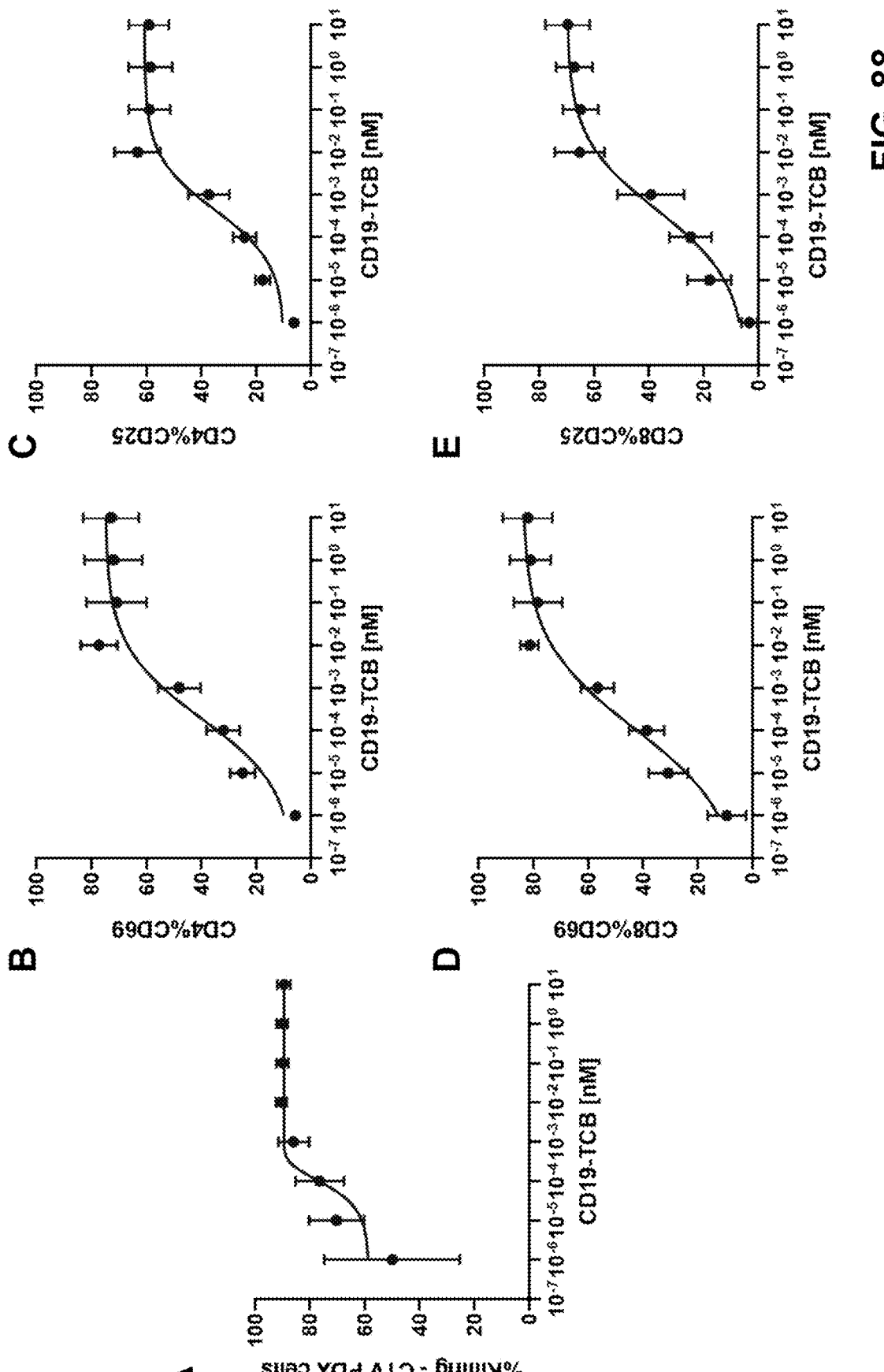

FIG. 88. CD19-TCB kills lymphoma PDX cells in vitro. Lymphoma PDX cells were thawed on the day of the assay, labelled with the CTV dye and cultured with PBMCs (E:T=10:1) in the presence of CD19-TCB for 24 hrs. (A) Killing of CTV labelled PDX cells was measured by flow cytometry in pooled technical replicates, mean of n=3 PBMCs donors+/−SD. (B-E) The expression of CD69 (B, D) and CD25 (C, E) on CD4+(B, C) and CD8+(D, E) T cells was measured by flow cytometry as a readout for T cell activation, pooled technical replicates, mean of n=3 PBMCs donors+/−SD.

Figure 89:
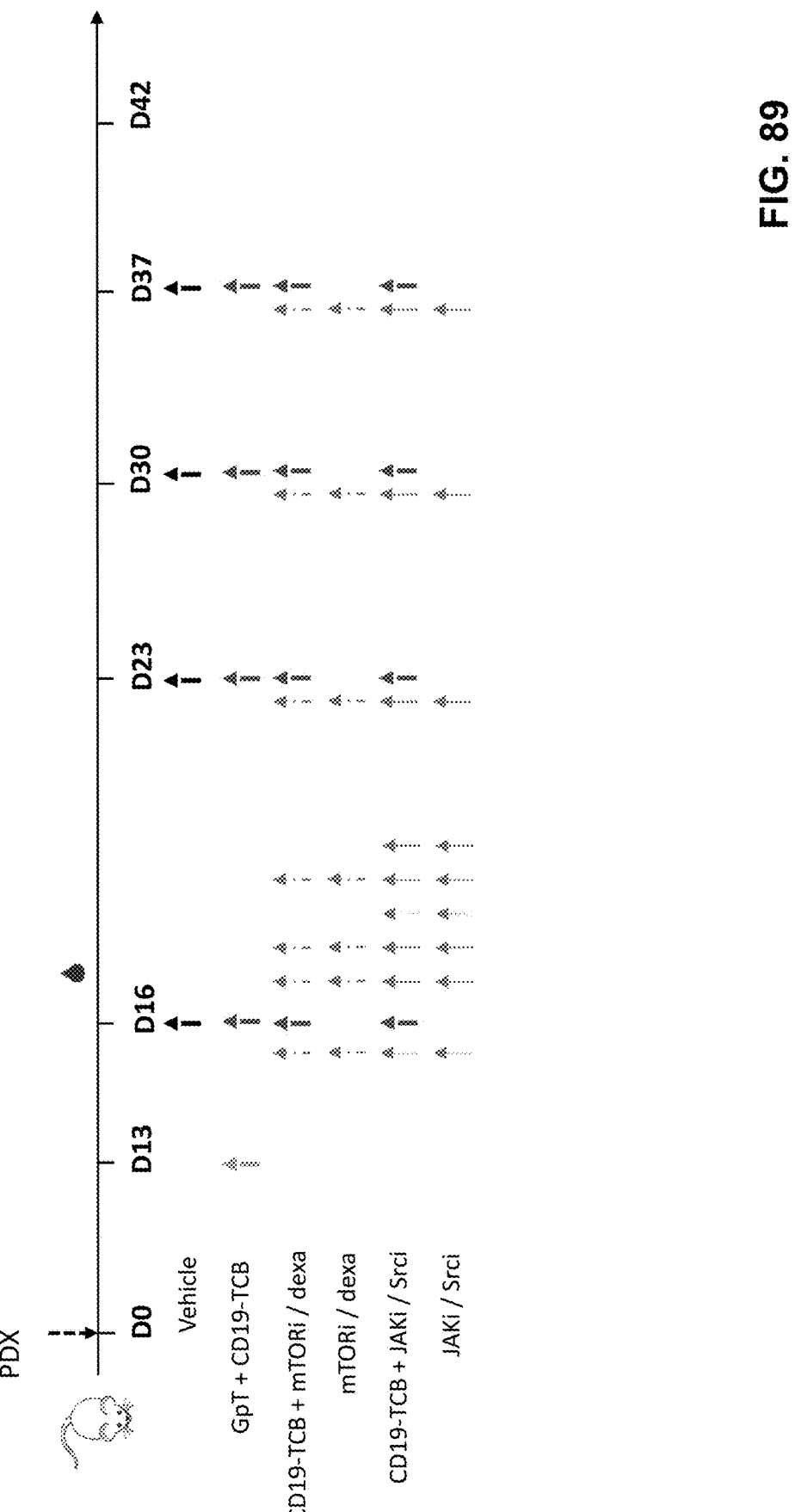

FIG. 89. In vivo experiment timelines and dosing schedule. Humanized NSG mice were engrafted with a lymphoma PDX (5 million cells, s.c.). When tumors reached 200 mm³ in size, mice were randomized in groups of 8 or 7 based on their tumor size and treated weekly with vehicle (i.v.), 0.5 mg/kg CD19-TCB (i.v.) alone, 0.5 mg/kg CD19-TCB (solid black arrows, i.v.) together with 20 mg/kg dasatinib ("Srci", dotted arrows, p.o), 5 mg/kg sirolimus ("mTORi", dashed arrows, p.o.), 30 mg/kg ruxolitinib ("JAKi", dotted arrows, p.o), 2 times 1 mg/kg, 0.5 mg/kg or 4 times 0.25 mg/kg dexamethasone ("dexa", dashed arrows, p.o), kinase inhibitors and dexamethasone alone, or pre-treated with 30 mg/kg obinutuzumab ("GpT", solid grey arrow, i.v.) 3 days before the first treatment with CD19-TCB. The kinase inhibitors were given twice on the day of the first CD19-TCB administration (D16, once 1 hour before CD19-TCB, and once afterwards), and then once (sirolimus) or twice (dasatinib, ruxolitinib) on the two following days (D17 and D18), as well as once 1 hour before each subsequent CD19-TCB administration.

Figure 90:

FIG. 90. Tumor growth curves of sirolimus alone or combined with CD19-TCB in comparison to vehicle, obinutuzumab pre-treatment (GpT) or CD19-TCB as a monotherapy. Tumor volumes were measured using a caliper two or three times per week, mean of n=6-8 mice+SD with *p≤0.05, p<0.01, *p<0.001 by 1 way ANOVA (Kruskal Wallis test).

Figure 91:
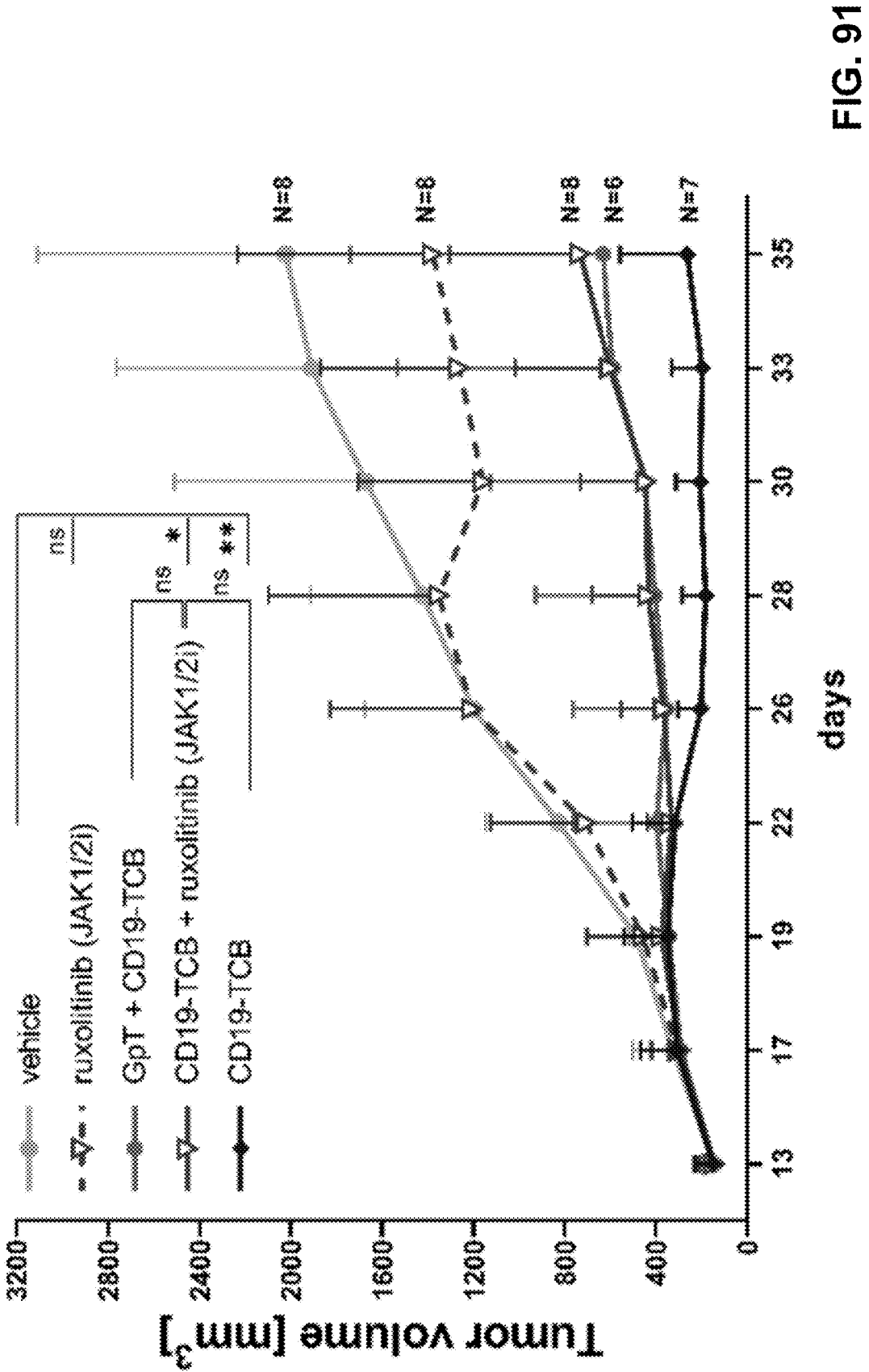

FIG. 91. Tumor growth curves of ruxolitinib alone or combined with CD19-TCB in comparison to vehicle, obinutuzumab pre-treatment (GpT) or CD19-TCB as a monotherapy. Tumor volumes were measured using a caliper two or three times per week, mean of n=6-8 mice+SD with *p≤0.05, p<0.01, *p<0.001 by 1 way ANOVA (Kruskal Wallis test).

Figure 92:
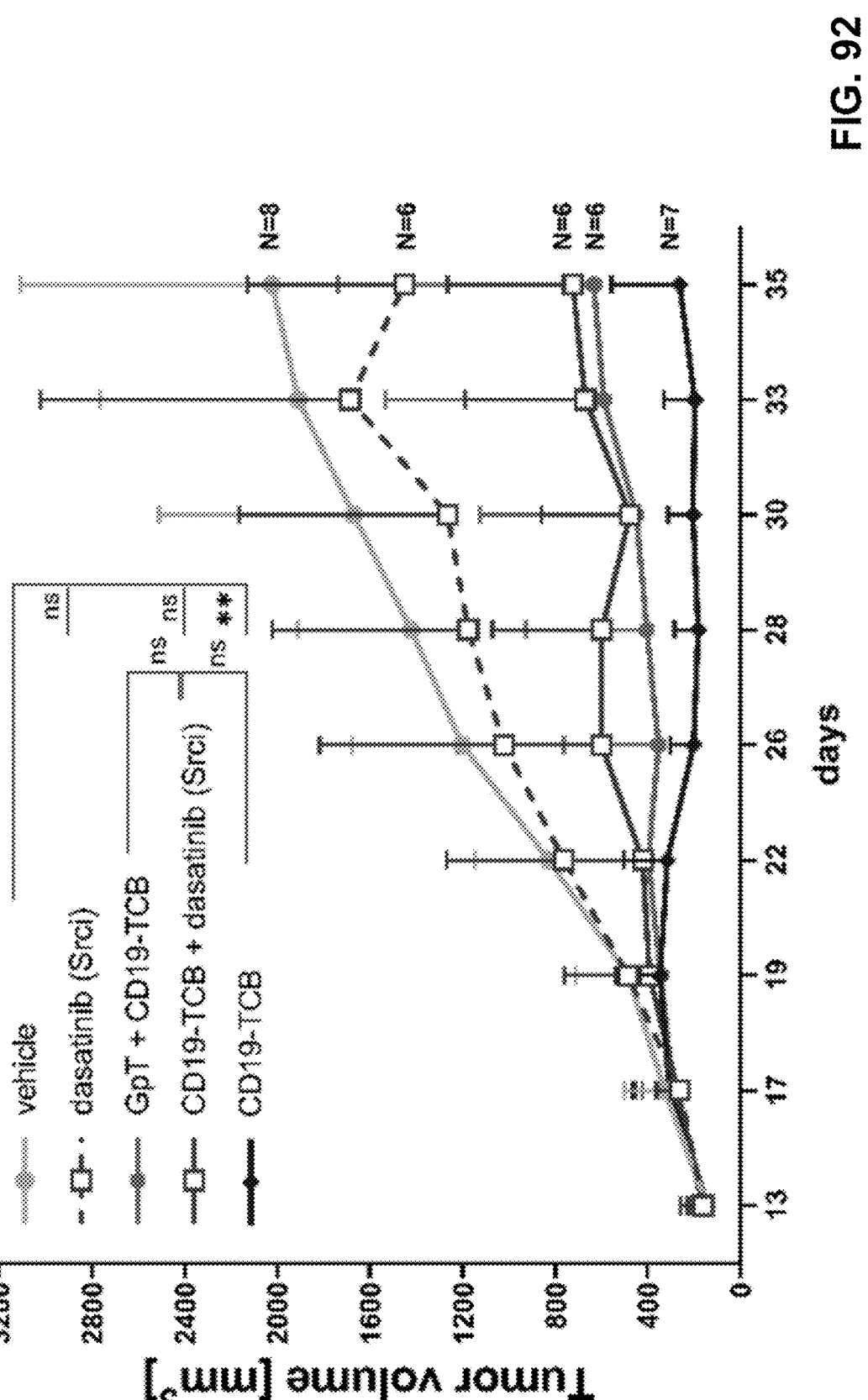

FIG. 92. Tumor growth curves of dasatinib alone or combined with CD19-TCB in comparison to vehicle, obinutuzumab pre-treatment (GpT) or CD19-TCB as a monotherapy. Tumor volumes were measured using a caliper two or three times per week, mean of n=6-8 mice+SD with *p≤0.05, p<0.01, *p<0.001 by 1 way ANOVA (Kruskal Wallis test).

Figure 93:
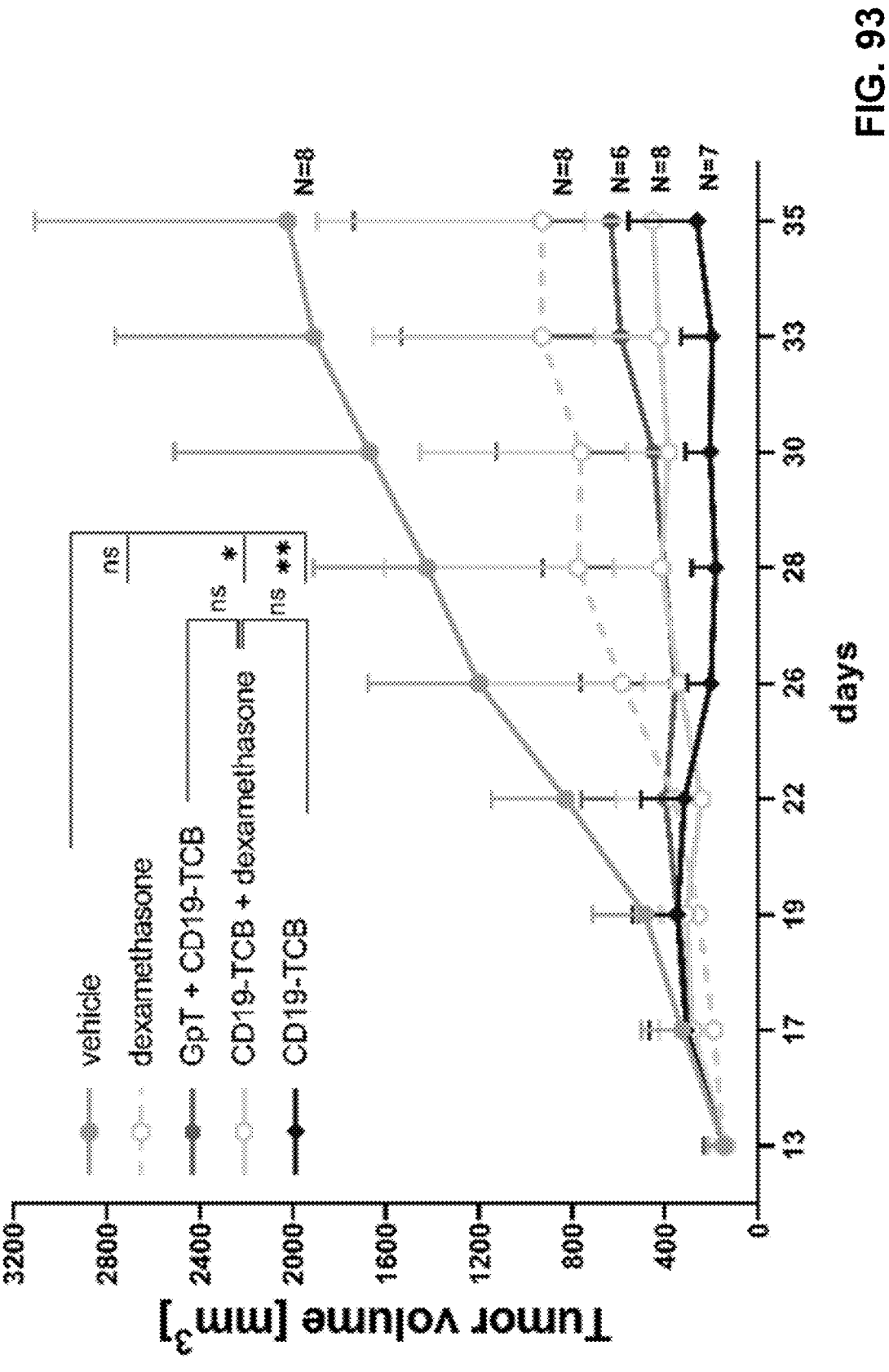

FIG. 93. Tumor growth curves of dexamethasone alone or combined with CD19-TCB in comparison to vehicle, obinutuzumab pre-treatment (GpT) or CD19-TCB as a monotherapy. Tumor volumes were measured using a caliper two or three times per week, mean of n=6-8 mice +SD with *p≤0.05, p<0.01, *p<0.001 by 1 way ANOVA (Kruskal Wallis test).

Figure 94:
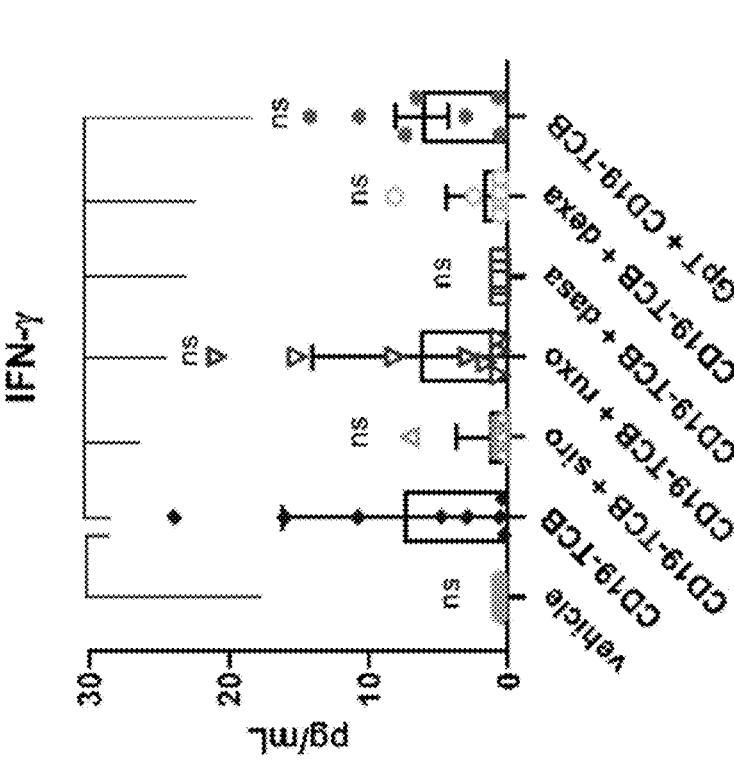
Figure 94:
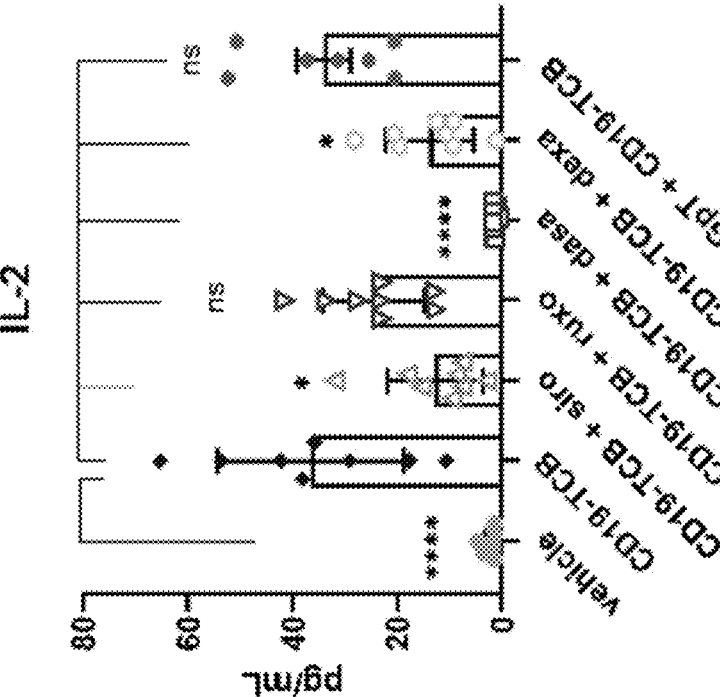
Figure 94:

FIG. 94. Effect of sirolimus (mTOR inhibitor), ruxolitinib (JAK1/2 inhibitor), dasatinib (Src inhibitor) and dexamethasone on CD19-TCB-mediated release of (A) IL-2, (B) IFN-γ, (C) TNF-α and (D) IL-6. Cytokine levels were measured by Luminex in serum collected 6 hrs post first infusion with CD19-TCB. Mean of n=6-8 mice+SD with *p≤0.05, p<0.01, *p<0.001 by 1 way ANOVA (Kruskal Wallis test).

Figure 95:

FIG. 95. In vivo experiment timelines and dosing schedule. Humanized NSG mice were treated with vehicle or 0.15 mg/kg CD20-TCB (i.v.) alone or in combination with different doses of mTOR inhibitors (p.o.) (2, 5 or 10 mg/kg sirolimus, 10 mg/kg temsirolimus and 10 mg/kg everolimus), JAK inhibitor (p.o.) (30 or 60 mg/kg ruxolitinib) and Src inhibitor (p.o.) (10 or 50 mg/kg dasatinib) or pre-treated with 30 mg/kg obinutuzumab (Gazyva®) (GpT) (i.v.). n=4 mice per group.

Figure 96:
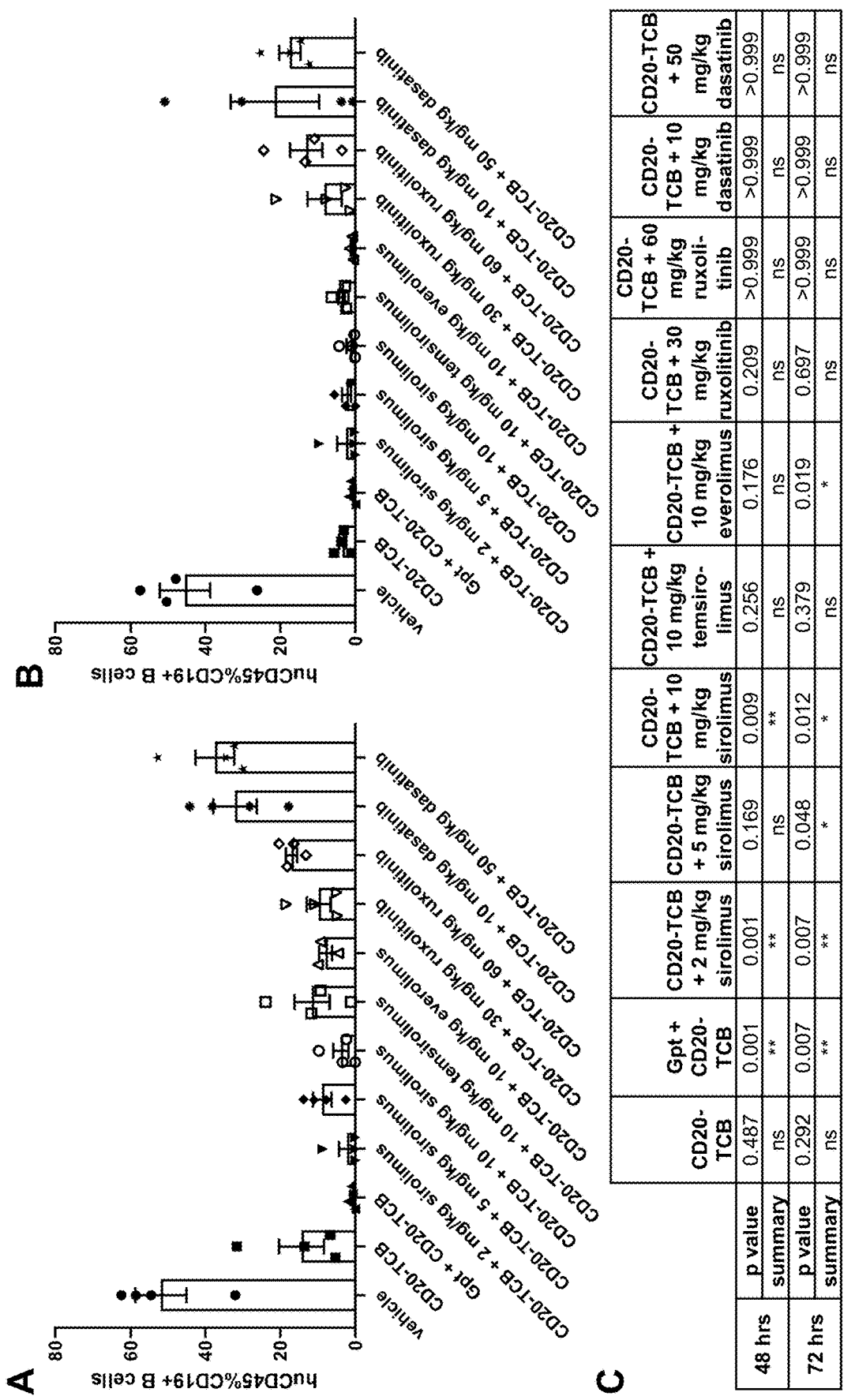

FIG. 96. Effect of obinutuzumab (Gazyva®) pre-treatment (GpT), ruxolitinib, dasatinib, sirolimus, everolimus, temsirolimus on CD20-TCB induced B cell depletion at 48 hrs (A) and 72 hrs (B) in the experiment described in FIG. 95. The proportion of CD19+ B cells among human CD45+ (huCD45) cells was measured by flow cytometry in the blood collected 48 hrs and 72 hrs post-treatment with CD20-TCB. Mean of n=4 mice or n=3 mice (everolimus group)+/−SEM. The statistical comparison to the vehicle group is summarized table (C) where the p values were calculated by Kruskal-Wallis test.

Figure 97:
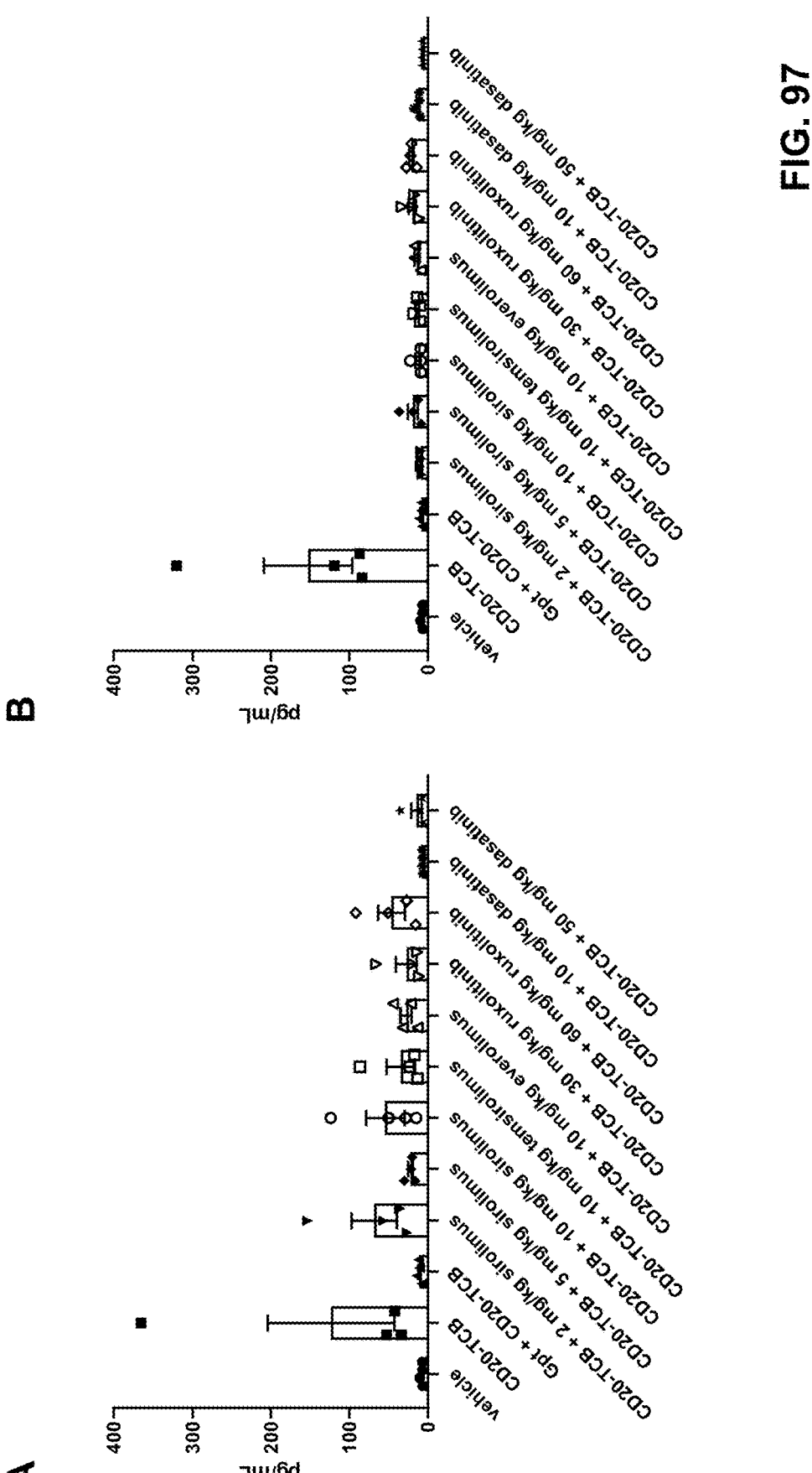

FIG. 97. Levels of IFN-γ in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

Figure 98:
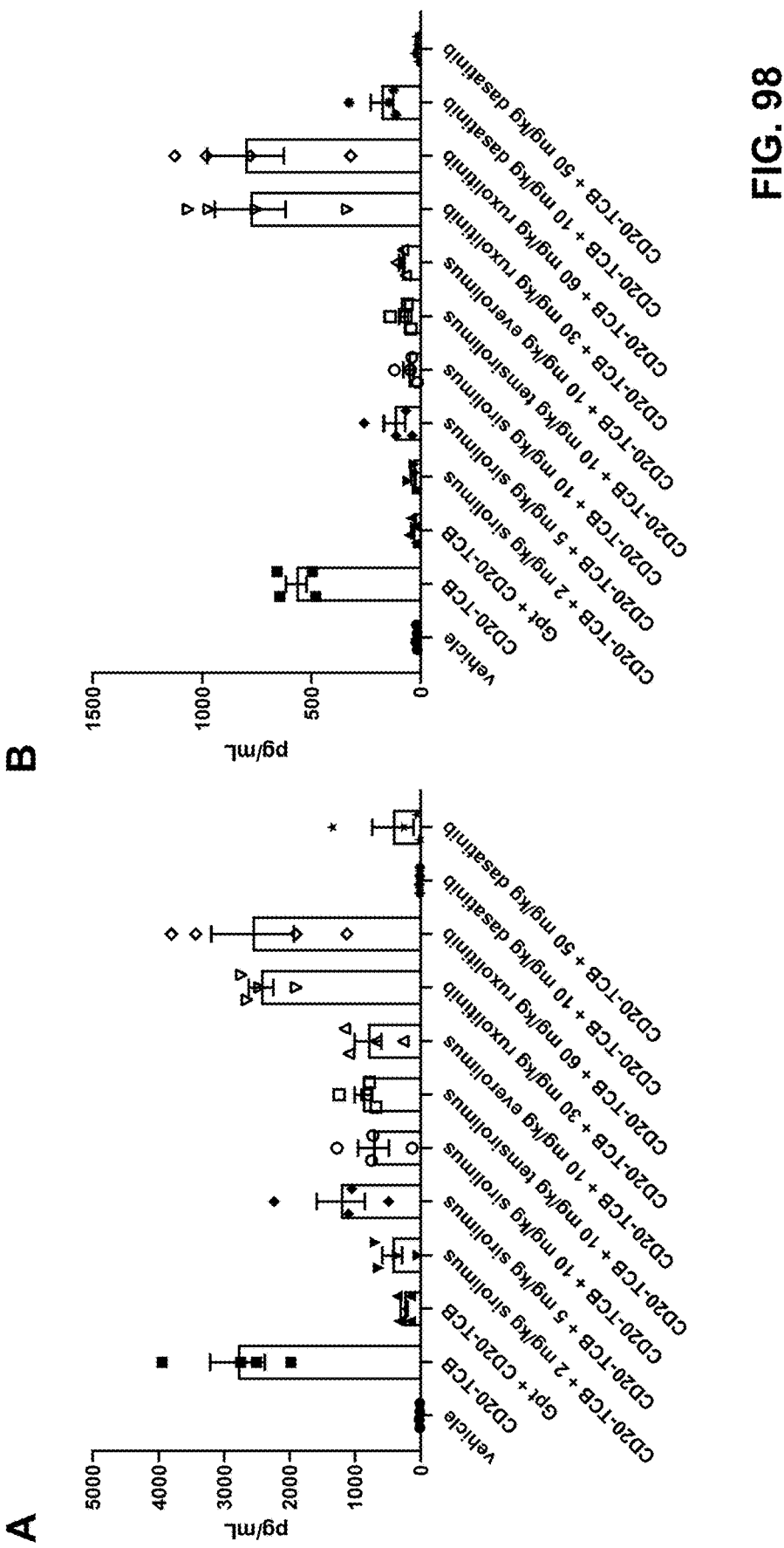

FIG. 98. Levels of IL-2 in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM for (everolimus group) at 24 hrs.

Figure 99:
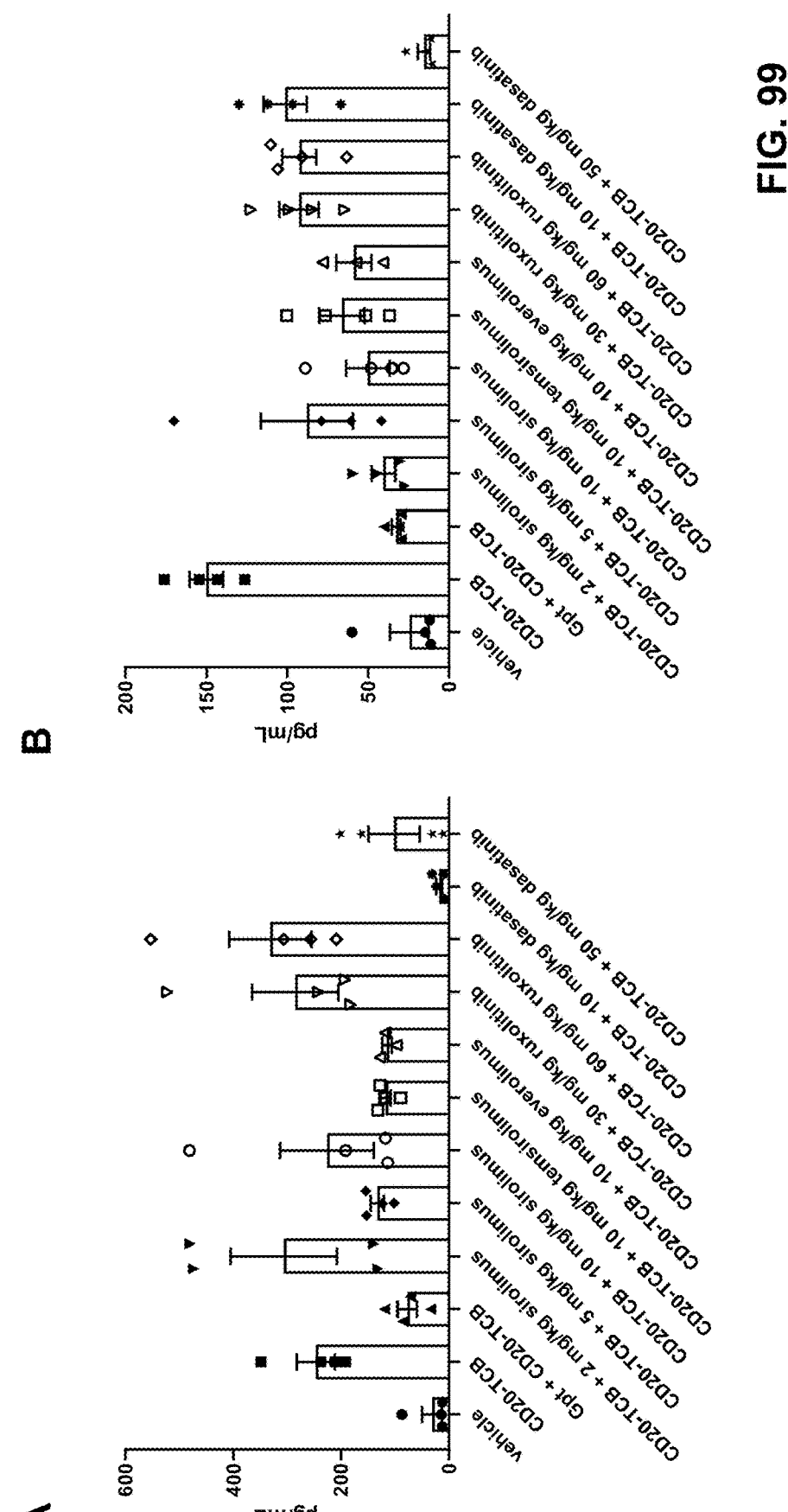

FIG. 99. Levels of TNF-α in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

Figure 100:
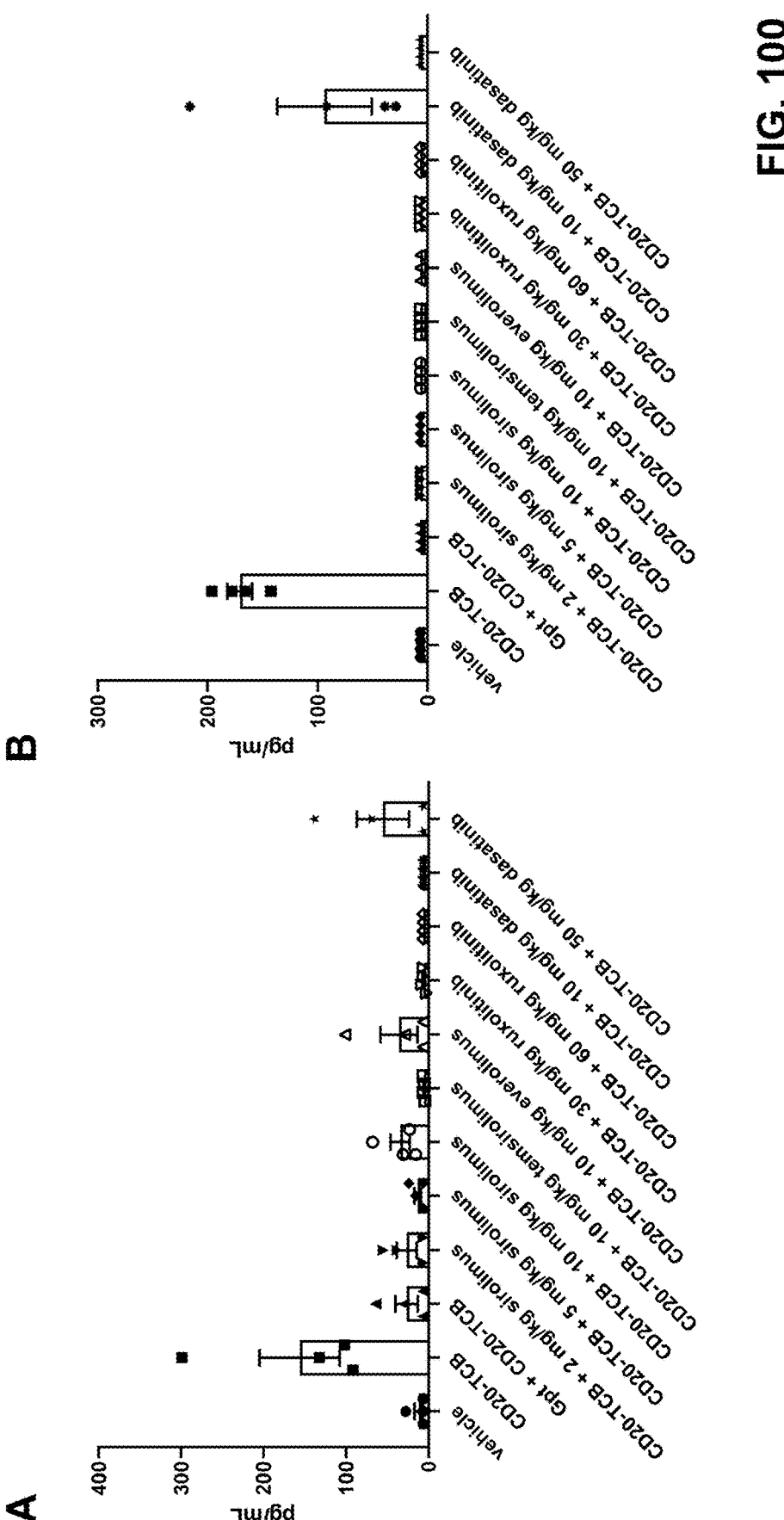

FIG. 100. Levels of IL-6 in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

Figure 101:
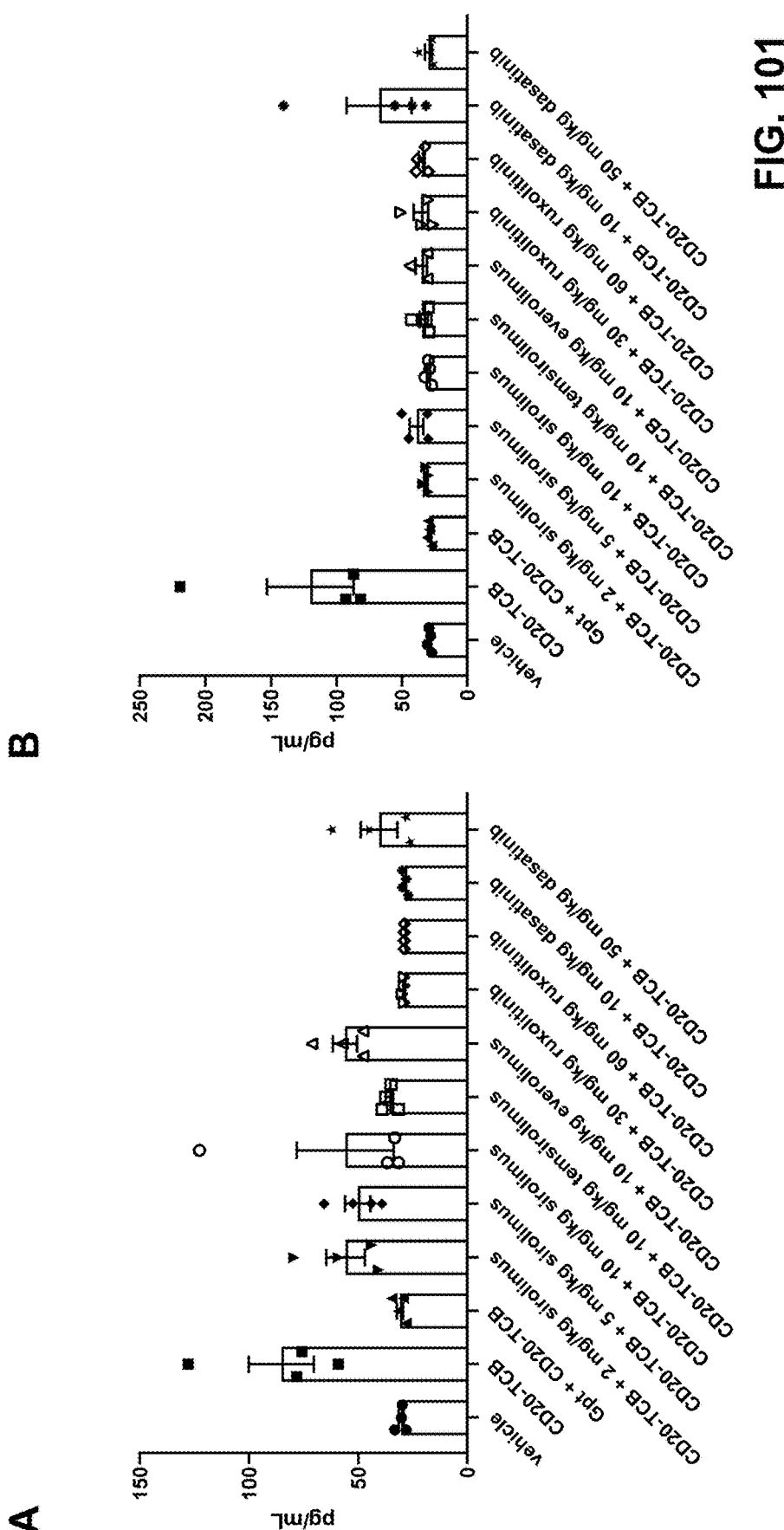

FIG. 101. Levels of IP-10 (CXCL10) in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

Figure 102:
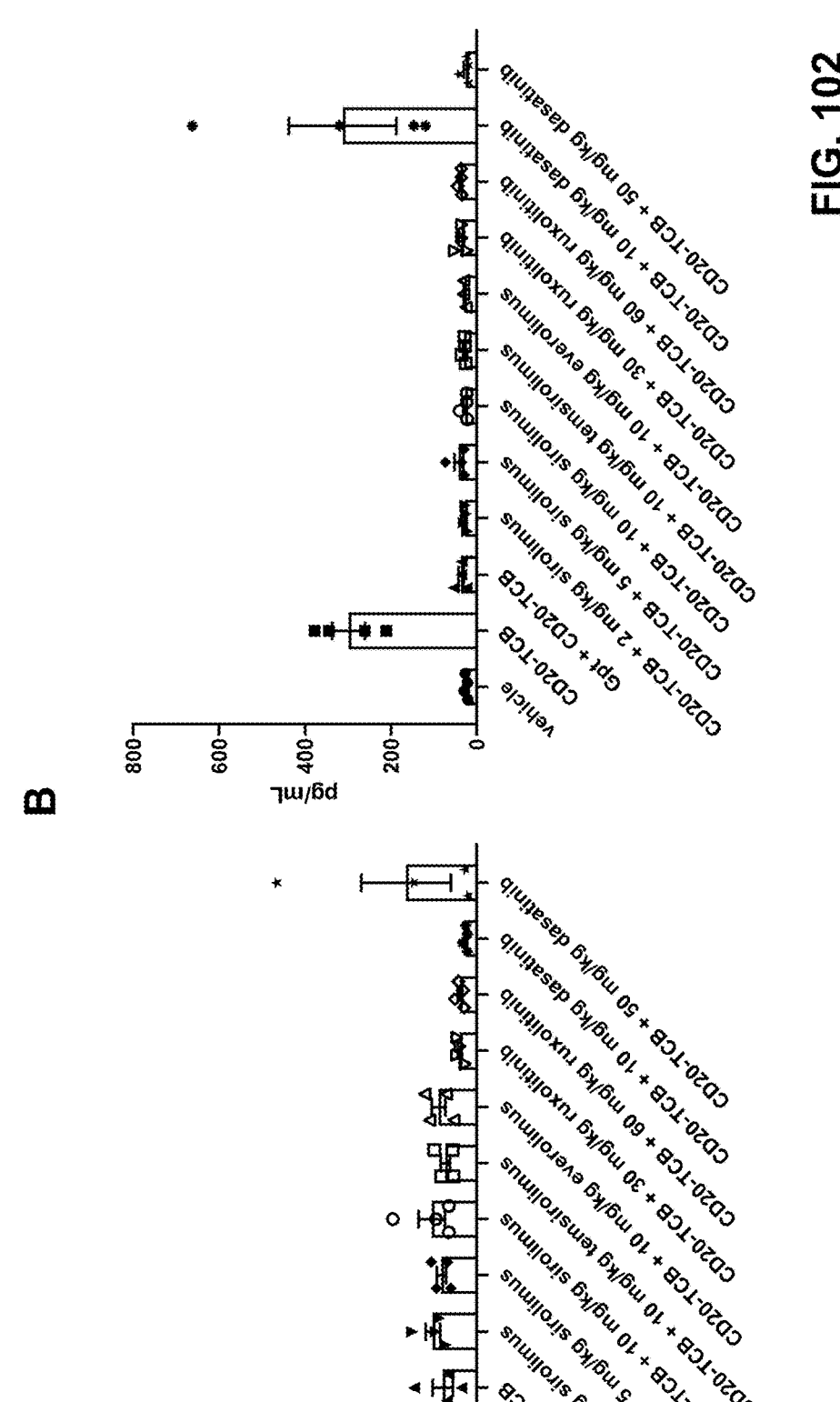

FIG. 102. Levels of MCP-1 (CCL2) in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

Figure 103:
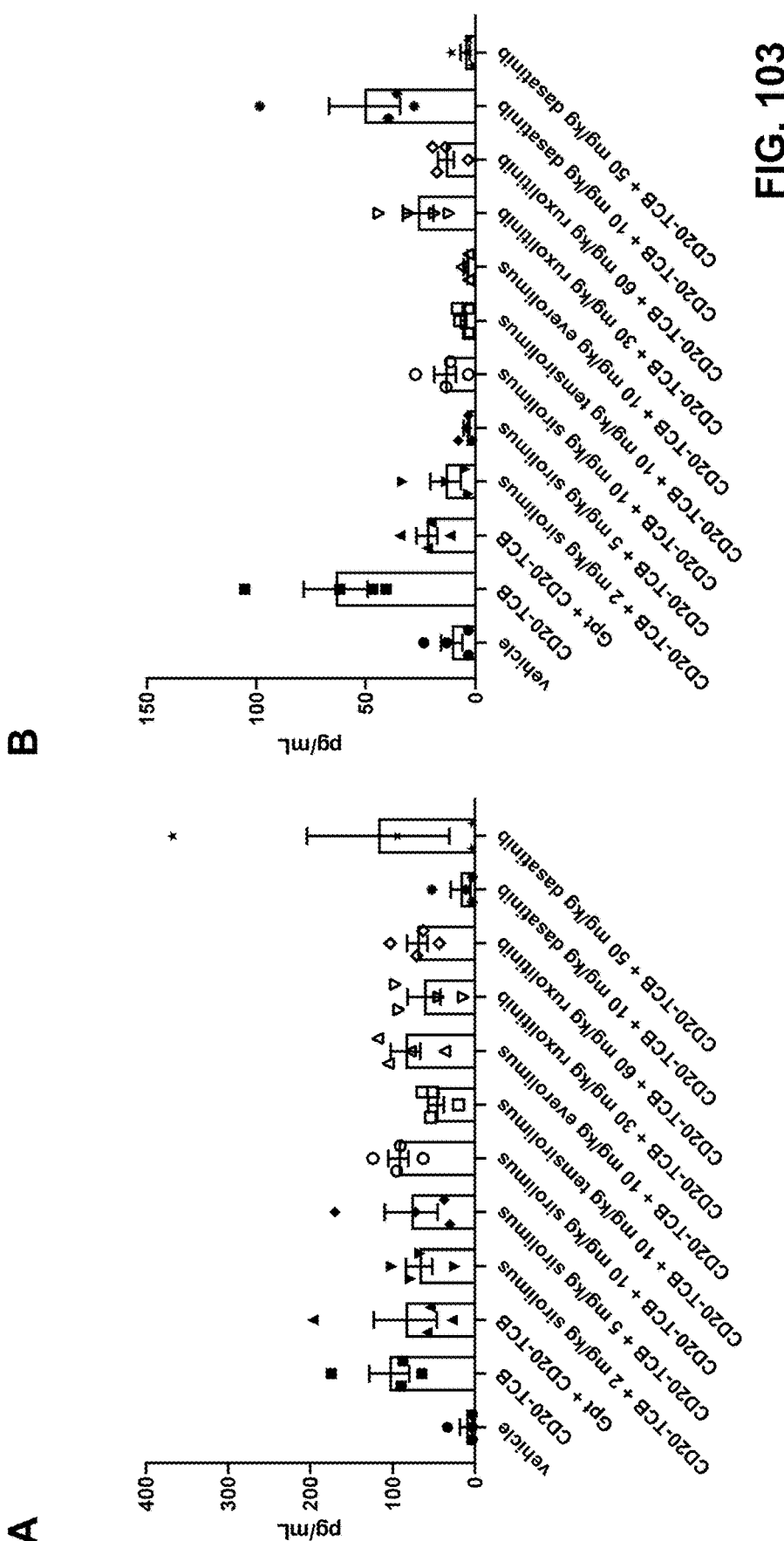

FIG. 103. Levels of IL-8 in the serum of the mice from the experiment described in FIG. 95, 4 hrs (A) and 24 hrs (B) after treatment with CD20-TCB alone or in combination with mTOR inhibitors (sirolimus, temsirolimus and everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

Figure 104:
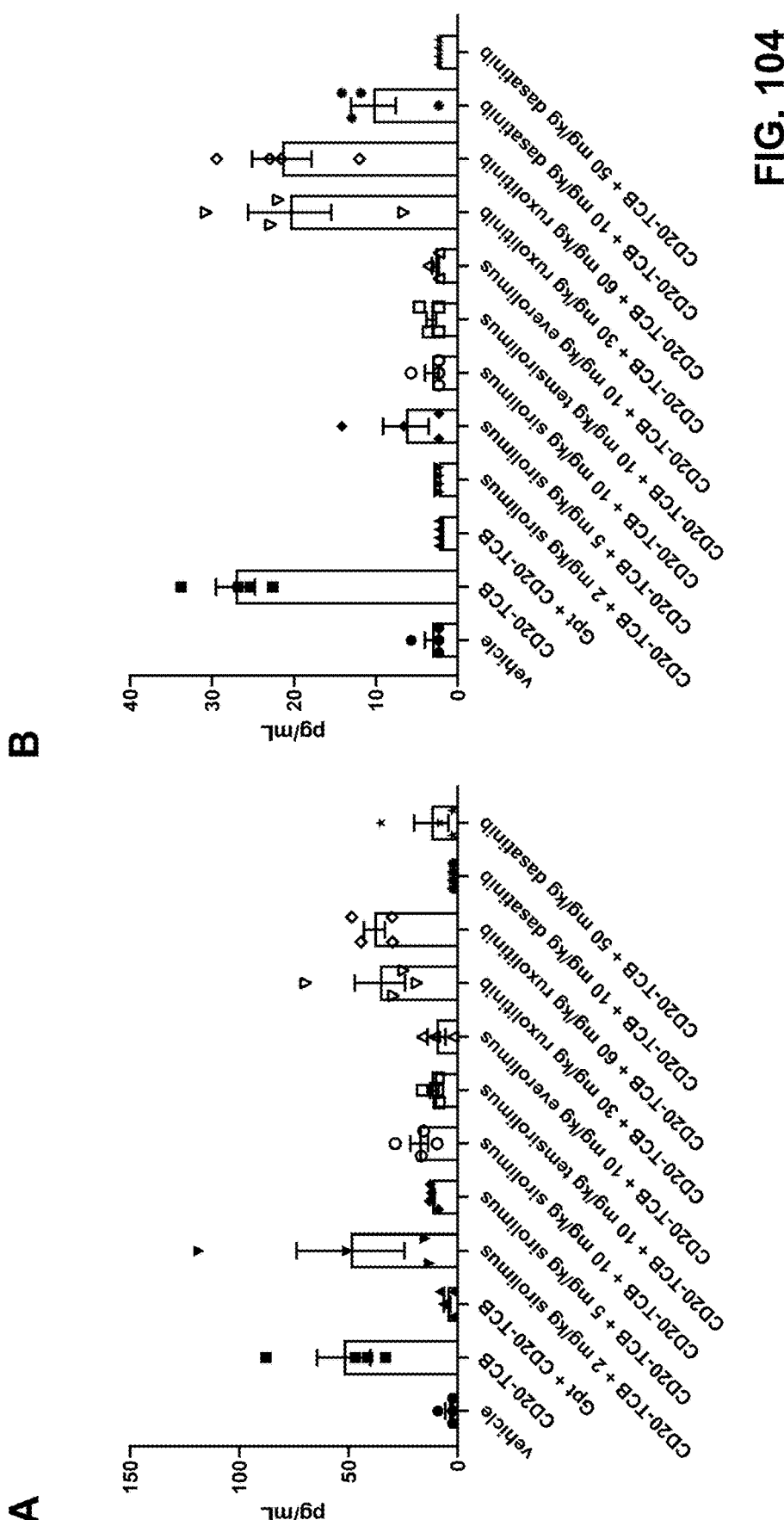

FIG. 104. Levels of GM-CSF in the serum of the mice from the experiment described in FIG. 95, 4 hrs (A) and 24 hrs (B) after treatment with CD20-TCB alone or in combination with mTOR inhibitors (sirolimus, temsirolimus, everolimus), JAK inhibitor (ruxolitinib), Src inhibitor (dasatinib) or obinutuzumab (Gazyva®) pre-treatment (GpT). Mean of n=4 mice+/−SEM, or n=3 mice+/−SEM (everolimus group) at 24 hrs.

EXAMPLES

The following are examples of methods and compositions of the invention. It is understood that various other aspects may be practiced, given the general description provided above.

Figure 1:
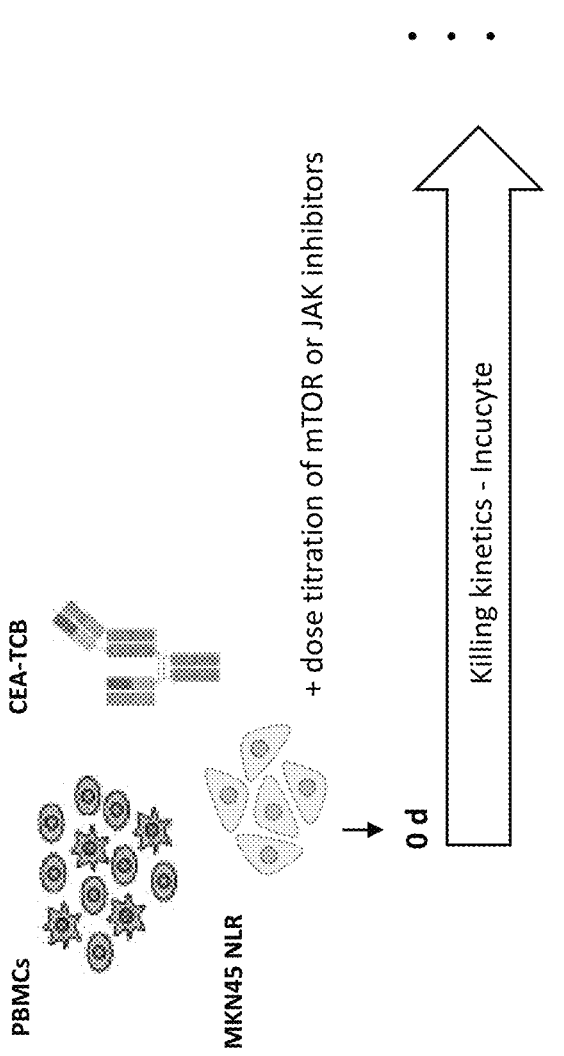
FIG. 1. Assay set-up. MKN45 NucLightRed (NLR) target cells were co-cultured with 10 nM CEA-TCB, mTOR or JAK inhibitor and peripheral blood mononuclear cells (PBMCs), E:T=50 000 PBMCs: 5 000 target cells. Kinetics of target cell killing was followed using an Incucyte® system (1 scan every 3 hours, zoom 10×, phase and red 400 ms acquisition time).
Figure 2:
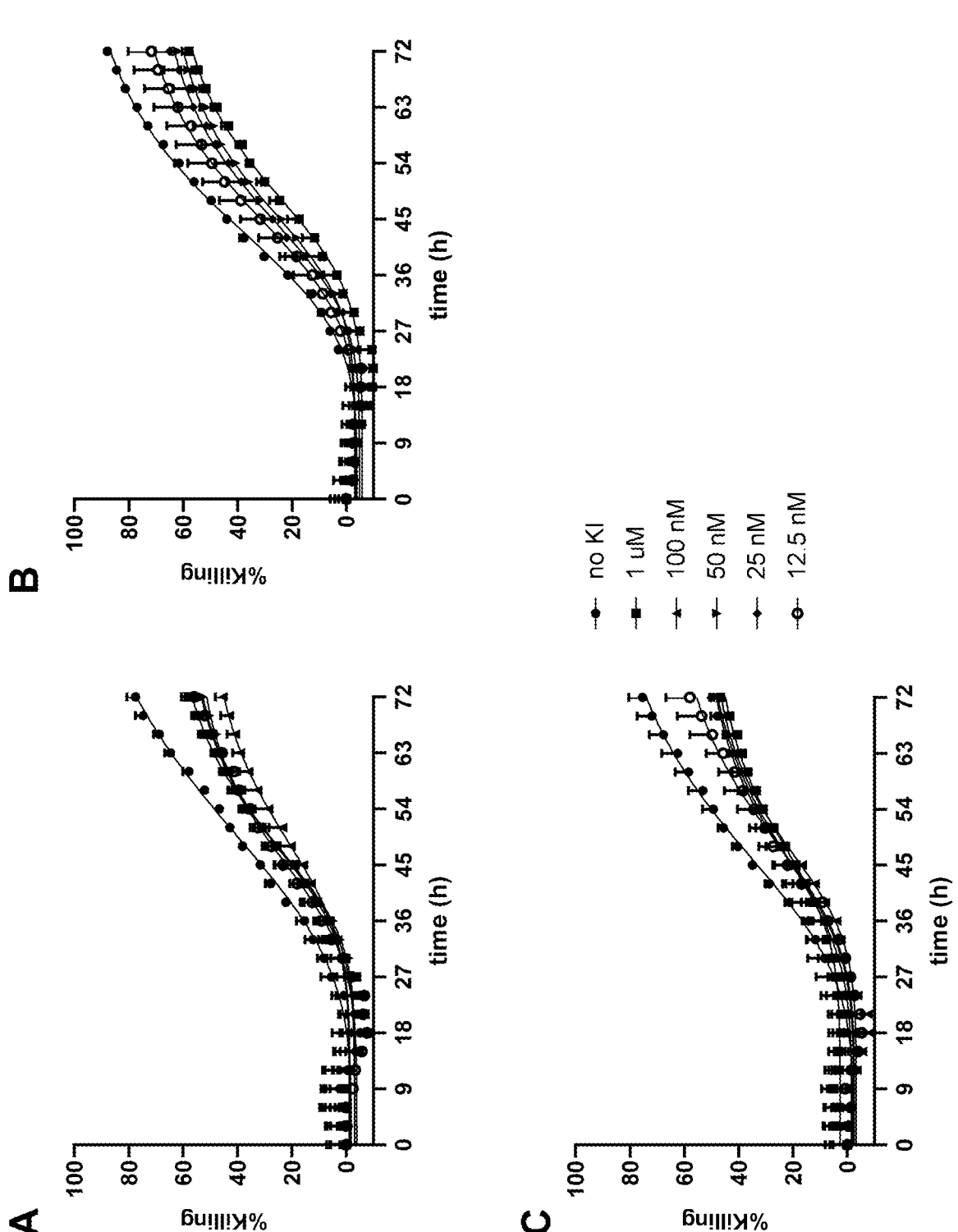
FIG. 2. Real-time killing of MKN45 NLR cells by 10 nM CEA-TCB in the presence of sirolimus (A), everolimus (B) and temsirolimus (C) concentrations ranging from 0 nM to 1000 nM in the assay described in FIG. 1. % Killing was measured by normalizing total red area with values at t=0 hour and target cells+PBMCs+mTOR inhibitor control wells for each time point. Means of technical replicates+SEM for 1 representative donor.
Figure 3:
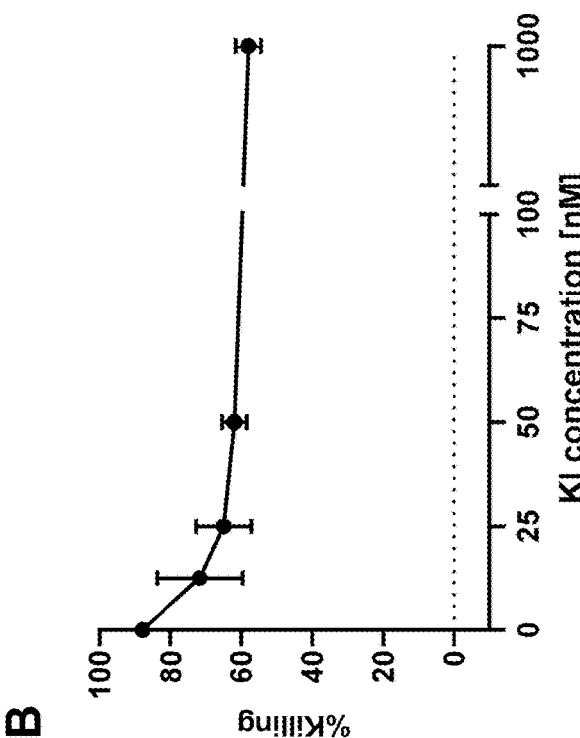
FIG. 3. Effect of escalating concentrations of sirolimus (A), everolimus (B) and temsirolimus (C) on TCB-mediated target cell killing measured at 72 h in the assay described in FIG. 1. % Killing at 72 h was measured by normalizing total red area with values at t=0 hour and target cells+PBMCs+ mTOR inhibitor control wells for each time point. Means of technical replicates +/−SD for 1 representative donor.
Figure 3:
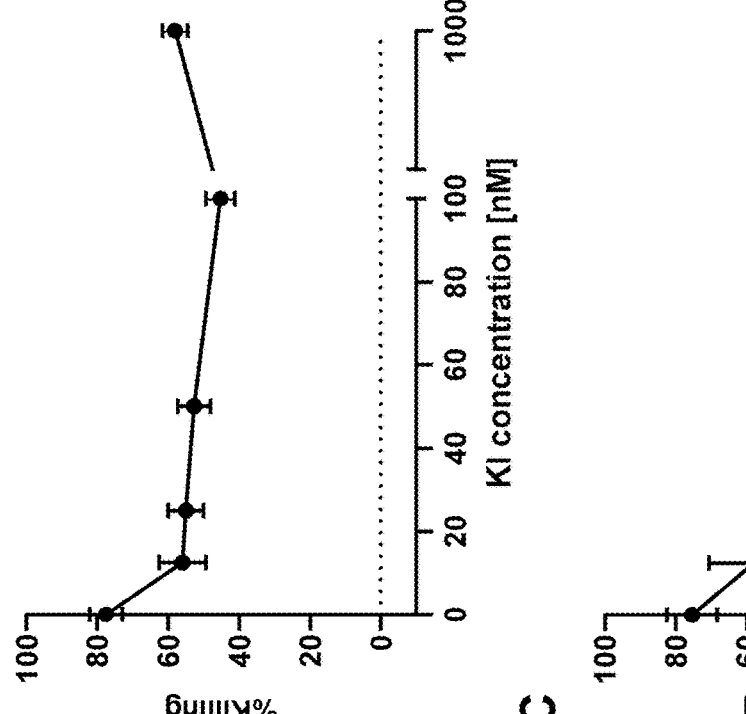
Figure 3:
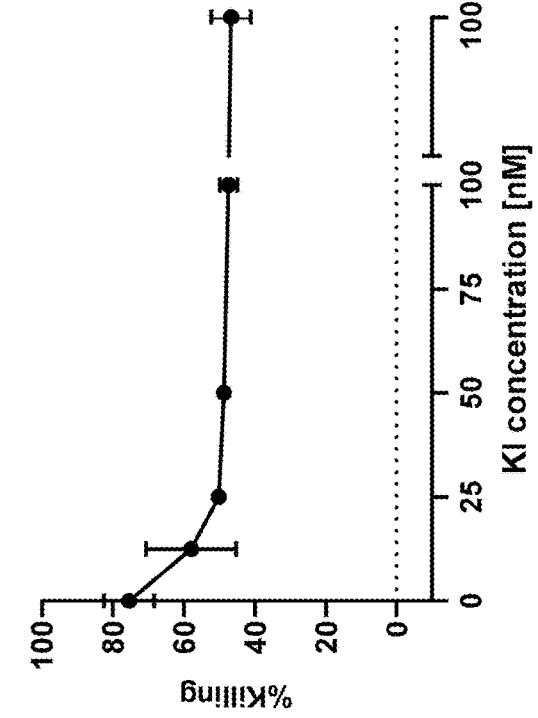

Example 1. mTOR Inhibitor Sirolimus Prevents TCB-Mediated Cytokine Release with Minimal Impact on TCB-Mediated Target Cell Killing To assess the inhibitory effect of sirolimus on TCB-mediated target-cell killing, we conducted killing assays using peripheral blood mononuclear cells (PBMCs), MKN45 NucLight Red (NLR) target cells and 10 nM CEA-TCB (SEQ ID NOs 4-23) in media supplemented with escalating concentrations of sirolimus (FIG. 1). The Incucyte® system (Essen Bioscience) was used to capture the loss of red fluorescent protein signal over time as a readout of target cell killing. Doses of sirolimus ranging from 1 μM (~915 ng/mL) to 12.5 nM (~11.4 ng/mL) only partially reduced MKN45 NLR target cell killing by 10 nM CEA-TCB (FIG. 2A and FIG. 3A).

At assay endpoint (72 h), PBMCs were stained with a live/dead stain in order to verify the impact of sirolimus on PBMC viability. At concentrations ranging from 1 μM (~915 ng/mL) to 12.5 nM (~11.4 ng/mL), sirolimus did not have a direct effect on PBMC viability in samples treated with 10 nM CEA-TCB (FIG. 4B). Expression of CD25 and CD69 on live CD4+ and CD8+ T cells was also measured by flow cytometry as a readout for T cell activation. Sirolimus did not affect expression of CD69 on CD8+ T cells, while it reduced it from ~45% to ~25% on CD4+ T cells at concentrations above 25 nM. At concentration above 25 nM, sirolimus reduced the expression of CD25 from ~45% to ~15% on CD4+ and from ~75% to 40% on CD8+ T cells (FIG. 6).

Lastly, the levels of cytokines were measured by Luminex in the supernatants of the assay to determine the impact of sirolimus on CEA-TCB-induced cytokine release. In the presence of any concentration of sirolimus, the levels of IFN-γ, TNF-α, IL-2, IL-6, MCP-1, IL-8, IL-10, IL-4 and GM-CSF in samples treated with 10 nM CEA-TCB were found very low in comparison to samples that did not receive any sirolimus treatment (FIG. 8). Sirolimus concentrations over the full range from 12.5 nM to 1 μM led to comparable impact on CEA-TCB induced cytokine release, showing that sirolimus strongly downregulated cytokine release.

Although sirolimus does not fully inhibit target cell killing and T cell activation triggered by the TCB, it strongly reduces cytokine release even at the lowest doses tested.

A similar experiment was conducted with another TCB. WSU DLCL2 cells were co-cultured together with PBMCs in the presence of 1 nM CD20-TCB (SEQ ID NOs 4-11, 24-35), and escalating sirolimus doses ranging from 0 nM to 1000 nM (FIG. 13). The killing of CTV labelled WSU target cells (FIG. 14C) as well as the expression of CD25 and CD69 on CD4+ and CD8+ T cells (FIG. 17) was measured at 24 h as a readout of the effect of sirolimus on TCB efficacy and T cell activation, respectively. Lastly, the levels of IFN-γ, IL-2, TNF-α, GM-CSF and IL-6 were measured by Luminex (FIG. 21) to assess the impact of escalating sirolimus concentrations on CD20-TCB-induced cytokine release. In line with the findings with CEA-TCB, sirolimus did not fully inhibit CD20-TCB-mediated target cell killing and T cell activation, while it strongly reduced cytokine release induced by CD20-TCB at concentrations above 12.5 nM.

Example 2. mTOR Inhibitor Temsirolimus is Prevents TCB-Mediated Cytokine Release with Minimal Impact on TCB-Mediated Target Cell Killing To assess the inhibitory effect of temsirolimus on TCB-mediated target cell killing, we conducted killing assays using peripheral blood mononuclear cells (PBMCs), NucLight Red (NLR) target cells and 10 nM CEA-TCB in media supplemented with escalating concentrations of temsirolimus (FIG. 1). The Incucyte® system (Essen Bioscience) was used to capture the loss of red fluorescent protein signal over time as a readout of target cell killing. Doses of temsirolimus ranging from 1 μM (~1031 ng/mL) to 12.5 nM (~12.9 ng/mL) only partially reduced MKN45 NLR target cell killing by 10 nM CEA-TCB (FIG. 2C and FIG. 3C).

At assay endpoint (72 h), PBMCs were stained with a live/dead stain in order to verify the impact of temsirolimus on PBMC viability. At concentrations ranging from 1 μM (~1031 ng/mL) to 12.5 nM (~12.9 ng/mL), temsirolimus did not have a direct effect on PBMC viability in samples treated with 10 nM CEA-TCB (FIG. 4C). Expression of CD25 and CD69 on live CD4+ and CD8+ T cells was also measured by flow cytometry as a readout for T cell activation. Temsirolimus did not affect expression of CD69 on CD8+ T cells, while it reduced it from ~45% to ~25% on CD4+ T cells at concentrations above 25 nM. At concentrations above 25 nM, temsirolimus reduced the expression of CD25 from ~45% to ~15% on CD4+ and from ~75% to 40% on CD8+ T cells (FIG. 7).

The levels of cytokines were measured by Luminex in the supernatants of the assay to determine the impact of temsirolimus on CEA-TCB-induced cytokine release. In the presence of any concentration of temsirolimus, the levels of IFN-γ, TNF-α, IL-2, IL-6, MCP-1, IL-8, IL-10, IL-4 and GM-CSF in samples treated with 10 nM CEA-TCB were found very low in comparison to samples that did not receive any temsirolimus treatment (FIG. 8). Temsirolimus concentrations over the full range from 12.5 nM to 1 μM led to comparable impact on CEA-TCB induced cytokine release, showing that temsirolimus strongly downregulated cytokine release.

Although temsirolimus does not fully inhibit target cell killing and T cells activation triggered by the TCB, it strongly reduces cytokine release even at the lowest doses tested.

A similar experiment was conducted with CD20-TCB. WSU DLCL2 cells were co-cultured together with PBMCs in the presence of 1 nM CD20-TCB, and escalating temsirolimus doses ranging from 0 nM to 1000 nM (FIG. 13). The killing of CTV labelled WSU target cells (FIG. 14B) as well as the expression of CD25 and CD69 on CD4+ and CD8+

(FIG. 16) was measured at 24 h as a readout of the effect of temsirolimus on TCB efficacy and T cell activation, respectively. Lastly, the levels of IFN-γ, IL-2, TNF-α, GM-CSF and IL-6 were measured by Luminex (FIG. 20) to assess the impact of escalating temsirolimus concentrations on CD20-TCB-induced cytokine release. In line with the findings with CEA-TCB, temsirolimus did not fully inhibit CD20-TCB-mediated target cell killing and T cell activation, while it strongly reduced cytokine release induced by CD20-TCB at concentrations above 12.5 nM.

Example 3. mTOR Inhibitor Everolimus Prevents TCB-Mediated Cytokine Release with Minimal Impact on TCB-Mediated Target Cell Killing To assess the inhibitory effect of everolimus on TCB-mediated target cell killing, we conducted killing assays using peripheral blood mononuclear cells (PBMCs), NucLight Red (NLR) target cells and 10 nM CEA-TCB in media supplemented with escalating concentrations of everolimus (FIG. 1). The Incucyte® system (Essen Bioscience) was used to capture the loss of red fluorescent protein signal over time as a readout of target cell killing. Doses of everolimus ranging from 1 μM (~959 ng/mL) to 12.5 nM (~12.0 ng/mL) only partially reduced MKN45 NLR target cell killing by 10 nM CEA-TCB (FIG. 2B and FIG. 3B).

Figure 5:
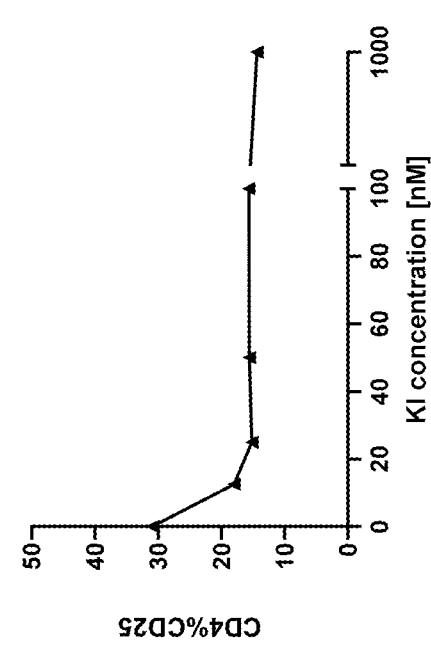
FIG. 5. Effect of escalating concentrations of everolimus on CD69 expression on CD4+(A) and CD8+(C) T cells and on CD25 expression on CD4+(B) and CD8+(D) T cells at 72 h after treatment with 10 nM CEA-TCB in the assay of FIG. 1. Technical replicates were pooled and expression of CD69 and CD25 on CD4+ and CD8+ T cells was measured by flow cytometry at 72 h. 1 representative donor.
Figure 5:
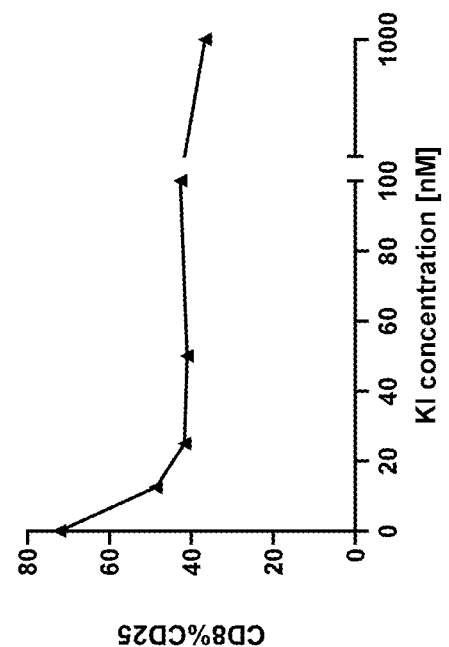
Figure 5:
Figure 5:
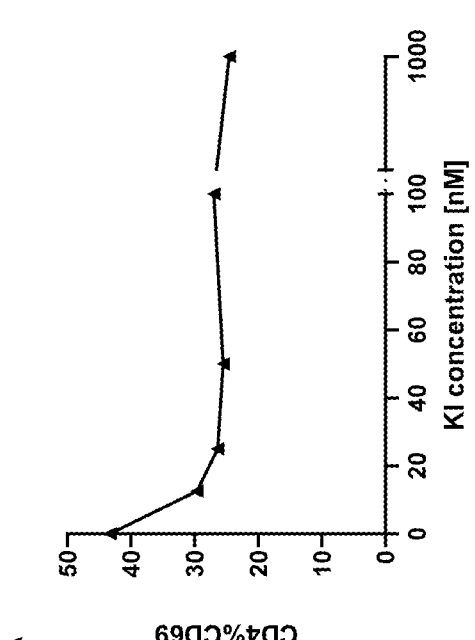
Figure 5:
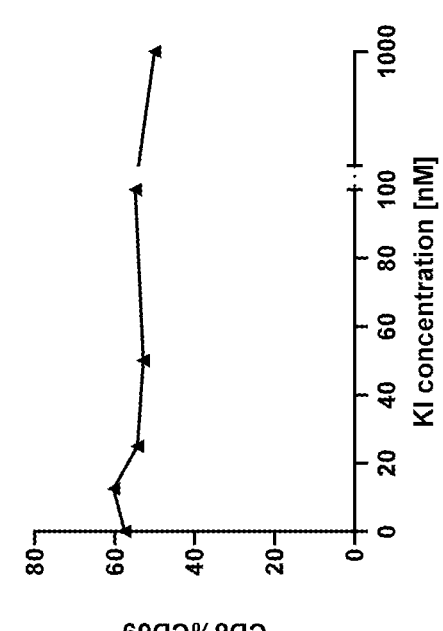

At assay endpoint (72 h), PBMCs were stained with a live/dead stain in order to verify the impact of everolimus on PBMC viability. At concentrations ranging from 1 μM (~959 ng/mL) to 12.5 nM (~12.0 ng/mL), everolimus did not have a direct effect on PBMC viability in samples treated with 10 nM CEA-TCB (FIG. 4A). Expression of CD25 and CD69 on live CD4+ and CD8+ T cells was also measured by flow cytometry as a readout for T cell activation. Everolimus did not affect expression of CD69 on CD8+ T cells, while it reduced it from ~45% to ~25% on CD4+ T cells at concentrations above 25 nM. At concentrations above 25 nM, everolimus reduced the expression of CD25 from ~45% to ~15% on CD4+ and from ~70% to 40% on CD8+ T cells (FIG. 5).

The levels of cytokines were measured by Luminex in the supernatants of the assay to determine the impact of everolimus on CEA-TCB-induced cytokine release. In the presence of any concentration of everolimus, the levels of IFN-γ, TNF-α, IL-2, IL-6, MCP-1, IL-8, IL-10, IL-4 and GM-CSF in samples treated with 10 nM CEA-TCB were found very low in comparison to samples that did not receive any everolimus treatment (FIG. 8). Everolimus concentrations over the full range from 12.5 nM to 1 μM led to comparable impact on CEA-TCB induced cytokine release, showing that everolimus strongly downregulated cytokine release.

Although everolimus does not fully inhibit target cell killing and T cell activation triggered by the TCB, it strongly reduces cytokine release even at the lowest doses tested.

A similar experiment was conducted with CD20-TCB. WSU DLCL2 cells were co-cultured together with PBMCs in the presence of 1 nM CD20-TCB, and escalating everolimus doses ranging from 0 nM to 1000 nM (FIG. 13). The killing of CTV labelled WSU target cells (FIG. 14D) as well as the expression of CD25 and CD69 on CD4+ and CD8+ (FIG. 18) was measured at 24 h as a readout of the effect of everolimus on TCB efficacy and T cell activation, respectively. Lastly, the levels of IFN-γ, IL-2, TNF-α, GM-CSF and IL-6 were measured by Luminex (FIG. 22) to assess the impact of escalating everolimus concentrations on CD20-TCB-induced cytokine release. In line with the findings with CEA-TCB, everolimus did not fully inhibit CD20-TCBmediated target cell killing and T cell activation, while it strongly reduced cytokine release induced by CD20-TCB for concentrations above 12.5 nM.

Example 4. JAK1/2 Inhibitor Ruxolitinib Prevents TCB-Mediated Cytokine Release with Minimal Impact on TCB-Mediated Target Cell Killing To assess the inhibitory effect of ruxolitinib on TCB-mediated target cell killing, we conducted killing assays using peripheral blood mononuclear cells (PBMCs), MKN45 NucLight Red (NLR) target cells and 10 nM CEA-TCB in media supplemented with escalating concentrations of ruxolitinib (FIG. 1). The Incucyte® system (Essen Bioscience) was used to capture the loss of red fluorescent protein signal over time as a readout of target cell killing. Doses of ruxolitinib ranging from 100 nM (~30.7 ng/mL) to 6.25 nM (~1.9 ng/mL) only partially reduced MKN45 NLR target cell killing by 10 nM CEA-TCB (FIGS. 9A and B).

At assay endpoint (69 h), PBMCs were stained with a live/dead stain in order to verify the impact of ruxolitinib on PBMC viability. At concentration ranging from 100 nM (~30.7 ng/mL) to 6.25 nM (~1.9 ng/mL), ruxolitinib did not have a direct effect on PBMC viability in samples treated with 10 nM CEA-TCB (FIG. 10). Expression of CD25 and CD69 on live CD4+ and CD8+T cells was also measured by flow cytometry as a readout for T cell activation. Ruxolitinib dose-dependently influenced the expression of CD25 and CD69 on both CD4+ and CD8+ T cells (FIG. 11). The effect of escalating doses of ruxolitinib on CD69 expression on CD4+ and CD8+ T cells was less pronounced than the effect on CD25 expression on CD4+ and CD8+ T cells.

The levels of cytokines were measured by Luminex in the supernatants of the assay to determine the impact of ruxolitinib on CEA-TCB-induced cytokine release. In the presence of escalating doses of ruxolitinib, the levels of IFN-γ, TNF-α, IL-2, IL-6, MCP-1, IL-8, IL-10, IL-4 and GM-CSF in samples treated with 10 nM CEA-TCB were found very low in comparison to samples that did not receive any ruxolitinib treatment (FIG. 12). Ruxolitinib strongly downregulated overall CEA-TCB induced cytokine release.

Although ruxolitinib does not fully inhibit target cell killing of and T cell activation triggered by the TCB, it strongly reduces cytokine release even at the lowest doses tested.

A similar experiment was conducted with CD20-TCB. WSU DLCL2 cells were co-cultured together with PBMCs in the presence of 1 nM CD20-TCB, and escalating ruxolitinib doses ranging from 0 nM to 1000 nM (FIG. 13). The killing of CTV labelled WSU target cells (FIG. 14A) as well as the expression of CD25 and CD69 on CD4+ and CD8+ (FIG. 15) was measured at 24 h as a readout of the effect of ruxolitinib on TCB efficacy and T cell activation, respectively. Lastly, the levels of IFN-γ, IL-2, TNF-α, GM-CSF and IL-6 were measured by Luminex (FIG. 19) to assess the impact of escalating sirolimus concentrations on CD20-TCB-induced cytokine release. Ruxolitinib did not fully inhibit CD20-TCB-mediated target cell killing and T cell activation while it strongly reduced IL-6 and IFN-γ release induced by CD20-TCB for concentrations above 25 nM nM. Unlike mTOR inhibitors, ruxolitinib did not have a strong effect on the release of TNF-α, IL-2 and GM-CSF.

Example 5. Effect of mTOR Inhibitors
(Temsirolimus, Sirolimus and Everolimus) and JAK
Inhibitors (Ruxolitinib) Vs. Anti-TNF-α Antibodies,
Anti-IL-6R Antibodies, Dexamethasone and
Dasatinib on TCB-Mediated Target Killing, T Cell
Activation and Cytokine Release To assess the impact of mTOR inhibitors (temsirolimus, sirolimus and everolimus) and JAK inhibitors (ruxolitinib) as compared to anti-TNF-α antibodies, anti-IL-6R antibodies, dexamethasone and dasatinib on TCB-mediated target cell killing, we conducted killing assays using peripheral blood mononuclear cells (PBMCs), MKN45 NucLight Red (NLR) target cells and 10 nM CEA-TCB in media supplemented with the different compounds (FIG. 1). The Incucyte® system (Essen Bioscience) was used to capture the loss of red fluorescent protein signal over time as a readout of target-cell killing. Neutralizing anti-TNF-α and anti-IL-6R antibodies (5 μg/ml) did not impact kinetics of target cell killing, nor maximal target cell killing in comparison the TCB alone. 50 nM JAK inhibitor (ruxolitinib), 50 nM mTOR inhibitors (temsirolimus, sirolimus and everolimus) had similar impact on target cell killing like 1 μM and 0.1 μM dexamethasone, and the addition of 50 nM dasatinib fully switched off TCB-induced target cell killing. (FIG. 23).

Figure 25:
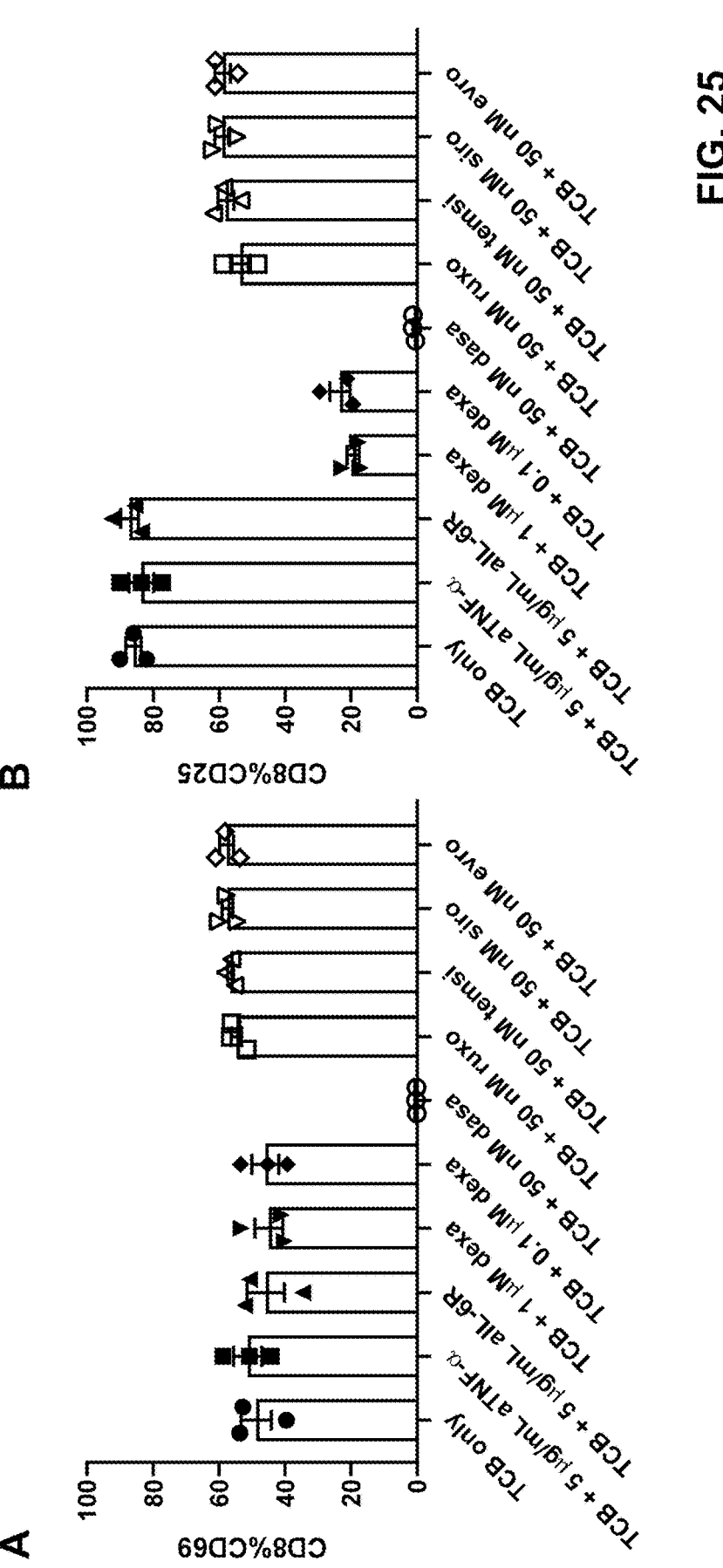

At assay endpoint (66 h), expression of CD25 and CD69 on CD4+ and CD8+ T cells was measured by flow cytometry to assess the impact of the different compounds on T cell activation. While the mTOR inhibitors (temsirolimus, sirolimus and everolimus) and the JAK inhibitor (ruxolitinib) had a milder impact on CD25 and CD69 expression on CD4+ and CD8+ T cells than dexamethasone or dasatinib, the anti-TNF-α and anti-IL-6R antibodies did not affect T cell activation (FIG. 24 and FIG. 25).

The levels of cytokines were measured by Luminex in the supernatants of the assay to determine the impact of the different compounds on CEA-TCB-induced cytokine release. The use of kinase inhibitors and dexamethasone led to an overall decrease of the TCB-induced cytokine release in comparison to neutralizing antibodies toward specific cytokines like TNF-α and IL-6 (FIG. 26). Dasatinib fully prevented CEA-TCB-induced cytokine release as well as T cell activation and target cell killing, while the mTOR inhibitors (temsirolimus, sirolimus and everolimus) and the JAK inhibitor (ruxolitinib) independently inhibited cytokine release with milder effect on T cell activation and target cell killing. The JAK1/2 inhibitor ruxolitinib reduced IL-2 levels less strongly that the mTOR inhibitors (temsirolimus, sirolimus and everolimus) (FIG. 26B).

The effect of the mTOR inhibitors (temsirolimus, sirolimus and everolimus) and the JAK inhibitor (ruxolitinib) on CEA-TCB-induced cytokine release is comparable to dexamethasone and dasatinib, and stronger as compared to anti-TNF-α and anti-IL-6R antibodies. On the other hand, the mTOR and JAK inhibitors have lower impacts on killing efficacy and T cell activation as compared to dasatinib.

A similar experiment was conducted with another TCB. WSU cells were co-cultured together with PBMCs in the presence of escalating doses of CD20-TCB, and mTOR inhibitors (temsirolimus, sirolimus, everolimus), JAK inhibitor (ruxolitinib), dasatinib, dexamethasone, anti-TNF-α antibody or anti-IL-6R antibody. The killing of B cells was measured as a readout for the impact of the various compounds on TCB efficacy at 24 h (FIGS. 27 and 28). The expression of CD25 and CD69 on CD4+ and CD8+ T cells was measured by flow cytometry as a readout for T cell activation at 24 h (FIGS. 29, 30 and 31). Lastly, the levels of cytokines (TNF-α, IFN-γ, IL-2, IL-6, IL-4, IL-10, GM-CSF and IL-1β) were analyzed by Luminex at assay endpoint to assess the impact of the different treatments on TCB-induced cytokine release (FIGS. 32 and 33). As seen with CEA-TCB, mTOR (temsirolimus, sirolimus and everolimus) and JAK (ruxolitinib) inhibitors have a comparable effect to dexamethasone and dasatinib on CD20-TCB-induced cytokine release and a stronger effect than anti-TNF-α and anti-IL-6R antibodies in reducing overall cytokine release. Unlike dasatinib, mTOR (temsirolimus, sirolimus and everolimus) and JAK (ruxolitinib) inhibitors did neither prevent the killing of B cells, nor switch off T cell activation induced by CD20-TCB, suggesting that they do not strongly influence the efficacy of the TCB.

In summary, mTOR and JAK inhibitors have lower impacts on killing efficacy and T cell activation than dasatinib (a Src inhibitor) or dexamethasone. Instead, their impact on killing efficacy and T cell activation is rather comparable impact to anti-TNF-α or anti-IL-6R antibodies. On the other hand, mTOR and JAK inhibitors, like dexamethasone and dasatinib, decrease cytokine release more potently than anti-TNF-α or anti-IL-6R antibodies. The differential activities of mTOR and JAK inhibitors show an uncoupling of TCB-induced cytokine release and cytotoxicity, suggesting these compounds may be attractive alternatives or complements to steroids or IL-6/IL-6R blockade for the mitigation of CRS.

Example 6. Effect of Sirolimus, Temsirolimus,
Everolimus and Ruxolitinib on CD20-TCB-Induced
Cytokine Release from Pre-Activated Effector Cells To assess whether mTOR inhibitors (temsirolimus, sirolimus and everolimus) and JAK inhibitor (ruxolitinib) can prevent further release of cytokine induced by the treatment of CD20-TCB, they were added in an in vitro killing assay after 18 hours of activation. In this assay, CTV labelled WSU DLCL2 tumors cells were co-cultured with PBMCs in the presence of escalating doses of CD20-TCB for 18 hours. At 18 hours, 100 nM ruxolitinib, 100 nM temsirolimus, 100 nM sirolimus or 100 nM everolimus were added in the system (FIG. 34). To verify if T cells were activated before the addition of 100 nM ruxolitinib, 100 nM temsirolimus, 100 nM sirolimus or 100 nM everolimus, tumor cell killing, T cell activation and cytokine release were measured at 18 h. To assess the impact of the addition 100 nM ruxolitinib, 100 nM temsirolimus, 100 nM sirolimus or 100 nM everolimus on TCB-induced cytokine release with respect to their impact on TCB efficacy; cytokine release, T cell activation and tumor cell killing were measured at 44 hours.

At 18 hours, treatment with CD20-TCB resulted in killing of CTV labelled WSU DLCL2 tumor cells (FIG. 35) as well as upregulation of CD25 on both CD4+ and CD8+ T cells (FIG. 36), indicating that T cells were activated before the addition of the different inhibitors in the assay system. The addition of 100 nM ruxolitinib, 100 nM temsirolimus, 100 nM sirolimus or 100 nM everolimus did not impact CTV labelled WSU DLCL2 tumor cell killing (FIG. 37) and T cell activation (FIG. 38) measured at 44 hours. However, the addition of mTOR inhibitors (temsirolimus, sirolimus and everolimus) stopped IL-2, IFN-γ, IL-6 and GM-CSF release and, to a lower extent, the release of TNF-α and IL-1β between 18 hours and 44 hours (FIG. 39). The addition of JAK inhibitor (ruxolitinib) prevented further production of IFN-γ, IL-6 and and, to a lower extent, production of GM-CSF and TNF-α but did not prevent further production of IL-2 between 18 hours and 44 hours (FIG. 39).

Furthermore, these results were confirmed for three donors at a fixed CD20-TCB concentration of 1 nM. The addition of 100 nM ruxolitinib, 100 nM temsirolimus, 100 nM sirolimus or 100 nM everolimus did not impact further CTV labelled WSU DLCL2 tumor cell killing (FIG. 40) and T cell activation (FIGS. 41 and 42) between 18 hours and 44 hours. However, the addition of 100 nM temsirolimus, 100 nM sirolimus or 100 nM everolimus prevented further release of IFN-γ, IL-2, IL-6 and to a lower extent TNF-α and IL-1β release between 18 hours and 44 hours (FIG. 43). The addition of 100 nM ruxolitinib prevented further release of IFN-γ and IL-6 and to a lower extent TNF-α and IL-1β but did not prevent IL-2 release (FIG. 43).

Overall, these data suggest that mTOR (temsirolimus, sirolimus and everolimus) as well as JAK (ruxolitinib) inhibitors can rapidly switch off CD20-TCB-induced cytokine release from pre-activated effector cells while not strongly affecting CD20-TCB efficacy.

Example 7. JAK1/2 Inhibitor Ruxolitinib Prevents TCB-Mediated Cytokine Release with Minimal Impact on TCB-Mediated Target Cell Killing The effect of ruxolitinib on TCB-induced tumor cell killing and cytokine release was assessed using an additional TCB, the MAGEA4-TCB (SEQ ID NOs 37-56). Similarly to Example 4, a killing assay was conducted using peripheral blood mononuclear cells (PBMCs), A375 NucLight Red (NLR) target-cells and 8 nM MAGEA4-TCB in media supplemented with escalating concentrations of ruxolitinib ranging from 0 nM to 100 nM. The Incucyte® system (Essen Bioscience) was used to capture the loss of red fluorescent protein signal over time as a readout of killing, allowing to evaluate the effect of ruxolitinib on MAGEA4-TCB-induced target-cell killing. Lastly, the supernatants were collected at assay endpoint (72 hours) and cytokines were measured by Luminex to assess the effect of escalating concentrations of ruxolitinib on MAGEA4-TCB-induced cytokine release.

While ruxolitinib did not prevent MAGEA4-TCB induced tumor cell killing (FIG. 44), the levels of IFN-γ (FIG. 45A), TNF-α (FIG. 45C), IL-8 (FIG. 45G), IL-6 (FIG. 45E), MCP-1 (FIG. 45H), IL-10 (FIG. 45I) and IL-1β (FIG. 45F) were reduced with increasing concentrations of ruxolitinib. The levels of GM-CSF (FIG. 45D) and IL-2 (FIG. 45B) were not impacted by ruxolitinib, in line with the data generated with CEA-TCB and CD20-TCB. Hence, the JAK1/2 inhibitor ruxolitinib could represent an attractive approach to mitigate MAGEA4-TCB-induced cytokine release while not affecting its efficacy, nor IL-2 and GM-CSF levels.

Example 8. mTOR Inhibitors Sirolimus, Temsirolimus and Everolimus Prevent TCB-Mediated Cytokine Release with Minimal Impact on TCB-Mediated Target Cell Killing The effect of sirolimus, temsirolimus and everolimus on TCB-induced tumor cell killing and cytokine release was assessed using an additional TCB, the MAGEA4-TCB. Similarly to Examples 1-3, a killing assay was conducted using peripheral blood mononuclear cells (PBMCs), A375 NucLight Red (NLR) target-cells and 8 nM MAGEA4-TCB in media supplemented with escalating concentrations of sirolimus, temsirolimus and everolimus ranging from 0 nM to 100 nM. The Incucyte® system (Essen Bioscience) was used to capture the loss of red fluorescent protein signal over time as a readout of target-cell killing. Lastly, the supernatants were collected at assay endpoint (72 hours) and cytokines were measured by Luminex to assess the effect of escalating concentrations of sirolimus, temsirolimus and everolimus on MAGEA4-TCB-induced cytokine release.

While sirolimus, temsirolimus and everolimus did not prevent MAGEA4-TCB induced tumor cell killing (FIG. 46A, B, C), the levels of most of the tested cytokines, including IFN-γ (FIG. 47A), IL-2 (FIG. 47B), TNF-α (FIG. 47C), IL-8 (FIG. 47G), IL-6 (FIG. 47E), MCP-1 (FIG. 47H) and IL-10 (FIG. 47I), were reduced with increasing concentrations of sirolimus, temsirolimus and everolimus. In line with the data generated with CEA-TCB and CD20-TCB, the mTOR inhibitors sirolimus, temsirolimus and everolimus could represent an attractive approach to mitigate MAGEA4-TCB-induced cytokine release while not impacting its efficacy.

Example 9. The JAK Inhibitor Baricitinib can Efficiently Prevent TCB-Induced Cytokine Release while not Affecting its Efficacy To assess the inhibitory effect of the JAK1/2 inhibitor baricitinib on CD20-TCB-mediated target-cell killing and cytokine release, peripheral blood mononuclear cells (PBMCs) were co-cultured with CTV labelled WSU target-cells and CD20-TCB in media supplemented with escalating concentrations of baricitinib. At 24 hours, tumor cell killing was measured by flow cytometry by exclusion of dead CTV cells. The supernatants were collected and cytokines were measured by Luminex. In addition, the expression of CD69 and CD25 on CD4+ and CD8+ T cells was measured by flow cytometry to assess the impact of baricitinib on T cell activation.

As a result, baricitinib concentrations ranging from 0 nM to 100 nM did not impair CD20-TCB-induced tumor cell killing (FIGS. 48 and 49) and T cell activation, as shown by the expression of CD25 and CD69 on CD4+(FIGS. 50A, C and 51) and CD8+(FIGS. 50B, D and 52) T cells. At a higher concentration of 1 μM, baricitinib slightly reduced CD20-TCB induced tumor cell killing. (FIGS. 48 and 49) and T cell activation (FIGS. 50A-D, 51 and 52). Similarly to the other JAK inhibitor ruxolitinib, escalating doses of baricitinib reduced the levels of IFN-γ, TNF-α, GM-CSF, IL-6 and IL-8 (FIGS. 53A, C, D, E and F, FIGS. 54A, C, D, E and F) but not IL-2 (FIG. 53B, FIG. 54B).

While baricitinib did not prevent the killing of CTV WSU tumor cells and T cell activation triggered by CD20-TCB, it strongly reduced CD20-TCB-induced cytokine release for doses ranging from 12.5 nM to 100 nM. Hence, the JAK inhibitor baricitinib, further to ruxolitinib, could be used to mitigate CD20-TCB-induced cytokine release while not affecting its efficacy.

Example 10. The Effect of the JAK Inhibitor Baricitinib on TCB-Induced Tumor Cell Killing, T Cell Activation and Cytokine Release is Comparable to the JAK Inhibitor Ruxolitinib To verify whether the effect of baricitinib on TCB-induced cytokine release, T cell activation and tumor cell killing is comparable to the effect of ruxolitinib, we conducted killing assays using peripheral blood mononuclear cells (PBMCs), MKN45 NucLight Red (NLR) target-cells and 10 and 1 nM CEA-TCB in media supplemented with escalating concentrations of ruxolitinib and baricitinib. The Incucyte® system (Essen Bioscience) was used to capture the loss of red fluorescent protein signal over time as a readout of target cell killing. At 72 hours, the expression of CD25 on CD4+ and CD8+ T cells was measured by flow cytometry to assess the impact of baricitinib and ruxolitinib on CEA-TCB-induced T cell activation. Lastly, the supernatants were collected at assay endpoint (72 hours) and cytokines were measured by Luminex to assess the effect of baricitinib vs. ruxolitinib on CEA-TCB-induced cytokine release. The percentage of cytokine inhibition was calculated as a percentage of cytokines found in the absence of kinase inhibitors and allowed to compare the effect of baricitinib and ruxolitinib on CEA-TCB-induced cytokine release.

Both baricitinib and ruxolitinib did not prevent the killing of MKN45 NLR tumor cell induced by 1 nM CEA-TCB (FIGS. 55A and B) for escalating concentrations ranging between 0 nM and 100 nM. At a higher concentration of 1 μM, both baricitinib and ruxolitinib partially prevented the killing of MKN45 NLR tumor cells (FIGS. 55A and B). Comparably to ruxolitinib, escalating concentrations of baricitinib reduced the expression of CD25 on CD4+(FIG. 56A) and CD8+(FIG. 56B) T cells, indicating that the effect of baricitinib on CEA-TCB-induced T cell activation is comparable to ruxolitinib. The degree of inhibition of IFN-γ, TNF-α, GM-CSF, IL-6 and IL-8 levels (FIGS. 57A, C, D, E and F) was the similar for escalating concentrations of ruxolitinib and baricitinib. In line with what was observed with ruxolitinib, escalating concentrations of baricitinib did not reduce IL-2 (FIG. 57B).

The comparison of baricitinib to ruxolitinib was done using another TCB, the MAGEA4-TCB. Similarly to CEA-TCB, killing assays were conducted using peripheral blood mononuclear cells (PBMCs), A375 NucLight Red (NLR) target-cells and 25 nM MAGEA4-TCB in media supplemented with escalating concentrations of ruxolitinib and baricitinib ranging from 0 nM to 100 nM. The Incucyte® system (Essen Bioscience) was used to capture the loss of red fluorescent protein signal over time as a readout of target-cell killing. Cytokines were measured by Luminex in the supernatants collected at assay endpoint (72 hours) to assess the effect of baricitinib vs. ruxolitinib on MAGEA4-TCB-induced cytokine release.

In line with the data generated with CEA-TCB, the effect of baricitinib (FIG. 58A) on MAGEA4-TCB-induced tumor cell killing was comparable to ruxolitinib (FIG. 58B) for escalating concentrations ranging from 0 nM to 100 nM. In addition, the effect of baricitinib (FIG. 59A-F) on MAGEA4-TCB-induced GM-CSF, IL-2, IFN-γ, IL-2, TNF-α, IL-1β and IL-6 release is also comparable to ruxolitinib (FIG. 60A-F) for concentrations ranging from 0 nM to 100 nM.

In summary, the effect of baricitinib on CEA-TCB and MAGEA4-TCB-induced tumor cell killing, T cell activation and cytokine release is comparable to the effect of ruxolitinib. Thus, further to ruxolitinib, baricitinib represents an attractive approach for the mitigation of TCB-induced cytokine release.

Example 11. JAK Inhibitor Ruxolitinib and mTOR Inhibitor Sirolimus Prevent CAR-T Cell-Induced Cytokine Release To assess the impact of JAK inhibitor ruxolitinib and mTOR inhibitor sirolimus on cytokine release induced by CAR-T cells, we conducted a killing assay where PGLALA and CD16 universal CAR-T cells (CAR-T cells with a CAR comprising an anti-P329G-Fc scFv (binding to PGLALA Fc) or CD16 (binding to wild-type Fc)) were co-cultured with CTV WSU tumor cells in the presence of escalating concentrations of PGLALA Fc and wild-type Fc anti-CD20 IgG in medium supplemented with 100 nM ruxolitinib or 100 nM sirolimus. To verify whether ruxolitinib and sirolimus interfered with tumor cell killing by CAR-T cells, we measured killing of CTV WSU tumor cells by flow cytometry at 24 hours. To verify whether ruxolitinib and sirolimus reduced the cytokine release induced by CAR-T cells, the cytokines were measured by Luminex in the supernatants of the assay at 72 hours.

As a result, neither sirolimus nor ruxolitinib prevented tumor cell killing by PGLALA (FIG. 61A) and CD16 (FIG. 61B) CAR-T cells. For both PGLALA (FIG. 62) and CD16 (FIG. 63) CAR-T cells, ruxolitinib reduced the release of IFN-γ (FIGS. 62B and 63B), TNF-α (FIGS. 62D and 63D) and GM-CSF (FIGS. 62A and 63A), but not IL-2 (FIGS. 62C and 63C), in line with findings with TCBs. Finally, sirolimus strongly reduced the release of all cytokines tested, namely IFN-γ (FIGS. 62B and 63B), TNF-α (FIGS. 62D and 63D), GM-CSF (FIGS. 62A and 63A) and IL-2 (FIGS. 62C and 63C).

Overall, this data suggest that JAK1/2 inhibitor ruxolitinib and mTOR inhibitor sirolimus could be an attractive approach to prevent cytokine release induced by CAR-T cells while not affecting CAR-T cell efficacy.

Example 12. mTOR Inhibitors Sirolimus, Temsirolimus and Everolimus and JAK Inhibitor Ruxolitinib do not Prevent CD19-TCB Dependent Killing and T Cell Activation while Strongly Reducing Cytokine Release The effect of the mTOR inhibitors sirolimus, everolimus and temsirolimus and the JAK1/2 inhibitor ruxolitinib on TCB-induced T cell cytotoxicity, T cell activation and cytokine release was assessed using another TCB, CD19-TCB (SEQ ID NOs 5, 7-9, 11, 64-74, 76-78, 80). PBMCs were co-cultured together with CellTrace™ Violet (CTV) labelled SUDLH-8 tumor cells and escalating concentrations of CD19-TCB in the presence of the different kinase inhibitors, including also the Src inhibitor dasatinib (FIG. 64). At assay endpoint (24 hrs), the killing of CTV labelled SUDLH-8 cells was measured by flow cytometry by exclusion of the dead SUDLH-8 cells with a Live/Dead stain. The expression of CD25 and CD69 on CD4+ and CD8+ T cells was also measured by flow cytometry as a readout for T cell activation. Lastly, the levels of cytokines were measured in the supernatants of the assay to evaluate the effect of mTOR, JAK and Src inhibitors on CD19-TCB-induced cytokine release.

As a result, unlike the Src inhibitor dasatinib, the mTOR and JAK inhibitors did not prevent CD19-TCB-dependent SUDLH-8 killing (FIG. 65A, FIG. 66). In line with the effect on killing, mTOR and JAK inhibitors did not block the expression of CD25 and CD69 on CD4+ and CD8+ T cells, as opposed to the Src inhibitor dasatinib (FIG. 65B-E, FIG. 67). Finally, the JAK1/2 inhibitor ruxolitinib prevented CD19-TCB-induced IFN-γ, TNF-α, IL-6 and GM-CSF release and, to a lower extent, IL-2 release while the mTOR imhibitors strongly reduced the release of all four cytokines (FIG. 68).

Overall, the differential activities of the mTOR, JAK and Src inhibitors revealed the uncoupling of CD19-TCB-induced T cell cytotoxicity and cytokine release. In addition, these data suggest that the mTOR inhibitors sirolimus, temsirolimus and everolimus as well as the JAK1/2 inhibitor ruxolitinib could mitigate CD19-TCB induced cytokine release while not preventing tumor cell killing and T cell activation. The Src inhibitor dasatinib would rather stand as an antidote for off-tumor toxicities or high grade CRS where a switch-off in T cell functionality would be required to block both cytokine release and killing.

Example 13. JAK Inhibitors Baricitinib and Tofacitinib have Comparable Effect to Ruxolitinib on CD19-TCB Induced Tumor Cell Killing, T Cell Activation and Cytokine Release To compare the effect of the JAK inhibitors baricitinib and tofacitinib to ruxolitinib on CD19-TCB-induced T cell cytoxicity, T cell activation and cytokine release, PBMCs were co-cultured together with CTV labelled SUDLH-8 tumor cells and escalating concentrations of CD19-TCB in the presence of 100 nM ruxolitinib, 100 nM baricitinib and 100 nM tofacitinib (FIG. 69). At assay endpoint (24 hrs), the killing of CTV labelled SUDLH-8 cells was measured by flow cytometry by exclusion of the dead SUDLH-8 cells with a Live/Dead stain. The expression of CD25 and CD69 on CD4+ and CD8+ T cells was also measured by flow cytometry as a readout for T cell activation. Lastly, the levels of cytokines were measured in the supernatants of the assay to assess the effect of the JAK inhibitors on CD19-TCB-induced cytokine release.

Similarly to ruxolitinib, baricitinib and tofacitinib did not prevent CD19-TCB dependent killing of CTV labelled SUDLH-8 tumor cells (FIG. 70), nor did they prevent the expression of CD25 and CD69 on CD4+(FIGS. 71A and B) and CD8+(FIGS. 71C and D) T cells. In addition, the JAK inhibitors baricitinib and tofacitinib prevented CD19-TCB-induced IFN-γ, TNF-α, IL-6 and GM-CSF release and, to a lower extent, IL-2 release (FIG. 72), comparably to ruxolitinib. Baricitinib and tofacitinib appeared to be as potent as ruxolitinib in preventing CD19-TCB-induced cytokine release while not blocking T cell activation and T cell cytotoxicity in vitro. Finally, this experiment suggests that baricitinib and tofacitinib could represent two additional JAK inhibitors for the mitigation of CD19-TCB-induced cytokine release as alternatives to ruxolitinib.

Example 14. Comparison of JAK Inhibitor Ruxolitinib, mTOR Inhibitors Sirolimus, Temsirolimus and Everolimus, and Src Inhibitor Dasatinib, to Current CRS Mitigation Approaches To verify whether the use of JAK and mTOR inhibitors would be comparable to current approaches used for the mitigation of TCB-induced cytokine release, we compared the effect of the kinase inhibitors to the corticosteroid dexamethasone and to the use of anti-TNF-α and anti-IL-6R antibodies in vitro. Therefore, PBMCs were co-cultured together with CTV labelled SUDLH-8 tumor cells and escalating concentrations of CD19-TCB in the presence of the mTOR, JAK and Src inhibitors, as well as dexamethasone, anti-TNF-α antibody (αTNF-α; Biolegend #502922 (antibody Mab11)) and anti-IL-6R antibody (aIL-6R; Roche in-house) (FIG. 73). At assay endpoint (24 hrs), the killing of CTV labelled SUDLH-8 cells was measured by flow cytometry by exclusion of the dead SUDLH-8 cells with a Live/Dead stain to evaluate the effect of the different mitigation approaches on CD19-TCB-dependent killing. Then, the expression of CD25 and CD69 on CD4+ and CD8+ T cells was also measured by flow cytometry as a readout for the effect on T cell activation. Lastly, the levels of cytokines were measured in the supernatants of the assay to address the effect of the JAK inhibitors on CD19-TCB-induced cytokine release. Comparably to dexamethasone, anti-TNF-α antibody and anti-IL-6R antibody, the mTOR inhibitors sirolimus, temsirolimus and everolimus, as well as the JAK1/2 inhibitor ruxolitinib, did not prevent CD19-TCB-dependent killing of CTV SUDLH-8 cells—unlike the Src inhibitor dasatinib (FIG. 74). In addition, the mTOR and JAK inhibitors, as well as dexamethasone, anti-TNF-α and anti-IL-6R, did not prevent the expression of CD25 (FIGS. 75A and C, FIGS. 76A and C) and CD69 (FIGS. 75B and D, FIGS. 76B and D) on CD4+ and CD8+ T cells, in contrast to the Src inhibitor dasatinib which fully blocked T cell activation. Lastly, the effect of the mTOR inhibitors sirolimus, temsirolimus and everolimus and the JAK1/2 inhibitor ruxolitinib on CD19-TCB-induced IFN-γ and TNF-α was comparable to the effect of dexamethasone (FIG. 77). The effect of the mTOR inhibitors on CD19-TCB-induced IL-2 and GM-CSF was comparable to the effect of dexamethasone, yet the effect of the JAK1/2 inhibitor ruxolitinib on these two cytokines was weaker (FIG. 77). The effect of the JAK and mTOR inhibitors in reducing CD19-TCB-induced IFN-γ, IL-2, TNF-α and GM-CSF was stronger than the effect of anti-IL-6R antibody, which only slightly decreased IFN-γ, IL-2, TNF-α and GM-CSF levels, or the effect of anti-TNF-α antibody which specifically reduced TNF-α and to a lower extent IFN-γ, IL-2 and GM-CSF. Finally, the Src inhibitor dasatinib shows complete inhibition of CD19-TCB-induced cytokine release (FIG. 77), correlating with the inhibition of killing and T cell activation.

In summary, this experiment suggests that the effect of the mTOR inhibitors sirolimus, temsirolimus and everolimus, as well as the JAK1/2 inhibitor ruxolitinib, is comparable to the effect of the corticosteroid dexamethasone to reduce CD19-TCB-dependent cytokine release, while not preventing T cell cytotoxicity and T cell activation. In addition, the effect of the mTOR inhibitors sirolimus, temsirolimus and everolimus and the JAK1/2 inhibitor ruxolitinib on CD19-TCB-induced cytokine release was shown to be stronger than the blockade of IL-6R and TNF-α. Taken together, this data highlights that the JAK and mTOR inhibitors could represent alternative approaches for the mitigation of CD19-TCB-induced cytokine release to the use of anti-IL-6R or anti-TNF-α antibodies or even corticosteroids.

Example 15. Effect of Sirolimus (as an Exemplary mTOR Inhibitor), Ruxolitinib (as an Exemplary JAK Inhibitor) and Dasatinib (as an Exemplary Src Inhibitor) on CD19-TCB-Induced Cytokine Release from Pre-Activated Effector Cells To assess whether the mTOR inhibitor sirolimus, the JAK1/2 inhibitor ruxolitinib and the Src inhibitor dasatinib can prevent further release of cytokines induced by the treatment of CD19-TCB, they were added in an in vitro killing assay after 24 hrs of activation (FIG. 78). In this assay CTV labelled NALM-6 tumors cells were co-cultured with PBMCs in the presence of escalating doses of CD19-TCB for 24 hrs. At 24 hrs, 100 nM ruxolitinib, 100 nM sirolimus or 100 nM dasatinib were added in the system. To verify if T cells were activated before the addition of the different kinase inhibitors, tumor cell killing and cytokine release were measured at 24 hrs (FIGS. 79 and 80). Lastly, cytokine release and tumor cell killing were measured at 48 hrs to assess the effect of the addition of 100 nM ruxolitinib, 100 nM sirolimus or 100 nM dasatinib on CD19-TCB-induced cytokine release as compared to the effect on killing.

At 24 hrs, the treatment with CD19-TCB resulted in killing of CTV labelled NALM-6 tumor cells (FIG. 79) and in the release of IFN-γ (FIG. 80A), TNF-α (FIG. 80B), IL-2 (FIG. 80C) and IL-6 (FIG. 80D), indicating that T cells were activated before the addition of the kinase inhibitors. The addition of 100 nM ruxolitinib or 100 nM sirolimus did not prevent CTV labelled NALM-6 tumor cell killing (FIG. 79) measured at 48 hrs, whereas the addition of 100 nM dasatinib moderately reduced the killing of NALM-6 tumor cells. However, the addition of 100 nM sirolimus or 100 nM dasatinib prevented further release of IFN-γ, TNF-α, IL-2 and IL-6 between 24 hrs and 48 hrs (FIG. 80), while the addition of 100 nM ruxolitinib only prevented further release of IFN-γ, TNF-α and IL-6 and, to a lower extent, IL-2 (FIG. 80). Overall, this experiment suggests that the mTOR inhibitor sirolimus as well as the JAK1/2 inhibitor ruxolitinib can rapidly stop CD19-TCB-induced cytokine release from pre-activated effector cells, while not affecting CD19-TCB efficacy. On the other hand, the Src inhibitor dasatinib can rapidly switch off CD19-TCB-induced cytokine release from pre-activated effector cells, while reducing also CD19-TCB-induced T cell cytotoxicity.

Example 16. The Effect of JAK Inhibitor Ruxolitinib, Src Inhibitor Dasatinib and mTOR Inhibitor Sirolimus in Reducing CD19-TCB Induced Cytokine Release in Humanized NSG Mice is Comparable to the Effect of the Corticosteroids Dexamethasone and Methylprednisolone and to the Pre-Treatment with Obinutuzumab The effect of the JAK1/2 inhibitor ruxolitinib, the mTOR inhibitor sirolimus, the Src inhibitor dasatinib, the pre-treatment with obinutuzumab (Gazyva®), and the corticosteroids dexamethasone and methylprednisolone on CD19-TCB-induced cytokine release vs. B cell depletion was evaluated in vivo. Therefore, humanized NSG mice were either pre-treated with obinutuzumab (Gazyva®) and then treated with 0.5 mg/kg CD19-TCB, or co-treated with 0.5 mg/kg CD19-TCB and (i) 4×5 mg/kg sirolimus, (ii) 6×30 mg/kg ruxolitinib, (iii) 6×50 mg/kg dasatinib, (iv) 2×1 mg/kg, 1×0.5 mg/kg and 1×0.25 mg/kg dexamethasone, or (v) 2×10 mg/kg, 1×5 mg/kg and 1×2.5 mg/kg methylprednisolone (FIG. 81). To best reproduce the pharmacodynamic profile of ruxolitinib, dasatinib and sirolimus in the clinic and to verify whether the resulting exposure would be sufficient to prevent CD19-TCB-induced cytokine release, dasatinib and ruxolitinib were given per os twice per day, and sirolimus was given per os twice per day on day 1 and then once per day.

At 48 hrs and 72 hrs, blood was collected by tail-vein bleeding and the CD20+ B cell count was measured by flow cytometry (FIGS. 82A and B) to assess the effect of the different treatments on CD19-TCB-induced B cell depletion. At 48 hrs and 72 hrs, the effect of the obinituzumab (Gazyva®) pre-treatment (GpT) followed by CD19-TCB treatment lead to a complete depletion of B cells, similarly to the treatment with CD19-TCB alone. On the other hand, ruxolitinib (ruxo) and sirolimus (siro), similarly to dexamethasone (dexa) and methylprednisolone (MP), slightly prevented B cell depletion, with a milder inhibitory effect than the Src inhibitor dasatinib (dasa), not fully preventing CD19-TCB efficacy (FIG. 82A). At 72 hrs, the effect of ruxolitinib and sirolimus was comparable to the effect dexamethasone but appeared stronger than methylprednisolone in preventing B cell depletion (FIG. 82B), indicating a small inhibitory effect on the activity of CD19-TCB. At 72 hrs, dasatinib did no longer fully block B cell depletion. Its half-life being around 6-7 hrs and dasatinib being given only twice per day, a lack of exposure could likely explain that CD19-TCB was partially active, resulting in B cell depletion. At experiment termination (72 hrs), spleens were collected and the B cell count was measured by flow-cytometry (FIG. 83). In line with the observations in the blood, ruxolitinib and sirolimus only partially prevented CD19-TCB-induced CD20+ B cell depletion, comparably to dexamethasone. However, their inhibitory effect was stronger than methylprednisolone (FIG. 83). At 72 hrs, dasatinib did not prevent CD20+ B cell depletion in the spleen, probably due to a lack of exposure (FIG. 83). As expected, the pre-treatment with obinutuzumab (Gazyva®) lead to a complete depletion of CD20+ B cells due to the dual activity of the two depleting antibodies (FIG. 83).

Finally, serum was collected from blood 6 hrs post treatment with CD19-TCB and the cytokine levels were measured by Luminex to assess the effect of the different treatments on CD19-TCB-induced cytokine release (FIG. 84). The effect of sirolimus, ruxolitinib, dexamethasone and methylprednisolone on CD19-TCB-induced IFN-γ (FIG. 84A) and IL-6 release (FIG. 84D) was comparable to the pre-treatement with obinutuzumab (Gazyva®). The effect of sirolimus, dexamethasone and methylprednisolone on CD19-TCB-induced IL-2 (FIG. 84B) and TNF-α (FIG. 84C) was comparable to the pre-treatement with Gazyva®. However, the effect of ruxolitinib appeared to be slightly weaker in reducing IL-2 and TNF-α. Overall, the effect of the mTOR and JAK inhibitors was found to be comparable to the effect the corticosteroids dexamethasone and methylprednisolone and to the pre-treatment with obinutuzumab (Gazyva®) in reducing CD19-TCB induced cytokine release with a milder effect of ruxolinib on IL-2 and TNF-α release.

In line with the in vitro findings, the co-treatment with ruxolitinib or sirolimus and CD19-TCB allowed to control CD19-TCB-induced cytokine release in humanized NSG mice while not fully preventing B cell depletion, similarly to dexamethasone and methylprednisolone. In addition, the effect of ruxolitinib, sirolimus, dexamethasone and methylprednisolone in preventing CD19-TCB-induced cytokine release was comparable to the pre-treatment with obinutuzumab (Gazyva®), although the latter induced a stronger B cell depletion.

Example 17. The JAK Inhibitor Fedratinib Prevents CEA-TCB-Mediated Cytokine Release with Minimal Impact on TCB-Mediated Target Cell Killing To assess the effect of another JAK inhibitor, fedratinib, on TCB-mediated target cell killing, T cell activation and cytokine release, we conducted a killing assay using peripheral blood mononuclear cells (PBMCs), NucLight Red (NLR) MKN45 tumor cells and 10 nM CEA-TCB in media supplemented with escalating concentrations of fedratinib. The Incucyte® system (Essen Bioscience) was used to capture the loss of red fluorescent protein signal over time as a readout of target cell killing. Doses of fedratinib ranging from 12.5 nM to 1 μM only partially reduced MKN45 NLR target cell killing by 10 nM CEA-TCB, with doses below 1 μM having only a minor effect (FIG. 85).

At assay endpoint (72 hrs), the expression of CD25 and CD69 on live CD4+ and CD8+ T cells was measured by flow cytometry as a readout for T cell activation. Fedratinib did not affect expression of CD69 and CD25 on CD4+ T cells (FIG. 86A, B) and CD8+ T cells (FIG. 86C, D) at concentrations below 1 μM.

The levels of cytokines were measured by Luminex in the supernatants of the assay to determine the effect of fedratinib on CEA-TCB-induced cytokine release. In the presence of concentrations of fedratinib ranging from 50 nM to 1 μM, the levels of IFN-γ, IL-2, TNF-α, IL-6 and IL-8 were reduced (FIG. 87).

Overall, this data suggests that fedratinib reduces CEA-TCB-induced cytokine release while not preventing T cell cytotoxicity and T cell activation.

Example 18. mTOR and JAK Inhibitors do not Suppress CD19-TCB Anti-Tumor Activity in Lymphoma PDX Bearing Mice To evaluate the impact of mTOR and JAK inhibition in comparison to Src inhibition, dexamethasone or pre-treatment with obinutuzumab (GpT) on CD19-TCB anti-tumor activity, we used a lymphoma patient derived xenograft (PDX) model in humanized NSG mice. First, we verified if the PDX cells were killed upon treatment with CD19-TCB in vitro, using a killing assay. The lymphoma PDX cells were co-cultured together with PBMCs (E:T=10:1) in the presence of CD19-TCB. The lymphoma PDX cells were efficiently depleted by CD19-TCB in vitro (FIG. 88A), resulting in T cell activation as shown by the expression of CD25 and CD69 on CD4+ and CD8+ T cells (FIG. 88 B-E). Then, PDX-bearing mice were treated with either vehicle, sirolimus (5 mg/kg), ruxolitinib (30 mg/kg), dasatinib (20 mg/kg), dexamethasone (2 times 1 mg/kg, 0.5 mg/kg, 4 times 0.25 mg/kg) alone or in combination with CD19-TCB (0.5 mg/kg), CD19-TCB (0.5 mg/kg) as a monotherapy or in combination with obinutuzumab pre-treatment (GpT) (30 mg/kg). The different kinase inhibitors and dexamethasone were given one hour prior to the first treatment with CD19-TCB and then once or twice per day for three days to suppress cytokine release, predominantly occurring upon the first infusion (FIG. 89). Moreover, they were also administered one hour before each subsequent treatment to prevent residual cytokine secretion (FIG. 89). Both, dexamethasone and sirolimus, given as a single agent, induced a reduction in tumor growth, yet not significant (FIGS. 90 and 93). When combined with CD19-TCB, the resulting anti-tumor activity was comparable to CD19-TCB alone, however sirolimus and dexamethasone suppressed IL-2, IFN-γ, TNF-α and IL-6 release upon the first infusion (FIGS. 90, 93 and 94). Similarly, co-treatment with ruxolitinib minimally interfered with CD19-TCB anti-tumor activity and decreased IL-6 and to a lower extent IFN-γ, TNF-α and IL-2 release (FIGS. 91 and 94). The effects of ruxolitinib, sirolimus and dexamethasone on cytokine levels appeared stronger than the effect of obinutuzumab pre-treatment, while their effects on anti-tumor efficacy are similar (FIGS. 90, 91, 93 and 94). Also dasatinib did not significantly suppress CD19-TCB anti-tumor efficacy while strongly reducing T-cell derived cytokines (IFN-γ, TNF-α, IL-2 and IL-6) upon the first infusion. This indicates that the transient use of dasatinib in the present experiment did not continuously block CD19-TCB-induced T cell cytotoxicity, as the inhibitory effect of dasatinib is reversible (FIGS. 92 and 94).

Taken together, this data shows that transient use of the JAK inhibitor ruxolitinib and the mTOR inhibitor sirolimus did not impair anti-tumor efficacy while suppressing T-cell mediated cytokine release upon first infusion of CD19-TCB, supporting the use of these compounds for the mitigation of TCB-related CRS.

Example 19. Effect of Ruxolitinib (JAK1/2 Inhibitor), mTOR Inhibitors (Sirolimus, Everolimus, Temsirolimus) and Dasatinib (Src Inhibitor) on CD20-TCB-Induced Cytokine Release and B Cell Depletion in Non-Tumor Bearing Humanized NSG Mice In this experiment, we verified if the in vivo combination of short PK/PD properties of small molecule kinase inhibitors with long PK/PD properties of CD20-TCB efficiently switches-off cytokine release in humanized NSG mice. Additionally, we also assessed the effect of JAK and mTOR inhibitors on CD20-TCB-mediated B cell depletion in comparison to the Src inhibitor dasatinib, by measuring CD19+ B cells in the peripheral blood.

Humanized NSG mice were treated with 0.15 mg/kg CD20-TCB alone or in combination with mTOR inhibitors (sirolimus, temsirolimus, everolimus), JAK inhibitor (ruxolitinib), Src inhibitor (dasatinib) or pre-treated with obinutuzumab)(Gazyva®, as described FIG. 95. Different doses of mTOR, JAK and Src kinase inhibitors were tested to determine the optimal dose that reduces CD20-TCB-induced cytokine release while minimally interfering with B cell depletion. The doses of 2, 5 and 10 mg/kg were tested for sirolimus and only the highest dose of 10 mg/kg was used for the other mTOR inhibitors temsirolimus and everolimus. The doses of 30 and 60 mg/kg were tested for ruxolitinib and the doses of 10 and 50 mg/kg were tested for dasatinib. To reproduce the clinical route of administration, the different kinase inhibitors were given orally (p.o.) once or twice per day as depicted in FIG. 95. Mice were bled 4 hours and 24 hours after the treatment with CD20-TCB (FIG. 95) to collect serum for cytokine level measurements by Luminex. Additionally, blood was collected 48 hours and 72 hours (termination) post treatment with CD20-TCB to measure the percentage of CD19+ B cells among human CD45+ cells by flow cytometry (FIG. 95).

As a result, the co-treatment with 2, 5, 10 mg/kg sirolimus, 10 mg/kg everolimus or 10 mg/kg temsirolimus (mTOR inhibitors) did not interfere with B cell depletion induced by CD20-TCB, as indicated by the percentage of CD19+ B cells among human CD45+ cells in the peripheral blood (FIG. 96A-C). However, mTOR inhibitors durably reduced CD20-TCB-induced cytokine release, as shown by the levels of IFN-γ (FIG. 97 A, B), IL-2 (FIG. 98 A, B), TNF-α (FIG. 99 A, B), IL-6 (FIG. 100 A, B), IP-10 (FIG. 101 A, B), MCP-1 (FIG. 102 A, B), IL-8 (FIG. 103 A, B) and GM-CSF (FIG. 104 A, B). Furthermore, the reduction of cytokine release by mTOR inhibitors was comparable to dasatinib and obinutuzumab (Gazyva®) pre-treatment in this model (FIG. 97-104). Overall, mTOR inhibitors strongly reduced CD20-TCB-mediated cytokine release while retaining B cell depletion at doses ranging from 2 to 10 mg/kg, unlike the Src inhibitor dasatinib that switched-off TCB activity up to 48 hours.

The co-treatment with 30 and 50 mg/kg of ruxolitinib (JAK1/2 inhibitor) slightly interfered with B cell depletion induced by CD20-TCB, as indicated by the percentage of CD19+ B cells among human CD45+ cells in the peripheral blood (FIG. 96A-C). The inhibitory effect on B cell depletion appears to be dependent on the dose of ruxolitinib. Besides, ruxolitinib durably reduced CD20-TCB-mediated cytokine release, except for IL-2 and GM-CSF release, as shown by the levels of IFN-γ (FIG. 97 A, B), IL-2 (FIG. 98 A, B), TNF-α (FIG. 99 A, B), IL-6 (FIG. 100 A, B), IP-10 (FIG. 101 A, B), MCP-1 (FIG. 102 A, B), IL-8 (FIG. 103 A, B) and GM-CSF (FIG. 104 A, B). Overall, the co-treatment with the JAK1/2 inhibitor ruxolitinib reduced CD20-TCB-mediated cytokine release, with the exception of IL-2 and GM-CSF, while minimally preventing B cell depletion at doses ranging from 30 to 60 mg/kg, unlike the Src inhibitor dasatinib that fully switched off TCB activity up to 48 hours.

In summary, this data show that the combination of mTOR and JAK inhibitors with CD20-TCB reduced cytokine release in humanized NSG, in line with the in vitro observations. The JAK inhibitor (ruxolitinib) and the mTOR inhibitors (sirolimus, everolimus and temsirolimus) minimally interfered with CD20-TCB-mediated B cell depletion as opposed to the Src inhibitor dasatinib. This indicates that they could represent a promising approach to prevent cytokine release upon the first infusion with CD20-TCB while retaining anti-tumor efficacy.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

The invention claimed is:

1. A method for preventing or mitigating an adverse effect related to the administration of a T cell bispecific antibody to an individual, comprising administering (a) a T cell bispecific antibody and (b) an inhibitor that inhibits mTOR signaling to the individual, wherein the adverse effect is prevented or mitigated, wherein the T cell bispecific antibody binds to CD3 and a target cell antigen, and wherein the method does not comprise administering a CAR-T cell, and wherein administering the inhibitor that inhibits mTOR signaling causes inhibition of an adverse effect related to administering the T cell bispecific antibody.

2. The method of claim 1, wherein the inhibitor that inhibits mTOR signaling comprises sirolimus, temsirolimus, or everolimus.

3. The method of claim 1, wherein the administration of the inhibitor does not cause inhibition of a desired effect related to administering the T cell bispecific antibody.

4. The method of claim 1, wherein the inhibition is a complete inhibition, a clinically meaningful inhibition, or a statistically significant inhibition.

5. The method of claim 1, wherein the adverse effect is:
(i) cytokine release syndrome (CRS);
(ii) fever;
(iii) hypotension;
(iv) hypoxia; or
(v) an elevated serum level of a cytokine.

6. The method of claim 5, wherein the adverse effect is an elevated serum level of a cytokine, wherein the cytokine is IL-6, IFN-γ, IL-10, TNF-α, GM-CSF, MCP-1, or IL-1β.

7. The method of claim 1, wherein the inhibitor is administered to the individual when the adverse effect clinically manifests.

8. The method of claim 1, wherein the inhibitor is administered before, concurrent with, or after administering the T cell bispecific antibody and is administered
(i) intermittently or continuously;
(ii) orally; or
(iii) parenterally.

9. The method of claim 8, wherein the inhibitor is administered parenterally, wherein the parenteral administration is intravenous administration.

10. The method of claim 1, wherein the T cell bispecific antibody is administered to the individual multiple times, and wherein the inhibitor is administered prior to, concurrent with, or subsequently to the first administration of the T cell bispecific antibody.

11. The method of claim 1, wherein the T cell bispecific antibody is administered intravenously and is a first administration of the T cell bispecific antibody.

12. The method of claim 1, wherein the target cell antigen is carcinoembryonic antigen (CEA), CD20, HLA-A2/MAGE-A4, or CD19.

13. The method of claim 12, wherein the target cell antigen is CEA, wherein the T cell bispecific antibody comprises:

(i) a first antigen binding moiety that binds to CD3 and comprises:
a heavy chain variable region comprising:
a heavy chain CDR (HCDR) 1 of SEQ ID NO: 4,
a HCDR2 of SEQ ID NO: 5, and
a HCDR3 of SEQ ID NO: 6; and
a light chain variable region comprising:
a light chain CDR (LCDR) 1 of SEQ ID NO: 7,
a LCDR2 of SEQ ID NO: 8, and
a LCDR3 of SEQ ID NO: 9;
and (ii) a second antigen binding moiety that binds to CEA and comprises:
a heavy chain variable region comprising:
a heavy chain CDR (HCDR) 1 of SEQ ID NO: 12,
a HCDR2 of SEQ ID NO: 13, and
a HCDR3 of SEQ ID NO: 14; and
a light chain variable region comprising:
a light chain CDR (LCDR) 1 of SEQ ID NO: 15,
a LCDR2 of SEQ ID NO: 16, and
a LCDR3 of SEQ ID NO: 17.

14. The method of claim 13, wherein the T cell bispecific antibody further comprises a third antigen binding moiety that binds to CEA, an Fc domain composed of a first and a second subunit, or both the third antigen binding moiety and the Fc domain.

15. The method of claim 14, wherein the third antigen binding moiety that binds to CEA comprises:
a heavy chain variable region comprising:
a heavy chain CDR (HCDR) 1 of SEQ ID NO: 12,
a HCDR2 of SEQ ID NO: 13, and
a HCDR3 of SEQ ID NO: 14; and
a light chain variable region comprising:
a light chain CDR (LCDR) 1 of SEQ ID NO: 15,
a LCDR2 of SEQ ID NO: 16, and
a LCDR3 of SEQ ID NO: 17;
wherein the first antigen binding moiety is a crossover Fab molecule wherein either the variable or the constant regions of the Fab light chain and the Fab heavy chain are exchanged; and
wherein the second and third antigen binding moieties are each a Fab molecule, and the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

16. The method of claim 13, wherein
(i) the first antigen binding moiety comprises a heavy chain variable region sequence that is at least about 95%, 96%, 97%, 98%, 99% or 100% identical to an amino acid sequence of SEQ ID NO: 10 and a light chain variable region sequence that is at least about 95%, 96%, 97%, 98%, 99% or 100% identical to an amino acid sequence of SEQ ID NO: 11, or (ii) the second antigen binding moiety comprises a heavy chain variable region sequence that is at least about 95%, 96%, 97%, 98%, 99% or 100% identical to the amino acid sequence of SEQ ID NO: 18 and a light chain variable region sequence that is at least about 95%, 96%, 97%, 98%, 99% or 100% identical to the amino acid sequence of SEQ ID NO: 19.

17. The method of claim 14, wherein the Fc domain comprises at least one of (i) a modification promoting the association of the first and the second subunit of the Fc domain or (ii) one or more amino acid substitutions that reduces binding to an Fc receptor or effector function.

18. The method of claim 12, wherein the target cell antigen is CD20, wherein the T cell bispecific antibody comprises:

(i) a first antigen binding moiety that binds to CD3 and comprises:
a heavy chain variable region comprising:
a heavy chain CDR (HCDR) 1 of SEQ ID NO: 4,
a HCDR2 of SEQ ID NO: 5, and
a HCDR3 of SEQ ID NO: 6; and
a light chain variable region comprising:
a light chain CDR (LCDR) 1 of SEQ ID NO: 7,
a LCDR2 of SEQ ID NO: 8, and
aLCDR3 of SEQ ID NO: 9;
and (ii) a second antigen binding moiety that binds to CD20 and comprises:
a heavy chain variable region comprising:
a heavy chain CDR (HCDR) 1 of SEQ ID NO: 24,
a HCDR2 of SEQ ID NO: 25, and
a HCDR3 of SEQ ID NO: 26; and
a light chain variable region comprising:
a light chain CDR (LCDR) 1 of SEQ ID NO: 27,
a LCDR2 of SEQ ID NO: 28 and
a LCDR3 of SEQ ID NO: 29.

19. The method of claim 18, wherein the T cell bispecific antibody further comprises a third antigen binding moiety that binds to CD20, an Fc domain composed of a first and a second subunit, or both the third antigen binding moiety and the Fc domain.

20. The method of claim 19, wherein the third antigen binding moiety that binds to CD20 comprises:
a heavy chain variable region comprising:
a heavy chain CDR (HCDR) 1 of SEQ ID NO: 24,
a HCDR2 of SEQ ID NO: 25, and
a HCDR3 of SEQ ID NO: 26; and
a light chain variable region comprising:
a light chain CDR (LCDR) 1 of SEQ ID NO: 27,
a LCDR2 of SEQ ID NO: 28 and
a LCDR3 of SEQ ID NO: 29,
wherein the first antigen binding moiety is a crossover Fab molecule wherein either the variable or the constant regions of the Fab light chain and the Fab heavy chain are exchanged; and
wherein the second and third antigen binding moieties are each a Fab molecule, and the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

21. The method of claim 18, wherein the T cell bispecific antibody comprises:

(i) the first antigen binding moiety comprises a heavy chain variable region sequence that is at least about 95%, 96%, 97%, 98%, 99% or 100% identical to the amino acid sequence of SEQ ID NO: 10 and a light chain variable region sequence that is at least about 95%, 96%, 97%, 98%, 99% or 100% identical to the amino acid sequence of SEQ ID NO: 11, or (ii) the second antigen binding moiety comprises a heavy chain variable region sequence that is at least about 95%, 96%, 97%, 98%, 99% or 100% identical to the amino acid sequence of SEQ ID NO: 30 and a light chain variable region sequence that is at least about 95%, 96%, 97%, 98%, 99% or 100% identical to the amino acid sequence of SEQ ID NO: 31.

22. The method of claim 20, wherein (i) the first antigen binding moiety is a crossover Fab molecule wherein the variable regions of the Fab light chain and the Fab heavy chain are exchanged, and (ii) the second binding moiety is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index); or (iii) the third binding moiety is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

23. The method of claim 19, wherein the Fc domain comprises at least one of (i) a modification promoting the association of the first and the second subunit of the Fc domain or (ii) one or more amino acid substitutions that reduces binding to an Fc receptor or effector function.

24. The method of claim 12, wherein the target cell antigen is HLA-A2/MAGE-A4, wherein the T cell bispecific antibody comprises:

(i) a first antigen binding moiety that binds to CD3 and comprises:
a heavy chain variable region comprising:
a heavy chain CDR (HCDR) 1 of SEQ ID NO: 37,
a HCDR2 of SEQ ID NO: 38, and
a HCDR3 of SEQ ID NO: 39; and
a light chain variable region comprising:
a light chain CDR (LCDR) 1 of SEQ ID NO: 40,
a LCDR2 of SEQ ID NO: 41 and
a LCDR3 of SEQ ID NO: 42;

and (ii) a second antigen binding moiety that binds to HLA-A2/MAGE-A4 and comprises:
a heavy chain variable region comprising:
a heavy chain CDR (HCDR) 1 of SEQ ID NO: 45,
a HCDR2 of SEQ ID NO: 46, and
a HCDR3 of SEQ ID NO: 47; and
a light chain variable region comprising:
a light chain CDR (LCDR) 1 of SEQ ID NO: 48,
a LCDR2 of SEQ ID NO: 49 and
a LCDR3 of SEQ ID NO: 50.

25. The method of claim 24, wherein the T cell bispecific antibody further comprises a third antigen binding moiety that binds to HLA-A2/MAGE-A4, an Fc domain composed of a first and a second subunit, or both the third antigen binding moiety and the Fc domain.

26. The method of claim 25, wherein the third antigen binding moiety that binds to HLA-A2/MAGE-A4 comprises:
a heavy chain variable region comprising:
a heavy chain CDR (HCDR) 1 of SEQ ID NO: 45,
a HCDR2 of SEQ ID NO: 46, and
a HCDR3 of SEQ ID NO: 47; and
a light chain variable region comprising:
a light chain CDR (LCDR) 1 of SEQ ID NO: 48,
a LCDR2 of SEQ ID NO: 49 and
a LCDR3 of SEQ ID NO: 50,
wherein the first antigen binding moiety is a crossover Fab molecule wherein either the variable or the constant regions of the Fab light chain and the Fab heavy chain are exchanged; and
wherein the second and third antigen binding moieties are each a Fab molecule, and the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

27. The method of claim 24, wherein the T cell bispecific antibody comprises:

(i) first antigen binding moiety of the T cell bispecific antibody comprises a heavy chain variable region sequence that is at least about 95%, 96%, 97%, 98%, 99% or 100% identical to the amino acid sequence of SEQ ID NO: 43 and a light chain variable region sequence that is at least about 95%, 96%, 97%, 98%, 99% or 100% identical to the amino acid sequence of SEQ ID NO: 44, or (ii) the second antigen binding moiety of the T cell bispecific antibody comprises a heavy chain variable region sequence that is at least about 95%, 96%, 97%, 98%, 99% or 100% identical to the amino acid sequence of SEQ ID NO: 51 and a light chain variable region sequence that is at least about 95%, 96%, 97%, 98%, 99% or 100% identical to the amino acid sequence of SEQ ID NO: 52.

28. The method of claim 26, wherein (i) the first antigen binding moiety is a crossover Fab molecule wherein the variable regions of the Fab light chain and the Fab heavy chain are exchanged, and (ii) the second binding moiety is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index); or (iii) the third binding moiety is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

29. The method of claim 25, wherein the Fc domain comprises at least one of (i) a modification promoting the association of the first and the second subunit of the Fc domain or (ii) one or more amino acid substitutions that reduces binding to an Fc receptor or effector function.

30. The method of claim 12, wherein the target antigen is CD19, wherein the T cell bispecific antibody comprises:

(i) a first antigen binding moiety that binds to CD3 and comprises:
a heavy chain variable region comprising:
a heavy chain CDR (HCDR) 1 of SEQ ID NO: 61,
a HCDR2 of SEQ ID NO: 5, and
a HCDR3 of SEQ ID NO: 62;
or a heavy chain variable region comprising:
a HCDR1 of SEQ ID NO: 64,
a HCDR2 of SEQ ID NO: 5, and
a HCDR3 of SEQ ID NO: 65; and
a light chain variable region comprising:
a light chain CDR (LCDR) 1 of SEQ ID NO: 7,
a LCDR2 of SEQ ID NO: 8, and
a LCDR3 of SEQ ID NO: 9;
and (ii) a second antigen binding moiety that binds to CD19 and comprises:
a heavy chain variable region comprising:
a heavy chain CDR (HCDR) 1 of SEQ ID NO: 67,
a HCDR2 of SEQ ID NO: 68, and
a HCDR3 of SEQ ID NO: 69; and
a light chain variable region comprising:
a light chain CDR (LCDR) 1 of SEQ ID NO: 70,
a LCDR2 of SEQ ID NO: 71, and
a LCDR3 of SEQ ID NO: 72.

31. The method of claim 30, wherein the T cell bispecific antibody further comprises a third antigen binding moiety that binds to CD19, an Fc domain composed of a first and a second subunit, or both the third antigen binding moiety and the Fc domain.

32. The method of claim 31, wherein the third antigen binding moiety that binds to CD19 comprises:
a heavy chain variable region comprising:
a heavy chain CDR (HCDR) 1 of SEQ ID NO: 67,
a HCDR2 of SEQ ID NO: 68, and
a HCDR3 of SEQ ID NO: 69; and
a light chain variable region comprising:
a light chain CDR (LCDR) 1 of SEQ ID NO: 70, a LCDR2 of SEQ ID NO: 71, and
a LCDR3 of SEQ ID NO: 72,
wherein the first antigen binding moiety is a crossover Fab molecule wherein either the variable or the constant regions of the Fab light chain and the Fab heavy chain are exchanged; and
wherein the second and third antigen binding moieties are each a Fab molecule, and the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

33. The method of claim 30, wherein
(i) the first antigen binding moiety comprises a heavy chain variable region sequence that is at least about 95%, 96%, 97%, 98%, 99% or 100% identical to an amino acid sequence of SEQ ID NO: 63 or SEQ ID NO: 66 and a light chain variable region sequence that is at least about 95%, 96%, 97%, 98%, 99% or 100% identical to an amino acid sequence of SEQ ID NO: 11, or (ii) the second antigen binding moiety comprises a heavy chain variable region sequence that is at least about 95%, 96%, 97%, 98%, 99% or 100% identical to the amino acid sequence of SEQ ID NO: 73 and a light chain variable region sequence that is at least about 95%, 96%, 97%, 98%, 99% or 100% identical to the amino acid sequence of SEQ ID NO: 74.

34. The method of claim 32, wherein
(i) the first antigen binding moiety is a crossover Fab molecule wherein the variable regions of the Fab light chain and the Fab heavy chain are exchanged, and
(ii) the second binding moiety is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index); or (iii) the third binding moiety is a conventional Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat) and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

35. The method of claim 31, wherein the Fc domain comprises at least one of (i) a modification promoting the association of the first and the second subunit of the Fc domain or (ii) one or more amino acid substitutions that reduces binding to an Fc receptor or effector function.

36. The method of claim 1, wherein the T cell bispecific antibody is cibisatamab or glofitamab.

37. The method of claim 1, wherein the administration of a T cell bispecific antibody to the individual treats a disease in the individual.

38. The method of claim 37, wherein the disease is cancer or an autoimmune disease.

39. The method of claim 38, wherein the cancer is:

(i) a carcinoembryonic antigen (CEA)-expressing cancer, or selected from the group consisting of colorectal cancer, lung cancer, pancreatic cancer, breast cancer, and gastric cancer;

(ii) a CD20-expressing cancer, a B-cell cancer, or selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL) and marginal zone lymphoma (MZL);

(iii) a MAGE-A4 expressing cancer; or (iv) a CD19-expressing cancer, a B-cell cancer, or selected from the group consisting of Non-Hodgkin lymphoma (NHL), acute lymphocytic leukemia (ALL) and chronic lymphocytic leukemia (CLL).

40. The method of claim 38, wherein the autoimmune disease is lupus.

41. The method of claim 40, wherein the autoimmune disease is systemic lupus erythematosus (SLE) or lupus nephritis (LN).

\* \* \* \* \*

SEQUENCE LISTING

```
<160> NUMBER OF SEQ ID NOS: 80

<210> SEQ ID NO 1
<211> LENGTH: 207
<212> TYPE: PRT
<213> ORGANISM: Homo sapiens

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205

<210> SEQ ID NO 2
<211> LENGTH: 198
<212> TYPE: PRT
<213> ORGANISM: Macaca fascicularis

<400> SEQUENCE: 2

Met Gln Ser Gly Thr Arg Trp Arg Val Leu Gly Leu Cys Leu Leu Ser
1               5                   10                  15
```

-continued

```
Ile Gly Val Trp Gly Gln Asp Gly Asn Glu Glu Met Gly Ser Ile Thr
             20                  25                  30

Gln Thr Pro Tyr Gln Val Ser Ile Ser Gly Thr Thr Val Ile Leu Thr
             35                  40                  45

Cys Ser Gln His Leu Gly Ser Glu Ala Gln Trp Gln His Asn Gly Lys
             50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                     85                  90                  95

Glu Asp Ala Ser His His Leu Tyr Leu Lys Ala Arg Val Cys Glu Asn
                 100                 105                 110

Cys Met Glu Met Asp Val Met Ala Val Ala Thr Ile Val Ile Val Asp
             115                 120                 125

Ile Cys Ile Thr Leu Gly Leu Leu Leu Leu Val Tyr Tyr Trp Ser Lys
         130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Pro Val Pro Asn
                 165                 170                 175

Pro Asp Tyr Glu Pro Ile Arg Lys Gly Gln Gln Asp Leu Tyr Ser Gly
             180                 185                 190

Leu Asn Gln Arg Arg Ile
         195

<210> SEQ ID NO 3
<211> LENGTH: 225
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1                   5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
             50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                     85                  90                  95

Lys Glu Tyr Lys Cys Lys Val Ser Asn Lys Ala Leu Pro Ala Pro Ile
                 100                 105                 110

Glu Lys Thr Ile Ser Lys Ala Lys Gly Gln Pro Arg Glu Pro Gln Val
             115                 120                 125

Tyr Thr Leu Pro Pro Ser Arg Asp Glu Leu Thr Lys Asn Gln Val Ser
         130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                 165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Thr Tyr Ala Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: Synthetic construct

<400> SEQUENCE: 5

Arg Ile Arg Ser Lys Tyr Asn Asn Tyr Ala Thr Tyr Tyr Ala Asp Ser
1               5                   10                  15

Val Lys Gly

<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

His Gly Asn Phe Gly Asn Ser Tyr Val Ser Trp Phe Ala Tyr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct

<400> SEQUENCE: 7

Gly Ser Ser Thr Gly Ala Val Thr Thr Ser Asn Tyr Ala Asn
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic construct

<400> SEQUENCE: 8

Gly Thr Asn Lys Arg Ala Pro
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic construct

<400> SEQUENCE: 9

Ala Leu Trp Tyr Ser Asn Leu Trp Val
1               5

<210> SEQ ID NO 10
<211> LENGTH: 125
<212> TYPE: PRT
<213> ORGANISM: Artificial Sequence
<220> FEATURE:
<223> OTHER INFORMATION: Synthetic construct

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 11
<211> LENGTH: 109
<212> TYPE: PRT
<213> ORGANISM: Artificial Sequence
<220> FEATURE:
<223> OTHER INFORMATION: Synthetic construct

<400> SEQUENCE: 11

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

-continued

```
<210> SEQ ID NO 12
<211> LENGTH: 5
<212> TYPE: PRT
<213> ORGANISM: Artificial Sequence
<220> FEATURE:
<223> OTHER INFORMATION: Synthetic construct

<400> SEQUENCE: 12

Glu Phe Gly Met Asn
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic construct

<400> SEQUENCE: 13

Trp Ile Asn Thr Lys Thr Gly Glu Ala Thr Tyr Val Glu Glu Phe Lys
1               5                   10                  15

Gly

<210> SEQ ID NO 14
<211> LENGTH: 12
<212> TYPE: PRT
<213> ORGANISM: Artificial Sequence
<220> FEATURE:
<223> OTHER INFORMATION: Synthetic construct

<400> SEQUENCE: 14

Trp Asp Phe Ala Tyr Tyr Val Glu Ala Met Asp Tyr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic construct

<400> SEQUENCE: 15

Lys Ala Ser Ala Ala Val Gly Thr Tyr Val Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic construct

<400> SEQUENCE: 16

Ser Ala Ser Tyr Arg Lys Arg
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic construct

<400> SEQUENCE: 17

His Gln Tyr Tyr Thr Tyr Pro Leu Phe Thr
1               5                   10
```

-continued

```
<210> SEQ ID NO 18
<211> LENGTH: 121
<212> TYPE: PRT
<213> ORGANISM: Artificial Sequence
<220> FEATURE:
<223> OTHER INFORMATION: Synthetic construct

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 19
<211> LENGTH: 108
<212> TYPE: PRT
<213> ORGANISM: Artificial Sequence
<220> FEATURE:
<223> OTHER INFORMATION: Synthetic construct

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 20
<211> LENGTH: 215
<212> TYPE: PRT
<213> ORGANISM: Artificial Sequence
<220> FEATURE:
<223> OTHER INFORMATION: Synthetic construct

<400> SEQUENCE: 20

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Ala Ala Val Gly Thr Tyr
        20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 451
<212> TYPE: PRT
<213> ORGANISM: Artificial Sequence
<220> FEATURE:
<223> OTHER INFORMATION: Synthetic construct

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
        20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
                355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450
```

```
<210> SEQ ID NO 22
<211> LENGTH: 214
<212> TYPE: PRT
<213> ORGANISM: Artificial Sequence
<220> FEATURE:
<223> OTHER INFORMATION: Synthetic construct

<400> SEQUENCE: 22

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
        50                  55                  60
```

```
Ser Gly Ser Leu Leu Gly Gly Lys Ala Ala Leu Thr Leu Ser Gly Ala
65              70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
                180                 185                 190

Ile Cys Asn Val Asn His Lys Pro Ser Asn Thr Lys Val Asp Lys Lys
    195                 200                 205

Val Glu Pro Lys Ser Cys
    210
```

```
<210> SEQ ID NO 23
<211> LENGTH: 694
<212> TYPE: PRT
<213> ORGANISM: Artificial Sequence
<220> FEATURE:
<223> OTHER INFORMATION: Synthetic construct

<400> SEQUENCE: 23
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205
```

-continued

```
Lys Pro Ser Asn Thr Lys Val Asp Lys Lys Val Glu Pro Lys Ser Cys
    210             215             220

Asp Gly Gly Gly Gly Ser Gly Gly Gly Gly Ser Glu Val Gln Leu Leu
225             230             235             240

Glu Ser Gly Gly Gly Leu Val Gln Pro Gly Gly Ser Leu Arg Leu Ser
            245             250             255

Cys Ala Ala Ser Gly Phe Thr Phe Ser Thr Tyr Ala Met Asn Trp Val
            260             265             270

Arg Gln Ala Pro Gly Lys Gly Leu Glu Trp Val Ser Arg Ile Arg Ser
        275             280             285

Lys Tyr Asn Asn Tyr Ala Thr Tyr Tyr Ala Asp Ser Val Lys Gly Arg
    290             295             300

Phe Thr Ile Ser Arg Asp Asp Ser Lys Asn Thr Leu Tyr Leu Gln Met
305             310             315             320

Asn Ser Leu Arg Ala Glu Asp Thr Ala Val Tyr Tyr Cys Val Arg His
            325             330             335

Gly Asn Phe Gly Asn Ser Tyr Val Ser Trp Phe Ala Tyr Trp Gly Gln
            340             345             350

Gly Thr Leu Val Thr Val Ser Ser Ala Ser Val Ala Ala Pro Ser Val
            355             360             365

Phe Ile Phe Pro Pro Ser Asp Glu Gln Leu Lys Ser Gly Thr Ala Ser
    370             375             380

Val Val Cys Leu Leu Asn Asn Phe Tyr Pro Arg Glu Ala Lys Val Gln
385             390             395             400

Trp Lys Val Asp Asn Ala Leu Gln Ser Gly Asn Ser Gln Glu Ser Val
            405             410             415

Thr Glu Gln Asp Ser Lys Asp Ser Thr Tyr Ser Leu Ser Ser Thr Leu
            420             425             430

Thr Leu Ser Lys Ala Asp Tyr Glu Lys His Lys Val Tyr Ala Cys Glu
            435             440             445

Val Thr His Gln Gly Leu Ser Ser Pro Val Thr Lys Ser Phe Asn Arg
    450             455             460

Gly Glu Cys Asp Lys Thr His Thr Cys Pro Pro Cys Pro Ala Pro Glu
465             470             475             480

Ala Ala Gly Gly Pro Ser Val Phe Leu Phe Pro Pro Lys Pro Lys Asp
            485             490             495

Thr Leu Met Ile Ser Arg Thr Pro Glu Val Thr Cys Val Val Val Asp
            500             505             510

Val Ser His Glu Asp Pro Glu Val Lys Phe Asn Trp Tyr Val Asp Gly
            515             520             525

Val Glu Val His Asn Ala Lys Thr Lys Pro Arg Glu Glu Gln Tyr Asn
    530             535             540

Ser Thr Tyr Arg Val Val Ser Val Leu Thr Val Leu His Gln Asp Trp
545             550             555             560

Leu Asn Gly Lys Glu Tyr Lys Cys Lys Val Ser Asn Lys Ala Leu Gly
            565             570             575

Ala Pro Ile Glu Lys Thr Ile Ser Lys Ala Lys Gly Gln Pro Arg Glu
            580             585             590

Pro Gln Val Tyr Thr Leu Pro Pro Cys Arg Asp Glu Leu Thr Lys Asn
            595             600             605

Gln Val Ser Leu Trp Cys Leu Val Lys Gly Phe Tyr Pro Ser Asp Ile
    610             615             620
```

-continued

```
Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
        690

<210> SEQ ID NO 24
<211> LENGTH: 5
<212> TYPE: PRT
<213> ORGANISM: Artificial Sequence
<220> FEATURE:
<223> OTHER INFORMATION: Synthetic construct

<400> SEQUENCE: 24

Tyr Ser Trp Ile Asn
1               5

<210> SEQ ID NO 25
<211> LENGTH: 17
<212> TYPE: PRT
<213> ORGANISM: Artificial Sequence
<220> FEATURE:
<223> OTHER INFORMATION: Synthetic construct

<400> SEQUENCE: 25

Arg Ile Phe Pro Gly Asp Gly Asp Thr Asp Tyr Asn Gly Lys Phe Lys
1               5                   10                  15

Gly

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

Asn Val Phe Asp Gly Tyr Trp Leu Val Tyr
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Synthetic construct

<400> SEQUENCE: 27

Arg Ser Ser Lys Ser Leu Leu His Ser Asn Gly Ile Thr Tyr Leu Tyr
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 28

Gln Met Ser Asn Leu Val Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic construct

<400> SEQUENCE: 29

Ala Gln Asn Leu Glu Leu Pro Tyr Thr
1               5

<210> SEQ ID NO 30
<211> LENGTH: 119
<212> TYPE: PRT
<213> ORGANISM: Artificial Sequence
<220> FEATURE:
<223> OTHER INFORMATION: Synthetic construct

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 31
<211> LENGTH: 112
<212> TYPE: PRT
<213> ORGANISM: Artificial Sequence
<220> FEATURE:
<223> OTHER INFORMATION: Synthetic construct

<400> SEQUENCE: 31

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Val Glu Ile Lys
            100                 105                 110
```

<210> SEQ ID NO 32
<211> LENGTH: 219
<212> TYPE: PRT
<213> ORGANISM: Artificial Sequence
<220> FEATURE:
<223> OTHER INFORMATION: Synthetic construct

<400> SEQUENCE: 32

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
            115                 120                 125

Lys Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 33
<211> LENGTH: 447
<212> TYPE: PRT
<213> ORGANISM: Artificial Sequence
<220> FEATURE:
<223> OTHER INFORMATION: Synthetic construct

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
            35                  40                  45
```

```
Gly Arg Ile Phe Pro Gly Asp Gly Asp Thr Asp Tyr Asn Gly Lys Phe
    50              55              60

Lys Gly Arg Val Thr Ile Thr Ala Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Asn Val Phe Asp Gly Tyr Trp Leu Val Tyr Trp Gly Gln Gly
            100             105             110

Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Glu Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
        195             200             205

Ser Asn Thr Lys Val Asp Glu Lys Val Glu Pro Lys Ser Cys Asp Lys
    210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Gly Ala Pro Ile Glu Lys
            325             330             335

Thr Ile Ser Lys Ala Lys Gly Gln Pro Arg Glu Pro Gln Val Cys Thr
        340             345             350

Leu Pro Pro Ser Arg Asp Glu Leu Thr Lys Asn Gln Val Ser Leu Ser
        355             360             365

Cys Ala Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Val Ser Lys Leu Thr Val Asp Lys
            405             410             415

Ser Arg Trp Gln Gln Gly Asn Val Phe Ser Cys Ser Val Met His Glu
        420             425             430

Ala Leu His Asn His Tyr Thr Gln Lys Ser Leu Ser Leu Ser Pro
        435             440             445
```

<210> SEQ ID NO 34
<211> LENGTH: 232

```
<212> TYPE: PRT
<213> ORGANISM: Artificial Sequence
<220> FEATURE:
<223> OTHER INFORMATION: Synthetic construct

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 35
<211> LENGTH: 672
<212> TYPE: PRT
<213> ORGANISM: Artificial Sequence
<220> FEATURE:
<223> OTHER INFORMATION: Synthetic construct

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Asn Val Phe Asp Gly Tyr Trp Leu Val Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
    130             135             140

Gly Cys Leu Val Glu Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Glu Lys Val Glu Pro Lys Ser Cys Asp Gly
    210             215             220

Gly Gly Gly Ser Gly Gly Gly Ser Gln Ala Val Val Thr Gln Glu
225             230             235             240

Pro Ser Leu Thr Val Ser Pro Gly Gly Thr Val Thr Leu Thr Cys Gly
            245             250             255

Ser Ser Thr Gly Ala Val Thr Thr Ser Asn Tyr Ala Asn Trp Val Gln
            260             265             270

Glu Lys Pro Gly Gln Ala Phe Arg Gly Leu Ile Gly Gly Thr Asn Lys
            275             280             285

Arg Ala Pro Gly Thr Pro Ala Arg Phe Ser Gly Ser Leu Leu Gly Gly
    290             295             300

Lys Ala Ala Leu Thr Leu Ser Gly Ala Gln Pro Glu Asp Glu Ala Glu
305             310             315             320

Tyr Tyr Cys Ala Leu Trp Tyr Ser Asn Leu Trp Val Phe Gly Gly Gly
            325             330             335

Thr Lys Leu Thr Val Leu Ser Ser Ala Ser Thr Lys Gly Pro Ser Val
            340             345             350

Phe Pro Leu Ala Pro Ser Ser Lys Ser Thr Ser Gly Gly Thr Ala Ala
            355             360             365

Leu Gly Cys Leu Val Lys Asp Tyr Phe Pro Glu Pro Val Thr Val Ser
    370             375             380

Trp Asn Ser Gly Ala Leu Thr Ser Gly Val His Thr Phe Pro Ala Val
385             390             395             400

Leu Gln Ser Ser Gly Leu Tyr Ser Leu Ser Ser Val Val Thr Val Pro
            405             410             415

Ser Ser Ser Leu Gly Thr Gln Thr Tyr Ile Cys Asn Val Asn His Lys
            420             425             430

Pro Ser Asn Thr Lys Val Asp Lys Lys Val Glu Pro Lys Ser Cys Asp
            435             440             445

Lys Thr His Thr Cys Pro Pro Cys Pro Ala Pro Glu Ala Ala Gly Gly
    450             455             460

Pro Ser Val Phe Leu Phe Pro Pro Lys Pro Lys Asp Thr Leu Met Ile
465             470             475             480

Ser Arg Thr Pro Glu Val Thr Cys Val Val Val Asp Val Ser His Glu
            485             490             495

Asp Pro Glu Val Lys Phe Asn Trp Tyr Val Asp Gly Val Glu Val His
            500             505             510
```

-continued

```
Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
        530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
                580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
        610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
                660                 665                 670

<210> SEQ ID NO 36
<211> LENGTH: 297
<212> TYPE: PRT
<213> ORGANISM: Homo sapiens

<400> SEQUENCE: 36

Met Thr Thr Pro Arg Asn Ser Val Asn Gly Thr Phe Pro Ala Glu Pro
1                   5                   10                  15

Met Lys Gly Pro Ile Ala Met Gln Ser Gly Pro Lys Pro Leu Phe Arg
                20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
        50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
                100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
        130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
                180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
        210                 215                 220
```

-continued

```
Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 37
<211> LENGTH: 5
<212> TYPE: PRT
<213> ORGANISM: Artificial Sequence
<220> FEATURE:
<223> OTHER INFORMATION: Synthetic construct

<400> SEQUENCE: 37

Gly Tyr Thr Met Asn
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic construct

<400> SEQUENCE: 38

Leu Ile Asn Pro Tyr Lys Gly Val Ser Thr Tyr Asn Gln Lys Phe Lys
1               5                   10                  15

Asp

<210> SEQ ID NO 39
<211> LENGTH: 13
<212> TYPE: PRT
<213> ORGANISM: Artificial Sequence
<220> FEATURE:
<223> OTHER INFORMATION: Synthetic construct

<400> SEQUENCE: 39

Ser Gly Tyr Tyr Gly Asp Ser Asp Trp Tyr Phe Asp Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic construct

<400> SEQUENCE: 40

Arg Ala Ser Gln Asp Ile Arg Asn Tyr Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic construct
```

<400> SEQUENCE: 41

Tyr Thr Ser Arg Leu Glu Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

Gln Gln Gly Asn Thr Leu Pro Trp Thr
1               5

<210> SEQ ID NO 43
<211> LENGTH: 122
<212> TYPE: PRT
<213> ORGANISM: Artificial Sequence
<220> FEATURE:
<223> OTHER INFORMATION: Synthetic construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Synthetic construct

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 45
<211> LENGTH: 4
<212> TYPE: PRT
<213> ORGANISM: Artificial Sequence
<220> FEATURE:
<223> OTHER INFORMATION: Synthetic construct

<400> SEQUENCE: 45

Lys Ala Met Ser
1

<210> SEQ ID NO 46
<211> LENGTH: 17
<212> TYPE: PRT
<213> ORGANISM: Artificial Sequence
<220> FEATURE:
<223> OTHER INFORMATION: Synthetic construct

<400> SEQUENCE: 46

Ser Ile Ser Pro Ser Gly Gly Ser Thr Tyr Tyr Asn Asp Asn Val Leu
1               5                   10                  15

Gly

<210> SEQ ID NO 47
<211> LENGTH: 7
<212> TYPE: PRT
<213> ORGANISM: Artificial Sequence
<220> FEATURE:
<223> OTHER INFORMATION: Synthetic construct

<400> SEQUENCE: 47

Asp Val Gly Phe Phe Asp Glu
1               5

<210> SEQ ID NO 48
<211> LENGTH: 11
<212> TYPE: PRT
<213> ORGANISM: Artificial Sequence
<220> FEATURE:
<223> OTHER INFORMATION: Synthetic construct

<400> SEQUENCE: 48

Arg Ala Ser Gln Ser Ile Ser Ser Tyr Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic construct

<400> SEQUENCE: 49

Asp Ala Ser Ile Arg Asp Ile
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic construct

<400> SEQUENCE: 50

Gln Gln Tyr Ser Ser Tyr Pro Tyr Thr
1               5

<210> SEQ ID NO 51
<211> LENGTH: 114
<212> TYPE: PRT
<213> ORGANISM: Artificial Sequence
<220> FEATURE:
<223> OTHER INFORMATION: Synthetic construct

<400> SEQUENCE: 51

Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
            20                  25                  30

Ser Trp Val Arg Gln Ala Pro Gly Lys Gly Leu Glu Trp Val Gly Ser
        35                  40                  45

Ile Ser Pro Ser Gly Gly Ser Thr Tyr Tyr Asn Asp Asn Val Leu Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
            85                  90                  95

Asp Val Gly Phe Phe Asp Glu Trp Gly Gln Gly Thr Leu Val Thr Val
            100                 105                 110

Ser Ser

<210> SEQ ID NO 52
<211> LENGTH: 107
<212> TYPE: PRT
<213> ORGANISM: Artificial Sequence
<220> FEATURE:
<223> OTHER INFORMATION: Synthetic construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ile Arg Asp Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
            85                  90                  95

Thr Phe Gly Gln Gly Thr Lys Leu Glu Ile Lys
            100                 105

<210> SEQ ID NO 53
<211> LENGTH: 214
<212> TYPE: PRT
<213> ORGANISM: Artificial Sequence
<220> FEATURE:
<223> OTHER INFORMATION: Synthetic construct -continued

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Ile Arg Asp Ile Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 54
<211> LENGTH: 442
<212> TYPE: PRT
<213> ORGANISM: Artificial Sequence
<220> FEATURE:
<223> OTHER INFORMATION: Synthetic construct
```

<400> SEQUENCE: 54

```
Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
                20                  25                  30

Ser Trp Val Arg Gln Ala Pro Gly Lys Gly Leu Glu Trp Val Gly Ser
            35                  40                  45

Ile Ser Pro Ser Gly Gly Ser Thr Tyr Tyr Asn Asp Asn Val Leu Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Val Gly Phe Phe Asp Glu Trp Gly Gln Gly Thr Leu Val Thr Val
            100                 105                 110

Ser Ser Ala Ser Thr Lys Gly Pro Ser Val Phe Pro Leu Ala Pro Ser
            115                 120                 125
```

-continued

```
Ser Lys Ser Thr Ser Gly Gly Thr Ala Ala Leu Gly Cys Leu Val Glu
    130             135                 140

Asp Tyr Phe Pro Glu Pro Val Thr Val Ser Trp Asn Ser Gly Ala Leu
145             150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Glu Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Cys Thr Leu Pro Pro Ser Arg
                340                 345                 350

Asp Glu Leu Thr Lys Asn Gln Val Ser Leu Ser Cys Ala Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro
            435                 440
```

<210> SEQ ID NO 55
<211> LENGTH: 229
<212> TYPE: PRT
<213> ORGANISM: Artificial Sequence
<220> FEATURE:
<223> OTHER INFORMATION: Synthetic construct

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
            35                  40                  45
```

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Val Ala Ala Pro
            115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
            195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 56
<211> LENGTH: 665
<212> TYPE: PRT
<213> ORGANISM: Artificial Sequence
<220> FEATURE:
<223> OTHER INFORMATION: Synthetic construct

<400> SEQUENCE: 56

Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
            20                  25                  30

Ser Trp Val Arg Gln Ala Pro Gly Lys Gly Leu Glu Trp Val Gly Ser
        35                  40                  45

Ile Ser Pro Ser Gly Gly Ser Thr Tyr Tyr Asn Asp Asn Val Leu Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Val Gly Phe Phe Asp Glu Trp Gly Gln Gly Thr Leu Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

-continued

```
Tyr Ser Leu Ser Ser Val Val Thr Val Pro Ser Ser Ser Leu Gly Thr
            180             185             190

Gln Thr Tyr Ile Cys Asn Val Asn His Lys Pro Ser Asn Thr Lys Val
            195             200             205

Asp Glu Lys Val Glu Pro Lys Ser Cys Asp Gly Gly Gly Gly Ser Gly
    210             215             220

Gly Gly Gly Ser Asp Ile Gln Met Thr Gln Ser Pro Ser Ser Leu Ser
225             230             235             240

Ala Ser Val Gly Asp Arg Val Thr Ile Thr Cys Arg Ala Ser Gln Asp
            245             250             255

Ile Arg Asn Tyr Leu Asn Trp Tyr Gln Gln Lys Pro Gly Lys Ala Pro
            260             265             270

Lys Leu Leu Ile Tyr Tyr Thr Ser Arg Leu Glu Ser Gly Val Pro Ser
            275             280             285

Arg Phe Ser Gly Ser Gly Ser Gly Thr Asp Tyr Thr Leu Thr Ile Ser
    290             295             300

Ser Leu Gln Pro Glu Asp Phe Ala Thr Tyr Tyr Cys Gln Gln Gly Asn
305             310             315             320

Thr Leu Pro Trp Thr Phe Gly Gln Gly Thr Lys Val Glu Ile Lys Ser
            325             330             335

Ser Ala Ser Thr Lys Gly Pro Ser Val Phe Pro Leu Ala Pro Ser Ser
            340             345             350

Lys Ser Thr Ser Gly Gly Thr Ala Ala Leu Gly Cys Leu Val Lys Asp
            355             360             365

Tyr Phe Pro Glu Pro Val Thr Val Ser Trp Asn Ser Gly Ala Leu Thr
    370             375             380

Ser Gly Val His Thr Phe Pro Ala Val Leu Gln Ser Ser Gly Leu Tyr
385             390             395             400

Ser Leu Ser Ser Val Val Thr Val Pro Ser Ser Ser Leu Gly Thr Gln
            405             410             415

Thr Tyr Ile Cys Asn Val Asn His Lys Pro Ser Asn Thr Lys Val Asp
            420             425             430

Lys Lys Val Glu Pro Lys Ser Cys Asp Lys Thr His Thr Cys Pro Pro
            435             440             445

Cys Pro Ala Pro Glu Ala Ala Gly Gly Pro Ser Val Phe Leu Phe Pro
    450             455             460

Pro Lys Pro Lys Asp Thr Leu Met Ile Ser Arg Thr Pro Glu Val Thr
465             470             475             480

Cys Val Val Val Asp Val Ser His Glu Asp Pro Glu Val Lys Phe Asn
            485             490             495

Trp Tyr Val Asp Gly Val Glu Val His Asn Ala Lys Thr Lys Pro Arg
            500             505             510

Glu Glu Gln Tyr Asn Ser Thr Tyr Arg Val Val Ser Val Leu Thr Val
            515             520             525

Leu His Gln Asp Trp Leu Asn Gly Lys Glu Tyr Lys Cys Lys Val Ser
            530             535             540

Asn Lys Ala Leu Gly Ala Pro Ile Glu Lys Thr Ile Ser Lys Ala Lys
545             550             555             560

Gly Gln Pro Arg Glu Pro Gln Val Tyr Thr Leu Pro Pro Cys Arg Asp
            565             570             575

Glu Leu Thr Lys Asn Gln Val Ser Leu Trp Cys Leu Val Lys Gly Phe
            580             585             590
```

-continued

```
Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
        610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro
                660                 665

<210> SEQ ID NO 57
<211> LENGTH: 317
<212> TYPE: PRT
<213> ORGANISM: Homo sapiens

<400> SEQUENCE: 57

Met Ser Ser Glu Gln Lys Ser Gln His Cys Lys Pro Glu Glu Gly Val
1                   5                   10                  15

Glu Ala Gln Glu Glu Ala Leu Gly Leu Val Gly Ala Gln Ala Pro Thr
                20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
        50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
                100                 105                 110

Lys Val Asp Glu Leu Ala His Phe Leu Leu Arg Lys Tyr Arg Ala Lys
        115                 120                 125

Glu Leu Val Thr Lys Ala Glu Met Leu Glu Arg Val Ile Lys Asn Tyr
        130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
                180                 185                 190

Asn Asn Gln Ile Phe Pro Lys Thr Gly Leu Leu Ile Ile Val Leu Gly
        195                 200                 205

Thr Ile Ala Met Glu Gly Asp Ser Ala Ser Glu Glu Glu Ile Trp Glu
        210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
                260                 265                 270

Leu Trp Gly Pro Arg Ala Leu Ala Glu Thr Ser Tyr Val Lys Val Leu
                275                 280                 285
```

-continued

Glu His Val Val Arg Val Asn Ala Arg Val Arg Ile Ala Tyr Pro Ser
    290                 295                 300

Leu Arg Glu Ala Ala Leu Leu Glu Glu Glu Glu Gly Val
305                 310                 315

<210> SEQ ID NO 58
<211> LENGTH: 10
<212> TYPE: PRT
<213> ORGANISM: Homo sapiens

<400> SEQUENCE: 58

Gly Val Tyr Asp Gly Arg Glu His Thr Val
1               5                   10

<210> SEQ ID NO 59
<211> LENGTH: 275
<212> TYPE: PRT
<213> ORGANISM: Homo sapiens

<400> SEQUENCE: 59

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
        210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 60
<211> LENGTH: 556
<212> TYPE: PRT
<213> ORGANISM: Homo sapiens

<400> SEQUENCE: 60

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365
```

```
Ala Gly Leu Gly Gly Thr Ala Pro Ser Tyr Gly Asn Pro Ser Ser Asp
    370             375             380

Val Gln Ala Asp Gly Ala Leu Gly Ser Arg Ser Pro Pro Gly Val Gly
385             390             395             400

Pro Glu Glu Glu Glu Gly Glu Gly Tyr Glu Glu Pro Asp Ser Glu Glu
            405             410             415

Asp Ser Glu Phe Tyr Glu Asn Asp Ser Asn Leu Gly Gln Asp Gln Leu
            420             425             430

Ser Gln Asp Gly Ser Gly Tyr Glu Asn Pro Glu Asp Glu Pro Leu Gly
        435             440             445

Pro Glu Asp Glu Asp Ser Phe Ser Asn Ala Glu Ser Tyr Glu Asn Glu
        450             455             460

Asp Glu Glu Leu Thr Gln Pro Val Ala Arg Thr Met Asp Phe Leu Ser
465             470             475             480

Pro His Gly Ser Ala Trp Asp Pro Ser Arg Glu Ala Thr Ser Leu Gly
            485             490             495

Ser Gln Ser Tyr Glu Asp Met Arg Gly Ile Leu Tyr Ala Ala Pro Gln
            500             505             510

Leu Arg Ser Ile Arg Gly Gln Pro Gly Pro Asn His Glu Glu Asp Ala
        515             520             525

Asp Ser Tyr Glu Asn Met Asp Asn Pro Asp Gly Pro Asp Pro Ala Trp
    530             535             540

Gly Gly Gly Gly Arg Met Gly Thr Trp Ser Thr Arg
545             550             555
```

```
<210> SEQ ID NO 61
<211> LENGTH: 5
<212> TYPE: PRT
<213> ORGANISM: Artificial Sequence
<220> FEATURE:
<223> OTHER INFORMATION: Synthetic construct

<400> SEQUENCE: 61

Ser Tyr Ala Met Asn
1               5

<210> SEQ ID NO 62
<211> LENGTH: 14
<212> TYPE: PRT
<213> ORGANISM: Artificial Sequence
<220> FEATURE:
<223> OTHER INFORMATION: Synthetic construct

<400> SEQUENCE: 62

His Thr Thr Phe Pro Ser Ser Tyr Val Ser Tyr Tyr Gly Tyr
1               5               10

<210> SEQ ID NO 63
<211> LENGTH: 125
<212> TYPE: PRT
<213> ORGANISM: Artificial Sequence
<220> FEATURE:
<223> OTHER INFORMATION: Synthetic construct

<400> SEQUENCE: 63

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Gln Phe Ser Ser Tyr
        20              25              30
```

-continued

```
Ala Met Asn Trp Val Arg Gln Ala Pro Gly Lys Gly Leu Glu Trp Val
    35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser
        115                 120                 125

<210> SEQ ID NO 64
<211> LENGTH: 5
<212> TYPE: PRT
<213> ORGANISM: Artificial Sequence
<220> FEATURE:
<223> OTHER INFORMATION: Synthetic construct

<400> SEQUENCE: 64

Ser Tyr Ala Met Asn
1               5

<210> SEQ ID NO 65
<211> LENGTH: 14
<212> TYPE: PRT
<213> ORGANISM: Artificial Sequence
<220> FEATURE:
<223> OTHER INFORMATION: Synthetic construct

<400> SEQUENCE: 65

Ala Ser Asn Phe Pro Ala Ser Tyr Val Ser Tyr Phe Ala Tyr
1               5                   10

<210> SEQ ID NO 66
<211> LENGTH: 125
<212> TYPE: PRT
<213> ORGANISM: Artificial Sequence
<220> FEATURE:
<223> OTHER INFORMATION: Synthetic construct

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg Ala Ser Asn Phe Pro Ala Ser Tyr Val Ser Tyr Phe
            100                 105                 110

Ala Tyr Trp Gly Gln Gly Thr Leu Val Thr Val Ser Ser
        115                 120                 125
```

-continued

```
<210> SEQ ID NO 67
<211> LENGTH: 5
<212> TYPE: PRT
<213> ORGANISM: Artificial Sequence
<220> FEATURE:
<223> OTHER INFORMATION: Synthetic construct

<400> SEQUENCE: 67

Asp Tyr Ile Met His
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic construct

<400> SEQUENCE: 68

Tyr Ile Asn Pro Tyr Asn Asp Gly Ser Lys Tyr Thr Glu Lys Phe Gln
1               5                   10                  15

Gly

<210> SEQ ID NO 69
<211> LENGTH: 12
<212> TYPE: PRT
<213> ORGANISM: Artificial Sequence
<220> FEATURE:
<223> OTHER INFORMATION: Synthetic construct

<400> SEQUENCE: 69

Gly Thr Tyr Tyr Tyr Gly Pro Gln Leu Phe Asp Tyr
1               5                   10

<210> SEQ ID NO 70
<211> LENGTH: 16
<212> TYPE: PRT
<213> ORGANISM: Artificial Sequence
<220> FEATURE:
<223> OTHER INFORMATION: Synthetic construct

<400> SEQUENCE: 70

Lys Ser Ser Gln Ser Leu Glu Thr Ser Thr Gly Thr Thr Tyr Leu Asn
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: Synthetic construct

<400> SEQUENCE: 71

Arg Val Ser Lys Arg Phe Ser
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic construct

<400> SEQUENCE: 72

Leu Gln Leu Leu Glu Asp Pro Tyr Thr
1               5
```

<210> SEQ ID NO 73
<211> LENGTH: 121
<212> TYPE: PRT
<213> ORGANISM: Artificial Sequence
<220> FEATURE:
<223> OTHER INFORMATION: Synthetic construct

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
                100                 105                 110

Gln Gly Thr Thr Val Thr Val Ser Ser
        115                 120

<210> SEQ ID NO 74
<211> LENGTH: 112
<212> TYPE: PRT
<213> ORGANISM: Artificial Sequence
<220> FEATURE:
<223> OTHER INFORMATION: Synthetic construct

<400> SEQUENCE: 74

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
                20                  25                  30

Thr Gly Thr Thr Tyr Leu Asn Trp Tyr Leu Gln Lys Pro Gly Gln Ser
            35                  40                  45

Pro Gln Leu Leu Ile Tyr Arg Val Ser Lys Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
                100                 105                 110

<210> SEQ ID NO 75
<211> LENGTH: 674
<212> TYPE: PRT
<213> ORGANISM: Artificial Sequence
<220> FEATURE:
<223> OTHER INFORMATION: Synthetic construct

<400> SEQUENCE: 75

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Asp Tyr
        20              25                  30

Ile Met His Trp Val Arg Gln Ala Pro Gly Gln Gly Leu Glu Trp Met
        35              40                  45

Gly Tyr Ile Asn Pro Tyr Asn Asp Gly Ser Lys Tyr Thr Glu Lys Phe
        50              55                  60

Gln Gly Arg Val Thr Met Thr Ser Asp Thr Ser Ile Ser Thr Ala Tyr
65              70                  75                  80

Met Glu Leu Ser Arg Leu Arg Ser Asp Asp Thr Ala Val Tyr Tyr Cys
                85              90                  95

Ala Arg Gly Thr Tyr Tyr Tyr Gly Pro Gln Leu Phe Asp Tyr Trp Gly
            100             105             110

Gln Gly Thr Thr Val Thr Val Ser Ser Ala Ser Thr Lys Gly Pro Ser
            115             120             125

Val Phe Pro Leu Ala Pro Ser Ser Lys Ser Thr Ser Gly Gly Thr Ala
    130             135             140

Ala Leu Gly Cys Leu Val Glu Asp Tyr Phe Pro Glu Pro Val Thr Val
145             150             155             160

Ser Trp Asn Ser Gly Ala Leu Thr Ser Gly Val His Thr Phe Pro Ala
                165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Glu Lys Val Glu Pro Lys Ser Cys
    210             215             220

Asp Gly Gly Gly Gly Ser Gly Gly Gly Gly Ser Gln Ala Val Val Thr
225             230             235             240

Gln Glu Pro Ser Leu Thr Val Ser Pro Gly Gly Thr Val Thr Leu Thr
            245             250             255

Cys Gly Ser Ser Thr Gly Ala Val Thr Thr Ser Asn Tyr Ala Asn Trp
            260             265             270

Val Gln Glu Lys Pro Gly Gln Ala Phe Arg Gly Leu Ile Gly Gly Thr
            275             280             285

Asn Lys Arg Ala Pro Gly Thr Pro Ala Arg Phe Ser Gly Ser Leu Leu
    290             295             300

Gly Gly Lys Ala Ala Leu Thr Leu Ser Gly Ala Gln Pro Glu Asp Glu
305             310             315             320

Ala Glu Tyr Tyr Cys Ala Leu Trp Tyr Ser Asn Leu Trp Val Phe Gly
            325             330             335

Gly Gly Thr Lys Leu Thr Val Leu Ser Ser Ala Ser Thr Lys Gly Pro
            340             345             350

Ser Val Phe Pro Leu Ala Pro Ser Ser Lys Ser Thr Ser Gly Gly Thr
            355             360             365

Ala Ala Leu Gly Cys Leu Val Lys Asp Tyr Phe Pro Glu Pro Val Thr
    370             375             380

Val Ser Trp Asn Ser Gly Ala Leu Thr Ser Gly Val His Thr Phe Pro
385             390             395             400

Ala Val Leu Gln Ser Ser Gly Leu Tyr Ser Leu Ser Ser Val Val Thr
            405             410             415

Val Pro Ser Ser Ser Leu Gly Thr Gln Thr Tyr Ile Cys Asn Val Asn
            420             425             430
```

-continued

```
His Lys Pro Ser Asn Thr Lys Val Asp Lys Lys Val Glu Pro Lys Ser
        435             440             445

Cys Asp Lys Thr His Thr Cys Pro Pro Cys Pro Ala Pro Glu Ala Ala
        450             455             460

Gly Gly Pro Ser Val Phe Leu Phe Pro Pro Lys Pro Lys Asp Thr Leu
465             470             475             480

Met Ile Ser Arg Thr Pro Glu Val Thr Cys Val Val Val Asp Val Ser
            485             490             495

His Glu Asp Pro Glu Val Lys Phe Asn Trp Tyr Val Asp Gly Val Glu
            500             505             510

Val His Asn Ala Lys Thr Lys Pro Arg Glu Glu Gln Tyr Asn Ser Thr
        515             520             525

Tyr Arg Val Val Ser Val Leu Thr Val Leu His Gln Asp Trp Leu Asn
        530             535             540

Gly Lys Glu Tyr Lys Cys Lys Val Ser Asn Lys Ala Leu Gly Ala Pro
545             550             555             560

Ile Glu Lys Thr Ile Ser Lys Ala Lys Gly Gln Pro Arg Glu Pro Gln
            565             570             575

Val Tyr Thr Leu Pro Pro Cys Arg Asp Glu Leu Thr Lys Asn Gln Val
            580             585             590

Ser Leu Trp Cys Leu Val Lys Gly Phe Tyr Pro Ser Asp Ile Ala Val
        595             600             605

Glu Trp Glu Ser Asn Gly Gln Pro Glu Asn Asn Tyr Lys Thr Thr Pro
        610             615             620

Pro Val Leu Asp Ser Asp Gly Ser Phe Phe Leu Tyr Ser Lys Leu Thr
625             630             635             640

Val Asp Lys Ser Arg Trp Gln Gln Gly Asn Val Phe Ser Cys Ser Val
            645             650             655

Met His Glu Ala Leu His Asn His Tyr Thr Gln Lys Ser Leu Ser Leu
        660             665             670

Ser Pro
```

```
<210> SEQ ID NO 76
<211> LENGTH: 674
<212> TYPE: PRT
<213> ORGANISM: Artificial Sequence
<220> FEATURE:
<223> OTHER INFORMATION: Synthetic construct

<400> SEQUENCE: 76
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asp Tyr
            20              25              30

Ile Met His Trp Val Arg Gln Ala Pro Gly Gln Gly Leu Glu Trp Met
        35              40              45

Gly Tyr Ile Asn Pro Tyr Asn Asp Gly Ser Lys Tyr Thr Glu Lys Phe
        50              55              60

Gln Gly Arg Val Thr Met Thr Ser Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Ala Arg Gly Thr Tyr Tyr Tyr Gly Pro Gln Leu Phe Asp Tyr Trp Gly
            100             105             110
```

-continued

```
Gln Gly Thr Thr Val Thr Val Ser Ser Ala Ser Thr Lys Gly Pro Ser
        115             120             125

Val Phe Pro Leu Ala Pro Ser Ser Lys Ser Thr Ser Gly Gly Thr Ala
    130             135             140

Ala Leu Gly Cys Leu Val Glu Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Glu Lys Val Glu Pro Lys Ser Cys
    210             215             220

Asp Gly Gly Gly Gly Ser Gly Gly Gly Gly Gln Ala Val Val Thr
225             230             235             240

Gln Glu Pro Ser Leu Thr Val Ser Pro Gly Gly Thr Val Thr Leu Thr
            245             250             255

Cys Gly Ser Ser Thr Gly Ala Val Thr Thr Ser Asn Tyr Ala Asn Trp
            260             265             270

Val Gln Glu Lys Pro Gly Gln Ala Phe Arg Gly Leu Ile Gly Gly Thr
            275             280             285

Asn Lys Arg Ala Pro Gly Thr Pro Ala Arg Phe Ser Gly Ser Leu Leu
    290             295             300

Gly Gly Lys Ala Ala Leu Thr Leu Ser Gly Ala Gln Pro Glu Asp Glu
305             310             315             320

Ala Glu Tyr Tyr Cys Ala Leu Trp Tyr Ser Asn Leu Trp Val Phe Gly
            325             330             335

Gly Gly Thr Lys Leu Thr Val Leu Ser Ser Ala Ser Thr Lys Gly Pro
            340             345             350

Ser Val Phe Pro Leu Ala Pro Ser Ser Lys Ser Thr Ser Gly Gly Thr
            355             360             365

Ala Ala Leu Gly Cys Leu Val Lys Asp Tyr Phe Pro Glu Pro Val Thr
    370             375             380

Val Ser Trp Asn Ser Gly Ala Leu Thr Ser Gly Val His Thr Phe Pro
385             390             395             400

Ala Val Leu Gln Ser Ser Gly Leu Tyr Ser Leu Ser Ser Val Val Thr
            405             410             415

Val Pro Ser Ser Ser Leu Gly Thr Gln Thr Tyr Ile Cys Asn Val Asn
            420             425             430

His Lys Pro Ser Asn Thr Lys Val Asp Lys Lys Val Glu Pro Lys Ser
            435             440             445

Cys Asp Lys Thr His Thr Cys Pro Pro Cys Pro Ala Pro Glu Ala Ala
    450             455             460

Gly Gly Pro Ser Val Phe Leu Phe Pro Pro Lys Pro Lys Asp Thr Leu
465             470             475             480

Met Ile Ser Arg Thr Pro Glu Val Thr Cys Val Val Val Asp Val Ser
            485             490             495

His Glu Asp Pro Glu Val Lys Phe Asn Trp Tyr Val Asp Gly Val Glu
            500             505             510

Val His Asn Ala Lys Thr Lys Pro Arg Glu Glu Gln Tyr Asn Ser Thr
            515             520             525
```

-continued

```
Tyr Arg Val Val Ser Val Leu Thr Val Leu His Gln Asp Trp Leu Asn
    530             535             540

Gly Lys Glu Tyr Lys Cys Lys Val Ser Asn Lys Ala Leu Gly Ala Pro
545             550             555             560

Ile Glu Lys Thr Ile Ser Lys Ala Lys Gly Gln Pro Arg Glu Pro Gln
                565             570             575

Val Tyr Thr Leu Pro Pro Cys Arg Asp Glu Leu Thr Lys Asn Gln Val
                580             585             590

Ser Leu Trp Cys Leu Val Lys Gly Phe Tyr Pro Ser Asp Ile Ala Val
                595             600             605

Glu Trp Glu Ser Asn Gly Gln Pro Glu Asn Asn Tyr Lys Thr Thr Pro
    610             615             620

Pro Val Leu Asp Ser Asp Gly Ser Phe Phe Leu Tyr Ser Lys Leu Thr
625             630             635             640

Val Asp Lys Ser Arg Trp Gln Gln Gly Asn Val Phe Ser Cys Ser Val
                645             650             655

Met His Glu Ala Leu His Asn His Tyr Thr Gln Lys Ser Leu Ser Leu
                660             665             670

Ser Pro
```

```
<210> SEQ ID NO 77
<211> LENGTH: 449
<212> TYPE: PRT
<213> ORGANISM: Artificial Sequence
<220> FEATURE:
<223> OTHER INFORMATION: Synthetic construct
```

```
<400> SEQUENCE: 77
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asp Tyr
                20              25              30

Ile Met His Trp Val Arg Gln Ala Pro Gly Gln Gly Leu Glu Trp Met
        35              40              45

Gly Tyr Ile Asn Pro Tyr Asn Asp Gly Ser Lys Tyr Thr Glu Lys Phe
    50              55              60

Gln Gly Arg Val Thr Met Thr Ser Asp Thr Ser Ile Ser Thr Ala Tyr
65              70              75              80

Met Glu Leu Ser Arg Leu Arg Ser Asp Asp Thr Ala Val Tyr Tyr Cys
                85              90              95

Ala Arg Gly Thr Tyr Tyr Tyr Gly Pro Gln Leu Phe Asp Tyr Trp Gly
                100             105             110

Gln Gly Thr Thr Val Thr Val Ser Ser Ala Ser Thr Lys Gly Pro Ser
        115             120             125

Val Phe Pro Leu Ala Pro Ser Ser Lys Ser Thr Ser Gly Gly Thr Ala
    130             135             140

Ala Leu Gly Cys Leu Val Glu Asp Tyr Phe Pro Glu Pro Val Thr Val
145             150             155             160

Ser Trp Asn Ser Gly Ala Leu Thr Ser Gly Val His Thr Phe Pro Ala
                165             170             175

Val Leu Gln Ser Ser Gly Leu Tyr Ser Leu Ser Ser Val Val Thr Val
                180             185             190

Pro Ser Ser Ser Leu Gly Thr Gln Thr Tyr Ile Cys Asn Val Asn His
        195             200             205
```

-continued

Lys Pro Ser Asn Thr Lys Val Asp Glu Lys Val Glu Pro Lys Ser Cys
    210             215             220

Asp Lys Thr His Thr Cys Pro Pro Cys Pro Ala Pro Glu Ala Ala Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
        275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Gly Ala Pro Ile
            325             330             335

Glu Lys Thr Ile Ser Lys Ala Lys Gly Gln Pro Arg Glu Pro Gln Val
            340             345             350

Cys Thr Leu Pro Pro Ser Arg Asp Glu Leu Thr Lys Asn Gln Val Ser
            355             360             365

Leu Ser Cys Ala Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Val Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro

<210> SEQ ID NO 78
<211> LENGTH: 219
<212> TYPE: PRT
<213> ORGANISM: Artificial Sequence
<220> FEATURE:
<223> OTHER INFORMATION: Synthetic construct

<400> SEQUENCE: 78

Asp Ile Val Met Thr Gln Thr Pro Leu Ser Leu Ser Val Thr Pro Gly
1               5               10              15

Gln Pro Ala Ser Ile Ser Cys Lys Ser Ser Gln Ser Leu Glu Thr Ser
            20              25              30

Thr Gly Thr Thr Tyr Leu Asn Trp Tyr Leu Gln Lys Pro Gly Gln Ser
        35              40              45

Pro Gln Leu Leu Ile Tyr Arg Val Ser Lys Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Leu Gln Leu
            85              90              95

Leu Glu Asp Pro Tyr Thr Phe Gly Gln Gly Thr Lys Leu Glu Ile Lys
            100             105             110

-continued

```
Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

```
<210> SEQ ID NO 79
<211> LENGTH: 232
<212> TYPE: PRT
<213> ORGANISM: Artificial Sequence
<220> FEATURE:
<223> OTHER INFORMATION: Synthetic construct

<400> SEQUENCE: 79
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

```
<210> SEQ ID NO 80
<211> LENGTH: 232
```

```
<212> TYPE: PRT
<213> ORGANISM: Artificial Sequence
<220> FEATURE:
<223> OTHER INFORMATION: Synthetic construct

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg Ala Ser Asn Phe Pro Ala Ser Tyr Val Ser Tyr Phe
            100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```